United States Patent
Chen et al.

(10) Patent No.: US 7,598,348 B2
(45) Date of Patent: Oct. 6, 2009

(54) ADIPONECTIN RECEPTOR VARIANT, ADIPOR2V2

(75) Inventors: Jian Chen, Princeton, NJ (US); Ning Lee, Hillsborough, NJ (US); Dong Cheng, Furlong, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/148,669

(22) Filed: Apr. 21, 2008

(65) Prior Publication Data

US 2008/0221305 A1 Sep. 11, 2008

Related U.S. Application Data

(62) Division of application No. 10/874,923, filed on Jun. 23, 2004, now Pat. No. 7,435,808.

(51) Int. Cl.
*C07K 14/72* (2006.01)
(52) U.S. Cl. ...................................... 530/350
(58) Field of Classification Search .................. None
See application file for complete search history.

(56) References Cited

U.S. PATENT DOCUMENTS

| 5,116,964 | A | 5/1992 | Capon et al. |
| 5,869,330 | A | 2/1999 | Scherer et al. |

FOREIGN PATENT DOCUMENTS

| WO | WO02/098898 | 12/2002 |
| WO | WO 9401548 A2 | 1/2004 |
| WO | WO2004/087874 A2 | 10/2004 |
| WO | WO2004/101618 A2 | 11/2004 |

OTHER PUBLICATIONS

Hillier, et al., "Generation and annotation of the DNA sequences of human chromosomes 2 and 4", Nature, vol. 434, pp. 724-731 (2005).
Denney, et al., "Assignment of a gene for uridine phosphorylase to chromosome 7", Cytogenet. Cell Genet., vol. 22, pp. 195-199 (1978).
Johansson, Magnus, "Identification of a novel human uridine phosphorylase", Biochem. Biophysic. Res. Comm., vol. 307, pp. 41-46 (2003).

(Continued)

*Primary Examiner*—Bridget E Bunner
*Assistant Examiner*—Zachary C Howard
(74) *Attorney, Agent, or Firm*—Stephen C. D'Amico

(57) ABSTRACT

The present invention provides novel polynucleotides encoding human AdipoR2v1 polypeptides, mouse AdipoR2v1 polypeptides, human AdipoR3 polypeptides, human AdipoR2v2 polypeptides, human AdipoR3v1 polypeptides, rat AdipoR1 polypeptides, rat AdipoR2 polypeptides, fragments and homologues thereof. Also provided are vectors, host cells, antibodies, and recombinant and synthetic methods for producing said polypeptides. The invention further relates to diagnostic and therapeutic methods for applying these novel human AdipoR2v1 polypeptides, mouse AdipoR2v1 polypeptides, human AdipoR3 polypeptides, human AdipoR2v2 polypeptides, human AdipoR3v1 polypeptides, rat AdipoR1 polypeptides, rat AdipoR2 polypeptides, to the diagnosis, treatment, and/or prevention of various diseases and/or disorders related to these polypeptides. The invention further relates to screening methods for identifying agonists and antagonists of the polynucleotides and polypeptides of the present invention.

10 Claims, 42 Drawing Sheets

• Isoforms

☐ Transmembrane domains

■ Novel hydrophobic sequence

OTHER PUBLICATIONS

Kanzaki, et al., "Expression of Uridine and Thymidine Phosphorylase Genes in Human Breast Carcinoma", Int. J. Cancer, vol. 97, pp. 631-635 (2002).

Miyashita, et al., "Uridine Phosphorylase is a Potential Prognostic Factor in Patients with Oral Squamous Cell Carcinoma", Cancer, vol. 94 (11), pp. 2959-2966 (2002).

Pizzorno, et al., "Homeostatic control of uridine and the role of uridine phosphorylase: a biological and clinical update", Biochim. Biophysica Acta, vol. 1587, pp. 133-144 (2002).

Russell, et al., "Uridine Phosphorylase Association with Vimentin", J. Biol. Chem., vol. 276 (16), pp. 13302-13307 (2001).

Temmink, et al., "The role of thymidine phosphorylase and uridine phosphorylase in (fluoro) pyrimidine metabolism in peripheral blood mononuclear cells", Int. J. Biochem. Cell Biol., vol. 38, pp. 1759-1765 (2006).

Watanabe, et al., "Cloning and Expression of Human Uridine Phosphorylase", Biochem. Biophysic. Res. Comm., vol. 216 (1), pp. 265-272 (1995).

NCBI Entrez Accession No. NM_003364 (gi:31742506), Temmink, et al., Nov. 17, 2006.

NCBI Entrez Accession No. NM_003364 (gi:4507838), Pizzorno, et al., May 7, 2003.

NCBI Entrez Accession No. NM_173355 (gi:34222223), Hillier, et al., Jun. 3, 2007.

NCBI Entrez Accession No. NM_173355 (gi:27597095), Johansson, M., Aug. 6, 2003.

NCBI Entrez Accession No. BF732341 (gi:12057499), NCI-CGAP, 1997.

Bork, 2000, "Powers and Pitfalls in Sequence Analysis: The 70% Hurdle", Genome Research, 10:398-400.

Bork, et al., 1996, "Go hunting in sequence databases but watch out for the traps", Trends in Genetics, 12 (10):425-427.

Brenner, 1999, "Errors in genome annotation", Trends in Genetics 15 (4):132-133.

Doerks, et al., 1998, "Protein annotation: detective work for function prediction", Trends in Genetics, 14 (6):248-250.

Kadowaki, 2005, Endocrine Reviews, 26 (3):439-451.

Locus BQ439997, NCBI Entrez Nucleotide Database, published May 24, 2002.

Ngo, et al., 1995, "The Protein Folding Problem and Tertiary Structure Prediction, Chapter 14: Computational Complexity Protein Structure Prediction, and the Levinthal Paradox", pp. 492-495.

Skolnick, et al., 2000, "From gene to protein structure and function: novel applications of computational approaches in the genomic era", Trends in Biotech., 18 (1):34-39.

Smith, et al., 1997, "The challenges of genome sequence annotation of 'The devil is in the details'", Nature Biotech., 15:1222-1223 sdsssss'.

Wells, 1990, "Additivity of Mutational Effects in Proteins", Biochemistry, 29 (37):8509-8517.

Altschul, et al., "Basic Local Alignment Search Tool", J. Mol. Biol., vol. 214, pp. 403-410 (1990).

Barger, et al., "p 38 Mitogen-activated Protein Kinase Activates Peroxisome Proliferator-activated Receptor α", J. Biol. Chem., vol. 276(48), pp. 44495-44501 (2001).

Berner, et al., "Adiponectin and its receptors are expressed in bone-forming cells", Bone, vol. 35, pp. 842-849 (2004).

Beylot, et al, "Expression of the adiponectin receptors AdipoR1 and AdipoR2 in lean rats and in obese Zucker rats", Metabolism Clin. Exper., vol. 55, pp. 396-401 (2006).

Blüher, et al., "Regulation of adiponectin receptor R1 and R2 gene expression in adipocytes of C57BL/6 mice", Biochem. Biophys. Res. Comm., vol. 329, pp. 1127-1132 (2005).

Blackshaw, et al., "Genomic Analysis of Mouse Retinal Development", PloS Biol., vol. 2(9) e247, pp. 1411-1431 (2004).

Broedl, et al., "Genetic variants of adiponectin receptor 2 are associated with increased adiponectin levels and decreased triglyceride/VLDL levels in patients with metabolic syndrome", Cardio. Diabetology, vol. 5(11), pp. 1-7 (2006).

Carninci, et al., "High-Efficiency Full-Length cDNA Cloning", Meth. Enzymology, vol. 303, pp. 19-44 (1999).

Carninci, et al., "Normalization and Subtraction of Cap-Trapper-Selected cDNAs to Prepare Full-Length cDNA Libraries for Rapid Discovery of New Genes", vol. 10, pp. 1617-1630 (2000).

Cheng, et al., "Identification of Acyl Coenzyme A:Monoacylglycerol Acyltransferase 3, an Intestinal Specific Enzyme Implicated in Dietary Fat Absorption", J. Biol. Chem., vol. 278(16), pp. 13611-13614 (2003).

Cheng, et al., "Human acyl-CoA: diacylglycerol acyltransferase is a tetrameric protein", Biochem. J., vol. 359, pp. 707-714 (2001).

Civitarese, et al., "Adiponectin receptors gene expression and insulin sensitivity in non-diabetic Mexican Americans with or without a family history of Type 2 diabetes", Diabetologia, vol. 47, pp. 816-820 (2004).

Dieudonne, et al., "Adiponectin mediates antiproliferative and apoptotic responses in human MCF7 breast cancer cells", Biochem. Biophys. Res. Comm., vol. 345, pp. 271-279 (2006).

Diez, et al., "The role of the novel adipocyte-derived hormone adiponectin in human disease", Eur. J. Endocrin, vol. 148, pp. 293-300 (2003).

Ding, et al., "Cloning and expression of porcine adiponectin and adiponectin receptor 1 and 2 genes in pigs", J. Anim. Sci., vol. 82, pp. 3162-3174 (2004).

Fang, et al., "Hyperglycemia- and hyperinsulinemia-induced alteration of adiponectin receptor expression and adiponectin effects in L6 myoblasts", J. Molec. Endocrin., vol. 35, pp. 465-476 (2005).

The Fantom Consortium, et al., "The Transcriptional Landscape of the Mammalian Genome", Science, vol. 309, pp. 1559-1563 (2005).

The Fantom Consortium and the Riken Genome Exploration Research Group Phase 1 & II Team, Nature, vol. 420, pp. 563-573 (2002).

Fasshauer, et al., "Growth hormone is a positive regulator of adiponectin receptor 2 in 3T3-L1 adipocytes", FEBS Ltrs., vol. 28035, pp. 27-32 (2004).

Fruebis, et al., "Proteolytic cleavage product of 30-kDa adipocyte complement-related protein increases fatty acid oxidation in muscle and causes weight loss in mice", PNAS, vol. 98(4), pp. 2005-2010 (2001).

Fry, et al., "Area Postrema Neurons are Modulated by the Adipocyte Hormone Adiponectin", J. Neurosci., vol. 26(38), pp. 9695-9702 (2006).

Fujimoto, et al., "Adiponectin is expressed in the brown adipose tissue and surrounding immature tissues in mouse embryos", Biochim. Biophysic Acta, vol. 1731, pp. 1-12 (2005).

Fujioka, et al., "Role of adiponectin receptors in endothelin-induced cellular hypertrophy in cultured cardiomyocytes and their expression in infarcted heart", Am. J. Physiol. Heart Circ. Physiol., vol. 290, pp. 2409-2416 (2006).

Inukai, et al., "Regulation of adiponectin receptor gene expression in diabetic mice", Am. J. Physiol. Endocrinol. Metab., vol. 288, pp. 876-882 (2005).

Kim, et al., "Increased adiponectin receptor-1 expression in adipose tissue of impaired glucose-tolerant obese subjects during weight loss", Eur. J. Endocrin., vol. 155, pp. 161-165 (2006).

Kubota, et al., "Disruption of Adiponectin Causes Insulin Resistance and Neointimal Formation", J. Biol. Chem., vol. 277(29), pp. 25863-25866 (2002).

Kyte, et al., "A Simple Method for Displaying the Hydropathic Character of a Protein", J. Mol. Biol., vol. 157, pp. 105-132 (1982).

Lord, et al., "Expression of adiponectin and its receptors in swine", J. Anim. Sci., vol. 83, pp. 565-578 (2005).

Mammalian Gene Collection Program Team, "Generation and initial analysis of more than 15,000 full-length human and mouse cDNA sequences", PNAS, vol. 99(26), pp. 16899-16903 (2002).

Maeda, et al., "Diet-induced insulin resistance in mice lacking adiponectin/ACRP30", Nature Med., vol. 8(7), pp. 731-737 (2002).

Mao, et al., "APPL1 binds to adiponectin receptors and mediates adiponectin signaling and function", Nature Cell Biol., vol. 8(5), pp. 516-523 (Supp. Figs. 1-4) (2006).

Michael, et al., "Restoration of insulin-sensitive glucose transporter (GLUT4) gene expression in muscle cells by the transcriptional coactivator PGC-1", PNAS, vol. 98, pp. 3820-3825 (2001).

Mistry, et al., "The regulation of adiponectin receptors in human prostate cancer cell lines", Biochem. Biophys. Res. Comm., vol. 348, pp. 832-838 (2006).

Neumeier, et al., "Adiponectin and its receptors in rodent models of fatty liver disease and liver cirrhosis", World J. Gastroen., vol. 12(34), pp. 5490-5494 (2006).

Ota, et al., "Complete sequencing and characterization of 21,243 full-length human cDNAs", Nature Gen., vol. 36(1), pp. 40-45 (2004).

Puigserver, et al., "Cytokine Stimulation of Energy Expenditure through p38 MAP Kinase Activation of PPARγ Coactivator-1", Molec. Cell, vol. 8, pp. 971-982 (2001).

Riken Genome Exploration Research Group and Genome Science Group (Genome Network Project Core Group) and the Fantom Consortium, "Antisense Transcription in the Mammalian Transcriptome", vol. 309, pp. 1564-1566 (2005).

The Riken Genome Exploration Research Group Phase II Team and the Fantom Consortium, "Functional annotation of a full-length mouse cDNA collection", Nature, vol. 409, pp. 685-690 (2001).

Shapiro, et al., "The crystal structure of a complement-1q family protein suggests an evolutionary link to tumor necrosis factor", Curr. Biol., vol. 8, pp. 335-338 (1998).

Shibata, et al., "Riken Integrated Sequence Analysis (RISA) System-384-Format Sequencing Pipeline with 384 Multicapillary Sequencer", Genome Research, vol. 10, pp. 1757-1771 (2000).

Siitonen, et al., "Association of sequence variations in the gene encoding adiponectin receptor 1 (ADIPOR1) with body size and insulin levels. The Finnish Diabetes Prevention Study", Diabetologia, vol. 49, pp. 1795-1805 (2006).

Soccio, et al., "Common Haplotypes at the Adiponectin Receptor 1 (ADIPOR1) Locus Are Associated With Increased Risk of Coronary Artery Disease in Type 2 Diabetes", Diabetes, vol. 55, pp. 2763-2770 (2006).

Staiger, et al., "Expression of Adiponectin Receptor mRNA in Human Skeletal Muscle Cells is Related to In Vivo Parameters of Glucose and Lipid Metabolism", Diabetes, vol. 53, pp. 2195-2201 (2004).

Sun, et al., "Regulation of adiponectin receptors in hepatocytes by the peroxisome proliferators-activated receptor-γ agonist rosiglitazone", Diabetologia, vol. 49, pp. 1303-1310 (2006).

Tomas, et al., "Enhanced muscle fat oxidation and glucose transport by ACRP30 globular domain: Acetyl-CoA carboxylase inhibition and AMP-activated protein kinase activation", PNAS, vol. 99, pp. 16309-16313 (2002).

Tsao, et al., "ACRP30, a new hormone controlling fat and glucose metabolism", Eur. J. Pharm., vol. 440, pp. 213-221 (2002).

Tsuchida, et al., "Insulin/Foxo1 Pathway Regulates Expression Levels of Adiponectin Receptors and Andiponectin Sensitivity", J. Biol. Chem., vol. 279(29), pp. 30817-30822 (2004).

Tsuchida, et al., "Peroxisome Proliferator-Activated Receptor (PPAR) α Activation Increases Adiponectin Receptors and Reduces Obesity-Related Inflammation in Adipose Tissue", Diabetes, vol. 54, pp. 3358-3370 (2005).

Waki, et al., "Impaired Multimerization of Human Adiponectin Mutants Associated with Diabetes", J. Biol. Chem., vol. 278(41), pp. 40352-40363 (2003).

Wang, et al., "Adiponectin Receptor 1 Gene (ADIPOR1) as a Candidate for Type 2 Diabetes and Insulin Resistance", Diabetes, vol. 53, pp. 2132-2136 (2004).

Warden, et al., "Linkage Mapping of 40 Randomly Isolated Liver cDNA Clones in the Mouse", Genomics, vol. 18, pp. 295-307 (1993).

Watahiki, et al., "Libraries enriched for alternatively spliced exons reveal splicing patterns in melanocytes and melanomas", Nature Methods, vol. 1(3), pp. 233-239 (2004).

Winzell, et al., "Dual action of adiponectin on insulin secretion in insulin-resistant mice", Biochem. Biophys. Res. Comm., vol. 321, pp. 154-160 (2004).

Yamauchi, et al., "The fat-derived hormone adiponectin reverses insulin resistance associated with both lipoatrophy and obesity", Nature Med., vol. 7(8), pp. 941-946 (2001).

Yamauchi, et al., "Adiponectin stimulates glucose utilization and fatty-acid oxidation by activating AMP-activated protein kinase", Nature Med., vol. 8(11), pp. 1288-1295 (2002).

Yamauchi, et al., "Globular Adiponectin Protected ob/ob Mice from Diabetes and ApoE-deficient Mice from Atherosclerosis", J. Biol. Chem., vol. 278(4), pp. 2461-2468 (2003).

Yamauchi, et al., "Cloning of adiponectin receptors that mediate antidiabetic metabolic effects", Nature, vol. 423, pp. 762-769 (2003) and Corrigendum on p. 1123 attached.

Zhou, et al., "Expression profiles of adiponectin receptors in mouse embryos", Gene Expression Patterns, vol. 5, pp. 711-715 (2005).

NCBI Entrez Accession No. AAH14875 (gi:15928831), Strausberg, et al., Jun. 19, 2006.

NCBI Entrez Accession No. AAH24094 (gi:54611225), Strausberg, et al., Dec. 2, 2006.

NCBI Entrez Accession No. AAH51858 (gi:30354285), Strausberg, et al., Aug. 11, 2006.

NCBI Entrez Accession No. AAH61838 (gi:38197440), Strausberg, et al., Jul. 15, 2006.

NCBI Entrez Accession No. AAR08368 (gi:38018645), Tang, et al., Oct. 3, 2005.

NCBI Entrez Accession No. AAR08378 (gi:38018665), Tang, et al., Nov. 3, 2003.

NCBI Entrez Accession No. AAZ76713 (gi:73487233), Fang, et al., Dec. 14, 2005.

NCBI Entrez Accession No. AAZ76714 (gi:73487235), Fang, et al., Dec. 14, 2005.

NCBI Entrez Accession No. AL049839 (gi:7009578), Heilig, et al., Apr. 29, 2001.

NCBI Entrez Accession No. BAC86881 (gi:34534009), Tanigami, et al., Sep. 14, 2006.

NCBI Entrez Accession No. BAC87473 (gi:34535916), Ninomiya, et al., Sep. 14, 2006.

NCBI Entrez Accession No. BC010743 (gi:14789613), Strausberg, et al., Jul. 15, 2006.

NCBI Entrez Accession No. BC014875 (gi:15928830), Strausberg, et al., Jun. 19, 2006.

NCBI Entrez Accession No. BC051858 (gi:34193849), Strausberg, et al., Aug. 11, 2006.

NCBI Entrez Accession No. BE785660 (gi:10206858), NIH-MGC, Oct. 20, 2000.

NCBI Entrez Accession No. BQ208259 (gi:20424724), Bonaldo, et al., May 2, 2002.

NCBI Entrez Accession No. BQ439997 (gi:21179073), NIH-MGC, May 24, 2002.

NCBI Entrez Accession No. CA339744 (gi:24557842), NCI-CGAP, Nov. 4, 2002.

NCBI Entrez Accession No. CB771587 (gi:29859978), Amgen Est Program, May 16, 2003.

NCBI Entrez Accession No. CB801151 (gi:29914128), Amgen Est Program, May 16, 2003.

NCBI Entrez Accession No. NM_015999 (gi:21361518), Soccio, et al., Nov. 26, 2006.

NCBI Entrez Accession No. NM_024551 (gi:38261972), Mistry, et al., Dec. 3, 2006.

NCBI Entrez Accession No. NM_197985 (gi:118130777), Neumeier, et al., Nov. 18, 2006.

NCBI Entrez Accession No. NP_001007193 (gi:55742866), Lord, et al., Nov. 18, 2006.

NCBI Entrez Accession No. NP_001033068 (gi:83816891), Fry, et al., Nov. 18, 2006.

NCBI Entrez Accession No. NP_057083 (gi:21361519), Soccio, et al., Nov. 26, 2006.

NCBI Entrez Accession No. NP_078827 (gi:38261973), Mistry, et al., Dec. 3, 2006.

NCBI Entrez Accession No. NP_116054 (gi:14249226), Strausberg, R., May 30, 2001.

NCBI Entrez Accession No. NP_997470 (gi:46485456), Fry, et al., Nov. 18, 2006.

NCBI Entrez Accession No. Q86V24 (gi:38372190), Ota, et al., Oct. 3, 2006.

NCBI Entrez Accession No. Q91VH1 (gi:38372245), Carninci, et al., Nov. 28, 2006.

NCBI Entrez Accession No. XM_063159 (gi:30153285), International Human Genome Sequencing Consortium, Apr. 28, 2003.

NCBI Entrez Accession No. XM_132831 (gi:28544681), NCBI Annotation Project, Feb. 24, 2003.
NCBI Entrez Accession No. XP_001096740 (gi:109095057), NCBI's Annotation Process, Jun. 14, 2006.
NCBI Entrez Accession No. XP_001096853 (gi:109095059), NCBI's Annotation Process, Jun. 14, 2006.
NCBI Entrez Accession No. XP_063159 (gi:30153286), International Human Genome Sequencing Consortium, Apr. 28, 2003.
NCBI Entrez Accession No. XP_129394 (gi:20910331), NCBI Annotation Project, Feb. 24, 2003.
NCBI Entrez Accession No. XP_232323 (gi:34858379), NCBI's Annotation Process, Apr. 15, 2005.
NCBI Entrez Accession No. XP_237893 (gi:34880233), NCBI's Annotation Process, Oct. 23, 2003.
NCBI Entrez Accession No. XP_508922 (gi:114642805), NCBI's Annotation Process, Sep. 15, 2006.
NCBI Entrez Accession No. XP_534929 (gi:73997564), NCBI's Annotation Process, Aug. 30, 2005.
NCBI Entrez Accession No. XP_537118 (gi:73960229), NCBI's Annotation Process, Aug. 30, 2005.
NCBI Entrez Accession No. XP_848356 (gi:73960225), NCBI's Annotation Process, Aug. 30, 2005.
NCBI Entrez Accession No. XP_854029 (gi:73997558), NCBI's Annotation Process, Aug. 30, 2005.
NCBI Entrez Accession No. XP_868131 (gi:73997560), NCBI's Annotation Process, Aug. 30, 2005.
NCBI Entrez Accession No. XP_868136 (gi:73997562), NCBI's Annotation Process, Aug. 30, 2005.
Pajvani, et al., "Complex Distribution, Not Absolute Amount of Adiponectin, Correlates with Thiazolidinedione-mediated Improvement in Insulin Sensitivity", J. Biol. Chem., vol. 279(13), pp. 12152-12162 (2004).

FIG. 1A

```
  1 CGGACGCGTGGGCGCGGCGGCGGCAGCGGCGGCGGCTACACCGGGCTTGGCCCCCTCCCT   60

61 CCTCCGTTCCCCCCTCCTCCCCCCTCCCCTCAGCGGTGGCTCCCAAGAAGTCCGAGACAC  120

121 GCGGATCAACTCACTATCCTGAAGGTCCATTCTCCCAAGAAGAGGGGACAGAAAGACAGA  180

181 TCTATTTGTAAGAAAGGCTTGGGTATCCCATGAACGAGCCAACAGAAAACCGATTGGGGT  240
  1                                 M  N  E  P  T  E  N  R  L  G  C   11

241 GCAGCAGGACTCCAGAGCCAGATATAAGGCTCAGAAAAGGGCACCAACTGGATGGTACAC  300
 12  S  R  T  P  E  P  D  I  R  L  R  K  G  H  Q  L  D  G  T  R   31

301 GAAGAGGTGATAATGACAGCCACCAAGGAGATTTGGAGCCCATTTTAGAGGCATCTGTTC  360
 32  R  G  D  N  D  S  H  Q  G  D  L  E  P  I  L  E  A  S  V  L   51

361 TATCTTCCCATCATAAAAAAAGCTCTGAGGAACATGAATACAGTGATGAAGCTCCTCAGG  420
 52  S  S  H  H  K  K  S  S  E  E  H  E  Y  S  D  E  A  P  Q  E   71

421 AAGATGAGGGCTTTATGGGCATGTCCCCTCTCTTACAAGCCCATCATGCTATGGAAAAAA  480
 72  D  E  G  F  M  G  M  S  P  L  L  Q  A  H  H  A  M  E  K  M   91

481 TGGAAGAATTTGTTTGTAAGGTATGGGAAGGTCGGTGGCGAGTGATCCCTCATGATGTAC  540
 92  E  E  F  V  C  K  V  W  E  G  R  W  R  V  I  P  H  D  V  L  111

541 TACCAGACTGGCTCAAGGATAATGACTTCCTCTTGCATGGACACCGGCCTCCTATGCCTT  600
112  P  D  W  L  K  D  N  D  F  L  L  H  G  H  R  P  P  M  P  S  131

601 CTTTCCGGGCCTGTTTTAAGAGCATTTTCAGAATACACACAGAAACAGGCAACATTTGGA  660
132  F  R  A  C  F  K  S  I  F  R  I  H  T  E  T  G  N  I  W  T̲  151

661 CACATCTCTTAGGTTGTGTATTCTTCCTGTGCCTGGGGATCTTTTATATGTTTCGCCCAA  720
152  H̲  L̲  L̲  G̲  C̲  V̲  F̲  F̲  L̲  C̲  L̲  G̲  I̲  F̲  Y̲  M̲  F̲  R̲  P̲  N̲  171

721 ATATCTCCTTTGTGGCCCCTCTGCAAGAGAAGGTGGTCTTTGGATTATTTTCTTAGGAG  780
172  I̲  S  F  V  A  P̲  L̲  Q̲  E̲  K̲  V̲  V̲  F̲  G̲  L̲  F̲  F̲  L̲  G̲  A̲  191

781 CCATTCTCTGCCTTTCTTTTTCATGGCTCTTCCACACAGTCTACTGCCACTCAGAGGGGG  840
192  I̲  L̲  C̲  L̲  S̲  F̲  S̲  W̲  L̲  F̲  H  T  V  Y  C  H  S  E  G  V  211
```

FIG. 1B

```
 841  TCTCTCGGCTCTTCTCTAAACTGGATTACTCTGGTATTGCTCTTCTGATTATGGGAAGTT   900
 212    S   R   L   F   S   K   L   D   Y   S   G   I   A   L   L   I   M   G   S   F    231

901  TTGTTCCTTGGCTTTATTATTCTTTCTACTGTAATCCACAACCTTGCTTCATCTACTTGA   960
 232    V   P   W   L   Y   Y   S   F   Y   C   N   P   Q   P   C   F   I   Y   L   I    251

961  TTGTCATCTGTGTGCTGGGCATTGCAGCCATTATAGTCTCCCAGTGGGACATGTTTGCCA  1020
 252    V   I   C   V   L   G   I   A   A   I   I   V   S   Q   W   D   M   F   A   T    271

1021  CCCCTCAGTATCGGGGAGTAAGAGCAGGAGTGTTTTTGGGCCTAGGCCTGAGTGGAATCA  1080
 272    P   Q   Y   R   G   V   R   A   G   V   F   L   G   L   G   L   S   G   I   I    291

1081  TTCCTACCTTGCACTATGTCATCTCGGAGGGGTTCCTTAAGGCCGCCACCATAGGGCAGA  1140
 292    P   T   L   H   Y   V   I   S   E   G   F   L   K   A   A   T   I   G   Q   I    311

1141  TAGGCTGGTTGATGCTGATGGCCAGCCTCTACATCACAGGAGCTGCCCTGTATGCTGCCC  1200
 312    G   W   L   M   L   M   A   S   L   Y   I   T   G   A   A   L   Y   A   A   R    331

1201  GGATCCCCGAACGCTTTTTCCCTGGCAAATGTGACATCTGGTTTCACTCTCATCAGCTGT  1260
 332    I   P   E   R   F   F   P   G   K   C   D   I   W   F   H   S   H   Q   L   F    351

1261  TTCATATCTTTGTGGTTGCTGGAGCTTTTGTTCACTTCCATGGTGTCTCAAACCTCCAGG  1320
 352    H   I   F   V   V   A   G   A   F   V   H   F   H   G   V   S   N   L   Q   E    371

1321  AGTTTCGTTTCATGATCGGCGGGGGCTGCAGTGAAGAGGATGCACTGTGATACCTACCAG  1380
 372    F   R   F   M   I   G   G   G   C   S   E   E   D   A   L                        386

1381  TCTCCAGGGACTATGACCCTAAACCAGGGCCTGCGGCACTTGCGGGCCTCCCTGCTGGCT  1440

1441  ACTGATGCCAGTACCAGAGGAGCCCCAAAACTTTGACAGCCTCGTGGGCTTTGTGACGGC  1500

1501  CCAGGGGCTCTGCGTGGTACATGACTGAGAAGAGAAAAACAAAAATAAATCATACCTCAA  1560

1561  AAAAAAAAAAAAAAAAAAAAAAAAA  1585
```

FIG. 2A

```
  1 CACAAGAATCCGTGGAGCTCAGCAGTACCCTCAGACTCTGGTCTACAACTCTGACAGGAT   60

61 TTGGGGTCAACTTACCATCCCTTAAAAATCCATTCTCCCAAGAAGAAGGGACAGAAAGAA  120

121 AGACCACTTTGTAAGAAAGGCTTTGGTATCCCATGAACGAGCCAGCCAAACACCGATTGG  180
  1                                   M  N  E  P  A  K  H  R  L  G   10

181 GGTGCACCAGGACTCCAGAGCCAGATATACGGCTCAGAAAAGGGCACCAACTTGATGATA  240
 11  C  T  R  T  P  E  P  D  I  R  L  R  K  G  H  Q  L  D  D  T   30

241 CAAGGGGAAGTAATAATGACAACTACCAAGGAGATTTGGAGCCCAGCTTAGAGACACCTG  300
 31  R  G  S  N  N  D  N  Y  Q  G  D  L  E  P  S  L  E  T  P  V   50

301 TTTGTTCTTCCTATTATGAAAATAGCCCGGAGGAGCCCGAGTGTCATGATGACAATTCCC  360
 51  C  S  S  Y  Y  E  N  S  P  E  E  P  E  C  H  D  D  N  S  Q   70

361 AGGAAGATGAAGGGTTTATGGGCATGTCCCCGCTCCTACAGGCCCATCATGCTATGGAAC  420
 71  E  D  E  G  F  M  G  M  S  P  L  L  Q  A  H  H  A  M  E  R   90

421 GAATGGAAGAGTTTGTTTGTAAGGTGTGGGAAGGCCGATGGCGAGTGATCCCTCACGATG  480
 91  M  E  E  F  V  C  K  V  W  E  G  R  W  R  V  I  P  H  D  V  110

481 TGCTACCGGATTGGCTTAAGGATAATGACTTCCTTCTCCATGGACACCGGCCTCCTATGC  540
111  L  P  D  W  L  K  D  N  D  F  L  L  H  G  H  R  P  P  M  P  130

541 CTTCCTTTCGGGCCTGTTTTAAGAGCATTTTTAGAATACACACAGAGACGGGCAACATTT  600
131  S  F  R  A  C  F  K  S  I  F  R  I  H  T  E  T  G  N  I  W  150

601 GGACACATCTCCTAGGTTGTGTATTCTTCCTGTGCCTGGGGATCTTTTATATGTTTCGCC  660
151  T  H  L  L  G  C  V  F  F  L  C  L  G  I  F  Y  M  F  R  P  170

661 CAAATATATCTTTTGTGGCCCCTCTGCAAGAGAAAGTGGTCTTTGGCTTGTTCTTCTTGG  720
171  N  I  S  F  V  A  P  L  Q  E  K  V  V  F  G  L  F  F  L  G  190

721 GAGCCATTCTCTGCCTTTCCTTTTCATGGCTCTTCCACACGGTGTACTGCCACTCAGAAG  780
191  A  I  L  C  L  S  F  S  W  L  F  H  T  V  Y  C  H  S  E  G  210

781 GGGTCTCCCGACTCTTCTCTAAATTGGATTACTCTGGTATTGCTCTTCTGATCATGGGAA  840
211  V  S  R  L  F  S  K  L  D  Y  S  G  I  A  L  L  I  M  G  S  230

841 GTTTTGTTCCTTGGCTTTATTATTCTTTCTACTGTAACCCACAACCTTGCTTCATCTACC  900
231  F  V  P  W  L  Y  Y  S  F  Y  C  N  P  Q  P  C  F  I  Y  L  250
```

FIG. 2B

```
 901  TGATTGTCATCTGTGTGCTGGGCATTGCAGCCATTATCGTCTCTCAGTGGGACATGTTTG   960
 251    I   V   I   C   V   L   G   I   A   A   I   I   V   S   Q   W   D   M   F   A     270

961  CCACCCCTCAGTATCGGGGGGTCAGAGCAGGAGTGTTCGTGGGCTTAGGCCTGAGTGGAA  1020
 271    T   P   Q   Y   R   G   V   R   A   G   V   F   V   G   L   G   L   S   G   I     290

1021  TCATCCCTACCTTGCATTATGTCATCTCAGAAGGGTTCCTGAAGGCTGCCACCATAGGGC  1080
 291    I   P   T   L   H   Y   V   I   S   E   G   F   L   K   A   A   T   I   G   Q     310

1081  AGATAGGCTGGCTAATGCTTATGGCTAGCCTCTATATCACCGGAGCTGCCCTCTATGCGG  1140
 311    I   G   W   L   M   L   M   A   S   L   Y   I   T   G   A   A   L   Y   A   A     330

1141  CCCGTATCCCTGAGCGCTTCTTTCCTGGCAAATGTGACATCTGGTTTCACTCTCATCAGC  1200
 331    R   I   P   E   R   F   F   P   G   K   C   D   I   W   F   H   S   H   Q   L     350

1201  TCTTCCACATCTTTGTGGTTGCTGGTGCCTTTGTTCACTTCCACGGAGTCTCAAACCTGC  1260
 351    F   H   I   F   V   V   A   G   A   F   V   H   F   H   G   V   S   N   L   Q     370

1261  AGGAATTTCGTTTCATGATTGGCGGGGGCTGCACTGAAGAGGATGCACTGTGATACTCTC  1320
 371    E   F   R   F   M   I   G   G   C   T   E   E   D   A   L                         386

1321  CAGGAACCAGGGACTCTGACCCTGAGCCAGGCCTGCAGGTCCTGCAGGCCTTCTTACTGG  1380

1381  CTGTCGGTGCCAGTGCCAGAGAAGCCCCAAAACTTGGACAGCCTCATGGGCCTTGTGTTG  1440

1441  GCCCAAGGGCTCCATGGGGTACAAGACTAAGAAGAGAAAAACAAAAATAAATCATACCTC  1500

1501  AAAGGATGGAATGCATCGATTAGGAGAGAAGGAGAAATGGCTCATCCCCTGGCTTCCTCT  1560

1561  TGGGATCTACCGATTGAAAGCAACTCTGCAAGACCCTCGCCTGACAGGCTGGCTTCTGAT  1620

1621  GTGATCGTATTTATTTGTAGAAGATGGGGAAACAGTTTAGTTGGTGGTCTTTCTTCTCCC  1680

1681  TTCCTTGCTCCTTGCAGCAGTAACATGTATGAGTACCATGCACCAACTGATCGTGCCATT  1740

1741  GGAGCTCCTTAAACAGTAATCACAACCAAGCTAGGGAACATTTGTATCCAATAAAGGGG   1800

1801  TGGGAGTGCGGTTTTAGGCACTCCTTTGGGAGAACAAAGAAATTAATGTAAATAAGATTT  1860

1861  CTAATTTACTGTTTAAATAAGAATTTATATAAACATTTAAGACATAGGGGCAGGGAGGGA  1920
```

FIG. 2C

```
1921  GGGAGACTTTTTTTAAAAAGAATGAAACATGCAAGTACCACACACTGTTTCAATTTTGCA  1980

1981  CAAGTGATGGGAGGAGGATGGAGTGGTAGCCCCAGAATGCACGATGTCTTGGTGCACCAA  2040

2041  GGTGCCTTCCCTAGGCCGATAACACTTGGACCCTGCTGGGGCAGAGTGGACAGCCCCAGC  2100

2101  CCAGGAACTTCCTGGCCACTCTCAAGACTGAGAGCCTTTGGGCATTCAGAGGGGAGGGA  2160

2161  TGTGGAAGTCGTGTGTGCTTTTCAATGGAAGCAGCACAGGTTGTCATAGTGGCTCTAGAG  2220

2221  AAAGTGTCATTTGGGAGACTGTTATGTAGGCTAGTGATGACCCTTTTGAAGAGTGAAGCC  2280

2281  ACCTGGTTCTACTGTAGATGTAGTAGAGACTTGATGAAGGGGAGGAGGACCTGGGGGCAT  2340

2341  CAGCATAGGACTGGTCTGCTTCTCCCTGGTGTCTCGTTTGACCAGGTGGTAGTTCTTATC  2400

2401  TGAATAGAGGTATGGCCATTTTCCAGACCCTCTCTGTGGAGCTCTGAGCCATTCTGCAAA  2460

2461  TTTTGCTCTATTGAGAATCACTGCCCTAACTGTCCTTCCTCCTGGAAATCAAAAACTGCC  2520

2521  CCCCCCCCCCAGCATCAAAGCTCCTTCGTGGAGCCGGCCACTAGTGAGATTCTGATGAG  2580

2581  CATGGGTCCCACCTGAAGTCATGCAGGCAGGTGTGGAGGACCATCCCTTGGACTAGGAAT  2640

2641  GGTGGCGCTTTTCTCTGGTGCAGGCTTGGCAGGCTTGGCATGACAACAGATTCTTCTCCC  2700

2701  GTTGAACAAGAAAGTCAGTAATACCTACTGTGGAGTTGTTAGCACGCACTGAATGCCATT  2760

2761  TGCAAGACCTGTGCTACAGAGTTGAAAAGGAAGTGGACTGTTATTACCAGGTAGTCGGAT  2820

2821  AGAATTAAACCCACAATTTTGAATTGCTGCTAGAAGTTACAAATAATTTCTTTGTCCTAG  2880

2881  GGCCTTCTTGTTATGGGTTTTAGAGAGTGGCAGTGAGTTGGGTCTTGGCTCCTAAGTGAG  2940

2941  AAACCAAGCACTTGAGTCTCTTAGACTCTAGGCCTCACTCCTTGGGGCTGGTGGGTATTG  3000

3001  CAGTGTAACATGGGCCTCGGGCATCCCAAAAGGGGTGCTGGGCAGTATGAGGAGGTCCTG  3060
```

FIG. 2D

```
3061  TTTTTACAGTAGTGTTTTCTTGGTCGTTGTTGTCCTTCCTCTACCTTCAGATCGCCACCC  3120

3121  AGCTGCAGCTGGGACCCAGGAAGGAGTCCATTGAAAACCTGGGAAGAACTTCAGAGTATT  3180

3181  GGGTTGTGGATAAGGTCACTGCCCTAGGTAGGCCCAACAGGAAGCTCTGGGTGAACAGCA  3240

3241  TTGTGCCAGACAACTAAGAACAGTGTTAATTCCTCAAGAAGCAGTTCATCAAGACAGTGT  3300

3301  CCATCCGGAAGGAAGCTCACCTAGGCTTGTGGTAGCAACAGCACATATCAGCAGCCAGAC  3360

3361  GCACTCTCTGGTCGTGCACTTTGGGACATGAGTTTGAGACGCTTCCTCATGACACCTACA  3420

3421  GGAGTAGAGGTCTTTGGGACTGGTCATCCCTCTTCCCAAAGCAGGGAGACTCTGGTTCAA  3480

3481  CATAGCACAAACTCTTAGGGAACCGAATCACCACCACCACTGTAGTCCAGTAACTTCCCT  3540

3541  TCGGTGTGTGTGTGTGGGCATGTGTGTGCCCTGTATGTCTGCGCAGCTCACTACCAACAG  3600

3601  CCTCCATGTGCACTTGACCTTGTGGTGCCTCCGGGAACTTTCCAGGTTGGCACCTGAATG  3660

3661  CCTTACTCTCAGCAGTCTGAGGCTCGCTTGCTCTGCGCACACATTTCAGTCTCCTTTTTT  3720

3721  GGCCCTAGGCTGGTTAGGAACCTGTACACCTTCACTCTCTCATCATTAAATAGTGGCCTT  3780

3781  TTTCAGTATTTCCTCTCTCCCCTCTATAAGTTGCTGAAATCACAAAGCACACTTTTGGGG  3840

3841  ATCATAGAAGGTTGGGGTTCCAGAAAGGCATCTCTGTGATGGTTCCATTCACTATGGGGA  3900

3901  TTTCCCTACTTGCTGTCTTCTTGATTTCTCTAATAAAAGAGCCAAATGGAAAATGAAAA  3960

3961  AAAAAAAAAAAAAAA  3975
```

FIG. 3

```
  1  ATGATTCTGTTGGAAGGCTTTGAGGAGAATGGGTGTGAATTTATGATTGCAGAGAAGGC    60
  1   M  I  L  L  E  G  F  E  E  N  G  C  E  F  M  I  A  E  K  G   20

61  AAATGGGTAATCACCAACCCAAACAAAGCTGAAGAAGAGCAAACATGCCCAGTGCCCCAG   120
 21   K  W  V  I  T  N  P  N  K  A  E  E  E  Q  T  C  P  V  P  Q   40

121  GAAGAAGAGGAGGAGGTGTGGGTACTGACACTTCCCCTGCAAGCCCACCACACCATGGAG   180
 41   E  E  E  E  V  W  V  L  T  L  P  L  Q  A  H  H  T  M  E      60

181  AAGATGGAGGAGTTTGTGTACAAGCCGCAGCTCCAGACAAGCTGCTGCCACCATCAATAT   240
 61   K  M  E  E  F  V  Y  K  P  Q  L  Q  T  S  C  C  H  H  Q  Y   80

241  GATGGGCTCCCTGACTGGCTGAAGGACAATGACTGTCTGCAGGACAATGACTGTCTGCTC   300
 81   D  G  L  P  D  W  L  K  D  N  D  C  L  Q  D  N  D  C  L  L  100

301  TATGGCCATAGACAACCCATGTCCTCCTTCTGGGCTTGCTTCAAGAGCATCTTCTATATC   360
101   Y  G  H  R  Q  P  M  S  S  F  W  A  C  F  K  S  I  F  Y  I  120

361  CATACAGAAACCGGCAGCAGCCGGACACATCTGCTTGGTTTCGTGCTGTTTCTCTTTTTG   420
121   H  T  E  T  G  S  S  R  T  H  L  L  G  F  V  L  F  L  F  L  140

421  GAAATCTTGACCATGCTCAGACCAAATATGTACTTCACGGCCCCTCTACAGGAGAAAGTG   480
141   E  I  L  T  M  L  R  P  N  M  Y  F  T  A  P  L  Q  E  K  V  160

481  ATTTGGAGGATATTCCTTTTGGAGAAAGTCTCTCGGACTTTTTCCAAACTGTACTATTCA   540
161   I  W  R  I  F  L  L  E  K  V  S  R  T  F  S  K  L  Y  Y  S  180

541  GGGATTGCTCCACTGCTCATAAGGAGCTTCGTCCCCTGGCTCTGTTACTCCTTCTACTGC   600
181   G  I  A  P  L  L  I  R  S  F  V  P  W  L  C  Y  S  F  Y  C  200

601  TCGCCACAGCCACGGCTCATCTACTTCTCCATCATCTATGTCCTGGGCATCTCTGCCATC   660
201   S  P  Q  P  R  L  I  Y  F  S  I  I  Y  V  L  G  I  S  A  I  220

661  ATTGTGACATGGGACCGGTTTGTCACTCCTAAGCACCGGCAGACAAGGGCAGGGGTGTTG   720
221   I  V  T  W  D  R  F  V  T  P  K  H  R  Q  T  R  A  G  V  L  240

721  CTGGGACTTGGCTTGAGCGGTATTGTGCCCACCATGCACTTTCCTATTGCTGAGGGTTTC   780
241   L  G  L  G  L  S  G  I  V  P  T  M  H  F  P  I  A  E  G  F  260

781  GTCAAGGCCACCACAGTGGGCCAGATGGGCTGGTTCTTCCTCGTGGCTGTGATGTACATC   840
261   V  K  A  T  T  V  G  Q  M  G  W  F  F  L  V  A  V  M  Y  I  280

841  ACCAGAGCTGGCCTTTATGCTGCTTAA   867
281   T  R  A  G  L  Y  A  A     288
```

FIG. 4A

```
                    1                                                50
hAdipoR1    (1)   -----------MSSHKGSVVAQGNGAPASNREADTVELAELGPLLEEKG
mAdipoR1    (1)   -----------MSSHKGSAGAQGNGAPSGNREADTVELAELGPLLEEKG
hAdipoR2    (1)   --------------------------------------------------
hAdipoR2v1  (1)   MNEPTENRLGCSRTPEPDIRLRKCHQLDGTRRGDNDSHQGDLEPILEASV
mAdipoR2    (1)   --------------------------------------------------
mAdipoR2v1  (1)   MNEPAKHRLGCTRTPEPDIRLRKGHQLDDTRGSNNDNYQGDLEPSLETPV 51                                              100
hAdipoR1    (39)  KRVIANPPKAEEQTCPVPQEEEEEVRVLTLPLQAHHAMEKMEEFVYKVW
mAdipoR1    (39)  KRAASSPAKAEDQACPVPQEEEEEVRVLTLPLQAHHAMEKMEEFVYKVW
hAdipoR2    (1)   -------------------------------MEKMEEFVCKVW
hAdipoR2v1  (51)  LSSHHKKSSEEHEYSDEAPQEDEG-FMGMSPLLQAHHAMEKMEEFVCKVW
mAdipoR2    (1)   -------------------------MGMSPLLQAHHAMERMEEFVCKVW
mAdipoR2v1  (51)  CSSYYENSPEEPECHDDNSQEDEG-FMGMSPLLQAHHAMERMEEFVCKVW 101                                             150
hAdipoR1    (89)  EGRWRVIPYDVLPDWLKDNDYLLHGHRPPMPSFRACFKSIFRIHTETGNI
mAdipoR1    (89)  EGRWRVIPYDVLPDWLKDNDYLLHGHRPPMPSFRACFKSIFRIHTETGNI
hAdipoR2    (13)  EGRWRVIPHDVLPDWLKDNDFLLHGHRPPMPSFRACFKSIFRIHTETGNI
hAdipoR2v1  (100) EGRWRVIPHDVLPDWLKDNDFLLHGHRPPMPSFRACFKSIFRIHTETGNI
mAdipoR2    (25)  EGRWRVIPHDVLPDWLKDNDFLLHGHRPPMPSFRACFKSIFRIHTETGNI
mAdipoR2v1  (100) EGRWRVIPHDVLPDWLKDNDFLLHGHRPPMPSFRACFKSIFRIHTETGNI 151                                             200
hAdipoR1    (139) WTHLLGFVLFLFLGILTMLRPNMYFMAPLQEKVVFGMFFLGAVLCLSFSW
mAdipoR1    (139) WTHLLGFVLFLFLGILTMLRPNMYFMAPLQEKVVFGMFFLGAVLCLSFSW
hAdipoR2    (63)  WTHLLGCVSFLCLGIFYMFRPNISFVAPLQEKVVFGLFFLGAILCLSFSW
hAdipoR2v1  (150) WTHLLGCVFFLCLGIFYMFRPNISFVAPLQEKVVFGLFFLGAILCLSFSW
mAdipoR2    (75)  WTHLLGCVFFLCLGIFYMFRPNISFVAPLQEKVVFGLFFLGAILCLSFSW
mAdipoR2v1  (150) WTHLLGCVFFLCLGIFYMFRPNISFVAPLQEKVVFGLFFLGAILCLSFSW 201                                             250
hAdipoR1    (189) LFHTVYCHSEKVSRTFSKLDYSGIALLIMGSFVPWLYYSFYCSPQPRLIY
mAdipoR1    (189) LFHTVYCHSEKVSRTFSKLDYSGIALLIMGSFVPWLYYSFYCSPQPRLIY
hAdipoR2    (113) LFHTVYCHSEGVSRLFSKLDYSGIALLIMGSFVPWLYYSFYCNPQPCFIY
hAdipoR2v1  (200) LFHTVYCHSEGVSRLFSKLDYSGIALLIMGSFVPWLYYSFYCNPQPCFIY
mAdipoR2    (125) LFHTVYCHSEGVSRLFSKLDYSGIALLIMGSFVPWLYYSFYCNPQPCFIY
mAdipoR2v1  (200) LFHTVYCHSEGVSRLFSKLDYSGIALLIMGSFVPWLYYSFYCNPQPCFIY 251                                             300
hAdipoR1    (239) LSIVCVLGISAIIVAQWDRFATPKHRQTRAGVFLGLGLSGVVPTMHFTIA
mAdipoR1    (239) LSIVCVLGISAIIVAQWDRFATPKHRQTRAGVFLGLGLSGVVPTMHFTIA
hAdipoR2    (163) LIVICVLGIAAIIVSQWDMFATPQYRGVRAGVFLGLGLSGIIPTLHYVIS
hAdipoR2v1  (250) LIVICVLGIAAIIVSQWDMFATPQYRGVRAGVFLGLGLSGIIPTLHYVIS
mAdipoR2    (175) LIVICVLGIAAIIVSQWDMFATPQYRGVRAGVFVGLGLSGIIPTLHYVIS
mAdipoR2v1  (250) LIVICVLGIAAIIVSQWDMFATPQYRGVRAGVFVGLGLSGIIPTLHYVIS 301                                             350
hAdipoR1    (289) EGFVKATTVGQMGWFLMAVMYITGAGLYAARIPERFFPGKFDIWFQSHQ
mAdipoR1    (289) EGFVKATTVGQMGWFLMAVMYITGAGLYAARIPERFFPGKFDIWFQSHQ
hAdipoR2    (213) EGFLKAATIGQIGWLMLMASLYITGAALYAARIPERFFPGKCDIWFHSHQ
hAdipoR2v1  (300) EGFLKAATIGQIGWLMLMASLYITGAALYAARIPERFFPGKCDIWFHSHQ
mAdipoR2    (225) EGFLKAATIGQIGWLMLMASLYITGAALYAARIPERFFPGKCDIWFHSHQ
mAdipoR2v1  (300) EGFLKAATIGQIGWLMLMASLYITGAALYAARIPERFFPGKCDIWFHSHQ
```

FIG. 4B

```
                351                                     387
hAdipoR1  (339) IFHVLVVAAAFVHFYGVSNLQEFRYGLEGGCTDDTLL
mAdipoR1  (339) IFHVLVVAAAFVHFYGVSNLQEFRYGLEGGCTDDSLL
hAdipoR2  (263) LFHIFVVAGAFVHFHGVSNLQEFRFMIGGGCSEEDAL
hAdipoR2v1(350) LFHIFVVAGAFVHFHGVSNLQEFRFMIGGGCSEEDAL
mAdipoR2  (275) LFHIFVVAGAFVHFHGVSNLQEFRFMIGGGCTEEDAL
mAdipoR2v1(350) LFHIFVVAGAFVHFHGVSNLQEFRFMIGGGCTEEDAL
```

FIG. 5

```
              1                                                  50
hAdipoR3  (1) ------------------MILLEGFEENGCEFMIAEKGKWVITNPNKAEE
hAdipoR1  (1) MSSHKGSVVAQGNGAPASNREADTVELAELGPLIEEKGKRVIANPPKAEE
hAdipoR2  (1) --------------------------------------------------

51                                                 100
hAdipoR3 (33) EQTCPVPQEEEEEVWVLTLPLQAHHTMEKMEEFVYKPQLQTSCCHHQYDG
hAdipoR1 (51) EQTCPVPQEEEEEVRVLTLPLQAHHAMEKMEEFVYK-VWEGRWRVIPYDV
hAdipoR2  (1) --------------------------MEKMEEFVCK-VWEGRWRVIPHDV 101                                                150
hAdipoR3 (83) LPDWLKDNDCLQDNDCLLYGHRQPMSSFWACFKSIFYIHTETGSSRTHLL
hAdipoR1 (100) LPDWLKDN------DYLLHGHRPPMPSFRACFKSIFRIHTETGNIWTHLL
hAdipoR2 (24) LPDWLKDN------DFLLHGHRPPMPSFRACFKSIFRIHTETGNIWTHLL 151                                                200
hAdipoR3 (133) GFVLFLFLEILTMLRPNMYFTAPLQEKVIWRIFLL---------------
hAdipoR1 (144) GFVLFLFLGILTMLRPNMYFMAPLQEKVVFGMFFLGAVLCLSFSWLFHTV
hAdipoR2 (68) GCVSFLCLGIFYMERPNISFVAPLQEKVVFGIFFLGAILCLSFSWLFHTV 201                                                250
hAdipoR3 (168) ----EKVSRTFSKLYYSGIAPLLIRSFVPWLCYSFYCSPQPRLIYFSIIY
hAdipoR1 (194) YCHSEKVSRTFSKLDYSGIALLIMGSFVPWLYYSFYCSPQPRLIYLSIVC
hAdipoR2 (118) YCHSEGVSRLFSKLDYSGIALLIMGSFVPWLYYSFYCNPQPCFIYLIVIC 251                                                300
hAdipoR3 (214) VLGISAIIVT-WDRFVTPKHRQTRAGVLLGLGLSGIVPTMHFPIAEGFVK
hAdipoR1 (244) VLGISAIIVAQWDRFATPKHRQTRAGVFLGLGLSGVVPTMHFTIAEGFVK
hAdipoR2 (168) VLGIAAIIVSQWDMFATPQYRGVRAGVFLGLGLSGIIPTLHYVISEGFLK 301                                                350
hAdipoR3 (263) ATTVGQMGWFFLVAVMYITRAGLYAA------------------------
hAdipoR1 (294) ATTVGQMGWFFLMAVMYITGAGLYAARIPERFFPGKFDIWFQSHQIFHVL
hAdipoR2 (218) AATIGQIGWLMLMASLYITGAALYAARIPERFFPGKCDIWFHSHQLFHIF 351                       382
hAdipoR3 (289) ----------------------------------
hAdipoR1 (344) VVAAAFVHFYGVSNLQEFRYGLEGGCTDDTLL
hAdipoR2 (268) VVAGAFVHFHGVSNLQEFRFMIGGGCSEEDAL
```

FIG. 10A

```
Top Sequence = hAdipoR2v1.tfa, 1585 bp
Bottom Sequence = hAdipoR2v1_genomic.sequence-Chromosome 12, 98001 bp 6-123      (2103-2220)    96%  ->
124-380    (65288-65544)  100% ->
381-500    (83872-83991)  100% ->
501-672    (88884-89055)  100% ->
673-859    (91481-91667)  100% ->
860-1047   (91919-92106)  100% ->
1048-1241  (94910-95103)  100% ->
1242-1561  (96974-97293)  99%

0         .         :         .         :         .         :         .         :         .         :
        6 GCGTGGGCGCGGCGGCGGCAGCGGCGGCGGCTACACCGGGCTTGGCCCCC
          |||      |||||||||||||||||||||||||||||||||||||||||
     2103 GCGGCATCGCGGCGGCGGCAGCGGCGGCGGCTACACCGGGCTTGGCCCCC

50         .         :         .         :         .         :         .         :         .         :
       56 TCCCTCCTCCGTTCCCCCCTCCTCCCCCCTCCCCTCAGCGGTGGCTCCCA
          ||||||||||||||||||||||||||||||||||||||||||||||||||
     2153 TCCCTCCTCCGTTCCCCCCTCCTCCCCCCTCCCCTCAGCGGTGGCTCCCA

100         .         :         .         :         .         :         .         :         .         :
      106 AGAAGTCCGAGACACGCG          GATCAACTCACTATCCTGAAGGT
          ||||||||||||||||||>>>...>>>|||||||||||||||||||||||
     2203 AGAAGTCCGAGACACGCGGTG...TAGGATCAACTCACTATCCTGAAGGT

150         .         :         .         :         .         :         .         :         .         :
      147 CCATTCTCCCAAGAAGAGGGGACAGAAAGACAGATCTATTTGTAAGAAAG
          ||||||||||||||||||||||||||||||||||||||||||||||||||
    65311 CCATTCTCCCAAGAAGAGGGGACAGAAAGACAGATCTATTTGTAAGAAAG

200         .         :         .         :         .         :         .         :         .         :
      197 GCTTGGGTATCCCATGAACGAGCCAACAGAAAACCGATTGGGGTGCAGCA
          ||||||||||||||||||||||||||||||||||||||||||||||||||
    65361 GCTTGGGTATCCCATGAACGAGCCAACAGAAAACCGATTGGGGTGCAGCA

250         .         :         .         :         .         :         .         :         .         :
      247 GGACTCCAGAGCCAGATATAAGGCTCAGAAAAGGGCACCAACTGGATGGT
          ||||||||||||||||||||||||||||||||||||||||||||||||||
    65411 GGACTCCAGAGCCAGATATAAGGCTCAGAAAAGGGCACCAACTGGATGGT

300         .         :         .         :         .         :         .         :         .         :
      297 ACACGAAGAGGTGATAATGACAGCCACCAAGGAGATTTGGAGCCCATTTT
          ||||||||||||||||||||||||||||||||||||||||||||||||||
    65461 ACACGAAGAGGTGATAATGACAGCCACCAAGGAGATTTGGAGCCCATTTT

350         .         :         .         :         .         :         .         :         .         :
      347 AGAGGCATCTGTTCTATCTTCCCATCATAAAAAA          AGCTCTG
          ||||||||||||||||||||||||||||||||||||>>>...>>>|||||||
    65511 AGAGGCATCTGTTCTATCTTCCCATCATAAAAAAGTA...CAGAGCTCTG
```

FIG. 10B

```
       400         .         :         .         :         .         :         .         :         .         :
       388 AGGAACATGAATACAGTGATGAAGCTCCTCAGGAAGATGAGGGCTTTATG
           ||||||||||||||||||||||||||||||||||||||||||||||||||
     83879 AGGAACATGAATACAGTGATGAAGCTCCTCAGGAAGATGAGGGCTTTATG

450         .         :         .         :         .         :         .         :         .         :
       438 GGCATGTCCCCTCTCTTACAAGCCCATCATGCTATGGAAAAAATGGAAGA
           ||||||||||||||||||||||||||||||||||||||||||||||||||
     83929 GGCATGTCCCCTCTCTTACAAGCCCATCATGCTATGGAAAAAATGGAAGA

500         .         :         .         :         .         :         .         :         .         :
       488 ATTTGTTTGTAAG              GTATGGGAAGGTCGGTGGCGAGTGATCC
           ||||||||||||>>>...>>>||||||||||||||||||||||||||||||
     83979 ATTTGTTTGTAAGGTA...CAGGTATGGGAAGGTCGGTGGCGAGTGATCC

550         .         :         .         :         .         :         .         :         .         :
       529 CTCATGATGTACTACCAGACTGGCTCAAGGATAATGACTTCCTCTTGCAT
           ||||||||||||||||||||||||||||||||||||||||||||||||||
     88912 CTCATGATGTACTACCAGACTGGCTCAAGGATAATGACTTCCTCTTGCAT

600         .         :         .         :         .         :         .         :         .         :
       579 GGACACCGGCCTCCTATGCCTTCTTTCCGGGCCTGTTTTAAGAGCATTTT
           ||||||||||||||||||||||||||||||||||||||||||||||||||
     88962 GGACACCGGCCTCCTATGCCTTCTTTCCGGGCCTGTTTTAAGAGCATTTT

650         .         :         .         :         .         :         .         :         .         :
       629 CAGAATACACACAGAAACAGGCAACATTTGGACACATCTCTTAG
           ||||||||||||||||||||||||||||||||||||||||||||>>>...
     89012 CAGAATACACACAGAAACAGGCAACATTTGGACACATCTCTTAGGTA...

700         .         :         .         :         .         :         .         :         .         :
       673     GTTGTGTATTCTTCCTGTGCCTGGGGATCTTTTATATGTTTCGCCCA
           >>>||||||||||||||||||||||||||||||||||||||||||||||||
     91478 TAGGTTGTGTATTCTTCCTGTGCCTGGGGATCTTTTATATGTTTCGCCCA

750         .         :         .         :         .         :         .         :         .         :
       720 AATATCTCCTTTGTGGCCCCTCTGCAAGAGAAGGTGGTCTTTGGATTATT
           ||||||||||||||||||||||||||||||||||||||||||||||||||
     91528 AATATCTCCTTTGTGGCCCCTCTGCAAGAGAAGGTGGTCTTTGGATTATT

800         .         :         .         :         .         :         .         :         .         :
       770 TTTCTTAGGAGCCATTCTCTGCCTTTCTTTTTCATGGCTCTTCCACACAG
           ||||||||||||||||||||||||||||||||||||||||||||||||||
     91578 TTTCTTAGGAGCCATTCTCTGCCTTTCTTTTTCATGGCTCTTCCACACAG

850         .         :         .         :         .         :         .         :         .         :
       820 TCTACTGCCACTCAGAGGGGGTCTCTCGGCTCTTCTCTAA              A
           ||||||||||||||||||||||||||||||||||||||||>>>...>>>|
     91628 TCTACTGCCACTCAGAGGGGGTCTCTCGGCTCTTCTCTAAGTA...TAGA

900         .         :         .         :         .         :         .         :         .         :
       861 CTGGATTACTCTGGTATTGCTCTTCTGATTATGGGAAGTTTTGTTCCTTG
           ||||||||||||||||||||||||||||||||||||||||||||||||||
     91920 CTGGATTACTCTGGTATTGCTCTTCTGATTATGGGAAGTTTTGTTCCTTG
```

FIG. 10C

```
 950           .         :         .         :         .         :         .         :         .         :
 911   GCTTTATTATTCTTTCTACTGTAATCCACAACCTTGCTTCATCTACTTGA
       ||||||||||||||||||||||||||||||||||||||||||||||||||
91970  GCTTTATTATTCTTTCTACTGTAATCCACAACCTTGCTTCATCTACTTGA

1000          .         :         .         :         .         :         .         :         .         :
 961   TTGTCATCTGTGTGCTGGGCATTGCAGCCATTATAGTCTCCCAGTGGGAC
       ||||||||||||||||||||||||||||||||||||||||||||||||||
92020  TTGTCATCTGTGTGCTGGGCATTGCAGCCATTATAGTCTCCCAGTGGGAC

1050          .         :         .         :         .         :         .         :         .         :
1011   ATGTTTGCCACCCCTCAGTATCGGGGAGTAAGAGCAG         GAGT
       |||||||||||||||||||||||||||||||||||||>>>...>>>||||
92070  ATGTTTGCCACCCCTCAGTATCGGGGAGTAAGAGCAGGTA...TAGGAGT

1100          .         :         .         :         .         :         .         :         .         :
1052   GTTTTTGGGCCTAGGCCTGAGTGGAATCATTCCTACCTTGCACTATGTCA
       ||||||||||||||||||||||||||||||||||||||||||||||||||
94914  GTTTTTGGGCCTAGGCCTGAGTGGAATCATTCCTACCTTGCACTATGTCA

1150          .         :         .         :         .         :         .         :         .         :
1102   TCTCGGAGGGGTTCCTTAAGGCCGCCACCATAGGGCAGATAGGCTGGTTG
       ||||||||||||||||||||||||||||||||||||||||||||||||||
94964  TCTCGGAGGGGTTCCTTAAGGCCGCCACCATAGGGCAGATAGGCTGGTTG

1200          .         :         .         :         .         :         .         :         .         :
1152   ATGCTGATGGCCAGCCTCTACATCACAGGAGCTGCCCTGTATGCTGCCCG
       ||||||||||||||||||||||||||||||||||||||||||||||||||
95014  ATGCTGATGGCCAGCCTCTACATCACAGGAGCTGCCCTGTATGCTGCCCG

1250          .         :         .         :         .         :         .         :         .         :
1202   GATCCCCGAACGCTTTTTCCCTGGCAAATGTGACATCTGG           T
       ||||||||||||||||||||||||||||||||||||||||>>>...>>>|
95064  GATCCCCGAACGCTTTTTCCCTGGCAAATGTGACATCTGGTA...CAGT

1300          .         :         .         :         .         :         .         :         .         :
1243   TTCACTCTCATCAGCTGTTTCATATCTTTGTGGTTGCTGGAGCTTTTGTT
       ||||||||||||||||||||||||||||||||||||||||||||||||||
96975  TTCACTCTCATCAGCTGTTTCATATCTTTGTGGTTGCTGGAGCTTTTGTT

1350          .         :         .         :         .         :         .         :         .         :
1293   CACTTCCATGGTGTCTCAAACCTCCAGGAGTTTCGTTTCATGATCGGCGG
       ||||||||||||||||||||||||||||||||||||||||||||||||||
97025  CACTTCCATGGTGTCTCAAACCTCCAGGAGTTTCGTTTCATGATCGGCGG

1400          .         :         .         :         .         :         .         :         .         :
1343   GGGCTGCAGTGAAGAGGATGCACTGTGATACCTACCAGTCTCCAGGGACT
       ||||||||||||||||||||||||||||||||||||||||||||||||||
97075  GGGCTGCAGTGAAGAGGATGCACTGTGATACCTACCAGTCTCCAGGGACT

1450          .         :         .         :         .         :         .         :         .         :
1393   ATGACCCTAAACCAGGGCCTGCGGCACTTGCGGGCCTCCCTGCTGGCTAC
       ||||||||||||||||||||||||||||||||||||||||||||||||||
97125  ATGACCCTAAACCAGGGCCTGCGGCACTTGCGGGCCTCCCTGCTGGCTAC
```

FIG. 10D

```
1500        .    :    .    :    .    :    .    :    .    :
1443 TGATGCCAGTACCAGAGGAGCCCCAAAACTTTGACAGCCTCGTGGGCTTT
     ||||||||||||||||||||||||||||||||||||||||||||||||||
97175 TGATGCCAGTACCAGAGGAGCCCCAAAACTTTGACAGCCTCGTGGGCTTT

1550        .    :    .    :    .    :    .    :    .    :
1493 GTGACGGCCCAGGGGCTCTGCGTGGTACATGACTGAGAAGAGAAAAACAA
     |||||||||| |||||||||||||||||||||||||||||||||||||||
97225 GTGACGGCCCAGTGGCTCTGCGTGGTACATGACTGAGAAGAGAAAAACAA

1600        .    :    .
1543 AAATAAATCATACCTCAAA
     |||||||||||||||||||
97275 AAATAAATCATACCTCAAA
```

FIG. 11

Human AdipoR2v1

| Protein | Genbank Accession | Identities | Similarities |
|---|---|---|---|
| human AdipoR1 protein | gi|NM_015999 | 66.4% | 77.0% |
| mouse AdipoR1 protein | gi|BCO14875 | 66.1% | 76.7% |
| human AdipoR2 protein | gi|NM_024551 | 77.2% | 77.2% |
| mouse AdipoR2 protein | gi|XM_132831 | 79.8% | 80.6% |

Mouse AdipoR2v1

| Protein | Genbank Accession | Identities | Similarities |
|---|---|---|---|
| human AdipoR1 protein | Gi|NM_015999 | 65.7% | 75.8% |
| mouse AdipoR1 protein | Gi|BCO14875 | 65.5% | 76.0% |
| human AdipoR2 protein | Gi|NM_024551 | 76.4% | 77.2% |
| mouse AdipoR2 protein | Gi|XM_132831 | 80.6% | 80.6% |
| Human AdipoR2v1 protein | N/A | 92.7% | 94.8% |

Human AdipoR3

| Protein | Genbank Accession | Identities | Similarities |
|---|---|---|---|
| human AdipoR1 protein | gi|NM_015999 | 57.1% | 60.5% |
| mouse AdipoR1 protein | gi|BCO14875 | 55.5% | 59.2% |
| human AdipoR2 protein | gi|NM_024551 | 40.1% | 46.2% |
| mouse AdipoR2 protein | gi|XM_132831 | 40.9% | 48.1% |
| Human AdipoR2v1 protein | N/A | 40.5% | 48.1% |
| Mouse AdipoR2v1 protein | N/A | 39.4% | 47.1% |

FIG. 12A

```
  1  ATGTCTTCTCACAAAGGGTCTGTGGTGGCAAGGAATGGGGCTCCTGCCAGTAACAGGGAA   60
  1   M  S  S  H  K  G  S  V  V  A  R  N  G  A  P  A  S  N  R  E    20

61  ACTGACATGGTGGAACTGGCTGAATCTGAATTGTCACCCCTGCTACAAGAGAAGGGCAAA  120
 21   T  D  M  V  E  L  A  E  S  E  L  S  P  L  L  Q  E  K  G  K    40

121  TGGGTAATCACCAACCCAAACAAAGCTGAAGAAGAGCAAACATGCCCAGTGCCCCAGGAA  180
 41   W  V  I  T  N  P  N  K  A  E  E  E  Q  T  C  P  V  P  Q  E    60

181  GAAGAGGAGGAGGTGTGGGTACTGACACTTCCCCTGCAAGCCCACCACACCATGGAGAAG  240
 61   E  E  E  E  V  W  V  L  T  L  P  L  Q  A  H  H  T  M  E  K    80

241  ATGGAGGAGTTTGTGTACAAGCTCCAGACAAGCTGCTGCCACCATCAATATGATGGGCTC  300
 81   M  E  E  F  V  Y  K  L  Q  T  S  C  C  H  H  Q  Y  D  G  L   100

301  CCTGACTGGCTGAAGGACAATGACTGTCTGCAGGACAATGACTGTCTGCTCTATGGCCAT  360
101   P  D  W  L  K  D  N  D  C  L  Q  D  N  D  C  L  L  Y  G  H   120

361  AGACAACCCATGTCCTCCTTCTGGGCTTGCTTCAAGAGCATCTTCTATATCCATACAGAA  420
121   R  Q  P  M  S  S  F  W  A  C  F  K  S  I  F  Y  I  H  T  E   140

421  ACCGGCAGCAGCCGGACACATCTGCTTGGTTTCGTGCTGTTTCTCTTTTTGGAAATCTTG  480
141   T  G  S  S  R  T  H  L  L  G  F  V  L  F  L  F  L  E  I  L   160

481  ACCATGCTCAGACCAAATATGTACTTCACGGCCCCTCTACAGGAGAAAGTGATTTGGAGG  540
161   T  M  L  R  P  N  M  Y  F  T  A  P  L  Q  E  K  V  I  W  R   180

541  ATATTCCTTTTGGGTGCAGTGCTCAGCCTCAGCTTCTCCTGGCTCGTCCGCACTGTCTAC  600
181   I  F  L  L  G  A  V  L  S  L  S  F  S  W  L  V  R  T  V  Y   200

601  TGTCATTCAGAGAAAGTCTCTCGGACTTTTTCCAAACTGTACTATTCAGGGATTGCTCCA  660
201   C  H  S  E  K  V  S  R  T  F  S  K  L  Y  Y  S  G  I  A  P   220

661  CTGCTCATAAGGAGCTTCGTCCCCTGGCTCTGTTACTCCTTCTACTGCTCGCCACAGCCA  720
221   L  L  I  R  S  F  V  P  W  L  C  Y  S  F  Y  C  S  P  Q  P   240

721  CGGCTCATCTACTTCTCCATCATCTATGTCCTGGGCATCTCTGCCATCATTGTGGACCAG  780
241   R  L  I  Y  F  S  I  I  Y  V  L  G  I  S  A  I  I  V  D  Q   260
```

FIG. 12B

```
 781  TGGGACCGGTTTGTCACTCCTAAGCACCGGCAGACAAGGGCAGGGGTGTTGCTGGGACTT   840
 261   W   D   R   F   V   T   P   K   H   R   Q   T   R   A   G   V   L   L   G   L    280

841  GGCTTGAGCGGTATTGTGCCCACCATGCACTTTCCTATTGCTGAGGGTTTCGTCAAGGCC   900
 281   G   L   S   G   I   V   P   T   M   H   F   P   I   A   E   G   F   V   K   A    300

901  ACCACAGTGGGCCAGATGGGCTGGTTCTTCCTCGTGGCTGTGATGTACATCACCAGAGCT   960
 301   T   T   V   G   Q   M   G   W   F   F   L   V   A   V   M   Y   I   T   R   A    320

961  GGCCTTTATGCTGCTTTAATTCCTGAGCGCTTCTTTCCTGGAAAATTAGACATATGGTTC  1020
 321   G   L   Y   A   A   L   I   P   E   R   F   F   P   G   K   L   D   I   W   F    340

1021  CAGTCTCAGCAGATTTTCCATGTCCTCATGGTGACGGTGGCCTTTGTCCACTTCTGTGGG  1080
 341   Q   S   Q   Q   I   F   H   V   L   M   V   T   V   A   F   V   H   F   C   G    360

1081  GTCTCCAACCTTCAGGAATTCCATTACAGCCGAGAAGGTGACTGCACTGATGACTCCCTT  1140
 361   V   S   N   L   Q   E   F   H   Y   S   R   E   G   D   C   T   D   D   S   L    380

1141  CTCTGA  1146
 381   L      381
```

FIG. 13A

```
  1  ATATCGTCGACCCACGCGTCCGGCGGCGGCGGCTACACCGGGCTTGGCCCCCTCCCTCCT    60

61  CCGTTCCCCCCTCCTCCCCCCTCCCCTCAGCGGTGGCTCCCAAGAAGTCCGAGACACGCG   120

121  GATCAACTCACTATCCTGAAGGTCCATTCTCCCAAGAAGAGGGGACAGAAAGACAGATCT   180

181  ATTTGTAAGAAAGGCTTGGGTATCCCATGAACGAGCCAACAGAAAACCGATTGGGGTGCA   240
  1                                 M   N   E   P   T   E   N   R   L   G   C   S    12

241  GCAGGACTCCAGAGCCAGATATAAGGCTCAGAAAAGGGCACCAACTGGATGGTACACGAA   300
 13    R   T   P   E   P   D   I   R   L   R   K   G   H   Q   L   D   G   T   R   R    32

301  GAGGTGATAATGACAGCCACCAAGGAGATTTGGAGCCCATTTTAGAGGCATCTGTTCTAT   360
 33    G   D   N   D   S   H   Q   G   D   L   E   P   I   L   E   A   S   V   L   S    52

361  CTTCCCATCATAAAAAAGCTCTGAGGAACATGAATACAGTGATGAAGCTCCTCAGGAAG   420
 53    S   H   H   K   K   S   S   E   E   H   E   Y   S   D   E   A   P   Q   E   D    72

421  ATGAGGGCTTTATGGGCATGTCCCCTCTCTTACAAGCCCATCATGCTATGGAAAAAATGG   480
 73    E   G   F   M   G   M   S   P   L   L   Q   A   H   H   A   M   E   K   M   E    92

481  AAGAATTTGTTTGTAAGGTATGGGAAGGTCGGTGGCGAGTGATCCCTCATGATGTACTAC   540
 93    E   F   V   C   K   V   W   E   G   R   W   R   V   I   P   H   D   V   L   P   112

541  CAGACTGGCTCAAGGATAATGACTTCCTCTTGCATGGACACCGGCCTCCTATGCCTTCTT   600
113    D   W   L   K   D   N   D   F   L   L   H   G   H   R   P   P   M   P   S   F   132

601  TCCGGGCCTGTTTTAAGAGCATTTTCAGAATACACACAGAAACAGGCAACATTTGGACAC   660
133    R   A   C   F   K   S   I   F   R   I   H   T   E   T   G   N   I   W   T   H   152

661  ATCTCTTAGGTTGTGTATTCTTCCTGTGCCTGGGGATCTTTTATATGTTTCGCCCAAATA   720
153    L   L   G   C   V   F   F   L   C   L   G   I   F   Y   M   F   R   P   N   I   172

721  TCTCCTTTGTGGCCCCTCTGCAAGAGAAGGTGGTCTTTGGATTATTTTCTTAGGAGCCA   780
173    S   F   V   A   P   L   Q   E   K   V   V   F   G   L   F   F   L   G   A   I   192

781  TTCTCTGCCTTTCTTTTTCATGGCTCTTCCACACAGTCTACTGCCACTCAGAGGGGGTCT   840
193    L   C   L   S   F   S   W   L   F   H   T   V   Y   C   H   S   E   G   V   S   212

841  CTCGGCTCTTCTCTAAACTGGATTACTCTGGTATTGCTCTTCTGATTATGGGAAGTTTTG   900
213    R   L   F   S   K   L   D   Y   S   G   I   A   L   L   I   M   G   S   F   V   232
```

FIG. 13B

```
 901 TTCCTTGGCTTTATTATTCTTTCTACTGTAATCCACAACCTTGCTTCATCTACTTGATTG  960
 233   P  W  L  Y  Y  S  F  Y  C  N  P  Q  P  C  F  I  Y  L  I  V   252

961 TCATCTGTGTGCTGGGCATTGCAGCCATTATAGTCTCCCAGTGGGACATGTTTGCCACCC 1020
 253   I  C  V  L  G  I  A  A  I  I  V  S  Q  W  D  M  F  A  T  P   272

1021 CTCAGTATCGGGGAGTAAGAGCAGATGGAGTCTTGCTTTGTAGCCCAGGCTGGAGTGCAG 1080
 273   Q  Y  R  G  V  R  A  D  G  V  L  L  C  S  P  G  W  S  A  V   292

1081 TGGTGCCATCTTGGCTCCTGACCTCAAGTGATCTGCCTGCCTCGGCCTCCCAAAGTGCTG 1140
 293   V  P  S  W  L  L  T  S  S  D  L  P  A  S  A  S  Q  S  A  G   312

1141 GGATTACAGGAGTGTTTTTGGGCCTAGGCCTGAGTGGAATCATTCCTACCTTGCACTATG 1200
 313   I  T  G  V  F  L  G  L  G  L  S  G  I  I  P  T  L  H  Y  V   332

1201 TCATCTCGGAGGGGTTCCTTAAGGCCGCCACCATAGGGCAGATAGGCTGGTTGATGCTGA 1260
 333   I  S  E  G  F  L  K  A  A  T  I  G  Q  I  G  W  L  M  L   352

1261 TGGCCAGCCTCTACATCACAGGAGCTGCCCTGTATGCTGCCCGGATCCCCGAACGCTTTT 1320
 353   A  S  L  Y  I  T  G  A  A  L  Y  A  A  R  I  P  E  R  F  F   372

1321 TCCCTGGCAAATGTGACATCTGGTTTCACTCTCATCAGCTGTTTCATATCTTTGTGGTTG 1380
 373   P  G  K  C  D  I  W  F  H  S  H  Q  L  F  H  I  F  V  V  A   392

1381 CTGGAGCTTTTGTTCACTTCCATGGTGTCTCAAACCTCCAGGAGTTTCGTTTCATGATCG 1440
 393   G  A  F  V  H  F  H  G  V  S  N  L  Q  E  F  R  F  M  I  G   412

1441 GCGGGGGCTGCAGTGAAGAGGATGCACTGTGATACCTACCAGTCTCCAGGGACTATGACC 1500
 413   G  G  C  S  E  E  D  A  L                                     421

1501 CTAAACCAGGGCCTGCGGCACTTGCGGGCCTCCCTGCTGGCTACTGATGCCAGTACCAGA 1560

1561 GGAGCCCCAAAACTTTGACAGCCTCGTGGGCTTTGTGACGGCCCAGGGGCTCTGCGTGGT 1620

1621 ACATGACTGAGAAGAGAAAAACAAAATAAATCATACCTCAAAAAAAAAAAAAAAGGGCG 1680

1681 GCCGCTCTAGAGTATCCCTCGAGGGGCCCAAGCTTACGCGTACCCAGCTTTCTTGTAC 1738
```

FIG. 14

```
                    1                                                50
AdipoR3.v1    (1)   MSSHKGSVVAR-NGAPASNRETDMVELAESELSPLLQEKGKWVITNPNKA
  hAdipoR1    (1)   MSSHKGSVVAQGNGAPASNREADTVELAE--LGPLLEEKGKRVIANPPKA
  hAdipoR3    (1)   --------------------MILLEGEEENGCEFMIAEKGKWVITNPNKA 51                                               100
AdipoR3.v1   (50)   EEEQTCPVPQEEEEEVWVLTLPLQAHHTMEKMEEFVYKLQTS--CCHHQY
  hAdipoR1   (49)   EEEQTCPVPQEEEEEVRVLTLPLQAHHAMEKMEEFVYKVWEGR-WRVIPY
  hAdipoR3   (31)   EEEQTCPVPQEEEEEVWVLTLPLQAHHTMEKMEEFVYKPQLQTSCCHHQY 101                                              150
AdipoR3.v1   (98)   DGLPDWLKDNDCLQDNDCLLYGHRQPMSSFWACFKSIFYIHTETGSSRTH
  hAdipoR1   (98)   DVLPDWLKD------NDYLLHGHRPPMPSFRACFKSIFRIHTETGNIWTH
  hAdipoR3   (81)   DGLPDWLKDNDCLQDNDCLLYGHRQPMSSFWACFKSIFYIHTETGSSRTH 151                                              200
AdipoR3.v1  (148)   LLGFVLFLFLEILTMLRPNMYFTAPLQEKVIWRIFLLGAVLSLSFSWLVR
  hAdipoR1  (142)   LLGFVLFLFLGILTMLRPNMYFMAPLQEKVVFGMFFLGAVLCLSFSWLFH
  hAdipoR3  (131)   LLGFVLFLFLEILTMLRPNMYFTAPLQEKVIWRIFLL-------------

201                                              250
AdipoR3.v1  (198)   TVYCHSEKVSRTFSKLYYSGIAPLLIRSFVPWLCYSFYCSPQPRLIYFSI
  hAdipoR1  (192)   TVYCHSEKVSRTFSKLDYSGIALLIMGSFVPWLYYSFYCSPQPRLIYLSI
  hAdipoR3  (168)   ------EKVSRTFSKLYYSGIAPLLIRSFVPWLCYSFYCSPQPRLIYFSI 251                                              300
AdipoR3.v1  (248)   IYVLGISAIIVDQWDRFVTPKHRQTRAGVLLGLGLSGIVPTMHFPIAEGF
  hAdipoR1  (242)   VCVLGISAIIVAQWDREATPKHRQTRAGVFLGLGLSGVVPTMHFTIAEGF
  hAdipoR3  (212)   IYVLGISAIIVT-WDRFVTPKHRQTRAGVLLGLGLSGIVPTMHFPIAEGF 301                                              350
AdipoR3.v1  (298)   VKATTVGQMGWFFLVAVMYITRAGLYAALIPERFFPGKLDIWFQSQQIFH
  hAdipoR1  (292)   VKATTVGQMGWFFLMAVMYITGAGLYAARIPERFFPGKFDIWFQSHQIFH
  hAdipoR3  (261)   VKATTVGQMGWFFLVAVMYITRAGLYAA----------------------

351                              384
AdipoR3.v1  (348)   VLMVTVAFVHFCGVSNLQEFHYSREGDCTDDSLL
  hAdipoR1  (342)   VLVVAAAFVHFYGVSNLQEFRYGLEGGCTDDTLL
  hAdipoR3  (289)   ----------------------------------
```

FIG. 15

```
                1                                                                    50
    AdipoR2.v2  (1)   MNEPTENRLGCSRTPEPDIRLRKGHQLDGTRRGDNDSHQGDLEPILEASV
     hAdipoR2v1 (1)   MNEPTENRLGCSRTPEPDIRLRKGHQLDGTRRGDNDSHQGDLEPILEASV
     mAdipoR2v1 (1)   MNEPAKHRLGCTRTPEPDIRLRKGHQLDDTRGSNNDNYQGDLEPSLETPV
       hAdipoR1 (1)   -----------MSSHKGSVVAQGNGAPASNREADTVELAELGPLLEEKG 51                                                                  100
    AdipoR2.v2 (51)   LSSHHKKSSEEHEYSDEAPQE-DEGFMGMSPLLQAHHAMEKMEEFVCKVW
     hAdipoR2v1(51)   LSSHHKKSSEEHEYSDEAPQE-DEGFMGMSPLLQAHHAMEKMEEFVCKVW
     mAdipoR2v1(51)   CSSYYENSPEEPCHDDNSQE-DEGFMGMSPLLQAHHAMERMEEFVCKVW
       hAdipoR1(39)   KRVIANPRKAEEEQTCPVPQEEEEEVRVETLPLQAHHAMEKMEEFVYKVW 101                                                                 150
    AdipoR2.v2(100)   EGRWRVIPHDVLPDWLKDNDFLLHGHRPPMPSFRACFKSIFRIHTETGNI
     hAdipoR2v1(100)  EGRWRVIPHDVLPDWLKDNDFLLHGHRPPMPSFRACFKSIFRIHTETGNI
     mAdipoR2v1(100)  EGRWRVIPHDVLPDWLKDNDFLLHGHRPPMPSFRACFKSIFRIHTETGNI
       hAdipoR1(89)   EGRWRVIPYDVLPDWLKDNDYLLHGHRPPMPSFRACFKSIFRIHTETGNI 151                                                                 200
    AdipoR2.v2(150)   WTHLLGCVFFLCLGIFYMFRPNISFVAPLQEKVVFGLFFLGAILCLSFSW
     hAdipoR2v1(150)  WTHLLGCVFFLCLGIFYMFRPNISFVAPLQEKVVFGLFFLGAILCLSFSW
     mAdipoR2v1(150)  WTHLLGCVFFLCLGIFYMFRPNISFVAPLQEKVVFGLFFLGAILCLSFSW
       hAdipoR1(139)  WTHLLGFVLFLFLGILTMLRPNMYFMAPLQEKVVFGMFFLGAVLCLSFSW 201                                                                 250
    AdipoR2.v2(200)   LFHTVYCHSEGVSRLFSKLDYSGIALLIMGSFVPWLYYSFYCNPQPCFIY
     hAdipoR2v1(200)  LFHTVYCHSEGVSRLFSKLDYSGIALLIMGSFVPWLYYSFYCNPQPCFIY
     mAdipoR2v1(200)  LFHTVYCHSEGVSRLFSKLDYSGIALLIMGSFVPWLYYSFYCNPQPCFIY
       hAdipoR1(189)  LFHTVYCHSEKVSRTFSKLDYSGIALLIMGSFVPWLYYSFYCSPQPRLIY 251                                                                 300
    AdipoR2.v2(250)   LIVICVLGIAAIIVSQWDMFATPQYRGVRADGVLLCSPGWSAVVPSWLLT
     hAdipoR2v1(250)  LIVICVLGIAAIIVSQWDMFATPQYRGVRAG-------------------
     mAdipoR2v1(250)  LIVICVLGIAAIIVSQWDMFATPQYRGVRAG-------------------
       hAdipoR1(239)  LSIVCVLGISAIIVAQWDRFATPKHROTRAG-------------------

301                                                                 350
    AdipoR2.v2(300)   SSDLPASASQSAGITGVFLGLGLSGIIPTLHYVISEGFLKAATIGQIGWL
     hAdipoR2v1(281)  ----------------VFLGLGLSGIIPTLHYVISEGFLKAATIGQIGWL
     mAdipoR2v1(281)  ----------------VFMGLGLSGIIPTLHYVISEGFLKAATIGQIGWL
       hAdipoR1(270)  ----------------VFLGLGLSGVVPTMHFTIAEGFVKATTVGQMGWL 351                                                                 400
    AdipoR2.v2(350)   MLMASLYITGAALYAARIPERFFPGKCDIWFHSHQLFHIFVVAGAFVHFH
     hAdipoR2v1(315)  MLMASLYITGAALYAARIPERFFPGKCDIWFHSHQLFHIFVVAGAFVHFH
     mAdipoR2v1(315)  MLMASLYITGAALYAARIPERFFPGKCDIWFHSHQLFHIFVVAGAFVHFH
       hAdipoR1(304)  MLMAVMYITGAGLYAARIPERFFPGKFDIWFQSHQIFHVLVVAAAFVHFY 401          422
    AdipoR2.v2(400)   GVSNLQEFRFMIGGGCSEEDAL
     hAdipoR2v1(365)  GVSNLQEFRFMIGGGCSEEDAL
     mAdipoR2v1(365)  GVSNLQEFRFMIGGGCTEEDAL
       hAdipoR1(354)  GVSNLQEFRYGLEGGCTDDTLL
```

FIG. 17A

```
hAdipoR2v2      1  mneptenrlgcsrtpepdirlrkghqldgtrrgdndshqgdlepileas
                   ++++++++++++++++++++++++++++++++++++++++++++++++
                   MNEPTENRLGCSRTPEPDIRLRKGHQLDGTRRGDNDSHQGDLEPILEAS
Chromosome12 63206 aagcagactgtaaacgcgaacaagcccggacaggagaccggtgcatggt
                   taaccaagtggggccacatgtgagaatagcgggaagaagatacttacc
                   gcgaaacaggccgtagatagcaagcagttaaatttcccaatggctagat hAdipoR2v2     50  vlsshhkk                    sseeheysdeapqedegf
                   ++++++++                    ++++++++++++++++++
                   VLSSHHKK                    SSEEHEYSDEAPQEDEGF
Chromosome12 63353 gcttccaaGTAAGTC   Intron 1   CAGatggcgtagggccgggt
                   ttccaaaa<0-----[63377:81703]-0>gcaaaaagaaccaaaagt
                   tatcttaa                    ctgatacttattgatgct hAdipoR2v2     76  mgmspllqahhamekmeefvck                       vweg
                   ++++++++++++++++++++++                       ++++
                   MGMSPLLQAHHAMEKMEEFVCK                       VWEG
Chromosome12 81758 agatcctcgccgagaaggtgtaGTAAGAG  Intron 2    CAGtgg
                   tgtccttacaactaataattga<0-----[81824:86715]-0>tgag
                   gcgctcaactttgaagaatttg                       agat hAdipoR2v2    102  rwrviphdvlpdwlkdndfllhghrppmpsfracfksifrihtetgniw
                   +++++++++++++++++++++++++++++++++++++++++++++++++
                   RWRVIPHDVLPDWLKDNDFLLHGHRPPMPSFRACFKSIFRIHTETGNIW
Chromosome12 86728 ctcgaccggccgtcagagtctcgccccacttcgttaaataacagagaat
                   gggttcaattcagtaaaatttagagcctcctgcgtagttgtacacgatg
                   ggagctttaaacgcgttcccgtacgttgttcgcttgctcaacaaacctg hAdipoR2v2    151  thll                        cvfflclgifymfrpnisf
                   ++++                        +++++++++++++++++++
                   THLL            g:G[ggt]    CVFFLCLGIFYMFRPNISF
Chromosome12 86875 acctGGTATGTA   Intron 3     TAGGTtgttctcgattatccaatt
                   catt <1-----[86888:89312]-1>  gttttgtgttattgcatct
                   atca                        taccgcggcttgtcatcct hAdipoR2v2    175  vaplqekvvfglfflgailclsfswlfhtvychsegvsrlfs
                   ++++++++++++++++++++++++++++++++++++++++++
                   VAPLQEKVVFGLFFLGAILCLSFSWLFHTVYCHSEGVSRLFS
Chromosome12 89372 ggcccgaggtgttttggactcttttctcagttctgggtcctt
                   tcctaaatttgttttgcttgtctcgttactagacagtcgttc
                   gctgagggctaatcaactcctttagcccaccccaggctgcct hAdipoR2v2    217                          ldysgiallimgsfvpwlyysfy
                                           +++++++++++++++++++++++
                         k:K[aaa]           LDYSGIALLIMGSFVPWLYYSFY
Chromosome12 89498 AAGTAAGTA   Intron 4    TAGAcgttgagccaagatgctctttt
                   <2-----[89500:89750]-2>  taacgtctttggttcgtaacta
                                            gtcttttgtgattttgttttcc
```

FIG. 17B

```
hAdipoR2v2      241  cnpqpcfiylivicvlgiaaiivsqwdmfatpqyrgvra
                     +++++++++++++++++++++++++++++++++++++++
                     CNPQPCFIYLIVICVLGIAAIIVSQWDMFATPQYRGVRA
Chromosome12  89821  tacccttattagatgcgaggaagtctgatgacctcggag
                     gacacgttattttgttgtcctttcagattcccaaggtgc
                     ttaatccccgtcctggctactaccggcgtcctgtgaaaa hAdipoR2v2      280                          gvllcspgwsavvpswlltssdl
                                             +++++++++++++++++++++++
                              d:D[gat]       GVLLCSPGWSAVVPSWLLTSSDL
Chromosome12  89938  GGTAAGAG   Intron 5    GAGATggtctacgtagggcttccatagc
                     <1-----[89939:91867]-1>  gtttggcgggcttccgttccgat
                                              acgttcacgtaggatgcgcattg hAdipoR2v2      304  pasasqsagit                     vflglglsgiip
                     +++++++++++                     ++++++++++++
                     PASASQSAGIT       g:G[gga]      VFLGLGLSGIIP
Chromosome12  91939  cgtgtcaggaaGGTGTGAG  Intron 6   TAGGAgttgcgcagaac
                     ccccccagcgtc <1-----[91973:92741]-1>  tttgtgtggttc
                     tcgccattgta                           gtgcacgtactt hAdipoR2v2      328  tlhyvisegflkaatigqigwlmlmaslyitgaalyaariperffpgkc
                     +++++++++++++++++++++++++++++++++++++++++++++++++
                     TLHYVISEGFLKAATIGQIGWLMLMASLYITGAALYAARIPERFFPGKC
Chromosome12  92780  atctgatggtcaggaagcagttacagactaagggctggcacgcttcgat
                     ctaattcagttaccctgatggttttcgtatcgcctaccgtcagttcgag
                     cgctccgggctgcccaggacgggggcccccaatcgttcgccactctcat hAdipoR2v2      377  diw               fhshqlfhifvvagafvhfhgvs
                     +++               +++++++++++++++++++++++
                     DIW               FHSHQLFHIFVVAGAFVHFHGVS
Chromosome12  92927  gatGTAAGTA   Intron 7    CAGtctccctcatggggtgctcggt
                     atg<0-----[92936:94805]-0>tacaattatttcgcttatagtc
                     ccg                           tcttggttctgttatttccttca hAdipoR2v2      403  nlqefrfmigggcseedal
                     +++++++++++++++++++
                     NLQEFRFMIGGGCSEEDAL
Chromosome12  94875  accgtctaagggtaggggc
                     ataatgtttgggggaaact
                     ccggttcgccgcctagtag
```

FIG. 18

Human AdipoR2v2

| Protein | Genbank Accession/ SEQ ID NO | Identities | Similarities |
|---|---|---|---|
| human AdipoR1 protein | gi|NM_015999 | 60.7% | 70.4% |
| human AdipoR2v1 protein | SEQ ID NO:2 | 91.4% | 91.4% |
| Human AdipoR3 | SEQ ID NO:6 | 37.1% | 44.2% |

Human AdipoR3v1

| Protein | Genbank Accession | Identities | Similarities |
|---|---|---|---|
| human AdipoR1 protein | gi|NM_015999 | 79.9% | 83.0% |
| human AdipoR2v1 protein | SEQ ID NO:2 | 53.9% | 63.9% |
| Human AdipoR3 | SEQ ID NO:6 | 70.2% | 71.0% |

FIG. 19A

```
                    Primer set A (SEQ ID NO:154)
Query:   1    atgtcttctcacaaagggtctgtggtggca-aggaatggggctcctgccagtaacaggga  59
              ||||||||||||||||||||||||||||| ||||||||||||||||||||||||||||||
Sbjct: 76966  atgtcttctcacaaagggtctgtggtggcataggaatggggctcctgccagtaacaggga  77025

Primer set B (SEQ ID NO:156)
Query:  60    aactgacatggtggaactggctgaa-tctgaattgtcacccctgctacaagagaagggca  118
              |||||||||||||||||||||||||  ||||||||  |||||||||||||||||||||||
Sbjct: 77026  aactgacatggtggaactggctgaactctgaactctggattgtgacccctgctacaagagaagggca  77085
                            (SEQ ID NO:155)

Query: 119    aatgggtaatcaccaacccaaacaaagctgaagaagagcaaacatgcccagtgccccagg  178
              ||||||||||||||||||||||||||||||||||||||||||||||||||||||||||||
Sbjct: 77086  aatgggtaatcaccaacccaaacaaagctgaagaagagcaaacatgcccagtgccccagg  77145

Query: 179    aagaagaggaggaggtgtgggtactgacacttcccctgcaagcccaccacaccatggaga  238
              ||||||||||||||||||||||||||||||||||||||||||||||||||||||||||||
Sbjct: 77146  aagaagaggaggaggtgtgggtactgacacttcccctgcaagcccaccacaccatggaga  77205

(SEQ ID NO:157)
Query: 239    agatggaggagtttgtgtacaag  261  ctccagacaagc  
              |||||||||||||||||||||||
Sbjct: 77206  agatggaggagtttgtgtacaag  77228

Primer set C (SEQ ID NO:158)
Aggagtttgtgtacaag
Query: 260    agctccagacaagctgctgccaccatcaatatgatgggctccctgactggctgaaggaca  319
              ||||||||||||||||||||||||||||||||||||||||||||||||||||||||||||
Sbjct: 78746  agctccagacaagctgctgccaccatcaatatgatgggctccctgactggctgaaggaca  78805

Query: 320    atgactgtctgcaggacaatgactgtctgctctatggccatagacaacccatgtcctcct  379
              ||||||||||||||||||||||||||||||||||||||||||||||||||||||||||||
Sbjct: 78806  atgactgtctgcaggacaatgactgtctgctctatggccatagacaacccatgtcctcct  78865

Query: 380    tctgggcttgcttcaagagcatcttctatatccatacagaaaccggcagcagccggacac  439
              ||||||||||||||||||||||||||||||||||||||||||||||||||||||||||||
Sbjct: 78866  tctgggcttgcttcaagagcatcttctatatccatacagaaaccggcagcagccggacac  78925

Query: 440    atctgcttggtttcgtgctgtttctcttttggaaatcttgaccatgctcagaccaaata  499
              ||||||||||||||||||||||||||||||||||||||||||||||||||||||||||||
Sbjct: 78926  atctgcttggtttcgtgctgtttctcttttggaaatcttgaccatgctcagaccaaata  78985

Query: 500    tgtacttcacggcccctctacaggagaaagtgatttggaggatattccttttgggtgcag  559
              ||||||||||||||||||||||||||||||||||||||||||||||||||||||||||||
Sbjct: 78986  tgtacttcacggcccctctacaggagaaagtgatttggaggatattccttttgggtgcag  79045
```

FIG. 19B

```
              Primer set D (SEQ ID NO:160)
Query:   560  tgctc-agcctcagcttctcctggctcgtccgcactgtctactgtcattcagagaaagtc  618
              |||||  |||||||||||||||||||||||||||||||||||||||||||||||||||||
Sbjct: 79046  tgctgtagcctcagcttctcctggctcgtccgcactgtctactgtcattcagagaaagtc  79105
              (SEQ ID NO:159)

Query:   619  tctcggacttttccaaactgtactattcagggattgctccactgctcataaggagcttc  678
              ||||||||||||||||||||||||||||||||||||||||||||||||||||||||||||
Sbjct: 79106  tctcggacttttccaaactgtactattcagggattgctccactgctcataaggagcttc  79165

Query:   679  gtccctggctctgttactccttctactgctcgccacagccacggctcatctacttctcc  738
              ||||||||||||||||||||||||||||||||||||||||||||||||||||||||||||
Sbjct: 79166  gtccctggctctgttactccttctactgctcgccacagccacggctcatctacttctcc  79225

Primer set E (SEQ ID NO:162)
Query:   739  atcatctatgtcctgggcatctctgccatcattgtggaccagtgggaccggtttgtcact  798
              |||||||||||||||||          |||||||||||||||||||||  ||||||||||
Sbjct: 79226  atcatctatgtcctgggcatctctgccatcattgtga--cagtgggaccggtttgtcact  79283
                                (SEQ ID NO:161)

Query:   799  cctaagcaccggcagacaagggcaggggtgttgctgggacttggcttgagcggtattgtg  858
              ||||||||||||||||||||||||||||||||||||||||||||||||||||||||||||
Sbjct: 79284  cctaagcaccggcagacaagggcaggggtgttgctgggacttggcttgagcggtattgtg  79343

Query:   859  cccaccatgcactttcctattgctgagggtttcgtcaaggccaccacagtgggccagatg  918
              ||||||||||||||||||||||||||||||||||||||||||||||||||||||||||||
Sbjct: 79344  cccaccatgcactttcctattgctgagggtttcgtcaaggccaccacagtgggccagatg  79403

Query:   919  ggctggttcttcctcgtggctgtgatgtacatcaccagagctggcctttatgctgcttta  978
              |||||||||||||||||||||||||||||||||||||||||||||||||||||||||| |
Sbjct: 79404  ggctggttcttcctcgtggctgtgatgtacatcaccagagctggcctttatgctgcttaa  79463

Query:   979  attcctgagcgcttctttcctggaaaattagacatatggttccagtctcagcagatttc  1038
              ||||||||||||||||||||||||||||||||||||||||||||||||||||||||||||
Sbjct: 79464  attcctgagcgcttctttcctggaaaattagacatatggttccagtctcagcagatttc  79523

Query:  1039  catgtcctcatggtgacggtggcctttgtccacttctgtggggtctccaaccttcaggaa  1098
              ||||||||||||||||||||||||||||||||||||||||||||||||||||||||||||
Sbjct: 79524  catgtcctcatggtgacggtggcctttgtccacttctgtggggtctccaaccttcaggaa  79583

Query:  1099  ttccattacagccgagaaggtgactgcactgatgactcccttctctga  1146
              ||||||||||||||||||||||||||||||||||||||||||||||||
Sbjct: 79584  ttccattacagccgagaaggtgactgcactgatgactcccttctctga  79631
                                               (SEQ ID NO:163)
```

FIG. 20A

```
  1  CCACGCGTCCGCCCACGCGTCCGCGGGCAGGGCGCTGAGGATCCGGCGCCCCTCGGCCGC   60

61  AGGCCGCCTCCAGAGCCGCGGGATGTAGCGCCCCGGCCTGCGGCCCCCAGCAGAGGCAGC  120

121  CAGCCAGGCCTGTCCATCATCACTGGGAGATCTCTGCCCTCTGGGGCTGAGAGACCCCAA  180

181  CCTCTCCTCAAGCTGAAGCTGCAAGGCACTGAGGTACCAGCCAGATGTCTTCCCACAAAG  240
  1                                                M  S  H  K  G    6

241  GATCTGCCGTGGCCCAGGGCAATGGGGCTCCTTCTAGTAACAGAGAAGCGGACACGGTGG  300
  7   S  A  V  A  Q  G  N  G  A  P  S  S  N  R  E  A  D  T  V  E   26

301  AGCTGGCTGAGCTGGGGCCCCTGCTGGAGGAGAAGGGTAAGCGGGCAGCCACCAGCCCAG  360
 27   L  A  E  L  G  P  L  L  E  E  K  G  K  R  A  A  T  S  P  A   46

361  CCAAGGCTGAAGAAGAACAAGCATGCCCCGTGCCTCAGGAGGAGGAGGAGGAGGTGCGGG  420
 47   K  A  E  E  E  Q  A  C  P  V  P  Q  E  E  E  E  E  V  R  V   66

421  TGCTGACCCTTCCTCTGCAAGCCCACCATGCCATGGAGAAGATGGAGGAGTTCGTATATA  480
 67   L  T  L  P  L  Q  A  H  H  A  M  E  K  M  E  E  F  V  Y  K   86

481  AGGTCTGGGAGGGGCGTTGGAGGGTCATCCCATACGATGTGCTTCCTGACTGGCTGAAAG  540
 87   V  W  E  G  R  W  R  V  I  P  Y  D  V  L  P  D  W  L  K  D  106

541  ACAATGACTACCTGCTACATGGCCACAGACCACCTATGCCCTCCTTCCGGGCTTGCTTCA  600
107   N  D  Y  L  L  H  G  H  R  P  P  M  P  S  F  R  A  C  F  K  126

601  AGAGCATCTTCCGCATCCACACAGAAACTGGCAACATCTGGACACATTTGCTTGGTTTTG  660
127   S  I  F  R  I  H  T  E  T  G  N  I  W  T  H  L  L  G  F  V  146

661  TGCTATTTCTCTTTCTGGGAATCTTGACCATGCTCAGACCAAATATGTACTTCATGGCTC  720
147   L  F  L  F  L  G  I  L  T  M  L  R  P  N  M  Y  F  M  A  P  166

721  CCCTCCAGGAGAAGGTGGTCTTCGGGATGTTCTTCCTGGGTGCAGTGCTCTGCCTCAGCT  780
167   L  Q  E  K  V  V  F  G  M  F  F  L  G  A  V  L  C  L  S  F  186

781  TCTCCTGGCTTTTCCACACCGTCTACTGTCATTCAGAGAAGGTCTCTCGCACTTTTTCCA  840
187   S  W  L  F  H  T  V  Y  C  H  S  E  K  V  S  R  T  F  S  K  206

841  AACTGGACTATTCAGGGATTGCTCTACTGATTATGGGGAGCTTCGTCCCCTGGCTCTATT  900
207   L  D  Y  S  G  I  A  L  L  I  M  G  S  F  V  P  W  L  Y  Y  226
```

FIG. 20B

```
 901  ACTCCTTCTACTGCTCCCCACAGCCACGGCTCATCTACCTCTCCATCGTCTGTGTCCTGG   960
 227    S   F   Y   C   S   P   Q   P   R   L   I   Y   L   S   I   V   C   V   L   G    246

961  GCATCTCTGCCATCATTGTGGCACAGTGGGACCGGTTTGCCACTCCCAAGCACCGGCAGA  1020
 247    I   S   A   I   I   V   A   Q   W   D   R   F   A   T   P   K   H   R   Q   T    266

1021  CAAGAGCAGGAGTGTTCCTGGGACTTGGCTTGAGTGGTGTTGTACCCACCATGCACTTTA  1080
 267    R   A   G   V   F   L   G   L   G   L   S   G   V   V   P   T   M   H   F   T    286

1081  CTATCGCTGAGGGCTTTGTCAAGGCCACCACAGTGGGCCAGATGGGCTGGTTCTTCCTCA  1140
 287    I   A   E   G   F   V   K   A   T   T   V   G   Q   M   G   W   F   F   L   M    306

1141  TGGCTGTGATGTACATCACCGGCGCTGGCCTTTATGCTGCTCGGATTCCTGAGCGCTTCT  1200
 307    A   V   M   Y   I   T   G   A   G   L   Y   A   A   R   I   P   E   R   F   F    326

1201  TTCCTGGAAAATTTGACATATGGTTCCAGTCTCATCAGATTTTCCATGTCCTGGTGGTGG  1260
 327    P   G   K   F   D   I   W   F   Q   S   H   Q   I   F   H   V   L   V   V   A    346

1261  CAGCGGCTTTCGTCCACTTCTATGGGGTGTCCAACCTACAGGAATTCCGTTACGGCCTAG  1320
 347    A   A   F   V   H   F   Y   G   V   S   N   L   Q   E   F   R   Y   G   L   E    366

1321  AGGGTGGATGTACCGATGACTCCCTTCTCTGAGCCTTCCCACCTGAGGGTTGGTGGAGGA  1380
 367    G   G   C   T   D   D   S   L   L                                                 375

1381  ACTTCCCCAAGTGCTTTTAAAAATAACTTCTTTGCTGAAGTACGAGAAAAAAAAAAAAAA  1440

```
  1  GCGGCTTCCCGGGCTCAGCAGATTGCCTGGGTCGGAAGGAGGGTCAACTCACCATCCCTT   60

61  ATAAATCCATTCTCCCAAGAAGAAGGGACAGAAAGAAAGACCACTTTGTAAGGAAGGCTT  120

121  TGGTATCCCATGAACGAGCCAACCGAACACCGATTGGGGTGCACCAGGACTCCAGAGCCA  180
  1           M   N   E   P   T   E   H   R   L   G   C   T   R   T   P   E   P    17

181  GATATAAGGCTCAGAAAAGGGCACCAACTTGATGATACAAGGGGAGGTAACAATGACAAC  240
 18   D   I   R   L   R   K   G   H   Q   L   D   D   T   R   G   G   N   N   D   N   37

241  CACCACGGAGATTTGGAGCCCAGTTTAGAGACACCTGTTTGTTCTTCCTACTATGAAAAT  300
 38   H   H   G   D   L   E   P   S   L   E   T   P   V   C   S   S   Y   Y   E   N   57

301  AGCCCCGAGGAACTCGAGTGTCATGATGACAACTCCCAAGAAGATGAAGGGTTTATGGGC  360
 58   S   P   E   E   L   E   C   H   D   D   N   S   Q   E   D   E   G   F   M   G   77

361  ATGTCCCCTCTCCTACAAGCCCATCATGCTATGGAACGAATGGAAGAGTTTGTTTGTAAG  420
 78   M   S   P   L   L   Q   A   H   H   A   M   E   R   M   E   E   F   V   C   K   97

421  GTGTGGGAAGGTCGATGGCGAGTGATCCCTCATGATGTGCTGCCAGATTGGCTTAAGGAC  480
 98   V   W   E   G   R   W   R   V   I   P   H   D   V   L   P   D   W   L   K   D  117

481  AATGACTTCCTTCTCCATGGACACCGGCCTCCTATGCCTTCTTTCCGGGCCTGTTTTAAG  540
118   N   D   F   L   L   H   G   H   R   P   P   M   P   S   F   R   A   C   F   K  137

541  AGCATCTTTAGAATACACACAGAGACGGGCAACATTTGGACACATCTCCTAGGTTGTGTA  600
138   S   I   F   R   I   H   T   E   T   G   N   I   W   T   H   L   L   G   C   V  157

601  TTCTTCCTGTGCCTGGGGATCTTTTATATGTTTCGCCCAAATATATCTTTTGTGGCCCCT  660
158   F   F   L   C   L   G   I   F   Y   M   F   R   P   N   I   S   F   V   A   P  177

661  CTGCAAGAGAAAGTGGTCTTCGGGTTGTTCTTCTTGGGAGCCATTCTCTGCCTTTCCTTT  720
178   L   Q   E   K   V   V   F   G   L   F   F   L   G   A   I   L   C   L   S   F  197

721  TCATGGCTCTTCCACACGGTGTACTGCCACTCAGAAGGGGTCTCCCGACTCTTCTCTAAA  780
198   S   W   L   F   H   T   V   Y   C   H   S   E   G   V   S   R   L   F   S   K  217

781  TTGGATTACTCTGGTATTGCTCTTCTGATCATGGGAAGTTTTGTTCCTTGGCTTTATTAT  840
218   L   D   Y   S   G   I   A   L   L   I   M   G   S   F   V   P   W   L   Y   Y  237
```

FIG. 21B

```
 841  TCTTTCTACTGTAACCCACAACCTTGCTTCATCTACCTGATTGTCATCTGTGTGCTGGGC   900
 238  S   F   Y   C   N   P   Q   P   C   F   I   Y   L   I   V   I   C   V   L   G   257

901  ATTGCAGCCATTATCGTCTCTCAGTGGGACATGTTTGCCACCCCTCAGTATCGGGGGGTC   960
 258  I   A   A   I   I   V   S   Q   W   D   M   F   A   T   P   Q   Y   R   G   V   277

961  AGAGCAGGAGTGTTCGTGGGCTTAGGTCTGAGTGGAATCATCCCTACCTTGCATTATGTC  1020
 278  R   A   G   V   F   V   G   L   G   L   S   G   I   I   P   T   L   H   Y   V   297

1021  ATCTCAGAAGGGTTCCTGAAGGCTGCCACCATAAGGCAGATAGGCTGGCTAATGCTCATG  1080
 298  I   S   E   G   F   L   K   A   A   T   I   R   Q   I   G   W   L   M   L   M   317

1081  GCTAGCCTCTATATCACAGGAGCTGCCCTCTACGCGGCCCGTATCCCTGAGCGCTTCTTT  1140
 318  A   S   L   Y   I   T   G   A   A   L   Y   A   A   R   I   P   E   R   F   F   337

1141  CCTGGCAAATGTGACATCTGGTTTCACTCTCATCAGCTCTTCCACATCTTTGTGGTTGCT  1200
 338  P   G   K   C   D   I   W   F   H   S   H   Q   L   F   H   I   F   V   V   A   357

1201  GGTGCCTTTGTTCACTTCCATGGAGTCTCAAACCTGCAGGAATTTCGTTTCATGATTGGT  1260
 358  G   A   F   V   H   F   H   G   V   S   N   L   Q   E   F   R   F   M   I   G   377

1261  GGGGGCTGCACTGAAAAAGATGCGCTGTGATACTCTCCAGGAACCAGGGACTTTGACCCT  1320
 378  G   G   C   T   E   K   D   A   L                                              386

1321  GAGCCAGGCCTGCAGCTCCCGCAGGCCTTCTTACTGGCTGTCTGTGCCA  1369
```

FIG. 22

```
              1                                                  50
hAdipoR1  (1) MSSHKGSVVAQGNGAPASNREADTVELAELGPLLEEKGKRVIANPPKAEE
mAdipoR1  (1) MSSHKGSAGAQGNGAPSCNREADTVELAELGPLLEEKGKRAASSPAKAEE
rAdipoR1  (1) MSSHKGSAVAQGNGAPSSNREADTVELAELGPLLEEKGKRAATSPAKAEE 51                                                 100
hAdipoR1 (51) EQTCPVPQEEEEEVRVLTLPLQAHHAMEKMEEFVYKVWEGRWRVIPYDVL
mAdipoR1 (51) DQACPVPQEEEEEVRVLTLPLQAHHAMEKMEEFVYKVWEGRWRVIPYDVL
rAdipoR1 (51) EQACPVPQEEEEEVRVLTLPLQAHHAMEKMEEFVYKVWEGRWRVIPYDVL 101                                                150
hAdipoR1 (101) PDWLKDNDYLLHGHRPPMPSFRACFKSIFRIHTETGNIWTHLLGFVLFLF
mAdipoR1 (101) PDWLKDNDYLLHGHRPPMPSFRACFKSIFRIHTETGNIWTHLLGFVLFLF
rAdipoR1 (101) PDWLKDNDYLLHGHRPPMPSFRACFKSIFRIHTETGNIWTHLLGFVLFLF 151                                                200
hAdipoR1 (151) LGILTMLRPNMYFMAPLQEKVVFGMFFLGAVLCLSFSWLFHTVYCHSEKV
mAdipoR1 (151) LGILTMLRPNMYFMAPLQEKVVFGMFFLGAVLCLSFSWLFHTVYCHSEKV
rAdipoR1 (151) LGILTMLRPNMYFMAPLQEKVVFGMFFLGAVLCLSFSWLFHTVYCHSEKV 201                                                250
hAdipoR1 (201) SRTFSKLDYSGIALLIMGSFVPWLYYSFYCSPQPRLIYLSIVCVLGISAI
mAdipoR1 (201) SRTFSKLDYSGIALLIMGSFVPWLYYSFYCSPQPRLIYLSIVCVLGISAI
rAdipoR1 (201) SRTFSKLDYSGIALLIMGSFVPWLYYSFYCSPQPRLIYLSIVCVLGISAI 251                                                300
hAdipoR1 (251) IVAQWDRFATPKHRQTRAGVFLGLGLSGVVPTMHFTIAEGFVKATTVGQM
mAdipoR1 (251) IVAQWDRFATPKHRQTRAGVFLGLGLSGVVPTMHFTIAEGFVKATTVGQM
rAdipoR1 (251) IVAQWDRFATPKHRQTRAGVFLGLGLSGVVPTMHFTIAEGFVKATTVGQM 301                                                350
hAdipoR1 (301) GWFFLMAVMYITGAGLYAARIPERFFPGKFDIWFQSHQIFHVLVVAAAFV
mAdipoR1 (301) GWFFLMAVMYITGAGLYAARIPERFFPGKFDIWFQSHQIFHVLVVAAAFV
rAdipoR1 (301) GWFFLMAVMYITGAGLYAARIPERFFPGKFDIWFQSHQIFHVLVVAAAFV 351              375
hAdipoR1 (351) HFYGVSNLQEFRYGLEGGCTDDTLL
mAdipoR1 (351) HFYGVSNLQEFRYGLEGGCTDDSLL
rAdipoR1 (351) HFYGVSNLQEFRYGLEGGCTDDSLL
```

FIG. 24

```
                    1                                                   50
rAdipoR2    (1)   MNEPTEHRLGCTRTPEPDIRLRKGHQLDDTRGGNNDNHHGDLEPSLETPV
hAdipoR2v1  (1)   MNEPTENRLGCSRTPEPDIRLRKGHQLDGTRRGDNDSHQGDLEPILEASV
hAdipoR2v2  (1)   MNEPTENRLGCSRTPEPDIRLRKGHQLDGTRRGDNDSHQGDLEPILEASV
mAdipoR2v1  (1)   MNEPAKHRLGCTRTPEPDIRLRKGHQLDDTRGSNNDNYQGDLEPSLETPV 51                                                  100
rAdipoR2    (51)  CSSYYENSPEELECHDDNSQEDEGFMGMSPLLQAHHAMERMEEFVCKVWE
hAdipoR2v1  (51)  TSSHHKKSSEEHEYSDEAPQEDEGFMGMSPLLQAHHAMEKMEEFVCKVWE
hAdipoR2v2  (51)  TSSHHKKSSEEHEYSDEAPQEDEGFMGMSPLLQAHHAMEKMEEFVCKVWE
mAdipoR2v1  (51)  CSSYYENSPEEPECHDDNSQEDEGFMGMSPLLQAHHAMERMEEFVCKVWE 101                                                 150
rAdipoR2    (101) GRWRVIPHDVLPDWLKDNDFLLHGHRPPMPSFRACFKSIFRIHTETGNIW
hAdipoR2v1  (101) GRWRVIPHDVLPDWLKDNDFLLHGHRPPMPSFRACFKSIFRIHTETGNIW
hAdipoR2v2  (101) GRWRVIPHDVLPDWLKDNDFLLHGHRPPMPSFRACFKSIFRIHTETGNIW
mAdipoR2v1  (101) GRWRVIPHDVLPDWLKDNDFLLHGHRPPMPSFRACFKSIFRIHTETGNIW 151                                                 200
rAdipoR2    (151) THLLGCVFFLCLGIFYMFRPNISFVAPLQEKVVFGLFFLGAILCLSFSWL
hAdipoR2v1  (151) THLLGCVFFLCLGIFYMFRPNISFVAPLQEKVVFGLFFLGAILCLSFSWL
hAdipoR2v2  (151) THLLGCVFFLCLGIFYMFRPNISFVAPLQEKVVFGLFFLGAILCLSFSWL
mAdipoR2v1  (151) THLLGCVFFLCLGIFYMFRPNISFVAPLQEKVVFGLFFLGAILCLSFSWL 201                                                 250
rAdipoR2    (201) FHTVYCHSEGVSRLFSKLDYSGIALLIMGSFVPWLYYSFYCNPQPCFIYL
hAdipoR2v1  (201) FHTVYCHSEGVSRLFSKLDYSGIALLIMGSFVPWLYYSFYCNPQPCFIYL
hAdipoR2v2  (201) FHTVYCHSEGVSRLFSKLDYSGIALLIMGSFVPWLYYSFYCNPQPCFIYL
mAdipoR2v1  (201) FHTVYCHSEGVSRLFSKLDYSGIALLIMGSFVPWLYYSFYCNPQPCFIYL 251                                                 300
rAdipoR2    (251) IVICVLGIAAIIVSQWDMFATPQYRGVRAG-------------------
hAdipoR2v1  (251) IVICVLGIAAIIVSQWDMFATPQYRGVRAG-------------------
hAdipoR2v2  (251) IVICVLGIAAIIVSQWDMFATPQYRGVRADGVLLCSPGWSAVVPSWLLTS
mAdipoR2v1  (251) IVICVLGIAAIIVSQWDMFATPQYRGVRAG-------------------

301                                                 350
rAdipoR2    (281) ---------------VFVGLGLSGIIPTLHYVISEGFLKAATIRQIGWLM
hAdipoR2v1  (281) ---------------VFLGLGLSGIIPTLHYVISEGFLKAATIGQIGWLM
hAdipoR2v2  (301) SDLPASASQSAGITGVFLGLGLSGIIPTLHYVISEGFLKAATIGQIGWLM
mAdipoR2v1  (281) ---------------VFVGLGLSGIIPTLHYVISEGFLKAATIGQIGWLM 351                                                 400
rAdipoR2    (316) LMASLYITGAALYAARIPERFFPGKCDIWFHSHQLFHIFVVAGAFVHFHG
hAdipoR2v1  (316) LMASLYITGAALYAARIPERFFPGKCDIWFHSHQLFHIFVVAGAFVHFHG
hAdipoR2v2  (351) LMASLYITGAALYAARIPERFFPGKCDIWFHSHQLFHIFVVAGAFVHFHG
mAdipoR2v1  (316) LMASLYITGAALYAARIPERFFPGKCDIWFHSHQLFHIFVVAGAFVHFHG 401           421
rAdipoR2    (366) VSNLQEFRFMIGGGCTEKDAL
hAdipoR2v1  (366) VSNLQEFRFMIGGGCSEEDAL
hAdipoR2v2  (401) VSNLQEFRFMIGGGCSEEDAL
mAdipoR2v1  (366) VSNLQEFRFMIGGGCTEEDAL
```

FIG. 26

Rat AdipoR1

| Protein | Genbank Accession/ SEQ ID NO | Identities | Similarities |
|---|---|---|---|
| human AdipoR1 protein | gi|NM_015999 | 97.6% | 98.1% |
| mouse AdipoR1 protein | gi|BCO14875 | 98.9% | 99.5% |

Rat AdipoR2

| Protein | Genbank Accession | Identities | Similarities |
|---|---|---|---|
| human AdipoR2v2 | SEQ ID NO:104 | 85.0% | 86.7% |
| human AdipoR2v1 protein | SEQ ID NO:2 | 93.0% | 94.8% |
| mouse AdipoR2v1 protein | SEQ ID NO:4 | 97.9% | 98.2% |

• Scheme:

ADIPONECTIN RECEPTOR VARIANT, ADIPOR2V2

This application is a divisional application of non-provisional application U.S. Ser. No. 10/874,923, filed Jun. 23, 2004, which claims benefit to provisional application U.S. Ser. No. 60/482,324 filed Jun. 25, 2003; to provisional application U.S. Ser. No. 60/486,036, filed Jul. 10, 2003; to provisional application U.S. Ser. No. 60/492,470, filed Aug. 4, 2003; to provisional application U.S. Ser. No. 60/508,225, filed Oct. 2, 2003; and to provisional application U.S. Ser. No. 60/552,084, filed Mar. 11, 2004; under 35 U.S.C. 119(e). The entire teachings of the referenced applications are incorporated herein by reference.

FIELD OF THE INVENTION

The present invention provides novel polynucleotides encoding human AdipoR2v1 polypeptides, mouse AdipoR2v1 polypeptides, human AdipoR3 polypeptides, human AdipoR2v2 polypeptides, human AdipoR3v1 polypeptides, rat AdipoR1 polypeptides, rat AdipoR2 polypeptides, fragments and homologues thereof. Also provided are vectors, host cells, antibodies, and recombinant and synthetic methods for producing said polypeptides. The invention further relates to diagnostic and therapeutic methods for applying these novel human AdipoR2v1 polypeptides, mouse AdipoR2v1 polypeptides, human AdipoR3 polypeptides, human AdipoR2v2 polypeptides, human AdipoR3v1 polypeptides, rat AdipoR1 polypeptides, rat AdipoR2 polypeptides, to the diagnosis, treatment, and/or prevention of various diseases and/or disorders related to these polypeptides. The invention further relates to screening methods for identifying agonists and antagonists of the polynucleotides and polypeptides of the present invention.

BACKGROUND OF THE INVENTION

Adiponectin/Acrp30/AdipoQ/apM1/GBP28 (Ad) is the most abundant adipose-specific hormone and acts as an anti-diabetic, anti-obese, anti-inflammatory and anti-atherogenic adipokine. It is a 30-kDa protein composed of 247 amino acids. It contains a secretory signal sequence at its amino terminus, followed by a non-homologous sequence region, a stretch of 22 collagen repeats and a globular domain, that constitute the majority of the polypeptide. The globular domain shares sequence homology with a family of proteins showing a modular design containing a characteristic C-terminal complement factor C1q-like globular domain. In addition to C1q, members of this family include the human type VIII and X collagens, precerebellin, and the hibernation-regulated protein HP-20, 25 and 27. A proteolytic cleavage product of Ad containing the globular head domain of Ad (gAd) has been found in human plasma. gAd had a higher binding affinity to skeletal muscle than full-length Ad, whereas full-length Ad had a higher binding affinity to liver. gAd may serve as an acute stimulator of FA oxidation by muscle. The secretion of Ad can be induced during adipogenesis and upon thiazolidinedione treatment, and be suppressed by TNF-alpha. In humans, the concentration of plasma Ad is 5-10 ug/ml (50-100 nM of homotrimer), and fluctuates much during the course of the day. Usually, females tend to have higher plasma Ad concentration than males (reviewed in Tsao et al, 2002). The crystal structure of Ad has been resolved at 2.1 A, and shows that Ad is a homotrimeric protein, which may further form a higher-order structure, comprising 4 trimers (Shapiro and Scherer, 1998). Ad is structurally similar to TNF-alpha even though they share no sequence similarity to each other.

In vitro and in vivo experiments have shown that adiponectin plays an important role in metabolism. In ob/bo, db/db, and lipoatrophic mice, the Ad level is very low. In rhesus monkeys, progression of obesity and insulin resistance has been associated with an decrease in plasma Ad and increase in leptin concentration. In humans, plasma Ad levels are inversely correlated with serum TG, atherogenic index, BMI/obesity, insulin resistance/T2D and coronary artery diseases. Ad levels rise with weight loss, caloric restriction, cold exposure, and thiazolidinedione treatment that restores insulin sensitivity. In both diabetic and non-diabetic patients, weight reduction caused a 42-65% increase in Ad levels. Ad preferably accumulates to the injured vascular wall, modulates endothelial function, and inhibits vascular smooth muscle proliferation and foam cell formation. Ad treatment also inhibits macrophage phagocytosis and TNF-alpha production (reviewed in Diez and Iglesias, 2003).

Administration of recombinant Ad caused glucose-lowering, ameliorated insulin resistance, suppressed FA influx into liver, and reduced serum TG in obese mice. In lipotropic mice, Ad had a synergistic effect with leptin in ameliorating insulin resistance. gAd, but not flAd, increased FA oxidation in muscle and caused weight loss (7%, 2 wk) without reducing food intake in mice (Fruebis et al, 2001). In muscle, AMPK is stimulated by globular (and full-length) Ad; in liver, only full-length Ad stimulates AMPK (Tomas et al., 2002; Yamauchi et al., 2002).

Both transgenic (gAd-Tg) and knock out mice (−/−) of Ad have been generated. The Ad −/− mice were insulin resistant and glucose intolerant. The transgenic mice also showed delayed clearance of FA from plasma, low FATP in muscle, and high TNFα in adipocytes and plasma. There was more neointimal formation in −/− mice in response to external injury, which can be attenuated via Adenovirus-mediated supplement of Ad (Kubota et al., 2002; Maeda et al., 2002). The gAd Tg mice were viable and normal. They showed ameliorated insulin resistance and hyperglycemia under HF diet. No change in body weight, plasma glucose and insulin levels. As gAd Tg were crossed with ob/ob mice, the progeny showed same body weight as ob/ob. However, their food intake was increased (~130%), and serum FFA & TG are reduced in compared with ob/ob. Interestingly, upon pair-feeding, the double mutants gained weigh much less than ob/ob, suggesting Ad caused changes in energy expenditure. These animals are also protected from diabetes, increased insulin sensitivity and secretion. The FA oxidation in skeletal muscle was also increased. gAd Tg ApoE −/− mice are partially protected from atherosclerotic lesion formation. However, they have similar plasma glucose and lipid levels as ApoE −/−, suggesting a direct role of Ad on vascular wall and macrophage (Yamauchi et al., 2003).

Genetic evidence also suggests that Ad is involved in metabolic regulation in humans. The gene of Ad is located on Chromosome 3q27, the strongest QTL linked to Metabolic Syndrome. In another study, this locus was also linked to early onset diabetes in French Caucasians. An intronic variant SNP276 was found to be associated with T2D and insulin resistance. Independently, a haplotype including SNP276 and SNP45 was associated with obesity and insulin resistance. Additionally, a missense mutation I164T is associated with low plasma Ad concentration, and T2D (reviewed in Tso et al., 2002).

The cloning of adiponectin receptors was recently described in a Nature research paper (Yamauchi et al, 2003).

Both receptors AdipoR1 and AdipoR2 were shown to have anti-diabetic metabolic effects. Both globular and full-length adiponectins can bind to and activate both receptors, signaling through increased AMP kinase activity, PPAR-α ligand activity, as well as fatty-acid oxidation and glucose uptake in muscle cells. Agonists for AdipoR1 and AdipoR2 would be important therapeutic reagents for the treatment of obesity, diabetes, atherosclerosis and inflammatory diseases.

The present invention is directed to the identification of the true full length DNA and protein sequences of both human and mouse AdipoR2 receptors. The published adiponectin receptor 1 (AdipoR1) is a protein containing 375 amino acids, while adiponectin receptor 2 (AdipoR2) contains 299 amino acids. As described herein, the human and mouse AdipoR2 receptors published by Yamauchi et al were missing additional 5' upstream coding sequences. The new NH2 terminus of human and mouse AdipoR2, as described herein, are 88 and 76 amino acids longer than the sequences described in the Yamauchi et al paper.

The present invention is also directed to a novel splice variant of the human AdipoR2 polypeptide, referred to as human AdipoR2v2.

In addition, the present invention discloses a third gene that is found in the human genome that has 80% identity to human AdipoR1 receptor, in addition to a novel variant of this sequence. The new Adipo gene and its variant have been termed AdipoR3, and AdipoR3v1, respectively. The predicted cDNA sequence of AdipoR3 contains 864 nucleotides and the predicted protein sequence of AdipoR3 contains 288 amino acids. The discoveries of the true full length cDNA and protein sequences for AdipoR2, the novel variants AdipoR2v1 and AdipoR2v2, and the AdipoR3 gene and its variant AdipoR3v1 in humans will greatly facilitate the understanding of the anti-diabetic, anti-obese, anti-atherogenic and anti-inflammatory function of adiponectin as well as its receptors.

Using the above examples, it is clear the availability of novel cloned adiponectin receptors provides an opportunity for adjunct or replacement therapy, and are useful for the identification of adiponectin receptor agonists, or stimulators (which might stimulate and/or bias adiponectin receptor action), as well as, in the identification of adiponectin receptor inhibitors. All of which might be therapeutically useful under different circumstances.

The present invention also relates to recombinant vectors, which include the isolated nucleic acid molecules of the present invention, and to host cells containing the recombinant vectors, as well as to methods of making such vectors and host cells, in addition to their use in the production of human AdipoR2v1 polypeptides, mouse AdipoR2v1 polypeptides, human AdipoR3 polypeptides, human AdipoR2v2 polypeptides, human AdipoR3v1 polypeptides, rat AdipoR1 polypeptides, rat AdipoR2 polypeptides, or peptides using recombinant techniques. Synthetic methods for producing the polypeptides and polynucleotides of the present invention are provided. Also provided are diagnostic methods for detecting diseases, disorders, and/or conditions related to the human AdipoR2v1 polypeptides, mouse AdipoR2v1 polypeptides, human AdipoR3 polypeptides, human AdipoR2v2 polypeptides, human AdipoR3v1 polypeptides, rat AdipoR1 polypeptides, rat AdipoR2 polypeptides, and polynucleotides, and therapeutic methods for treating such diseases, disorders, and/or conditions. The invention further relates to screening methods for identifying binding partners of the polypeptides.

BRIEF SUMMARY OF THE INVENTION

The present invention provides isolated nucleic acid molecules, that comprise, or alternatively consist of, a polynucleotide encoding the human AdipoR2.v1 protein having the amino acid sequence shown in FIGS. 1A-B (SEQ ID NO:2), respectively, or the amino acid sequence encoded by the cDNA clone, human AdipoR2.v1 (also referred to as hAdipoR2.v1), deposited as ATCC Deposit Number PTA-6088 on Jun. 18$^{th}$, 2004.

The present invention provides isolated nucleic acid molecules, that comprise, or alternatively consist of, a polynucleotide encoding the mouse AdipoR2.v1 protein having the amino acid sequence shown in FIGS. 2A-D (SEQ ID NO:4), respectively, or the amino acid sequence encoded by the cDNA clone, mouse AdipoR2.v1 (also referred to as mAdipoR2.v1).

The present invention provides isolated nucleic acid molecules, that comprise, or alternatively consist of, a polynucleotide encoding the human AdipoR3 protein having the amino acid sequence shown in FIG. 3 (SEQ ID NO:6), respectively, or the amino acid sequence encoded by the cDNA clone, human AdipoR3.

The present invention provides isolated nucleic acid molecules, that comprise, or alternatively consist of, a polynucleotide encoding the human AdipoR3v1 protein having the amino acid sequence shown in FIGS. 12A-B (SEQ ID NO:101), respectively, or the amino acid sequence encoded by the cDNA clone, human AdipoR3v1 (also referred to as hAdipoR3v1).

The present invention provides isolated nucleic acid molecules, that comprise, or alternatively consist of, a polynucleotide encoding the human AdipoR2v2 protein having the amino acid sequence shown in FIGS. 13A-B (SEQ ID NO:103), respectively, or the amino acid sequence encoded by the cDNA clone, human AdipoR2v2 (also referred to as hAdipoR2v2), deposited as ATCC Deposit Number PTA-6088 on Jun. 18$^{th}$, 2004.

The present invention provides isolated nucleic acid molecules, that comprise, or alternatively consist of, a polynucleotide encoding the rat AdipoR1 protein having the amino acid sequence shown in FIGS. 20A-B (SEQ ID NO:165), respectively, or the amino acid sequence encoded by the cDNA clone, rat AdipoR1 (also referred to as rAdipoR1).

The present invention provides isolated nucleic acid molecules, that comprise, or alternatively consist of, a polynucleotide encoding the rat AdipoR2 protein having the amino acid sequence shown in FIGS. 21A-B (SEQ ID NO:167), respectively, or the amino acid sequence encoded by the cDNA clone, rat AdipoR2 (also referred to as rAdipoR2).

The present invention also relates to recombinant vectors, which include the isolated nucleic acid molecules of the present invention, and to host cells containing the recombinant vectors, as well as to methods of making such vectors and host cells, in addition to their use in the production of AdipoR2v1, mouse AdipoR2v1, human AdipoR3, human AdipoR2v2, human AdipoR3v1, rat AdipoR1, and/or rat AdipoR2 or peptides using recombinant techniques. Synthetic methods for producing the polypeptides and polynucleotides of the present invention are provided. Also provided are diagnostic methods for detecting diseases, disorders, and/or conditions related to the AdipoR2v1, mouse AdipoR2v1, human AdipoR3, human AdipoR2v2, human AdipoR3v1, rat AdipoR1, and/or rat AdipoR2 and polynucleotides, and therapeutic methods for treating such diseases, disorders, and/or conditions. The invention further relates to screening methods for identifying binding partners of the polypeptides.

The invention further provides an isolated human AdipoR2.v1 polypeptide having an amino acid sequence encoded by a polynucleotide described herein.

The invention further provides an isolated mouse AdipoR2.v1 polypeptide having an amino acid sequence encoded by a polynucleotide described herein.

The invention further provides an isolated human AdipoR3 polypeptide having an amino acid sequence encoded by a polynucleotide described herein.

The invention further provides an isolated human AdipoR2v2 polypeptide having an amino acid sequence encoded by a polynucleotide described herein.

The invention further provides an isolated human AdipoR3v1 polypeptide having an amino acid sequence encoded by a polynucleotide described herein.

The invention further provides an isolated rat AdipoR1 polypeptide having an amino acid sequence encoded by a polynucleotide described herein.

The invention further provides an isolated rat AdipoR2 polypeptide having an amino acid sequence encoded by a polynucleotide described herein.

The invention further relates to a polynucleotide encoding a polypeptide fragment of SEQ ID NO:2, 4, 6, 102, 104, 165, or 167, or a polypeptide fragment encoded by the cDNA sequence included in the deposited clone, which is hybridizable to SEQ ID NO:1, 3, 5, 101, 103, 164, or 166.

The invention further relates to a polynucleotide encoding a polypeptide domain of SEQ ID NO:2, 4, 6, 102, 104, 165, or 167 or a polypeptide domain encoded by the cDNA sequence included in the deposited clone, which is hybridizable to SEQ ID NO:1, 3, 5, 101, 103, 164, or 166.

The invention further relates to a polynucleotide encoding a polypeptide epitope of SEQ ID NO:2, 4, 6, 102, 104, 165, or 167 or a polypeptide epitope encoded by the cDNA sequence included in the deposited clone, which is hybridizable to SEQ ID NO:1, 3, 5, 101, 103, 164, or 166.

The invention further relates to a polynucleotide encoding a polypeptide of SEQ ID NO:2, 4, 6, 102, 104, 165, or 167 or the cDNA sequence included in the deposited clone, which is hybridizable to SEQ ID NO:1, 3, 5, 101, 103, 164, or 166, having biological activity.

The invention further relates to a polynucleotide which is a variant of SEQ ID NO:1, 3, 5, 101, 103, 164, or 166.

The invention further relates to a polynucleotide which is an allelic variant of SEQ ID NO:1, 3, 5, 101, 103, 164, or 166.

The invention further relates to a polynucleotide which encodes a species homologue of the SEQ ID NO:2, 4, 6, 102, 104, 165, or 167.

The invention further relates to a polynucleotide which represents the complimentary sequence (antisense) of SEQ ID NO:1, 3, 5, 101, 103, 164, or 166.

The invention further relates to a polynucleotide capable of hybridizing under stringent conditions to any one of the polynucleotides specified herein, wherein said polynucleotide does not hybridize under stringent conditions to a nucleic acid molecule having a nucleotide sequence of only A residues or of only T residues.

The invention further relates to an isolated nucleic acid molecule of SEQ ID NO:2, 4, 6, 102, 104, 165, or 167, wherein the polynucleotide fragment comprises a nucleotide sequence encoding an adiponectin receptor.

The invention further relates to an isolated nucleic acid molecule of SEQ ID NO:1, 3, 5, 101, 103, 164, or 166, wherein the polynucleotide fragment comprises a nucleotide sequence encoding the sequence identified as SEQ ID NO:2, 4, 6, 102, 104, 165, or 167 or the polypeptide encoded by the cDNA sequence included in the deposited clone, which is hybridizable to SEQ ID NO:1, 3, 5, 101, 103, 164, or 166.

The invention further relates to an isolated nucleic acid molecule of SEQ ID NO:1, 3, 5, 101, 103, 164, or 166, wherein the polynucleotide fragment comprises the entire nucleotide sequence of SEQ ID NO:1, 3, 5, 101, 103, 164, or 166 or the cDNA sequence included in the deposited clone, which is hybridizable to SEQ ID NO:1, 3, 5, 101, 103, 164, or 166.

The invention further relates to an isolated nucleic acid molecule of SEQ ID NO:1, 3, 5, 101, 103, 164, or 166, wherein the nucleotide sequence comprises sequential nucleotide deletions from either the C-terminus or the N-terminus.

The invention further relates to an isolated polypeptide comprising an amino acid sequence that comprises a polypeptide fragment of SEQ ID NO:2, 4, 6, 102, 104, 165, or 167 or the encoded sequence included in the deposited clone.

The invention further relates to a polypeptide fragment of SEQ ID NO:2, 4, 6, 102, 104, 165, or 167 or the encoded sequence included in the deposited clone, having biological activity.

The invention further relates to a polypeptide domain of SEQ ID NO:2, 4, 6, 102, 104, 165, or 167 or the encoded sequence included in the deposited clone.

The invention further relates to a polypeptide epitope of SEQ ID NO:2, 4, 6, 102, 104, 165, or 167 or the encoded sequence included in the deposited clone.

The invention further relates to a full length protein of SEQ ID NO:2, 4, 6, 102, 104, 165, or 167 or the encoded sequence included in the deposited clone.

The invention further relates to a variant of SEQ ID NO:2, 4, 6, 102, 104, 165, or 167.

The invention further relates to an allelic variant of SEQ ID NO:2, 4, 6, 102, 104, 165, or 167.

The invention further relates to a species homologue of SEQ ID NO:2, 4, 6, 102, 104, 165, or 167.

The invention further relates to the isolated polypeptide of SEQ ID NO:2, 4, 6, 102, 104, 165, or 167, wherein the full length protein comprises sequential amino acid deletions from either the C-terminus or the N-terminus.

The invention further relates to an isolated antibody that binds specifically to the isolated polypeptide of SEQ ID NO:2, 4, 6, 102, 104, 165, or 167.

The invention further relates to a method for preventing, treating, or ameliorating a medical condition, comprising administering to a mammalian subject a therapeutically effective amount of the polypeptide of SEQ ID NO:2, 4, 6, 102, 104, 165, or 167 or the polynucleotide of SEQ ID NO:1, 3, 5, 101, 103, 164, or 166.

The invention further relates to a method of diagnosing a pathological condition or a susceptibility to a pathological condition in a subject comprising the steps of (a) determining the presence or absence of a mutation in the polynucleotide of SEQ ID NO:1, 3, 5, 101, 103, 164, or 166; and (b) diagnosing a pathological condition or a susceptibility to a pathological condition based on the presence or absence of said mutation.

The invention further relates to a method of diagnosing a pathological condition or a susceptibility to a pathological condition in a subject comprising the steps of (a) determining the presence or amount of expression of the polypeptide of SEQ ID NO:2, 4, 6, 102, 104, 165, or 167 in a biological sample; and (b) diagnosing a pathological condition or a susceptibility to a pathological condition based on the presence or amount of expression of the polypeptide.

The invention further relates to a method for identifying a binding partner to the polypeptide of SEQ ID NO:2, 4, 6, 102, 104, 165, or 167 comprising the steps of (a) contacting the polypeptide of SEQ ID NO:2, 4, 6, 102, 104, 165, or 167 with a binding partner; and (b) determining whether the binding partner effects an activity of the polypeptide.

The invention further relates to a gene corresponding to the cDNA sequence of SEQ ID NO:1, 3, 5, 101, 103, 164, or 166.

The invention further relates to a method of identifying an activity in a biological assay, wherein the method comprises the steps of (a) expressing SEQ ID NO:1, 3, 5, 101, 103, 164, or 166 in a cell, (b) detecting an activity in a biological assay.

The invention further relates to a process for making polynucleotide sequences encoding gene products having altered activity selected from the group consisting of SEQ ID NO:2, 4, 6, 102, 104, 165, or 167 activity comprising the steps of (a) shuffling a nucleotide sequence of SEQ ID NO:1, 3, 5, 101, 103, 164, or 166, (b) expressing the resulting shuffled nucleotide sequences and, (c) selecting for altered activity selected from the group consisting of SEQ ID NO:2, 4, 6, 102, 104, 165, or 167 activity as compared to the activity selected from the group consisting of SEQ ID NO:2, 4, 6, 102, 104, 165, or 167 activity of the gene product of said unmodified nucleotide sequence.

The invention further relates to a shuffled polynucleotide sequence produced by a shuffling process, wherein said shuffled DNA molecule encodes a gene product having enhanced tolerance to an inhibitor of any one of the activities selected from the group consisting of SEQ ID NO:2, 4, 6, 102, 104, 165, or 167 activity.

The invention further relates to a method for preventing, treating, or ameliorating a medical condition with the polypeptide provided as SEQ ID NO:2, 4, 6, 102, 104, 165, or 167, in addition to, its encoding nucleic acid, wherein the medical condition is a reproductive disorder.

The invention further relates to a method for preventing, treating, or ameliorating a medical condition with the polypeptide provided as SEQ ID NO:2, 4, 6, 102, 104, 165, or 167, in addition to, its encoding nucleic acid, wherein the medical condition is a disorder related to aberrant G-protein coupled signaling.

The invention further relates to a method for preventing, treating, or ameliorating a medical condition with the polypeptide provided as SEQ ID NO:2, 4, 6, 102, 104, 165, or 167, in addition to, its encoding nucleic acid, wherein the medical condition is selected from the group consisting of: metabolic disorders, inflammatory disorders, cardiovascular disorders, obesity, diabetes, type I diabetes, type II diabetes, gestational diabetes, early onset diabetes, insulin resistance, disorders in which glucose-lowering would be beneficial, disorders in which amelioration of insulin resistance would be beneficial, disorders in which suppressed FA influx into liver would be beneficial, disorders in which reduced serum TG would be beneficial, myocardial infarction, heart failure, atherosclerosis, arteriosclerosis, disorders disclosed herein in the "Cardiovascular Disorders" section, disorders in which adiponectin levels are below normal, disorders that would benefit from increased adiponectin levels, disorders associated with aberrant vascular smooth muscle proliferation, disorders associated with aberrant foam cell formation, disorders in which inhibition of macrophage phagocytosis would be beneficial, disorders in which inhibition of TNF-alpha production would be beneficial, dyslipidemia, diabetic dyslipidemia, mixed dyslipidemia, hypercholesteremia, hypertriglyceridemia, hyperlipidemia, and anorexia nervosa.

The invention further relates to a method for preventing, treating, or ameliorating a medical condition with the polypeptide provided as SEQ ID NO:2, 4, 6, 102, 104, 165, or 167, in addition to, its encoding nucleic acid, wherein the medical condition is selected from the group consisting of: arthritis, rheumatoid arthritis, osteoarthritis, prosthetic joint failure, ulcerative colitis, Crohn's disease, inflammatory bowel and gastrointestinal diseases, gastritis, mucosal inflammation resulting from infection, enteropathy provoked by non-steroidal anti-inflammatory drugs, adult respiratory distress syndrome, asthma, cystic fibrosis, chronic obstructive pulmonary disease, myocarditis, multiple sclerosis, inflammation associated with diabetes melitus, glomerulonephritis, dermatitis, psoriasis, eczema, urticaria, burn injury, glaucoma, organ rejection, multi-organ diseases, systemic lupus erythematosis, sepsis, inflammatory sequelae of viral or bacterial infections, inflammatory conditions associated with atherosclerosis following hypoxic or ischaemic insults (with or without reperfusion, particularly in the brain or in ischaemic heart disease.

The invention further relates to a method of identifying a compound that modulates the biological activity of human AdipoR2v1, mouse AdipoR2v1, human AdipoR3, human AdipoR2v2, human AdipoR3v, rat AdipoR1, and/or rat AdipoR2, comprising the steps of, (a) combining a candidate modulator compound with human AdipoR2v1, mouse AdipoR2v1, human AdipoR3, human AdipoR2v2, human AdipoR3v, rat AdipoR1, and/or rat AdipoR2 having the sequence set forth in SEQ ID NO:2, 4, 6, 102, 104, 165, or 167; and, (b) measuring an effect of the candidate modulator compound on the activity of human AdipoR2v1, mouse AdipoR2v1, human AdipoR3, human AdipoR2v2, human AdipoR3v, rat AdipoR1, and/or rat AdipoR2.

The invention further relates to a method of identifying a compound that modulates the biological activity of human AdipoR2v1, mouse AdipoR2v1, human AdipoR3, human AdipoR2v2, human AdipoR3v, rat AdipoR1, and/or rat AdipoR2, comprising the steps of, (a) combining a candidate modulator compound with human AdipoR2v1, mouse AdipoR2v1, human AdipoR3, human AdipoR2v2, human AdipoR3v, rat AdipoR1, and/or rat AdipoR2 having the sequence set forth in SEQ ID NO:2, 4, 6, 102, 104, 165, or 167; and, (b) measuring an effect of the candidate modulator compound on the activity of human AdipoR2v1, mouse AdipoR2v1, human AdipoR3, human AdipoR2v2, human AdipoR3v, rat AdipoR1, and/or rat AdipoR2, wherein said method optionally includes the addition of adiponectin to human AdipoR2v1, mouse AdipoR2v1, human AdipoR3, human AdipoR2v2, human AdipoR3v, rat AdipoR1, and/or rat AdipoR2 either before or after addition of said candidate modulator compound.

The invention further relates to a method of identifying an antagonist compound that modulates the biological activity of human AdipoR2v1, mouse AdipoR2v1, human AdipoR3, human AdipoR2v2, human AdipoR3v, rat AdipoR1, and/or rat AdipoR2, comprising the steps of, (a) combining a candidate modulator compound with human AdipoR2v1, mouse AdipoR2v1, human AdipoR3, human AdipoR2v2, human AdipoR3v, rat AdipoR1, and/or rat AdipoR2 having the sequence set forth in SEQ ID NO:2, 4, 6, 102, 104, 165, or 167 subsequent to addition of adiponectin; and, (b) identifying antagonist compounds by measuring an effect of the candidate modulator compound on the activity of human AdipoR2v1, mouse AdipoR2v1, human AdipoR3, human AdipoR2v2, human AdipoR3v, rat AdipoR1, and/or rat AdipoR2, wherein said identified antagonist compound decreases adiponectin dependent human AdipoR2v1, mouse AdipoR2v1, human AdipoR3, human AdipoR2v2, human AdipoR3v, rat AdipoR1, and/or rat AdipoR2 activity.

The invention further relates to a method of identifying an agonist compound that modulates the biological activity of human AdipoR2v1, mouse AdipoR2v1, human AdipoR3, human AdipoR2v2, human AdipoR3v, rat AdipoR1, and/or rat AdipoR2, comprising the steps of, (a) combining a candidate modulator compound with human AdipoR2v1, mouse AdipoR2v1, human AdipoR3, human AdipoR2v2, human AdipoR3v, rat AdipoR1, and/or rat AdipoR2 having the sequence set forth in SEQ ID NO:2, 4, 6, 102, 104, 165, or 167 subsequent to addition of adiponectin; and, (b) identifying agonist compounds by measuring an effect of the candidate modulator compound on the activity of human AdipoR2v1, mouse AdipoR2v1, human AdipoR3, human AdipoR2v2, human AdipoR3v, rat AdipoR1, and/or rat AdipoR2, wherein said identified agonist compound increases adiponectin dependent human AdipoR2v1, mouse AdipoR2v1, human AdipoR3, human AdipoR2v2, human AdipoR3v, rat AdipoR1, and/or rat AdipoR2 activity.

The invention further relates to a method of identifying a compound that modulates the biological activity of an adiponectin receptor, comprising the steps of, (a) combining a candidate modulator compound with a host cell expressing human AdipoR2v1, mouse AdipoR2v1, human AdipoR3, human AdipoR2v2, human AdipoR3v, rat AdipoR1, and/or rat AdipoR2 having the sequence as set forth in SEQ ID NO:2, 4, 6, 102, 104, 165, or 167; and, (b) measuring an effect of the candidate modulator compound on the activity of the expressed human AdipoR2v1, mouse AdipoR2v1, human AdipoR3, human AdipoR2v2, human AdipoR3v, rat AdipoR1, and/or rat AdipoR2.

The invention further relates to a method of identifying a compound that modulates the biological activity of an adiponectin receptor, comprising the steps of, (a) combining a candidate modulator compound with a host cell expressing human AdipoR2v1, mouse AdipoR2v1, human AdipoR3, human AdipoR2v2, human AdipoR3v, rat AdipoR1, and/or rat AdipoR2 having the sequence as set forth in SEQ ID NO:2, 4, 6, 102, 104, 165, or 167; and, (b) measuring an effect of the candidate modulator compound on the activity of the expressed human AdipoR2v1, mouse AdipoR2v1, human AdipoR3, human AdipoR2v2, human AdipoR3v, rat AdipoR1, and/or rat AdipoR2, wherein said method optionally includes the addition of adiponectin to human AdipoR2v1, mouse AdipoR2v1, human AdipoR3, human AdipoR2v2, human AdipoR3v, rat AdipoR1, and/or rat AdipoR2 either before or after addition of said candidate modulator compound.

The invention further relates to a method of identifying an antagonist compound that modulates the biological activity of an adiponectin receptor, comprising the steps of, (a) combining a candidate modulator compound with a host cell expressing human AdipoR2v1, mouse AdipoR2v1, human AdipoR3, human AdipoR2v2, human AdipoR3v, rat AdipoR1, and/or rat AdipoR2 having the sequence as set forth in SEQ ID NO:2, 4, 6, 102, 104, 165, or 167 subsequent to addition of adiponectin; and, (b) measuring an effect of the candidate modulator compound on the activity of the expressed human AdipoR2v1, mouse AdipoR2v1, human AdipoR3, human AdipoR2v2, human AdipoR3v, rat AdipoR1, and/or rat AdipoR2, wherein said identified antagonist compound decreases adiponectin dependent human AdipoR2v1, mouse AdipoR2v1, human AdipoR3, human AdipoR2v2, human AdipoR3v, rat AdipoR1, and/or rat AdipoR2 activity.

The invention further relates to a method of identifying an agonist compound that modulates the biological activity of an adiponectin receptor, comprising the steps of, (a) combining a candidate modulator compound with a host cell expressing human AdipoR2v1, mouse AdipoR2v1, human AdipoR3, human AdipoR2v2, human AdipoR3v, rat AdipoR1, and/or rat AdipoR2 having the sequence as set forth in SEQ ID NO:2, 4, 6, 102, 104, 165, or 167 subsequent to addition of adiponectin; and, (b) measuring an effect of the candidate modulator compound on the activity of the expressed human AdipoR2v1, mouse AdipoR2v1, human AdipoR3, human AdipoR2v2, human AdipoR3v, rat AdipoR1, and/or rat AdipoR2, wherein said identified agonist compound increases adiponectin dependent human AdipoR2v1, mouse AdipoR2v1, human AdipoR3, human AdipoR2v2, human AdipoR3v, rat AdipoR1, and/or rat AdipoR2 activity.

The invention further relates to a method of identifying a compound that modulates the biological activity of human AdipoR2v1, mouse AdipoR2v1, human AdipoR3, human AdipoR2v2, human AdipoR3v, rat AdipoR1, and/or rat AdipoR2, comprising the steps of, (a) combining a candidate modulator compound with a host cell containing a vector described herein, wherein human AdipoR2v1, mouse AdipoR2v1, human AdipoR3, human AdipoR2v2, human AdipoR3v, rat AdipoR1, and/or rat AdipoR2 is expressed by the cell; and, (b) measuring an effect of the candidate modulator compound on the activity of the expressed human AdipoR2v1, mouse AdipoR2v1, human AdipoR3, human AdipoR2v2, human AdipoR3v, rat AdipoR1, and/or rat AdipoR2.

The invention further relates to a method of identifying a compound that modulates the biological activity of human AdipoR2v1, mouse AdipoR2v1, human AdipoR3, human AdipoR2v2, human AdipoR3v, rat AdipoR1, and/or rat AdipoR2, comprising the steps of, (a) combining a candidate modulator compound with a host cell containing a vector described herein, wherein human AdipoR2v1, mouse AdipoR2v1, human AdipoR3, human AdipoR2v2, human AdipoR3v, rat AdipoR1, and/or rat AdipoR2 is expressed by the cell; and, (b) measuring an effect of the candidate modulator compound on the activity of the expressed human AdipoR2v1, mouse AdipoR2v1, human AdipoR3, human AdipoR2v2, human AdipoR3v, rat AdipoR1, and/or rat AdipoR2, wherein said method optionally includes the addition of adiponectin to human AdipoR2v1, mouse AdipoR2v1, human AdipoR3, human AdipoR2v2, human AdipoR3v, rat AdipoR1, and/or rat AdipoR2 either before or after addition of said candidate modulator compound.

The invention further relates to a method of identifying an antagonist compound that modulates the biological activity of human AdipoR2v1, mouse AdipoR2v1, human AdipoR3, human AdipoR2v2, human AdipoR3v, rat AdipoR1, and/or rat AdipoR2, comprising the steps of, (a) combining a candidate modulator compound with a host cell containing a vector described herein, wherein human AdipoR2v1, mouse AdipoR2v1, human AdipoR3, human AdipoR2v2, human AdipoR3v, rat AdipoR1, and/or rat AdipoR2 is expressed by the cell, subsequent to addition of adiponectin, and, (b) measuring an effect of the candidate modulator compound on the activity of the expressed human AdipoR2v1, mouse AdipoR2v1, human AdipoR3, human AdipoR2v2, human AdipoR3v, rat AdipoR1, and/or rat AdipoR2, wherein said identified antagonist compound decreases adiponectin dependent human AdipoR2v1, mouse AdipoR2v1, human AdipoR3, human AdipoR2v2, human AdipoR3v, rat AdipoR1, and/or rat AdipoR2 activity.

The invention further relates to a method of identifying an agonist compound that modulates the biological activity of human AdipoR2v1, mouse AdipoR2v1, human AdipoR3, human AdipoR2v2, human AdipoR3v, rat AdipoR1, and/or rat AdipoR2, comprising the steps of, (a) combining a candidate modulator compound with a host cell containing a vector described herein, wherein human AdipoR2v1, mouse AdipoR2v1, human AdipoR3, human AdipoR2v2, human AdipoR3v, rat AdipoR1, and/or rat AdipoR2 is expressed by the cell, subsequent to addition of adiponectin, and, (b) measuring an effect of the candidate modulator compound on the activity of the expressed human AdipoR2v1, mouse AdipoR2v1, human AdipoR3, human AdipoR2v2, human AdipoR3v, rat AdipoR1, and/or rat AdipoR2, wherein said identified agonist compound increases adiponectin dependent human AdipoR2v1, mouse AdipoR2v1, human AdipoR3, human AdipoR2v2, human AdipoR3v, rat AdipoR1, and/or rat AdipoR2 activity.

The invention further relates to a method of screening for a compound that is capable of modulating the biological activity of human AdipoR2v1, mouse AdipoR2v1, human AdipoR3, human AdipoR2v2, human AdipoR3v, rat AdipoR1, and/or rat AdipoR2, comprising the steps of: (a) providing a host cell described herein; (b) determining the biological activity of human AdipoR2v1, mouse AdipoR2v1, human AdipoR3, human AdipoR2v2, human AdipoR3v, rat AdipoR1, and/or rat AdipoR2 in the absence of a modulator compound; (c) contacting the cell with the modulator compound; and (d) determining the biological activity of human AdipoR2v1, mouse AdipoR2v1, human AdipoR3, human AdipoR2v2, human AdipoR3v, rat AdipoR1, and/or rat AdipoR2 in the presence of the modulator compound; wherein a difference between the activity of human AdipoR2v1, mouse AdipoR2v1, human AdipoR3, human AdipoR2v2, human AdipoR3v, rat AdipoR1, and/or rat AdipoR2 in the presence of the modulator compound and in the absence of the modulator compound indicates a modulating effect of the compound.

The invention further relates to a method of screening for a compound that is capable of modulating the biological activity of human AdipoR2v1, mouse AdipoR2v1, human AdipoR3, human AdipoR2v2, human AdipoR3v, rat AdipoR1, and/or rat AdipoR2, comprising the steps of: (a) providing a host cell described herein; (b) determining the biological activity of human AdipoR2v1, mouse AdipoR2v1, human AdipoR3, human AdipoR2v2, human AdipoR3v, rat AdipoR1, and/or rat AdipoR2 in the absence of a modulator compound; (c) contacting the cell with the modulator compound; and (d) determining the biological activity of human AdipoR2v1, mouse AdipoR2v1, human AdipoR3, human AdipoR2v2, human AdipoR3v, rat AdipoR1, and/or rat AdipoR2 in the presence of the modulator compound; wherein a difference between the activity of human AdipoR2v1, mouse AdipoR2v1, human AdipoR3, human AdipoR2v2, human AdipoR3v, rat AdipoR1, and/or rat AdipoR2 in the presence of the modulator compound and in the absence of the modulator compound indicates a modulating effect of the compound, wherein said method optionally includes the addition of adiponectin to human AdipoR2v1, mouse AdipoR2v1, human AdipoR3, human AdipoR2v2, human AdipoR3v, rat AdipoR1, and/or rat AdipoR2 either before or after addition of said candidate modulator compound.

The invention further relates to a compound that modulates the biological activity of human AdipoR2v1, mouse AdipoR2v1, human AdipoR3, human AdipoR2v2, human AdipoR3v, rat AdipoR1, and/or rat AdipoR2 as identified by the methods described herein.

As used herein the terms "modulate" or "modulates" refer to an increase or decrease in the amount, quality or effect of a particular activity, DNA, RNA, or protein of human AdipoR2v1, mouse AdipoR2v1, human AdipoR3, human AdipoR2v2, human AdipoR3v, rat AdipoR1, and/or rat AdipoR2.

BRIEF DESCRIPTION OF THE FIGURES/DRAWINGS

FIGS. 1A-B show the polynucleotide sequence (SEQ ID NO:1) and deduced amino acid sequence (SEQ ID NO:2) of the novel human adiponectin receptor, human AdipoR2v1, of the present invention. The standard one-letter abbreviation for amino acids is used to illustrate the deduced amino acid sequence. The polynucleotide sequence contains a sequence of 1585 nucleotides (SEQ ID NO:1), encoding a polypeptide of 386 amino acids (SEQ ID NO:2). An analysis of the human AdipoR2v1 polypeptide determined that it comprised the following features: seven transmembrane domains (TM1 to TM7) located from about amino acid 151 to about amino acid 172 (TM1; SEQ ID NO:67); from about amino acid 177 to about amino acid 201 (TM2; SEQ ID NO:68); from about amino acid 221 to about amino acid 235 (TM3; SEQ ID NO:69); from about amino acid 247 to about amino acid 266 (TM4; SEQ ID NO:70); from about amino acid 279 to about amino acid 299 (TM5; SEQ ID NO:71); from about amino acid 307 to about amino acid 327 (TM6; SEQ ID NO:72); and/or from about amino acid 347 to about amino acid 364 (TM7; SEQ ID NO:73) of SEQ ID NO:2. It is anticipated that the human AdipoR2v1 polypeptide is a functional receptor for adiponectin as described more particularly elsewhere herein.

FIGS. 2A-D show the polynucleotide sequence (SEQ ID NO:3) and deduced amino acid sequence (SEQ ID NO:4) of the novel human adiponectin receptor, mouse AdipoR2v1, of the present invention. The standard one-letter abbreviation for amino acids is used to illustrate the deduced amino acid sequence. The polynucleotide sequence contains a sequence of 3975 nucleotides (SEQ ID NO:3), encoding a polypeptide of 386 amino acids (SEQ ID NO:4). An analysis of the mouse AdipoR2v1 polypeptide determined that it comprised the following features: seven transmembrane domains (TM1 to TM7) located from about amino acid 151 to about amino acid 172 (TM1; SEQ ID NO:74); from about amino acid 177 to about amino acid 201 (TM2; SEQ ID NO:75); from about amino acid 217 to about amino acid 235 (TM3; SEQ ID NO:76); from about amino acid 243 to about amino acid 266 (TM4; SEQ ID NO:77); from about amino acid 279 to about amino acid 303 (TM5; SEQ ID NO:78); from about amino acid 307 to about amino acid 327 (TM6; SEQ ID NO:79); and/or from about amino acid 348 to about amino acid 364 (TM7; SEQ ID NO:80) of SEQ ID NO:4. It is anticipated that the mouse AdipoR2v1 polypeptide is a functional receptor for adiponectin as described more particularly elsewhere herein.

FIG. 3 shows the polynucleotide sequence (SEQ ID NO:5) and deduced amino acid sequence (SEQ ID NO:6) of the novel human adiponectin receptor, human AdipoR3, of the present invention. The standard one-letter abbreviation for amino acids is used to illustrate the deduced amino acid sequence. The polynucleotide sequence contains a sequence of 867 nucleotides (SEQ ID NO:5), encoding a polypeptide of 288 amino acids (SEQ ID NO:6). An analysis of the human AdipoR3 polypeptide determined that it comprised the following features: six transmembrane domains (TM1 to TM6) located from about amino acid 131 to about amino acid 149 (TM1; SEQ ID NO:81); from about amino acid 157 to about amino acid 172 (TM2; SEQ ID NO:82); from about amino acid 179 to about amino acid 197 (TM3; SEQ ID NO:83); from about amino acid 204 to about amino acid 225 (TM4;

SEQ ID NO:84); from about amino acid 240 to about amino acid 263 (TM5; SEQ ID NO:85); and/or from about amino acid 266 to about amino acid 288 (TM6; SEQ ID NO:86) of SEQ ID NO:6. It is anticipated that the human AdipoR3 polypeptide is a functional receptor for adiponectin as described more particularly elsewhere herein.

FIGS. 4A-B shows the regions of identity and similarity between the encoded human AdipoR2v1 polypeptide (SEQ ID NO:2) and mouse AdipoR2v1 polypeptide (SEQ ID NO:4) to the human AdipoR1 protein (hAdipoR1; GenbankAccession No: gi|NM_015999; SEQ ID NO:7); the mouse AdipoR1 protein (mAdipoR1; Genbank Accession No: gi|BCO14875; SEQ ID NO:8); the human AdipoR2 protein (hAdipoR2; Genbank Accession No: gi|NM_024551; SEQ ID NO:9); and the mouse AdipoR2 protein (mAdipoR2; Genbank Accession No: gi|XM_132831; SEQ ID NO:10). The alignment was performed using the CLUSTALW algorithm using default parameters as described herein (Vector NTI suite of programs). The darkly shaded amino acids represent regions of matching identity. The lightly shaded amino acids represent regions of matching similarity. Dots ("•") between residues indicate gapped regions of non-identity for the aligned polypeptides. The conserved cysteines between human AdipoR2v1, mouse AdipoR2v1, human AdipoR3, human AdipoR2v2, human AdipoR3v, rat AdipoR1, and/or rat AdipoR2 to the other adiponectin receptors are noted.

FIG. 5 shows the regions of identity and similarity between the encoded human AdipoR3 polypeptide (SEQ ID NO:6) to the human AdipoR1 protein (hAdipoR1; GenbankAccession No: gi|NM_015999; SEQ ID NO:7); and the human AdipoR2 protein (hAdipoR2; Genbank Accession No: gi|NM_024551; SEQ ID NO:9). The alignment was performed using the CLUSTALW algorithm using default parameters as described herein (Vector NTI suite of programs). The darkly shaded amino acids represent regions of matching identity. The lightly shaded amino acids represent regions of matching similarity. Dots ("•") between residues indicate gapped regions of non-identity for the aligned polypeptides. The conserved cysteines between human AdipoR3 to the other adiponectin receptors are noted.

Figure 8:
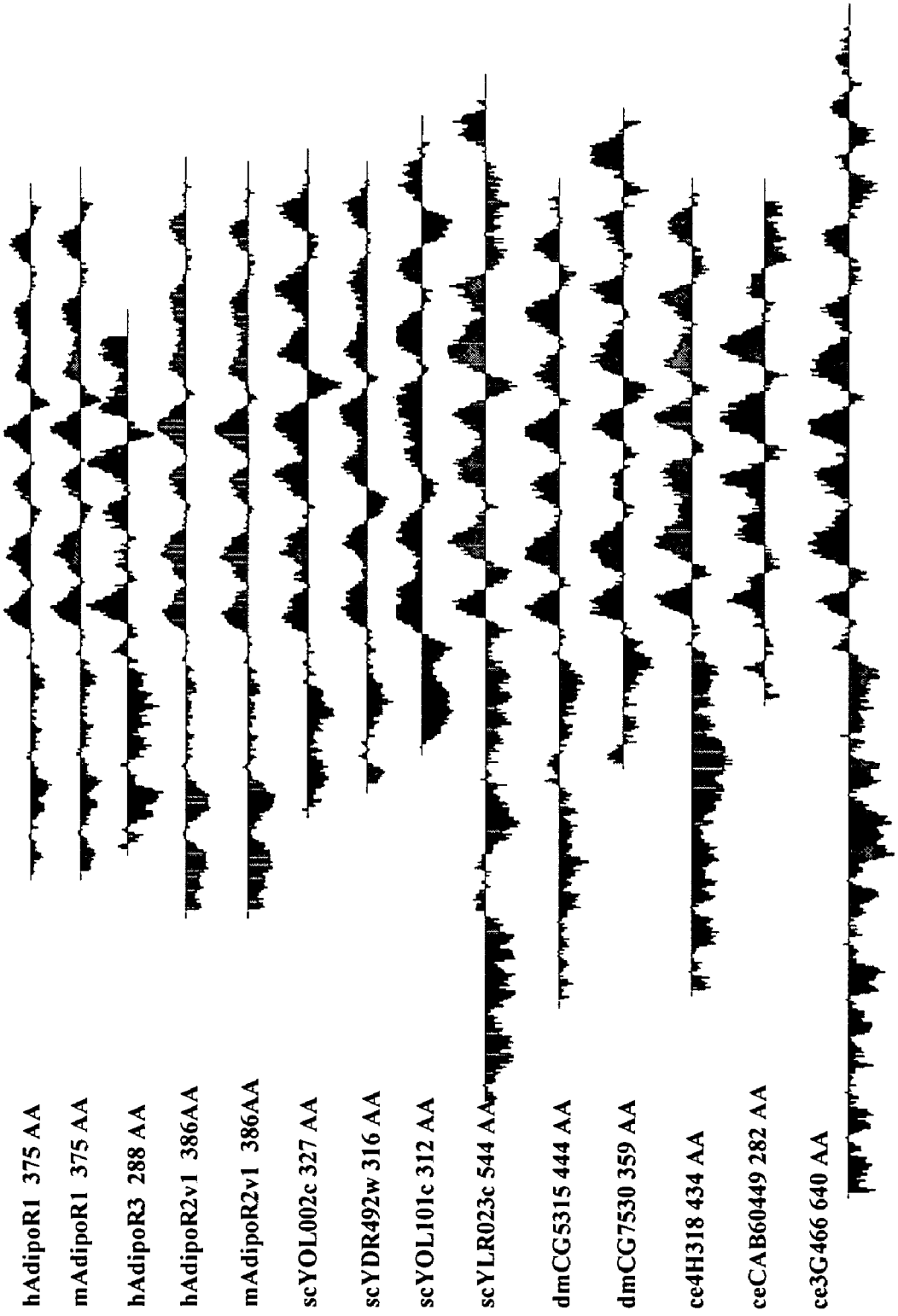

FIG. 8 shows an alignment of various hydropathy plots between the human AdipoR2.v1 polypeptide (SEQ ID NO:2), the mouse AdipoR2.v1 polypeptide (SEQ ID NO:4), and the human AdipoR3 polypeptide (SEQ ID NO:6) of the present invention to various other hydropathy plots of Adipo receptors known in the art. As shown, the additional amino acids that extend the human AdipoR2.v1 and mouse AdipoR2.v1 N-terminal sequences of the present invention over the known human and mouse AdidoR2 sequences reported in the art, share very similar hydropathy to other Adipo receptors. The latter is consistent with the human AdipoR2.v1 and mouse AdipoR2.v1 polypeptide sequences representing the physiologically relevant forms of the AdipoR2 receptor in both humans and mice.

Figure 9:
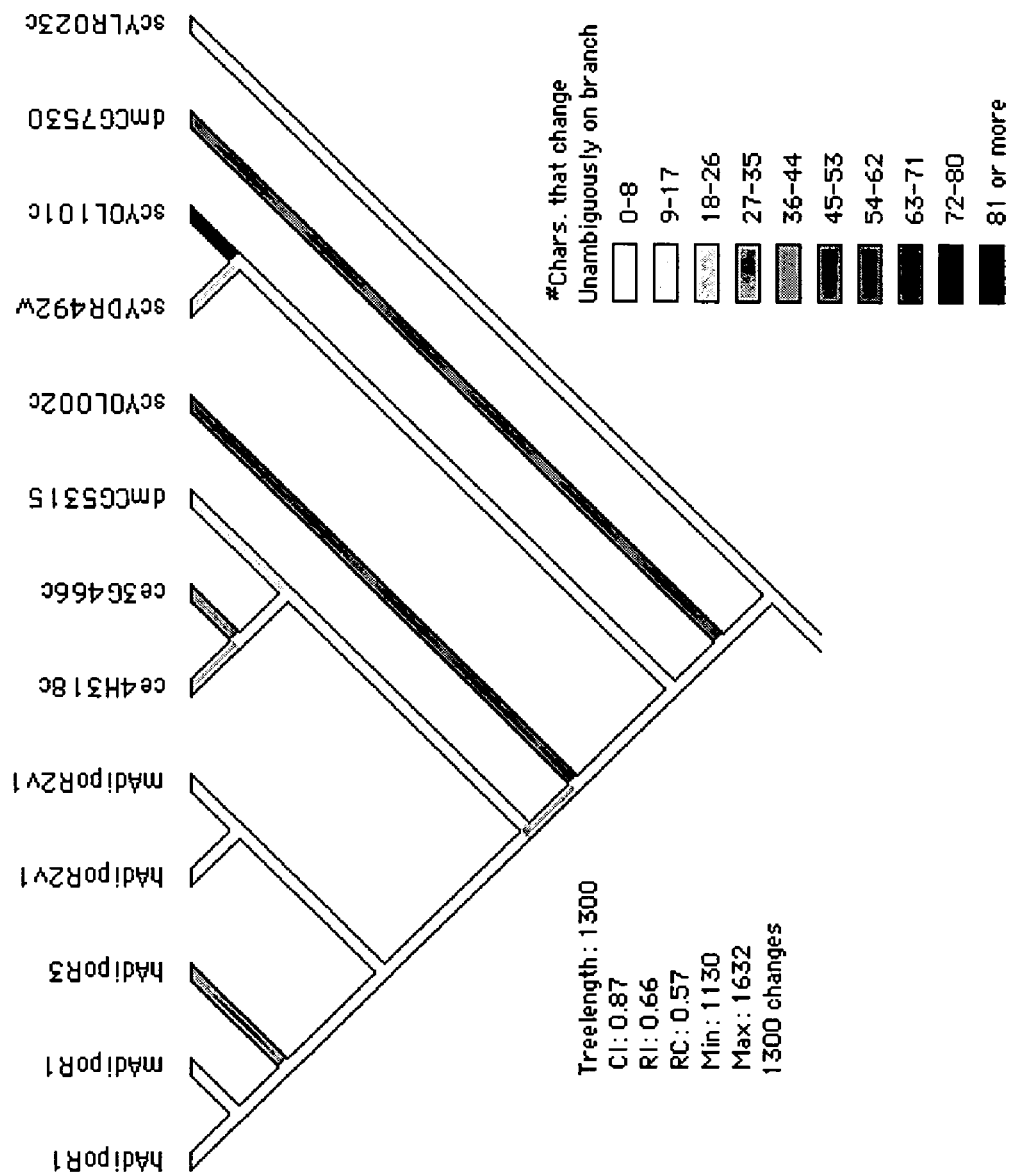

FIG. 9 illustrates a phylogenetic tree comparing the overall similarity of the human AdipoR2.v1 polypeptide (SEQ ID NO:2), the mouse AdipoR2.v1 polypeptide (SEQ ID NO:4), and the human AdipoR3 polypeptide (SEQ ID NO:6) of the present invention to the polypeptide sequences of various other Adipo receptors known in the art.

FIGS. 10A-D illustrates the location of each of the exons of the human AdipoR2v1 polynucleotide of the present invention on the corresponding region of the human genome (NCBI human genome version 30). The top sequence represents portions of the human AdipoR2v1 polynucleotide sequence (SEQ ID NO:1), while the bottom sequence represents a portion of the human genome from human chromosome 12p13.33 region (SEQ ID NO:100) that corresponds to the region in which the human AdipoR2v1 gene resides. Exon locations are denoted by ">>> ... >>>", and the start and stop codons are denoted by bold underlining. The positions of each exon, within both SEQ ID NO:1 as well as within Chromosome 12p13.33, are specified at the top of FIG. 10A. The Figure proves that the reported sequence of the human AdipoR2 sequence is not correct and that the sequence of the human AdipoR2v1 polynucleotide of the present invention is the correct and physiologically relevant sequence of this receptor.

FIG. 11 shows a table illustrating the percent identity and percent similarity between the AdipoR2v1, mouse AdipoR2v1, human AdipoR3, human AdipoR2v2, human AdipoR3v1, rat AdipoR1, and/or rat AdipoR2 of the present invention with other adiponectin receptors. The percent identity and percent similarity values were determined using the CLUSTALW algorithm using default parameters as described herein (Vector NTI suite of programs).

FIGS. 12A-B shows the polynucleotide sequence (SEQ ID NO:101) and deduced amino acid sequence (SEQ ID NO:102) of the novel human adiponectin receptor, human AdipoR3v1, of the present invention. The standard one-letter abbreviation for amino acids is used to illustrate the deduced amino acid sequence. The polynucleotide sequence contains a sequence of 1146 nucleotides (SEQ ID NO:101), encoding a polypeptide of 381 amino acids (SEQ ID NO:102). It is anticipated that the human AdipoR3v1 polypeptide is a functional receptor for adiponectin as described more particularly elsewhere herein.

FIGS. 13A-B show the polynucleotide sequence (SEQ ID NO:103) and deduced amino acid sequence (SEQ ID NO:104) of the novel human adiponectin receptor, human AdipoR2v2, of the present invention. The standard one-letter abbreviation for amino acids is used to illustrate the deduced amino acid sequence. The polynucleotide sequence contains a sequence of 1738 nucleotides (SEQ ID NO:103), encoding a polypeptide of 421 amino acids (SEQ ID NO:104). An analysis of the human AdipoR2v2 polypeptide determined that it comprised the following features: eight transmembrane domains (TM1 to TM8) located from about amino acid 150 to about amino acid 174 (TM1; SEQ ID NO:121); from about amino acid 176 to about amino acid 208 (TM2; SEQ ID NO:122); from about amino acid 217 to about amino acid 237 (TM3; SEQ ID NO:123); from about amino acid 243 to about amino acid 268 (TM4; SEQ ID NO:124); from about amino acid 282 to about amino acid 304 (TM5; SEQ ID NO:125); from about amino acid 308 to about amino acid 336 (TM6; SEQ ID NO:126); from about amino acid 337 to about amino acid 365 (TM7; SEQ ID NO:127); and/or from about amino acid 382 to about amino acid 400 (TM8; SEQ ID NO:128) of SEQ ID NO:104. It is anticipated that the human AdipoR2v2 polypeptide is a functional receptor for adiponectin as described more particularly elsewhere herein.

FIG. 14 shows the regions of identity and similarity between the encoded human AdipoR3v1 polypeptide (SEQ ID NO:102) to human AdipoR1 protein (hAdipoR1; GenbankAccession No: gi|NM_015999; SEQ ID NO:7); and the human AdipoR3 protein (AdipoR3; SEQ ID NO:9). The alignment was performed using the CLUSTALW algorithm using default parameters as described herein (Vector NTI suite of programs). The darkly shaded amino acids represent regions of matching identity. The lightly shaded amino acids represent regions of matching similarity. Dots ("•") between residues indicate gapped regions of non-identity for the aligned polypeptides. The conserved cysteines between human AdipoR3v1 with other adiponectin receptors are noted.

FIG. 15 shows the regions of identity and similarity between the encoded human AdipoR2v2 polypeptide (SEQ ID NO:104) to the human AdipoR1 protein (hAdipoR1; GenbankAccession No: gi|NM_015999; SEQ ID NO:7); the human AdipoR2v1 protein of the present invention (hAdipoR2v1; SEQ ID NO:2); and the mouse AdipoR2v1 protein of the present invention (mAdipoR2v1; SEQ ID NO:4). The alignment was performed using the CLUSTALW algorithm using default parameters as described herein (Vector NTI suite of programs). The darkly shaded amino acids represent regions of matching identity. The lightly shaded amino acids represent regions of matching similarity. Dots ("•") between residues indicate gapped regions of non-identity for the aligned polypeptides. The conserved cysteines between human AdipoR2v2 with other adiponectin receptors are noted.

Figure 16:
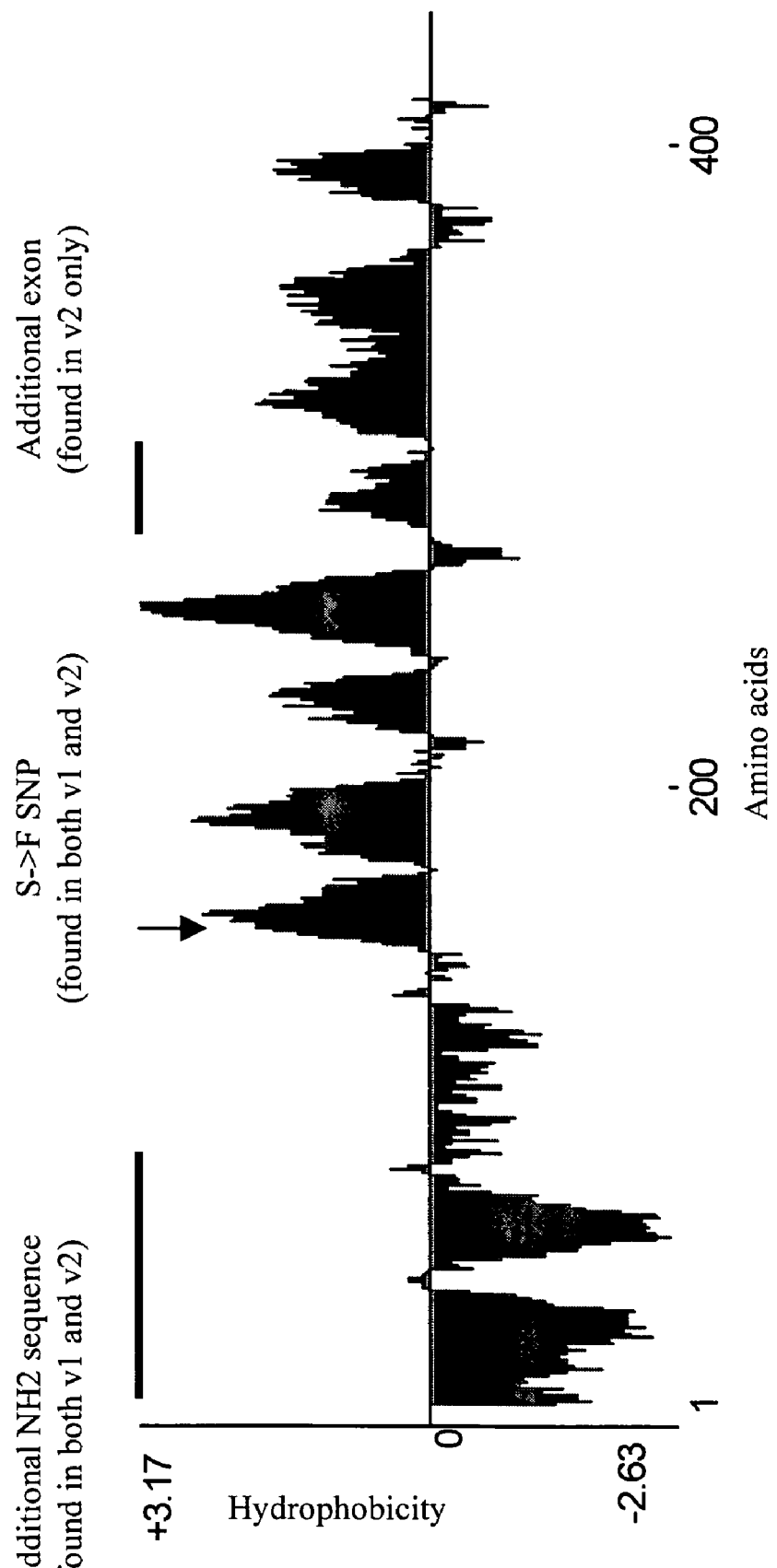

FIG. 16 shows a hydrophobicity plot of the human AdipoR2v2 polypeptide according to the BioPlot Hydrophobicity algorithm of Vector NTI (version 5.5). The seven hydrophilic peaks are consistent with the human AdipoR2v2 polypeptide being an adiponectin receptor.

FIGS. 17A-B illustrates the location of each of the exons and introns of the human AdipoR2v2 polynucleotide of the present invention on the corresponding region of the human genome (NCBI human genome version 30). The top sequence represents portions of the human AdipoR2v2 polypeptide sequence (SEQ ID NO:104), while the bottom sequence represents a portion of the human genome from human chromosome 12p13.33 region in all three open reading frames that corresponds to the region in which the human AdipoR2v2 gene resides. Intron locations are denoted by "< . . . >" with the locations noted within each bracket. The Figure illustrates that the AdipoR2v2 splice variant is supported by the human genomic sequence.

FIG. 18 shows a table illustrating the percent identity and percent similarity between the human AdipoR2v2 and AdipoR3v1 polypeptides of the present invention with other adiponectin receptors. The percent identity and percent similarity values were determined using the CLUSTALW algorithm using default parameters as described herein (Vector NTI suite of programs).

FIGS. 19A-B show a schematic representation of the strategy that could be used to clone the polynucleotide encoding the human AdipoR3v1 polypeptide of the present invention. The top strand ("Query") of the alignment represents the encoding polynucleotide of the human AdipoR3v1 polypeptide of the present invention (SEQ ID NO:101), while the bottom strand ("Sbjct") of the alignment represents the genomic sequence of relevant portions of the region of the genome containing the human AdipoR3v1 polypeptide coding region (Genbank Accession No: gi|AL049839.3.1.214527; SEQ ID NO:153). The identity of Primer Sets A, B, C, D, and E are labeled. The sequence of each primer is highlighted with the forward primer of each set being represented in light shading, and the reverse primer of each set being represented by dark shading. The SEQ ID NO for each sequence is provided either above or below each highlighted sequence. Detailed descriptions of the cloning method are provided in Example 4 herein.

FIGS. 20A-B show the polynucleotide sequence (SEQ ID NO:164) and deduced amino acid sequence (SEQ ID NO:165) of the novel rat adiponectin receptor, rat AdipoR1, of the present invention. The standard one-letter abbreviation for amino acids is used to illustrate the deduced amino acid sequence. The polynucleotide sequence contains a sequence of 1442 nucleotides (SEQ ID NO:164), encoding a polypeptide of 375 amino acids (SEQ ID NO:165). An analysis of the rat AdipoR1 polypeptide determined that it comprised the following features: seven transmembrane domains (TM1 to TM7) located from about amino acid 137 to about amino acid 162 (TM1; SEQ ID NO:168); from about amino acid 167 to about amino acid 192 (TM2; SEQ ID NO:169); from about amino acid 208 to about amino acid 227 (TM3; SEQ ID NO:170); from about amino acid 234 to about amino acid 255 (TM4; SEQ ID NO:171); from about amino acid 270 to about amino acid 292 (TM5; SEQ ID NO:172); from about amino acid 298 to about amino acid 320 (TM6; SEQ ID NO:173); and/or from about amino acid 337 to about amino acid 354 (TM7; SEQ ID NO:174) of SEQ ID NO:165. It is anticipated that the rat AdipoR1 polypeptide is a functional receptor for adiponectin as described more particularly elsewhere herein.

FIGS. 21A-B show the polynucleotide sequence (SEQ ID NO:166) and deduced amino acid sequence (SEQ ID NO:167) of the novel rat adiponectin receptor, rat AdipoR2, of the present invention. The standard one-letter abbreviation for amino acids is used to illustrate the deduced amino acid sequence. The polynucleotide sequence contains a sequence of 1369 nucleotides (SEQ ID NO:166), encoding a polypeptide of 386 amino acids (SEQ ID NO:167). An analysis of the rat AdipoR2 polypeptide determined that it comprised the following features: seven transmembrane domains (TM1 to TM7) located from about amino acid 151 to about amino acid 172 (TM1; SEQ ID NO:175); from about amino acid 177 to about amino acid 201 (TM2; SEQ ID NO:176); from about amino acid 217 to about amino acid 235 (TM3; SEQ ID NO:177); from about amino acid 243 to about amino acid 266 (TM4; SEQ ID NO:178); from about amino acid 279 to about amino acid 303 (TM5; SEQ ID NO:179); from about amino acid 307 to about amino acid 327 (TM6; SEQ ID NO:180); and/or from about amino acid 348 to about amino acid 364 (TM7; SEQ ID NO:181) of SEQ ID NO:167. It is anticipated that the rat AdipoR2 polypeptide is a functional receptor for adiponectin as described more particularly elsewhere herein.

FIG. 22 shows the regions of identity and similarity between the encoded rat AdipoR1 polypeptide (SEQ ID NO:165) to the human AdipoR1 protein (hAdipoR1; GenbankAccession No: gi|NM_015999; SEQ ID NO:7); and the mouse AdipoR1 protein (mAdipoR1; Genbank Accession No: gi|BCO14875; SEQ ID NO:8). The alignment was performed using the CLUSTALW algorithm using default parameters as described herein (Vector NTI suite of programs). The darkly shaded amino acids represent regions of matching identity. The lightly shaded amino acids represent regions of matching similarity. Dots ("•") between residues indicate gapped regions of non-identity for the aligned polypeptides. The conserved cysteines between the rat AdipoR1 polypeptide with other the human and mouse AdipoR1 receptors are noted.

Figure 23:
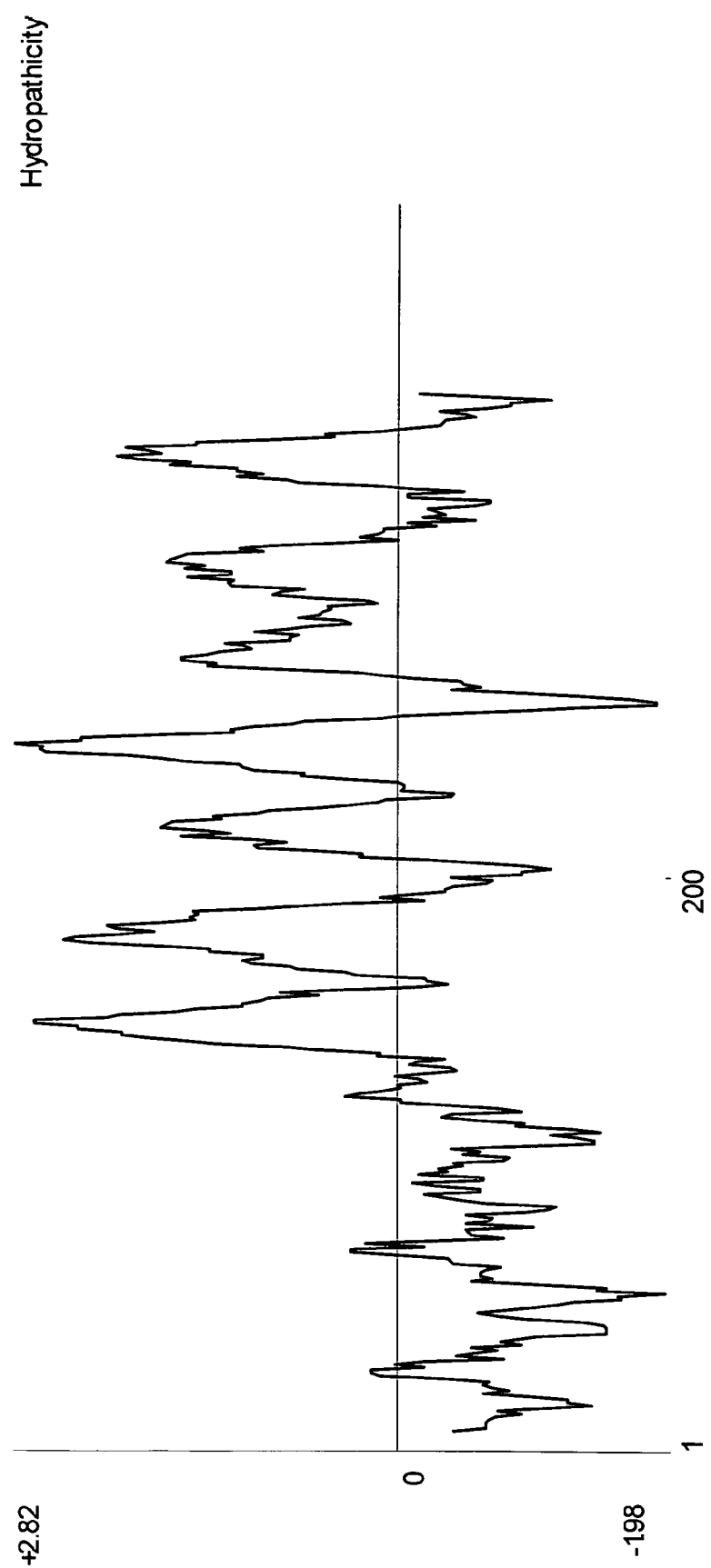

FIG. 23 shows a hydrophobicity plot of the rat AdipoR1 polypeptide of the present invention (SEQ ID NO:165) according to the BioPlot Hydrophobicity algorithm of Vector NTI (version 5.5). The seven hydrophilic peaks are consistent with the rat AdipoR1 polypeptide being an adiponectin receptor.

FIG. 24 shows the regions of identity and similarity between the encoded rat AdipoR2 polypeptide (SEQ ID NO:167) to the human AdipoR2v2 polypeptide of the present invention (SEQ ID NO:104); the human AdipoR2v1 protein of the present invention (hAdipoR2v1; SEQ ID NO:2); and the mouse AdipoR2v1 protein of the present invention (mAdipoR2v1; SEQ ID NO:4). The alignment was performed using the CLUSTALW algorithm using default parameters as described herein (Vector NTI suite of programs). The darkly shaded amino acids represent regions of matching identity. The lightly shaded amino acids represent regions of matching similarity. Dots ("•") between residues indicate gapped regions of non-identity for the aligned polypeptides. The conserved cysteines between the rat AdipoR2 polypeptide with other the human and mouse AdipoR2v1 and human AdipoR2v2 receptors are noted.

Figure 25:
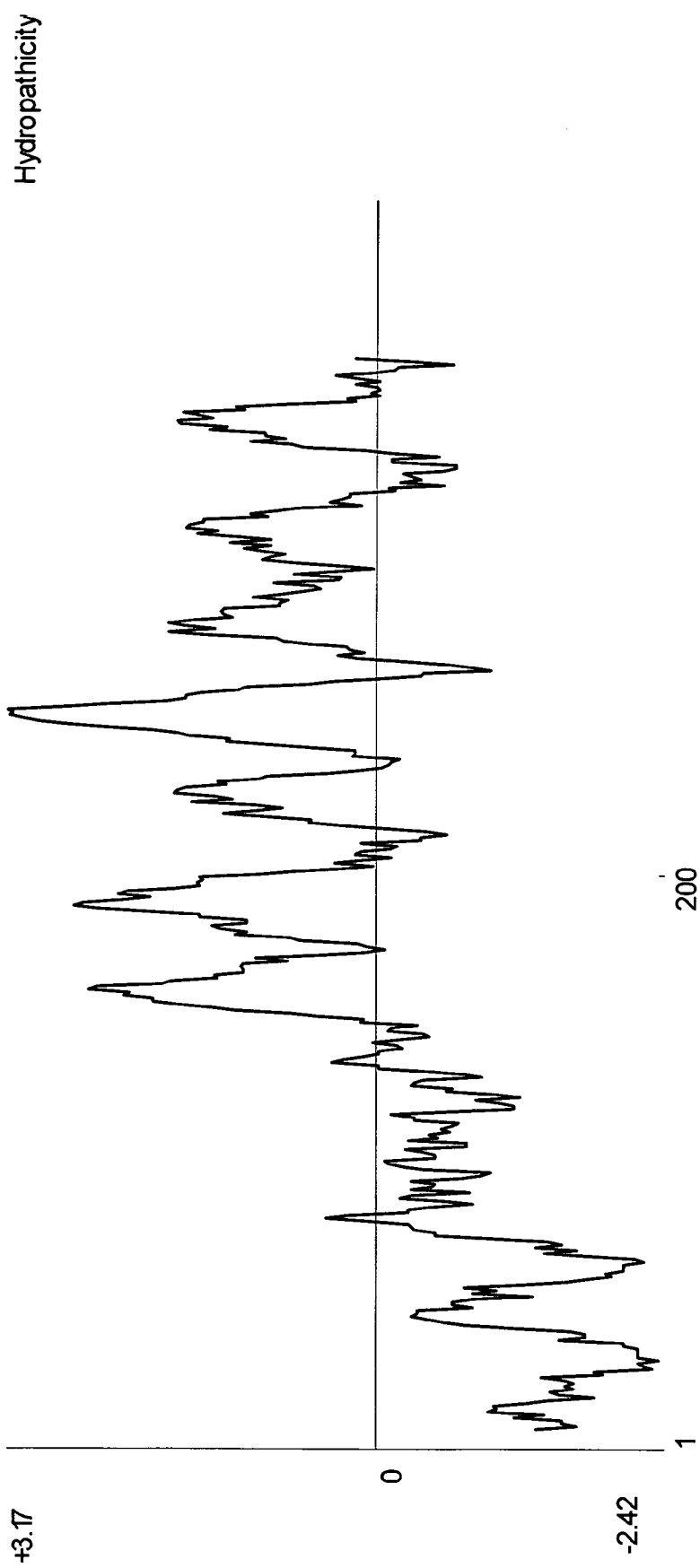

FIG. 25 shows a hydrophobicity plot of the rat AdipoR2 polypeptide of the present invention (SEQ ID NO:167) according to the BioPlot Hydrophobicity algorithm of Vector NTI (version 5.5). The seven hydrophilic peaks are consistent with the rat AdipoR2 polypeptide being an adiponectin receptor.

FIG. 26 shows a table illustrating the percent identity and percent similarity between the rat AdipoR1 and rat AdipoR2 polypeptides of the present invention with other adiponectin receptors. The percent identity and percent similarity values were determined using the CLUSTALW algorithm using default parameters as described herein (Vector NTI suite of programs).

Figure 27:
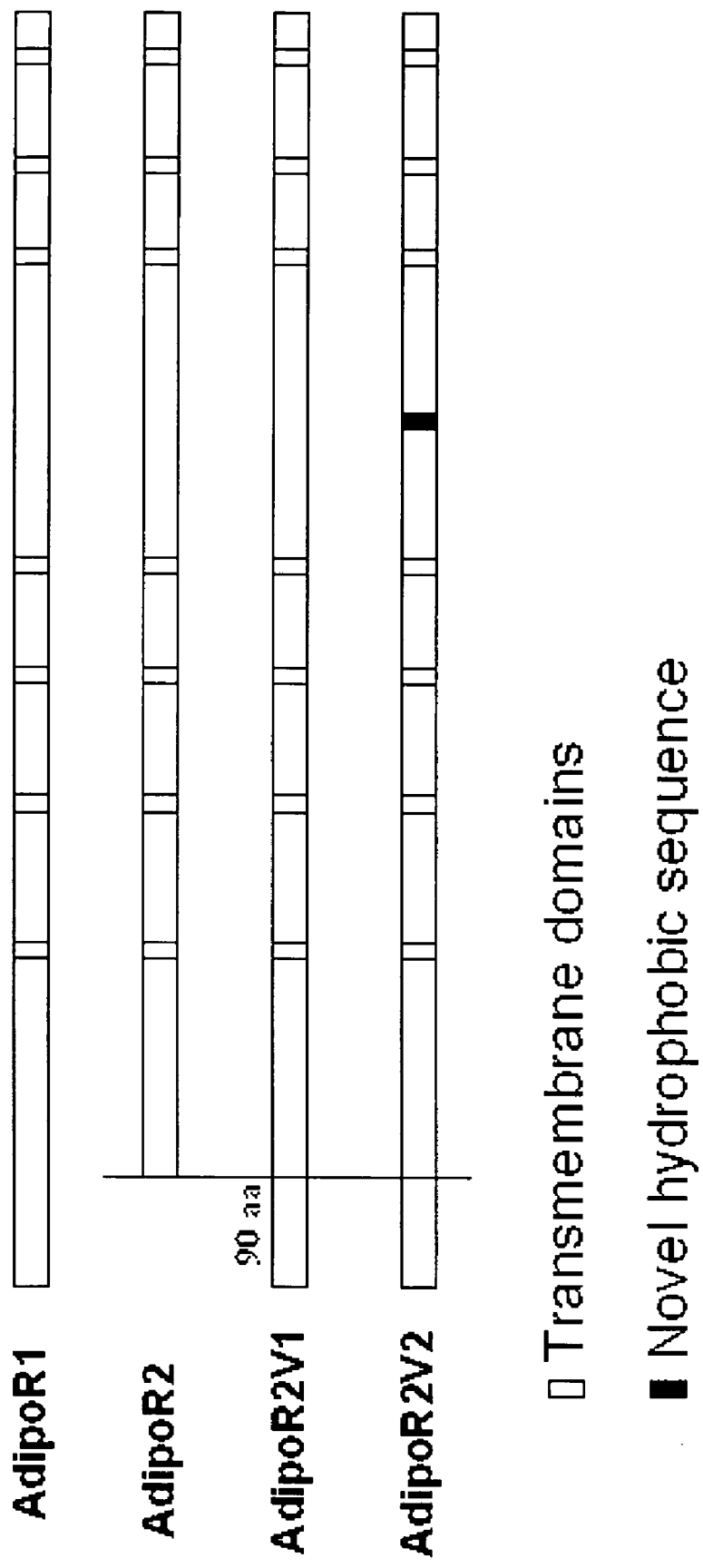

FIG. 27 shows a schematic illustrating the structure of the novel human AdipoR2v1 and human AdipoR2v2 receptor polypeptides to the structure of the AdipoR1 and AdipoR2 published by Yamauchi et al (Nature, 423:762-769 (2003)). As shown, the novel human AdipoR2v2 receptor of the present invention contains a unique hydrophobic domain in the region intervening the two transmembrane domain regions of the polypeptide.

Figure 28A:
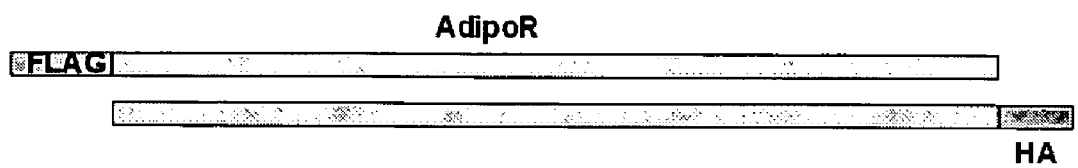

FIG. 28A shows a schematic of the epitope tagged AdipoR receptors. As shown, the AdipoR receptors were modified to include an N-terminal FLAG tag, in addition to a C-terminal HA tag. The human AdipoR1 and human AdipoR2 receptors, in addition to the novel human AdipoR2v1 and human AdipoR2v2 receptors of the present invention were modified according to this schematic. Modifications were performed as described in Example 6 herein.

Figure 28B:
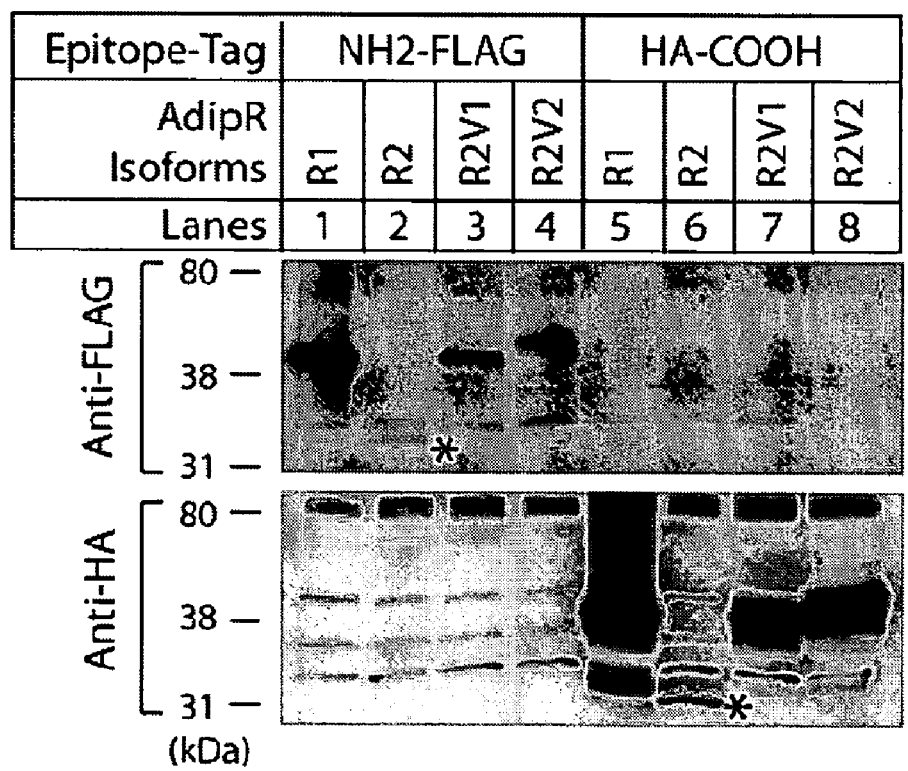

FIG. 28B shows the results of western blot experiments for the FLAG and HA epitope tagged AdipoR receptors described in FIG. 28A and elsewhere herein. As shown, anti-FLAG and anti-HA antibodies detected strong expression of the FLAG and HA epitope tagged human AdipoR1 receptor ("R1"), the FLAG and HA epitope tagged novel human AdipoR2v1 receptor ("R2V1"), and the FLAG and HA epitope tagged human AdipoR2v2 receptor ("R2V2"). However, the expressed level of FLAG and HA epitope tagged human AdipoR2 ("R2") was significantly lower than that observed for the other receptors. This result suggests that the AdipoR2 form of this receptor is less stable than the other Adipo receptors, and that the novel AdipoR2v1 and AdipoR2v2 forms are likely more abundant and physiologically relevant than the AdipoR2 form identified by Yamuchi et al. The intense band in each Adipo lane represents the over-expressed FLAG and HA epitope tagged Adipo receptors. The band marked with an asterisk ("*") represents the over-expressed FLAG and HA epitope tagged human AdipoR2 receptor. Western blot experiments were performed as described in Example 6 herein.

DETAILED DESCRIPTION OF THE INVENTION

The present invention may be understood more readily by reference to the following detailed description of the preferred embodiments of the invention and the Examples included herein.

The invention provides novel human and mouse sequences that encode what the inventors believe are the physiologically relevant forms of the AdipoR2 adiponectin receptors of human, mice, and rat. The invention also provides novel human sequences that encode a previously unidentified adiponectin receptor referred to herein as the human AdipoR3 receptor, in addition to a novel variant, AdipoR3v1. Such receptors have been implicated in a number of diseases and/or disorders, which are known in the art or otherwise described herein.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In specific embodiments, the polynucleotides of the invention are at least 15, at least 30, at least 50, at least 100, at least 125, at least 150, at least 175, at least 200, at least 225, at least 250, at least 275, at least 300, at least 325, at least 350, at least 375, at least 400, at least 425, at least 450, at least 475, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:1, 3, 5, 101, 103, 164, or 166, or the cDNA contained within the clone deposited with the ATCC. For example, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:1, 3, 5, 101, 103, 164, or 166 was often generated by overlapping sequences contained in one or more clones (contig analysis). A representative clone containing all of the sequence for SEQ ID NO:1, 3, 5, 101, 103, 164, or 166 was deposited with the American Type Culture Collection ("ATCC"). As shown in Table I, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure. The deposited clone is inserted in the pSport1 (Life Technologies) using the NotI and SalI restriction endonuclease sites as described herein.

Unless otherwise indicated, all nucleotide sequences determined by sequencing a DNA molecule herein were determined using an automated DNA sequencer (such as the Model 373, preferably a Model 3700, from Applied Biosystems, Inc.), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A-B (SEQ ID NO:1, 3, 5, 101, 103, 164, or 166), a nucleic acid molecule of the present invention encoding the human AdipoR2v1, mouse AdipoR2v1, human AdipoR3, human AdipoR2v2, human AdipoR3v, rat AdipoR1, and/or rat AdipoR2 polypeptide may be obtained using standard cloning and screening procedures, such as those for cloning cDNAs using mRNA as starting material.

A "polynucleotide" of the present invention also includes those polynucleotides capable of hybridizing, under stringent hybridization conditions, to sequences contained in SEQ ID NO:1, 3, 5, 101, 103, 164, or 166, the complement thereof, or the cDNA within the clone deposited with the ATCC. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20× SSPE=3M NaCl; 0.2M NaH2PO4; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide" since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, 2nd Ed., T. E. Creighton, W.H. Freeman and Company, New York (1993); Posttranslational Covalent Modification of Proteins, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

"SEQ ID NO:X" refers to a polynucleotide sequence while "SEQ ID NO:Y" refers to a polypeptide sequence, both sequences are identified by an integer specified in Table I.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

The term "organism" as referred to herein is meant to encompass any organism referenced herein, though preferably to eukaryotic organisms, more preferably to mammals, and most preferably to humans.

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young (Mol. Endocrinol., 9(10):1321-9, (1995); and Ann. N.Y. Acad. Sci., 7; 766:279-81, (1995)).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify gene expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further preferred embodiments, methods are provided for evolving the polynucleotides and polypeptides of the present invention using molecular evolution techniques in an effort to create and identify novel variants with desired structural, functional, and/or physical characteristics.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

Polynucleotides and Polypeptides of the Invention

Features of the Polypeptide Encoded by
Polynucleotide No:1

The polypeptide of this polynucleotide provided as SEQ ID NO:2 (FIGS. 1A-B), encoded by the polynucleotide sequence according to SEQ ID NO:1 (FIGS. 1A-B), and/or encoded by the polynucleotide contained within the deposited clone, human AdipoR2v1 (also referred to as hAdipoR2v1), is believed to represent the physiologically relevant form of the human AdipoR2 polypeptide.

An alignment of the human AdipoR2v1 polypeptide of the present invention with the human AdipoR1 protein (hAdipoR1; GenbankAccession No: gi|NM_015999; SEQ ID NO:7); the mouse AdipoR1 protein (mAdipoR1; Genbank Accession No: gi|BCO14875; SEQ ID NO:8); the human AdipoR2 protein (hAdipoR2; Genbank Accession No: gi|NM_024551; SEQ ID NO:9); and the mouse AdipoR2 protein (mAdipoR2; Genbank Accession No: gi|XM_132831; SEQ ID NO:10) is provided in FIGS. 4A-B.

The human AdipoR2v1 polypeptide (SEQ ID NO:2) of the present invention differs from the sequence of the human AdipoR2 receptor reported by Yamauchi et al (Nature, 423: 762-769 (2003)) by having an additional 88 amino acids in the N-terminus of the polypeptide. An alignment of the hydropathy plots of AdipoR1 and AdipoR2 polypeptide sequences from other species with the human AdipoR2v1 polypeptide (SEQ ID NO:2) of the present invention (see FIG. 8) provides convincing evidence that the sequence of the human AdipoR2 receptor reported by Yamauchi et al is truncated and that the human AdipoR2v1 polypeptide of the present invention is the true, physiologically relevant full-length form of this receptor. Additionally, the polynucleotide sequence of the human AdipoR2v1 polypeptide of the present invention is supported by the human genome (NCBI human genome version 30) as shown in FIGS. 10A-D.

An additional schematic representation of the human AdipoR2v1 polypeptide sequence compared to the human AdipoR1, human AdipoR2, and human AdipoR2v2 polypeptides is provided in FIG. 27.

As noted by Yamauchi et al, the human AdipoR1 and AdipoR2 polypeptide sequences are "highly structurally related", and share 80% identity overall between the sequences. Both AdipoR1 and AdipoR2 serve as receptors for both globular and full-length adiponectin. Importantly, Yamauchi et al point out that AdipoR1 represents a high affinity receptor for globular adiponectin, while AdipoR2 only represents an intermediate affinity receptor for globular adiponectin.

As shown in the hydropathy plot alignments of FIG. 4, the N-terminus of the AdipoR2 receptor is significantly shorter than the N-terminus of the AdipoR1 receptor. It is possible that the functional dimorphism between the AdipoR1 and AdipoR2 receptors in terms of their binding affinity for adiponectin is due to the truncation of the AdipoR2 receptor sequence as originally reported by Yamauchi et al.

The inventors believe that the human AdipoR2v1 polypeptide of the present invention is the physiologically relevant form of the AdipoR2 sequence. Likewise, the AdipoR2v1 polypeptide is expected to share the same biological activity as the reported AdipoR2 sequence. Preferably, the AdipoR2v1 polypeptide is expected to have increased biological activity relative to the reported AdipoR2 sequence. Such increased biological function may be in the form of increased binding affinity for adiponectin, increased binding affinity for globular adiponectin, increased binding affinity for full-length adiponectin, increased association rate constant for adiponectin, increased association rate constant for globular adiponectin, increased association rate constant for full-length adiponectin, decreased dissociation rate constant for adiponectin, decreased dissociation rate constant for globular adiponectin, decreased dissociation rate constant for full-length adiponectin, increased ability to regulate AMPK phosphorylation, increased ability to regulate ACC phosphorylation, increased ability to regulate MAPK phosphorylation, increased ability to regulate p38 MAPK phosphorylation, among others.

Alternatively, the ability of the AdipoR2v1 sequence of the present invention to bind to adiponectin may be less than the reported AdipoR2 sequence. Thus, the AdipoR2v1 polypeptide may have increased biological activity relative to the reported AdipoR2 sequence. Such increased biological function may be in the form of decreased binding affinity for adiponectin, decreased binding affinity for globular adiponectin, decreased binding affinity for full-length adiponectin, decreased association rate constant for adiponectin, decreased association rate constant for globular adiponectin, decreased association rate constant for full-length adiponectin, increased dissociation rate constant for adiponectin, increased dissociation rate constant for globular adiponectin, increased dissociation rate constant for full-length adiponectin, decreased ability to regulate AMPK phosphorylation, decreased ability to regulate ACC phosphorylation, decreased ability to regulate MAPK phosphorylation, decreased ability to regulate p38 MAPK phosphorylation, among others.

The determined nucleotide sequence of the human AdipoR2v1 cDNA in FIGS. 1A-B (SEQ ID NO:1) contains an open reading frame encoding a protein of about 386 amino acid residues, with a deduced molecular weight of about 43.8 kDa. The amino acid sequence of the predicted human AdipoR2v1 polypeptide is shown in FIGS. 1A-B (SEQ ID NO:2). By virtue of the human AdipoR2v1 protein representing an N-terminally extended form of the human AdipoR2 polypeptide, the human AdipoR2v1 polypeptide shown in FIGS. 1A-B was determined to share significant identity and similarity to other adiponectin receptors, as shown in FIGS. 4A-B. The percent identity and similarity values between the human AdipoR2v1 polypeptide to these known adiponectin receptors is provided in FIG. 11.

Consistent with the inventors description of the human AdipoR2v1 polypeptide representing the physiologically relevant form of the AdipoR2 polypeptide, the inventors determined that overexpressed forms of the human AdipoR2 protein are inherently unstable when expressed in COS-7 mammalian cell lines compared to the human AdipoR2v1 and AdipoR2v2 polypeptides, as shown in FIG. 28B and described in Example 6. Specifically, pcDNA3 expression constructs were created for human AdipoR1, human AdipoR2, human AdipoR2v1, and human AdipoR2v2. Two constructs were created for each Adipo receptor with one construct containing the encoding region of the FLAG tag epitope at the N-terminus of each receptor, and the other construct containing the coding region of the influenza hemagluttin (HA) epitope tag at the C-terminus. The plasmids were transfected into COS-7 cell lines, overexpressed, and the extracts run out on a SDS-PAGE gel. Each gel was transferred to nylon membrane and probes with anti-FLAG and/or anti-HA antibody. As shown in FIG. 28B, regardless of whether the epitope was tagged at either the N- or C-terminus, the level of human AdipoR2 receptor detected was consistently at very low levels. By comparison, the level of human AdipoR1, human AdipoR2v1, and human AdipoR2v2 polypeptides detected were very high. Accordingly, it is believed that the human AdipoR2 polypeptide is significantly less stable than the human AdipoR2v1 and human AdipoR2v2 receptors, particularly considering the only difference between each receptor construct is the sequence of each receptor itself since the promoter and context of expression for each AdipoR2 isoform were the same. These results support the notion that the human AdipoR2 polypeptide described by Yamauchi is an artifact and that the human AdipoR2v1 and human AdipoR2v2 are the physiologically relevant forms of this receptor. This analysis is also consistent with the human AdipoR1 receptor described by Yamauchi as being physiologically relevant.

The human AdipoR2v1 polypeptide was predicted to comprise seven transmembrane domains (TM1 to TM7) located from about amino acid 151 to about amino acid 172 (TM1; SEQ ID NO:67); from about amino acid 177 to about amino acid 201 (TM2; SEQ ID NO:68); from about amino acid 221 to about amino acid 235 (TM3; SEQ ID NO:69); from about amino acid 247 to about amino acid 266 (TM4; SEQ ID NO:70); from about amino acid 279 to about amino acid 299 (TM5; SEQ ID NO:71); from about amino acid 307 to about amino acid 327 (TM6; SEQ ID NO:72); and/or from about amino acid 347 to about amino acid 364 (TM7; SEQ ID NO:73) of SEQ ID NO:2 (FIGS. 1A-B). In this context, the term "about" may be construed to mean 1, 2, 3, 4, 5, 6, 7, 8, 9, or 10 amino acids beyond the N-Terminus and/or C-terminus of the above referenced transmembrane domain polypeptides.

In preferred embodiments, the following transmembrane domain polypeptides are encompassed by the present invention: THLLGCVFFLCLGIFYMFRPNI (SEQ ID NO:67), PLQEKVVFGLFFLGAILCLSFSWLF (SEQ ID NO:68), SGIALLIMGSFVPWL (SEQ ID NO:69), FIYLIVICVLGIAAIIVSQW (SEQ ID NO:70), AGVFLGLGLSGIIPTLHYVIS (SEQ ID NO:71), TIGQIGWLMLMASLYITGAAL (SEQ ID NO:72), and/or SHQLFHIFVVAGAFVHFH (SEQ ID NO:73). Polynucleotides encoding these polypeptides are also provided. The present invention also encompasses the use of these human AdipoR2v1 transmembrane domain polypeptides as immunogenic and/or antigenic epitopes as described elsewhere herein.

The present invention also encompasses the polypeptide sequences that intervene between each of the predicted human AdipoR2v1 transmembrane domains. Since these regions are solvent accessible either extracellularly or intracellularly, they are particularly useful for designing antibodies specific to each region. Such antibodies may be useful as antagonists or agonists of the human AdipoR2v1 full-length polypeptide and may modulate its activity.

In preferred embodiments, the following inter-transmembrane domain polypeptides are encompassed by the present invention: HTVVYCHSEGVSRLFSKLDY (SEQ ID NO:87), YYSFYCNPQPC (SEQ ID NO:88), DMFATPQYRGVR (SEQ ID NO:89), EGFLKAA (SEQ ID NO:90), and/or YAARIPERFFPGKCDIWFH (SEQ ID NO:91). Polynucleotides encoding these polypeptides are also provided. The present invention also encompasses the use of these human AdipoR2v1 intratransmembrane domain polypeptides as immunogenic and/or antigenic epitopes as described elsewhere herein.

In preferred embodiments, the present invention encompasses the use of N-terminal deletions, C-terminal deletions, or any combination of N-terminal and C-terminal deletions of any one or more of the human AdipoR2v1 TM1 thru TM7 transmembrane domain polypeptides as antigenic and/or immunogenic epitopes.

In preferred embodiments, the present invention also encompasses the use of N-terminal deletions, C-terminal deletions, or any combination of N-terminal and C-terminal deletions of any one or more of the amino acids intervening (i.e., extracellular or intracellular loops) the human AdipoR2v1 TM1 thru TM7 transmembrane domain polypeptides as antigenic and/or immunogenic epitopes.

Although the human AdipoR2 receptor has seven transmembrane domains, it is believed to be structurally, topologically, and functionally distinct from G-protein coupled receptors. Yamauchi et al demonstrated that the N-terminus of AdipoR2 is intracellular, as opposed to GPCRs which typically have their N-terminus extracellular. In addition, AdipoR2 does not appear to couple to G-proteins, but rather activate unique sets of signalling molecules such as PPAR-alpha, AMPK, and p38 MAPK.

Likewise, the human AdipoR2v1 receptor of the present invention is also thought to be structurally, topologically, and functionally distinct from G-protein coupled receptors. Alternatively, the human AdipoR2v1 receptor of the present invention may share at least some biological function with GPCRs.

The human AdipoR2v1 polypeptide was also determined to comprise several conserved cysteines which are denoted by dark shading, in addition to other identical residues, as shown in FIGS. 4A-B. Conservation of cysteines at key amino acid residues is indicative of conserved structural features, which may correlate with conservation of protein function and/or activity.

The present invention also encompasses polynucleotides encoding at least 300 consecutive amino acids of the human AdipoR2v1 polypeptide of the present invention (SEQ ID NO:2). Preferably the polynucleotides encode a polypeptide having at least some adiponectin receptor activity. The present invention also encompasses polynucleotides having at least 900 consecutive nucleotides of SEQ ID NO:1, wherein said polynucleotides preferably encode a polypeptide having at least some adiponectin receptor activity.

The present invention also is directed to the novel human AdipoR2v1 receptor polypeptide fragment located from amino acid 1 to amino 87 of SEQ ID NO:2. The present invention also is directed to the novel human AdipoR2v1 receptor polynucleotide from nucleotide 1 to nucleotide 470 of SEQ ID NO:1.

The present invention also is directed to the carboxy terminus of the novel human AdipoR2v1 receptor polypeptide fragment located from amino acid 365 to amino acid 386 of SEQ ID NO:2. The present invention also is directed to the novel human AdipoR2v1 receptor polynucleotide from nucleotide 1302 to nucleotide 1367 of SEQ ID NO:1. The present invention also encompasses the use of this carboxy terminal fragment polypeptide as an antigenic and/or immunogenic epitope. Antibodies to this particular carboxy terminal epitope of AdipoR2v1 would be useful therapeutically to modulate the activity of the AdipoR2v1 polypeptide.

Since the human AdipoR2v1 polypeptide represents a variant form of the human AdipoR2 protein (hAdipoR2; Genbank Accession No: gi|NM_024551; SEQ ID NO:9), it is expected that the expression pattern of the human AdipoR2v1 polypeptide of the present invention is the same or similar to the expression pattern of the human AdipoR2 protein.

The human AdipoR2 protein was determined to be expressed predominately in liver (Yamauchi et al., 2003). Likewise, the expression pattern of the human AdipoR2v1 polypeptide is also expected to be expressed predominately in liver.

The human AdipoR2v1 polynucleotides and polypeptides of the present invention, including modulators and/or fragments thereof, have uses that include detecting, prognosing, treating, preventing, and/or ameliorating the following diseases and/or disorders: metabolic disorders, inflammatory disorders, cardiovascular disorders, obesity, diabetes, type I diabetes, type II diabetes, gestational diabetes, early onset diabetes, insulin resistance, disorders in which glucose-lowering would be beneficial, disorders in which amelioration of insulin resistance would be beneficial, disorders in which suppressed FA influx into liver would be beneficial, disorders in which reduced serum TG would be beneficial, myocardial infarction, heart failure, atherosclerosis, arteriosclerosis, disorders disclosed herein in the "Cardiovascular Disorders" section, disorders in which adiponectin levels are below normal, disorders that would benefit from increased adiponectin levels, disorders associated with aberrant vascular smooth muscle proliferation, disorders associated with aberrant foam cell formation, disorders in which inhibition of macrophage phagocytosis would be beneficial, disorders in which inhibition of TNF-alpha production would be beneficial, dyslipidemia, diabetic dyslipidemia, mixed dyslipidemia, hypercholesteremia, hypertriglyceridemia, hyperlipidemia, and anorexia nervosa.

The human AdipoR2v1 polynucleotides and polypeptides of the present invention, including modulators and/or fragments thereof, have uses that include detecting, prognosing, treating, preventing, and/or ameliorating the following inflammatory diseases and/or disorders: arthritis, rheumatoid arthritis, osteoarthritis, prosthetic joint failure, ulcerative colitis, Crohn's disease, inflammatory bowel and gastrointestinal diseases, gastritis, mucosal inflammation resulting from infection, enteropathy provoked by non-steroidal anti-inflammatory drugs, adult respiratory distress syndrome, asthma, cystic fibrosis, chronic obstructive pulmonary disease, myocarditis, multiple sclerosis, inflammation associated with diabetes melitus, glomerulonephritis, dermatitis, psoriasis, eczema, urticaria, burn injury, glaucoma, organ rejection, multi-organ diseases, systemic lupus erythematosis, sepsis, inflammatory sequelae of viral or bacterial infections, inflammatory conditions associated with atherosclerosis following hypoxic or ischaemic insults (with or without reperfusion, particularly in the brain or in ischaemic heart disease.

The human AdipoR2v1 polynucleotides and polypeptides of the present invention, including modulators and/or fragments thereof, have uses that include modulating signal transduction activity, in various cells, tissues, and organisms, and particularly in mammalian liver.

Human AdipoR2v1 polynucleotides and polypeptides of the present invention, including modulators and/or fragments thereof, have uses that include detecting, prognosing, treating, preventing, and/or ameliorating the following additional cardiovascular disorders: congestive heart failure, arrthymias, cardiomyopathy, microvascular disease, embolism, thromobosis, pulmonary edema, palpitation, dyspnea, angina, hypotension, syncope, heart murmur, aberrant ECG, hypertrophic cardiomyopathy, the Marfan syndrome, sudden death, prolonged QT syndrome, congenital defects, cardiac viral infections, valvular heart disease, and hypertension.

Similarly, human AdipoR2v1 polynucleotides and polypeptides may be useful for ameliorating cardiovascular diseases and symptoms which result indirectly from various non-cardiovascular effects, which include, but are not limited to, the following, obesity, smoking, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, have uses which include, directly or indirectly, treating, preventing, diagnosing, and/or prognosing the following, non-limiting, cardiovascular infections: blood stream invasion, bacteremia, sepsis, *Streptococcus pneumoniae* infection, group a streptococci infection, group b streptococci infection, *Enterococcus* infection, nonenterococcal group D streptococci infection, nonenterococcal group C streptococci infection, nonenterococcal group G streptococci infection, *Streptococcus viridans* infection, *Staphylococcus aureus* infection, coagulase-negative staphylococci infection, gram-negative Bacilli infection, Enterobacteriaceae infection, *Pseudomonas* spp. Infection, *Acinobacter* spp. Infection, *Flavobacterium meningosepticum* infection, *Aeromonas* spp. Infection, *Stenotrophomonas maltophilia* infection, gram-negative coccobacilli infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous *Mycobacteria* infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

Human AdipoR2v1 polypeptides and polynucleotides have additional uses which include diagnosing diseases related to the over and/or under expression of human AdipoR2v1 by identifying mutations in the human AdipoR2v1 gene by using human AdipoR2v1 sequences as probes or by determining human AdipoR2v1 protein or mRNA expression levels. human AdipoR2v1 polypeptides, may be useful for screening compounds that affect the activity of the protein. Human AdipoR2v1 peptides can also be used for the generation of specific antibodies and as bait in yeast two hybrid screens to find proteins that specifically interact with human AdipoR2v1 (described elsewhere herein).

In preferred embodiments, the following N-terminal human AdipoR2v1 deletion polypeptides are encompassed by the present invention: M1-L386, N2-L386, E3-L386, P4-L386, T5-L386, E6-L386, N7-L386, R8-L386, L9-L386, G10-L386, C11-L386, S12-L386, R13-L386, T14-L386, P15-L386, E16-L386, P17-L386, D18-L386, I19-L386, R20-L386, L21-L386, R22-L386, K23-L386, G24-L386, H25-L386, Q26-L386, L27-L386, D28-L386, G29-L386, T30-L386, R31-L386, R32-L386, G33-L386, D34-L386, N35-L386, D36-L386, S37-L386, H38-L386, Q39-L386, G40-L386, D41-L386, L42-L386, E43-L386, P44-L386, I45-L386, L46-L386, E47-L386, A48-L386, S49-L386, V50-L386, L51-L386, S52-L386, S53-L386, H54-L386, H55-L386, K56-L386, K57-L386, S58-L386, S59-L386, E60-L386, E61-L386, H62-L386, E63-L386, Y64-L386, S65-L386, D66-L386, E67-L386, A68-L386, P69-L386, Q70-L386, E71-L386, D72-L386, E73-L386, G74-L386, F75-L386, M76-L386, G77-L386, M78-L386, S79-L386, P80-L386, L81-L386, L82-L386, Q83-L386, A84-L386, H85-L386, H86-L386, A87-L386, M88-L386, E89-L386, K90-L386, M91-L386, E92-L386, E93-L386, F94-L386, V95-L386, C96-L386, K97-L386, V98-L386, W99-L386, E100-L386, G101-L386, R102-L386, W103-L386, R104-L386, V105-L386, I106-L386, P107-L386, H108-L386, D109-L386, V110-L386, L111-L386, P112-L386, D113-L386, W114-L386, L115-L386, K116-L386, D117-L386, N118-L386, D119-L386, F120-L386, L121-L386, L122-L386, H123-L386, G124-L386, H125-L386, R126-L386, P127-L386, P128-L386, M129-L386, P130-L386, S131-L386, F132-L386, R133-L386, A134-L386, C135-L386, F136-L386, K137-L386, S138-L386, I139-L386, F140-L386, R141-L386, I142-L386, H143-L386, T144-L386, E145-L386, T146-L386, G147-L386, N148-L386, I149-L386, W150-L386, T151-L386, H152-L386, L153-L386, L154-L386, G155-L386, C156-L386, V157-L386, F158-L386, F159-L386, L160-L386, C161-L386, L162-L386, G163-L386, I164-L386, F165-L386, Y166-L386, M167-L386, F168-L386, R169-L386, P170-L386, N171-L386, I172-L386, S173-L386, F174-L386, V175-L386, A176-L386, P177-L386, L178-L386, Q179-L386, E180-L386, K181-L386, V182-L386, V183-L386, F184-L386, G185-L386, L186-L386, F187-L386, F188-L386, L189-L386, G190-L386, A191-L386, I192-L386, L193-L386, C194-L386, L195-L386, S196-L386, F197-L386, S198-L386, W199-L386, L200-L386, F201-L386, H202-L386, T203-L386, V204-L386, Y205-L386, C206-L386, H207-L386, S208-

L386, E209-L386, G210-L386, V211-L386, S212-L386, R213-L386, L214-L386, F215-L386, S216-L386, K217-L386, L218-L386, D219-L386, Y220-L386, S221-L386, G222-L386, I223-L386, A224-L386, L225-L386, L226-L386, I227-L386, M228-L386, G229-L386, S230-L386, F231-L386, V232-L386, P233-L386, W234-L386, L235-L386, Y236-L386, Y237-L386, S238-L386, F239-L386, Y240-L386, C241-L386, N242-L386, P243-L386, Q244-L386, P245-L386, C246-L386, F247-L386, I248-L386, Y249-L386, L250-L386, I251-L386, V252-L386, I253-L386, C254-L386, V255-L386, L256-L386, G257-L386, I258-L386, A259-L386, A260-L386, I261-L386, I262-L386, V263-L386, S264-L386, Q265-L386, W266-L386, D267-L386, M268-L386, F269-L386, A270-L386, T271-L386, P272-L386, Q273-L386, Y274-L386, R275-L386, G276-L386, V277-L386, R278-L386, A279-L386, G280-L386, V281-L386, F282-L386, L283-L386, G284-L386, L285-L386, G286-L386, L287-L386, S288-L386, G289-L386, I290-L386, I291-L386, P292-L386, T293-L386, L294-L386, H295-L386, Y296-L386, V297-L386, I298-L386, S299-L386, E300-L386, G301-L386, F302-L386, L303-L386, K304-L386, A305-L386, A306-L386, T307-L386, I308-L386, G309-L386, Q310-L386, I311-L386, G312-L386, W313-L386, L314-L386, M315-L386, L316-L386, M317-L386, A318-L386, S319-L386, L320-L386, Y321-L386, I322-L386, T323-L386, G324-L386, A325-L386, A326-L386, L327-L386, Y328-L386, A329-L386, A330-L386, R331-L386, I332-L386, P333-L386, E334-L386, R335-L386, F336-L386, F337-L386, P338-L386, G339-L386, K340-L386, C341-L386, D342-L386, I343-L386, W344-L386, F345-L386, H346-L386, S347-L386, H348-L386, Q349-L386, L350-L386, F351-L386, H352-L386, I353-L386, F354-L386, V355-L386, V356-L386, A357-L386, G358-L386, A359-L386, F360-L386, V361-L386, H362-L386, F363-L386, H364-L386, G365-L386, V366-L386, S367-L386, N368-L386, L369-L386, Q370-L386, E371-L386, F372-L386, R373-L386, F374-L386, M375-L386, I376-L386, G377-L386, G378-L386, G379-L386, and/or C380-L386 of SEQ ID NO:2. Polynucleotide sequences encoding these polypeptides are also provided. The present invention also encompasses the use of these N-terminal human AdipoR2v1 deletion polypeptides as immunogenic and/or antigenic epitopes as described elsewhere herein.

In preferred embodiments, the following C-terminal human AdipoR2v1 deletion polypeptides are encompassed by the present invention: M1-L386, M1-A385, M1-D384, M1-E383, M1-E382, M1-S381, M1-C380, M1-G379, M1-G378, M1-G377, M1-I376, M1-M375, M1-F374, M1-R373, M1-F372, M1-E371, M1-Q370, M1-L369, M1-N368, M1-S367, M1-V366, M1-G365, M1-H364, M1-F363, M1-H362, M1-V361, M1-F360, M1-A359, M1-G358, M1-A357, M1-V356, M1-V355, M1-F354, M1-I353, M1-H352, M1-F351, M1-L350, M1-Q349, M1-H348, M1-S347, M1-H346, M1-F345, M1-W344, M1-I343, M1-D342, M1-C341, M1-K340, M1-G339, M1-P338, M1-F337, M1-F336, M1-R335, M1-E334, M1-P333, M1-I332, M1-R331, M1-A330, M1-A329, M1-Y328, M1-L327, M1-A326, M1-A325, M1-G324, M1-T323, M1-I322, M1-Y321, M1-L320, M1-S319, M1-A318, M1-M317, M1-L316, M1-M315, M1-L314, M1-W313, M1-G312, M1-I311, M1-Q310, M1-G309, M1-I308, M1-T307, M1-A306, M1-A305, M1-K304, M1-L303, M1-F302, M1-G301, M1-E300, M1-S299, M1-I298, M1-V297, M1-Y296, M1-H295, M1-L294, M1-T293, M1-P292, M1-I291, M1-I290, M1-G289, M1-S288, M1-L287, M1-G286, M1-L285, M1-G284, M1-L283, M1-F282, M1-V281, M1-G280, M1-A279, M1-R278, M1-V277, M1-G276, M1-R275, M1-Y274, M1-Q273, M1-P272, M1-T271, M1-A270, M1-F269, M1-M268, M1-D267, M1-W266, M1-Q265, M1-S264, M1-V263, M1-I262, M1-I261, M1-A260, M1-A259, M1-I258, M1-G257, M1-L256, M1-V255, M1-C254, M1-I253, M1-V252, M1-I251, M1-L250, M1-Y249, M1-I248, M1-F247, M1-C246, M1-P245, M1-Q244, M1-P243, M1-N242, M1-C241, M1-Y240, M1-F239, M1-S238, M1-Y237, M1-Y236, M1-L235, M1-W234, M1-P233, M1-V232, M1-F231, M1-S230, M1-G229, M1-M228, M1-I227, M1-L226, M1-L225, M1-A224, M1-I223, M1-G222, M1-S221, M1-Y220, M1-D219, M1-L218, M1-K217, M1-S216, M1-F215, M1-L214, M1-R213, M1-S212, M1-V211, M1-G210, M1-E209, M1-S208, M1-H207, M1-C206, M1-Y205, M1-V204, M1-T203, M1-H202, M1-F201, M1-L200, M1-W199, M1-S198, M1-F197, M1-S196, M1-L195, M1-C194, M1-L193, M1-I192, M1-A191, M1-G190, M1-L189, M1-F188, M1-F187, M1-L186, M1-G185, M1-F184, M1-V183, M1-V182, M1-K181, M1-E180, M1-Q179, M1-L178, M1-P177, M1-A176, M1-V175, M1-F174, M1-S173, M1-I172, M1-N171, M1-P170, M1-R169, M1-F168, M1-M167, M1-Y166, M1-F165, M1-I164, M1-G163, M1-L162, M1-C161, M1-L160, M1-F159, M1-F158, M1-V157, M1-C156, M1-G155, M1-L154, M1-L153, M1-H152, M1-T151, M1-W150, M1-I149, M1-N148, M1-G147, M1-T146, M1-E145, M1-T144, M1-H143, M1-I142, M1-R141, M1-F140, M1-I139, M1-S138, M1-K137, M1-F136, M1-C135, M1-A134, M1-R133, M1-F132, M1-S131, M1-P130, M1-M129, M1-P128, M1-P127, M1-R126, M1-H125, M1-G124, M1-H123, M1-L122, M1-L121, M1-F120, M1-D119, M1-N118, M1-D117, M1-K116, M1-L115, M1-W114, M1-D113, M1-P112, M1-L111, M1-V110, M1-D109, M1-H108, M1-P107, M1-I106, M1-V105, M1-R104, M1-W103, M1-R102, M1-G101, M1-E100, M1-W99, M1-V98, M1-K97, M1-C96, M1-V95, M1-F94, M1-E93, M1-E92, M1-M91, M1-K90, M1-E89, M1-M88, M1-A87, M1-H86, M1-H85, M1-A84, M1-Q83, M1-L82, M1-L81, M1-P80, M1-S79, M1-M78, M1-G77, M1-M76, M1-F75, M1-G74, M1-E73, M1-D72, M1-E71, M1-Q70, M1-P69, M1-A68, M1-E67, M1-D66, M1-S65, M1-Y64, M1-E63, M1-H62, M1-E61, M1-E60, M1-S59, M1-S58, M1-K57, M1-K56, M1-H55, M1-H54, M1-S53, M1-S52, M1-L51, M1-V50, M1-S49, M1-A48, M1-E47, M1-L46, M1-I45, M1-P44, M1-E43, M1-L42, M1-D41, M1-G40, M1-Q39, M1-H38, M1-S37, M1-D36, M1-N35, M1-D34, M1-G33, M1-R32, M1-R31, M1-T30, M1-G29, M1-D28, M1-L27, M1-Q26, M1-H25, M1-G24, M1-K23, M1-R22, M1-L21, M1-R20, M1-I19, M1-D18, M1-P17, M1-E16, M1-P15, M1-T14, M1-R13, M1-S12, M1-C11, M1-G10, M1-L9, M1-R8, and/or M1-N7 of SEQ ID NO:2. Polynucleotide sequences encoding these polypeptides are also provided. The present invention also encompasses the use of these C-terminal human AdipoR2v1 deletion polypeptides as immunogenic and/or antigenic epitopes as described elsewhere herein.

Alternatively, preferred polypeptides of the present invention may comprise polypeptide sequences corresponding to, for example, internal regions of the human AdipoR2v1 polypeptide (e.g., any combination of both N- and C-terminal human AdipoR2v1 polypeptide deletions) of SEQ ID NO:2. For example, internal regions could be defined by the equation: amino acid NX to amino acid CX, wherein NX refers to any N-terminal deletion polypeptide amino acid of human AdipoR2v1 (SEQ ID NO:2), and where CX refers to any C-terminal deletion polypeptide amino acid of human AdipoR2v1 (SEQ ID NO:2). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the human AdipoR2v1 polypeptide.

The human AdipoR2v1 polypeptide of the present invention was determined to comprise several phosphorylation sites based upon the Motif algorithm (Genetics Computer Group, Inc.). The phosphorylation of such sites may regulate some biological activity of the human AdipoR2v1 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the human AdipoR2v polypeptide to associate with other polypeptides, particularly the cognate ligand for human AdipoR2v1, such as adiponectin, or its ability to modulate certain cellular signally pathways such as AMPK, p38 MAPK, MAPK, and/or ACC.

Specifically, the human AdipoR2v1 polypeptide was predicted to comprise one tyrosine phosphorylation site using the Motif algorithm (Genetics Computer Group, Inc.). Such sites are phosphorylated at the tyrosine amino acid residue. The consensus pattern for tyrosine phosphorylation sites are as follows: [RK]-x(2)-[DE]-x(3)-Y, or [RK]-x(3)-[DE]-x(2)-Y, where Y represents the phosphorylation site and 'x' represents an intervening amino acid residue. Additional information specific to tyrosine phosphorylation sites can be found in Patschinsky T., Hunter T., Esch F. S., Cooper J. A., Sefton B. M., Proc. Natl. Acad. Sci. U.S.A. 79:973-977 (1982); Hunter T., J. Biol. Chem. 257:4843-4848 (1982), and Cooper J. A., Esch F. S., Taylor S. S., Hunter T., J. Biol. Chem. 259:7835-7841 (1984), which are hereby incorporated herein by reference.

In preferred embodiments, the following tyrosine phosphorylation site polypeptides are encompassed by the present invention: Y LSSHHKKSSEEHEYSDEAP (SEQ ID NO:13), and/or Y SSHHKKSSEEHEYSDEAP (SEQ ID NO:14). Polynucleotides encoding these polypeptides are also provided. The present invention also encompasses the use of these human AdipoR2v1 tyrosine phosphorylation site polypeptides as immunogenic and/or antigenic epitopes as described elsewhere herein.

The human AdipoR2v1 polypeptide was predicted to comprise two PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. 260: 12492-12499 (1985); which are hereby incorporated by reference herein.

In preferred embodiments, the following PKC phosphorylation site polypeptides are encompassed by the present invention: HQLDGTRRGDNDS (SEQ ID NO:11), and/or RPPMPSFRACFKS (SEQ ID NO:12). Polynucleotides encoding these polypeptides are also provided. The present invention also encompasses the use of the human AdipoR2v1 PKC phosphorylation site polypeptides as immunogenic and/or antigenic epitopes as described elsewhere herein.

The human AdipoR2v1 polypeptide was predicted to comprise four casein kinase II phosphorylation sites using the Motif algorithm (Genetics Computer Group, Inc.). Casein kinase II (CK-2) is a protein serine/threonine kinase whose activity is independent of cyclic nucleotides and calcium. CK-2 phosphorylates many different proteins. The substrate specificity [1] of this enzyme can be summarized as follows: (1) Under comparable conditions Ser is favored over Thr.; (2) An acidic residue (either Asp or Glu) must be present three residues from the C-terminal of the phosphate acceptor site; (3) Additional acidic residues in positions +1, +2, +4, and +5 increase the phosphorylation rate. Most physiological substrates have at least one acidic residue in these positions; (4) Asp is preferred to Glu as the provider of acidic determinants; and (5) A basic residue at the N-terminal of the acceptor site decreases the phosphorylation rate, while an acidic one will increase it.

A consensus pattern for casein kinase II phosphorylations site is as follows: [ST]-x(2)-[DE], wherein 'x' represents any amino acid, and S or T is the phosphorylation site.

Additional information specific to casein kinase II phosphorylation site-II domains may be found in reference to the following publication: Pinna L. A., Biochim. Biophys. Acta 1054:267-284 (1990); which is hereby incorporated herein in its entirety.

In preferred embodiments, the following casein kinase II phosphorylation site polypeptide is encompassed by the present invention: SHHKKSSEEHEYSD (SEQ ID NO:15), VSRLFSKLDYSGIA (SEQ ID NO:16), AAIIVSQWDMFATP (SEQ ID NO:17), and/or IGGGCSEEDAL (SEQ ID NO:18). Polynucleotides encoding these polypeptides are also provided. The present invention also encompasses the use of this casein kinase II phosphorylation site polypeptide as an immunogenic and/or antigenic epitope as described elsewhere herein.

The human AdipoR2v1 polypeptide was predicted to comprise one cAMP- and cGMP-dependent protein kinase phosphorylation site using the Motif algorithm (Genetics Computer Group, Inc.). There has been a number of studies relative to the specificity of cAMP- and cGMP-dependent protein kinases. Both types of kinases appear to share a preference for the phosphorylation of serine or threonine residues found close to at least two consecutive N-terminal basic residues.

A consensus pattern for cAMP- and cGMP-dependent protein kinase phosphorylation sites is as follows: [RK](2)-x-[ST], wherein "x" represents any amino acid, and S or T is the phosphorylation site.

Additional information specific to cAMP- and cGMP-dependent protein kinase phosphorylation sites may be found in reference to the following publication: Fremisco J. R., Glass D. B., Krebs E. G, J. Biol. Chem. 255:4240-4245 (1980); Glass D. B., Smith S. B., J. Biol. Chem. 258:14797-14803 (1983); and Glass D. B., El-Maghrabi M. R., Pilkis S. J., J. Biol. Chem. 261:2987-2993 (1986); which is hereby incorporated herein in its entirety.

In preferred embodiments, the following cAMP- and cGMP-dependent protein kinase phosphorylation site polypeptide is encompassed by the present invention: LSSHHKKSSEEHEY (SEQ ID NO:19). Polynucleotides encoding this polypeptide are also provided. The present invention also encompasses the use of this cAMP- and cGMP-dependent protein kinase phosphorylation site polypeptide as an immunogenic and/or antigenic epitope as described elsewhere herein.

The human AdipoR2v1 polypeptide has been shown to comprise two glycosylation site according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine glycosylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673-702 (1972); Pless D. D., Lennarz W. J., Proc. Natl. Acad. Sci. U.S.A. 74:134-138 (1977); Bause E., Biochem. J. 209:331-336 (1983); Gavel Y., von Heijne G., Protein Eng. 3:433-442 (1990); and Miletich J. P., Broze G. J. Jr., J. Biol. Chem. 265:11397-11404 (1990).

In preferred embodiments, the following asparagine glycosylation site polypeptides are encompassed by the present invention: TRRGDNDSHQGDLE (SEQ ID NO:19), and/or YMFRPNISFVAPLQ (SEQ ID NO:20). Polynucleotides encoding these polypeptides are also provided. The present invention also encompasses the use of these human AdipoR2v1 asparagine glycosylation site polypeptides as immunogenic and/or antigenic epitopes as described elsewhere herein.

The human AdipoR2v1 polypeptide was predicted to comprise eight N-myristoylation sites using the Motif algorithm (Genetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA: protein N-myristoyl transferase (NMT), has been derived from the sequence of known N-myristoylated proteins and from studies using synthetic peptides. The specificity seems to be the following: i.) The N-terminal residue must be glycine; ii.) In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-{EDRKHPFYW}-x(2)-[STAGCN]-{P}, wherein 'x' represents any amino acid, and G is the N-myristoylation site.

Additional information specific to N-myristoylation sites may be found in reference to the following publication: Towler D. A., Gordon J. I., Adams S. P., Glaser L., Annu. Rev. Biochem. 57:69-99 (1988); and Grand R. J. A., Biochem. J. 258:625-638 (1989); which is hereby incorporated herein in its entirety.

In preferred embodiments, the following N-myristoylation site polypeptides are encompassed by the present invention: GHQLDGTRRGDNDSHQ (SEQ ID NO:22), IHTETGNIWTHLLGCV (SEQ ID NO:23), GLFFLGAILCLSFSWL (SEQ ID NO:24), TPQYRGVRAGVFLGLG (SEQ ID NO:25), RGVRAGVFLGLGLSGI (SEQ ID NO:26), AGVFLGLGLSGIIPTL (SEQ ID NO:27), GLGLSGIIPTLHYVIS (SEQ ID NO:28), and/or FRFMIGGGCSEEDAL (SEQ ID NO:29). Polynucleotides encoding these polypeptides are also provided. The present invention also encompasses the use of these N-myristoylation site polypeptides as immunogenic and/or antigenic epitopes as described elsewhere herein.

The human AdipoR2v1 polypeptide has been shown to comprise one RGD cell attachment site domain according to the Motif algorithm (Genetics Computer Group, Inc.). The sequence Arg-Gly-Asp, found in fibronectin, is crucial for its interaction with its cell surface receptor, an integrin. What has been called the 'RGD' tripeptide is also found in the sequences of a number of other proteins, where it has been shown to play a role in cell adhesion. Non-limiting examples of these proteins are the following: some forms of collagens, fibrinogen, vitronectin, von Willebrand factor (VWF), snake disintegrins, and slime mold discoidins. The 'RGD' tripeptide is also found in other proteins where it may serve the same purpose. A consensus pattern for RGD cell attachment sites is the following: R-G-D. Additional information relating to RGD cell attachment site domains may be found in reference to the following publications, which are hereby incorporated by reference herein: Ruoslahti E., Pierschbacher M. D., Cell 44:517-518 (1986); and d'Souza S. E., Ginsberg M. H., Plow E. F., Trends Biochem. Sci. 16:246-250 (1991).

In preferred embodiments, the following RGD cell attachment site domain polypeptide is encompassed by the present invention: LDGTRRGDNDSHQ (SEQ ID NO:42). Polynucleotides encoding these polypeptides are also provided. The present invention also encompasses the use of this RGD cell attachment site domain polypeptide as an immunogenic and/or antigenic epitope as described elsewhere herein.

The present invention encompasses the identification of compounds and drugs which stimulate human AdipoR2v1 on the one hand (i.e., agonists) and which inhibit the function of human AdipoR2v1 on the other hand (i.e., antagonists). In general, such screening procedures involve providing appropriate cells which express the receptor polypeptide of the present invention on the surface thereof. Such cells may include, for example, cells from mammals, yeast, Drosophila or E. coli. In a preferred embodiment, a polynucleotide encoding the receptor of the present invention may be employed to transfect cells to thereby express the human AdipoR2v1 polypeptide. The expressed receptor may then be contacted with a test compound to observe binding, stimulation or inhibition of a functional response.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 1571 of SEQ ID NO:1, b is an integer between 15 to 1585, where both a and b correspond to the positions of nucleotide residues shown in SEQ ID NO:1, and where b is greater than or equal to a+14

Features of the Polypeptide Encoded by Polynucleotide No:2

The polypeptide of this polynucleotide provided as SEQ ID NO:4 (FIGS. 2A-D), encoded by the polynucleotide sequence according to SEQ ID NO:3 (FIGS. 2A-D), and/or encoded by the polynucleotide contained within the deposited clone, mouse AdipoR2v1 (also referred to as mAdipoR2v1), is believed to represent the physiologically relevant form of the mouse AdipoR2 polypeptide.

An alignment of the mouse AdipoR2v1 polypeptide of the present invention with the human AdipoR1 protein (hAdipoR1; GenbankAccession No: gi|NM_015999; SEQ ID NO:7); the mouse AdipoR1 protein (mAdipoR1; Genbank Accession No: gi|BCO14875; SEQ ID NO:8); the human AdipoR2 protein (hAdipoR2; Genbank Accession No: gi|NM_024551; SEQ ID NO:9); and the mouse AdipoR2 protein (mAdipoR2; Genbank Accession No: gi|XM_132831; SEQ ID NO:30) is provided in FIGS. 4A-B.

The mouse AdipoR2v1 polypeptide (SEQ ID NO:4) of the present invention differs from the sequence of the human AdipoR2 receptor by having an additional 76 amino acids in the N-terminus of the polypeptide. An alignment of the hydropathy plots of AdipoR1 and AdipoR2 polypeptide sequences from other species with the mouse AdipoR2v1 polypeptide (SEQ ID NO:4) of the present invention (see FIG. 8) provides convincing evidence that the sequence of the mouse AdipoR2 receptor reported by Yamauchi et al is truncated and that the mouse AdipoR2v1 polypeptide of the present invention is the true, physiologically relevant full-length form of this receptor.

As noted by Yamauchi et al, the human AdipoR1 and AdipoR2 polypeptide sequences are "highly structurally related", and share 80% identity overall between the sequences. Both AdipoR1 and AdipoR2 serve as receptors for both globular and full-length adiponectin. Importantly, Yamauchi et al point out that AdipoR1 represents a high affinity receptor for globular adiponectin, while AdipoR2 only represents an intermediate affinity receptor for globular adiponectin.

As shown in the hydropathy plot alignments of FIG. 4, the N-terminus of the AdipoR2 receptor is significantly shorter than the N-terminus of the AdipoR1 receptor. It is possible that the functional dimorphism between the AdipoR1 and AdipoR2 receptors in terms of their binding affinity for adiponectin is due to the truncation of the AdipoR2 receptor sequence as originally reported by Yamauchi et al. The inventors believe that the mouse AdipoR2v1 polypeptide of the present invention is the physiologically relevant form of the mouse AdipoR2 sequence. Likewise, the mouse AdipoR2v1 polypeptide is expected to share the same biological activity as the reported for the mouse AdipoR2 sequence. Preferably, the AdipoR2v1 polypeptide is expected to have increased biological activity relative to the reported AdipoR2 sequence. Such increased biological function may be in the form of increased binding affinity for adiponectin, increased binding affinity for globular adiponectin, increased binding affinity for full-length adiponectin, increased association rate constant for adiponectin, increased association rate constant for globular adiponectin, increased association rate constant for full-length adiponectin, decreased dissociation rate constant for adiponectin, decreased dissociation rate constant for globular adiponectin, decreased dissociation rate constant for full-length adiponectin, increased ability to regulate AMPK phosphorylation, increased ability to regulate ACC phosphorylation, increased ability to regulate MAPK phosphorylation, increased ability to regulate p38 MAPK phosphorylation, among others.

Alternatively, the ability of the AdipoR2v1 sequence of the present invention to bind to adiponectin may be less than the reported AdipoR2 sequence. Thus, the AdipoR2v1 polypeptide may have increased biological activity relative to the reported AdipoR2 sequence. Such increased biological function may be in the form of decreased binding affinity for adiponectin, decreased binding affinity for globular adiponectin, decreased binding affinity for full-length adiponectin, decreased association rate constant for adiponectin, decreased association rate constant for globular adiponectin, decreased association rate constant for full-length adiponectin, increased dissociation rate constant for adiponectin, increased dissociation rate constant for globular adiponectin, increased dissociation rate constant for full-length adiponectin, decreased ability to regulate AMPK phosphorylation, decreased ability to regulate ACC phosphorylation, decreased ability to regulate MAPK phosphorylation, decreased ability to regulate p38 MAPK phosphorylation, among others.

The determined nucleotide sequence of the mouse AdipoR2v1 cDNA in FIGS. 2A-D (SEQ ID NO:3) contains an open reading frame encoding a protein of about 386 amino acid residues, with a deduced molecular weight of about 44.0 kDa. The amino acid sequence of the predicted mouse AdipoR2v1 polypeptide is shown in FIGS. 2A-D (SEQ ID NO:4). By virtue of the mouse AdipoR2v1 protein representing an N-terminally extended form of the human AdipoR2 polypeptide, the mouse AdipoR2v1 polypeptide shown in FIGS. 2A-D was determined to share significant identity and similarity to other adiponectin receptors, as shown in FIGS. 4A-B. The percent identity and similarity values between the mouse AdipoR2v1 polypeptide to these known adiponectin receptors is provided in FIG. 11.

The mouse AdipoR2v1, mouse AdipoR2v1, human AdipoR3, human AdipoR2v2, human AdipoR3v1, rat AdipoR1, and/or rat AdipoR2 polypeptide was predicted to comprise seven transmembrane domains (TM1 to TM7) located from about amino acid 151 to about amino acid 172 (TM1; SEQ ID NO:74); from about amino acid 177 to about amino acid 201 (TM2; SEQ ID NO:75); from about amino acid 217 to about amino acid 235 (TM3; SEQ ID NO:76); from about amino acid 243 to about amino acid 266 (TM4; SEQ ID NO:77); from about amino acid 279 to about amino acid 303 (TM5; SEQ ID NO:78); from about amino acid 307 to about amino acid 327 (TM6; SEQ ID NO:79); and/or from about amino acid 348 to about amino acid 364 (TM7; SEQ ID NO:80) of SEQ ID NO:4 (FIGS. 2A-D). In this context, the term "about" may be construed to mean 1, 2, 3, 4, 5, 6, 7, 8, 9, or 10 amino acids beyond the N-Terminus and/or C-terminus of the above referenced transmembrane domain polypeptides.

In preferred embodiments, the following transmembrane domain polypeptides are encompassed by the present invention: THLLGCVFFLCLGIFYMFRPNI (SEQ ID NO:74), PLQEKVVFGLFFLGAILCLSFSWLF (SEQ ID NO:75), KLDYSGIALLIMGSFVPWL (SEQ ID NO:76), PQPCFIYLIVICVLGIAAIIVSQW (SEQ ID NO:77), AGVFVGLGLSGIIPTLHYVISEGFL (SEQ ID NO:78), TIGQIGWLMLMASLYITGAAL (SEQ ID NO:79), and/or HQLFHIFVVAGAFVHFH (SEQ ID NO:80). Polynucleotides encoding these polypeptides are also provided. The present invention also encompasses the use of these mouse AdipoR2v1 transmembrane domain polypeptides as immunogenic and/or antigenic epitopes as described elsewhere herein.

The present invention also encompasses the polypeptide sequences that intervene between each of the predicted mouse AdipoR2v1 transmembrane domains. Since these regions are solvent accessible either extracellularly or intracellularly, they are particularly useful for designing antibodies specific to each region. Such antibodies may be useful as antagonists or agonists of the mouse AdipoR2v1 full-length polypeptide and may modulate its activity.

In preferred embodiments, the following inter-transmembrane domain polypeptides are encompassed by the present invention: HTVYCHSEGVSRLFS (SEQ ID NO:92), YYSFYCN (SEQ ID NO:93), DMFATPQYRGVR (SEQ ID NO:94), and/or YAARIPERFFPGKCDIWFHS (SEQ ID NO:95). Polynucleotides encoding these polypeptides are also provided. The present invention also encompasses the use of these mouse AdipoR2v1 transmembrane domain polypeptides as immunogenic and/or antigenic epitopes as described elsewhere herein.

In preferred embodiments, the present invention encompasses the use of N-terminal deletions, C-terminal deletions, or any combination of N-terminal and C-terminal deletions of any one or more of the mouse AdipoR2v1 TM1 thru TM7 transmembrane domain polypeptides as antigenic and/or immunogenic epitopes.

In preferred embodiments, the present invention also encompasses the use of N-terminal deletions, C-terminal deletions, or any combination of N-terminal and C-terminal deletions of any one or more of the amino acids intervening (i.e., extracellular or intracellular loops) the mouse AdipoR2v1 TM1 thru TM7 transmembrane domain polypeptides as antigenic and/or immunogenic epitopes.

Although the mouse AdipoR2 receptor has seven transmembrane domains, it is believed to be structurally, topologically, and functionally distinct from G-protein coupled receptors. Yamauchi et al demonstrated that the N-terminus of AdipoR2 is intracellular, as opposed to GPCRs which typically have their N-terminus extracellular. In addition, AdipoR2 does not appear to couple to G-proteins, but rather activate unique sets of signalling molecules such as PPAR-alpha, AMPK, and p38 MAPK.

Likewise, the mouse AdipoR2v1 receptor of the present invention is also thought to be structurally, topologically, and functionally distinct from G-protein coupled receptors. Alternatively, the mouse AdipoR2v1 receptor of the present invention may share at least some biological function with GPCRs.

The mouse AdipoR2v1 polypeptide was also determined to comprise several conserved cysteines which are denoted by dark shading, in addition to other identical residues, as shown in FIGS. 4A-B. Conservation of cysteines at key amino acid residues is indicative of conserved structural features, which may correlate with conservation of protein function and/or activity.

The present invention also encompasses polynucleotides encoding at least 312 consecutive amino acids of the mouse AdipoR2v1 polypeptide of the present invention (SEQ ID NO:4). Preferably the polynucleotides encode a polypeptide having at least some adiponectin receptor activity. The present invention also encompasses polynucleotides having at least 936 consecutive nucleotides of SEQ ID NO:3, wherein said polynucleotides preferably encode a polypeptide having at least some adiponectin receptor activity.

The present invention also is directed to the novel mouse AdipoR2v1 receptor polypeptide fragment located from amino acid 1 to amino 75 of SEQ ID NO:4. The present invention also is directed to the novel mouse AdipoR2v1 receptor polynucleotide from nucleotide 1 to nucleotide 377 of SEQ ID NO:3.

The present invention also is directed to the carboxy terminus of the novel mouse AdipoR2v1 receptor polypeptide fragment located from amino acid 365 to amino acid 386 of SEQ ID NO:4. The present invention also is directed to the novel mouse AdipoR2v receptor polynucleotide from nucleotide 1245 to nucleotide 1310 of SEQ ID NO:3. The present invention also encompasses the use of this carboxy terminal fragment polypeptide as an antigenic and/or immunogenic epitope. Antibodies to this particular carboxy terminal epitope of AdipoR2v1 would be useful therapeutically to modulate the activity of the AdipoR2v1 polypeptide.

Since the mouse AdipoR2v1 polypeptide represents a variant form of the human AdipoR2 protein (hAdipoR2; Genbank Accession No: gi|NM_024551; SEQ ID NO:9), it is expected that the expression pattern of the mouse AdipoR2v1 polypeptide of the present invention is the same or similar to the expression pattern of the human AdipoR2 protein.

The human AdipoR2 protein was determined to be expressed predominately in liver (Yamauchi et al., 2003). Likewise, the expression pattern of the mouse AdipoR2v1 polypeptide is also expected to be expressed predominately in liver.

The mouse AdipoR2v1 polynucleotides and polypeptides of the present invention, including modulators and/or fragments thereof, have uses that include detecting, prognosing, treating, preventing, and/or ameliorating the following diseases and/or disorders: metabolic disorders, inflammatory disorders, cardiovascular disorders, obesity, diabetes, type I diabetes, type II diabetes, gestational diabetes, early onset diabetes, insulin resistance, disorders in which glucose-lowering would be beneficial, disorders in which amelioration of insulin resistance would be beneficial, disorders in which suppressed FA influx into liver would be beneficial, disorders in which reduced serum TG would be beneficial, myocardial infarction, heart failure, atherosclerosis, arteriosclerosis, disorders disclosed herein in the "Cardiovascular Disorders" section, disorders in which adiponectin levels are below normal, disorders that would benefit from increased adiponectin levels, disorders associated with aberrant vascular smooth muscle proliferation, disorders associated with aberrant foam cell formation, disorders in which inhibition of macrophage phagocytosis would be beneficial, disorders in which inhibition of TNF-alpha production would be beneficial, dyslipidemia, diabetic dyslipidemia, mixed dyslipidemia, hypercholesteremia, hypertriglyceridemia, hyperlipidemia, and anorexia nervosa.

The mouse AdipoR2v1 polynucleotides and polypeptides of the present invention, including modulators and/or fragments thereof, have uses that include detecting, prognosing, treating, preventing, and/or ameliorating the following inflammatory diseases and/or disorders: arthritis, rheumatoid arthritis, osteoarthritis, prosthetic joint failure, ulcerative colitis, Crohn's disease, inflammatory bowel and gastrointestinal diseases, gastritis, mucosal inflammation resulting from infection, enteropathy provoked by non-steroidal anti-inflammatory drugs, adult respiratory distress syndrome, asthma, cystic fibrosis, chronic obstructive pulmonary disease, myocarditis, multiple sclerosis, inflammation associated with diabetes melitus, glomerulonephritis, dermatitis, psoriasis, eczema, urticaria, burn injury, glaucoma, organ rejection, multi-organ diseases, systemic lupus erythematosis, sepsis, inflammatory sequelae of viral or bacterial infections, inflammatory conditions associated with atherosclerosis following hypoxic or ischaemic insults (with or without reperfusion, particularly in the brain or in ischaemic heart disease.

The mouse AdipoR2v1 polynucleotides and polypeptides of the present invention, including modulators and/or fragments thereof, have uses that include modulating signal transduction activity, in various cells, tissues, and organisms, and particularly in mammalian liver.

Mouse AdipoR2v1 polynucleotides and polypeptides of the present invention, including modulators and/or fragments thereof, have uses that include detecting, prognosing, treating, preventing, and/or ameliorating the following additional cardiovascular disorders: congestive heart failure, arrthymias, cardiomyopathy, microvascular disease, embolism, thromobosis, pulmonary edema, palpitation, dyspnea, angina, hypotension, syncope, heart murmur, aberrant ECG, hypertrophic cardiomyopathy, the Marfan syndrome, sudden death, prolonged QT syndrome, congenital defects, cardiac viral infections, valvular heart disease, and hypertension.

Similarly, mouse AdipoR2v1 polynucleotides and polypeptides may be useful for ameliorating cardiovascular diseases and symptoms which result indirectly from various non-cardiovascular effects, which include, but are not limited to, the following, obesity, smoking, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, have uses which include, directly or indirectly, treating, preventing, diagnosing, and/or prognosing the following, non-limiting, cardiovascular infections: blood stream invasion, bacteremia, sepsis, *Streptococcus pneumoniae* infection, group a streptococci infection, group b streptococci infection, *Enterococcus* infection, nonenterococcal group D streptococci infection, nonenterococcal group C streptococci infection, nonenterococcal group G streptococci infection, *Streptococcus viridans* infection, *Staphylococcus aureus* infection, coagulase-negative staphylococci infection, gram-negative Bacilli infection, Enterobacteriaceae infection, *Pseudomonas* spp. Infection, *Acinobacter* spp. Infection, *Flavobacterium meningosepticum* infection, *Aeromonas* spp. Infection, *Stenotrophomonas maltophilia* infection, gram-negative coccobacilli infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous *Mycobacteria* infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

Mouse AdipoR2v1 polypeptides and polynucleotides have additional uses which include diagnosing diseases related to the over and/or under expression of mouse AdipoR2v1 by identifying mutations in the mouse AdipoR2v1 gene by using mouse AdipoR2v1 sequences as probes or by determining mouse AdipoR2v1 protein or mRNA expression levels. mouse AdipoR2v1 polypeptides, may be useful for screening compounds that affect the activity of the protein. Human AdipoR2v1 peptides can also be used for the generation of specific antibodies and as bait in yeast two hybrid screens to find proteins that specifically interact with mouse AdipoR2v1 (described elsewhere herein).

In preferred embodiments, the following N-terminal mouse AdipoR2.v1 deletion polypeptides are encompassed by the present invention: M1-L386, N2-L386, E3-L386, P4-L386, A5-L386, K6-L386, H7-L386, R8-L386, L9-L386, G10-L386, C11-L386, T12-L386, R13-L386, T14-L386, P15-L386, E16-L386, P17-L386, D18-L386, I19-L386, R20-L386, L21-L386, R22-L386, K23-L386, G24-L386, H25-L386, Q26-L386, L27-L386, D28-L386, D29-L386, T30-L386, R31-L386, G32-L386, S33-L386, N34-L386, N35-L386, D36-L386, N37-L386, Y38-L386, Q39-L386, G40-L386, D41-L386, L42-L386, E43-L386, P44-L386, S45-L386, L46-L386, E47-L386, T48-L386, P49-L386, V50-L386, C51-L386, S52-L386, S53-L386, Y54-L386, Y55-L386, E56-L386, N57-L386, S58-L386, P59-L386, E60-L386, E61-L386, P62-L386, E63-L386, C64-L386, H65-L386, D66-L386, D67-L386, N68-L386, S69-L386, Q70-L386, E71-L386, D72-L386, E73-L386, G74-L386, F75-L386, M76-L386, G77-L386, M78-L386, S79-L386, P80-L386, L81-L386, L82-L386, Q83-L386, A84-L386, H85-L386, H86-L386, A87-L386, M88-L386, E89-L386, R90-L386, M91-L386, E92-L386, E93-L386, F94-L386, V95-L386, C96-L386, K97-L386, V98-L386, W99-L386, E100-L386, G101-L386, R102-L386, W103-L386, R104-L386, V105-L386, I106-L386, P107-L386, H108-L386, D109-L386, V110-L386, L111-L386, P112-L386, D113-L386, W114-L386, L115-L386, K116-L386, D117-L386, N118-L386, D119-L386, F120-L386, L121-L386, L122-L386, H123-L386, G124-L386, H125-L386, R126-L386, P127-L386, P128-L386, M129-L386, P130-L386, S131-L386, F132-L386, R133-L386, A134-L386, C135-L386, F136-L386, K137-L386, S138-L386, I139-L386, F140-L386, R141-L386, I142-L386, H143-L386, T144-L386, E145-L386, T146-L386, G147-L386, N148-L386, I149-L386, W150-L386, T151-L386, H152-L386, L153-L386, L154-L386, G155-L386, C156-L386, V157-L386, F158-L386, F159-L386, L160-L386, C161-L386, L162-L386, G163-L386, I164-L386, F165-L386, Y166-L386, M167-L386, F168-L386, R169-L386, P170-L386, N171-L386, I172-L386, S173-L386, F174-L386, V175-L386, A176-L386, P177-L386, L178-L386, Q179-L386, E180-L386, K181-L386, V182-L386, V183-L386, F184-L386, G185-L386, L186-L386, F187-L386, F188-L386, L189-L386, G190-L386, A191-L386, I192-L386, L193-L386, C194-L386, L195-L386, S196-L386, F197-L386, S198-L386, W199-L386, L200-L386, F201-L386, H202-L386, T203-L386, V204-L386, Y205-L386, C206-L386, H207-L386, S208-L386, E209-L386, G210-L386, V211-L386, S212-L386, R213-L386, L214-L386, F215-L386, S216-L386, K217-L386, L218-L386, D219-L386, Y220-L386, S221-L386, G222-L386, I223-L386, A224-L386, L225-L386, L226-L386, I227-L386, M228-L386, G229-L386, S230-L386, F231-L386, V232-L386, P233-L386, W234-L386, L235-L386, Y236-L386, Y237-L386, S238-L386, F239-L386, Y240-L386, C241-L386, N242-L386, P243-L386, Q244-L386, P245-L386, C246-L386, F247-L386, I248-L386, Y249-L386, L250-L386, I251-L386, V252-L386, I253-L386, C254-L386, V255-L386, L256-L386, G257-L386, I258-L386, A259-L386, A260-L386, I261-L386, I262-L386, V263-L386, S264-L386, Q265-L386, W266-L386, D267-L386, M268-L386, F269-L386, A270-L386, T271-L386, P272-L386, Q273-L386, Y274-L386, R275-L386, G276-L386, V277-L386, R278-L386, A279-L386, G280-L386, V281-L386, F282-L386, V283-L386, G284-L386, L285-L386, G286-L386, L287-L386, S288-L386, G289-L386, I290-L386, I291-L386, P292-L386, T293-L386, L294-L386, H295-L386, Y296-L386, V297-L386, I298-L386, S299-L386, E300-L386, G301-L386, F302-L386, L303-L386, K304-L386, A305-L386, A306-L386, T307-L386, I308-L386, G309-L386, Q310-L386, I311-L386, G312-L386, W313-L386, L314-L386, M315-L386, L316-L386, M317-L386, A318-L386, S319-L386, L320-L386, Y321-L386, I322-L386, T323-L386, G324-L386, A325-L386, A326-L386, L327-L386, Y328-L386, A329-L386, A330-L386, R331-L386, I332-L386, P333-L386, E334-L386, R335-L386, F336-L386, F337-L386, P338-L386, G339-L386, K340-L386, C341-L386, D342-L386, I343-L386, W344-L386, F345-L386, H346-L386, S347-L386, H348-L386, Q349-L386, L350-L386, F351-L386, H352-L386, I353-L386, F354-L386, V355-L386, V356-L386, A357-L386, G358-L386, A359-L386, F360-L386, V361-L386, H362-L386, F363-L386, H364-L386, G365-L386, V366-L386, S367-L386, N368-L386, L369-L386, Q370-L386, E371-L386, F372-L386, R373-L386, F374-L386, M375-L386, I376-L386, G377-L386, G378-L386, G379-L386, and/or C380-L386 of SEQ ID NO:4. Polynucleotide sequences encoding these polypeptides are also provided. The present invention also encompasses the use of these N-terminal mouse AdipoR2.v1 deletion polypeptides as immunogenic and/or antigenic epitopes as described elsewhere herein.

In preferred embodiments, the following C-terminal mouse AdipoR2.v1 deletion polypeptides are encompassed by the present invention: M1-L386, M1-A385, M1-D384, M1-E383, M1-E382, M1-T381, M1-C380, M1-G379, M1-G378, M1-G377, M1-I376, M1-M375, M1-F374, M1-R373, M1-F372, M1-E371, M1-Q370, M1-L369, M1-N368, M1-S367, M1-V366, M1-G365, M1-H364, M1-F363, M1-H362, M1-V361, M1-F360, M1-A359, M1-G358, M1-A357, M1-V356, M1-V355, M1-F354, M1-I353, M1-H352, M1-F351, M1-L350, M1-Q349, M1-H348, M1-S347, M1-H346, M1-F345, M1-W344, M1-I343, M1-D342, M1-C341, M1-K340, M1-G339, M1-P338, M1-F337, M1-F336, M1-R335, M1-E334, M1-P333, M1-I332, M1-R331, M1-A330, M1-A329, M1-Y328, M1-L327, M1-A326, M1-A325, M1-G324, M1-T323, M1-I322, M1-Y321, M1-L320, M1-S319, M1-A318, M1-M317, M1-L316, M1-M315, M1-L314, M1-W313, M1-G312, M1-I311, M1-Q310, M1-G309, M1-I308, M1-T307, M1-A306, M1-A305, M1-K304, M1-L303, M1-F302, M1-G301, M1-E300, M1-S299, M1-I298, M1-V297, M1-Y296, M1-H295, M1-L294, M1-T293, M1-P292, M1-I291, M1-I290, M1-G289, M1-S288, M1-L287, M1-G286, M1-L285, M1-G284, M1-V283, M1-F282, M1-V281, M1-G280, M1-A279, M1-R278, M1-V277, M1-G276, M1-R275, M1-Y274, M1-Q273, M1-P272, M1-T271, M1-A270, M1-F269, M1-M268, M1-D267, M1-W266, M1-Q265, M1-S264, M1-V263, M1-I262, M1-I261, M1-A260, M1-A259, M1-I258, M1-G257, M1-L256, M1-V255, M1-C254, M1-I253, M1-V252, M1-I251, M1-L250, M1-Y249, M1-I248, M1-F247, M1-C246, M1-P245, M1-Q244, M1-P243, M1-N242, M1-C241, M1-Y240, M1-F239, M1-S238, M1-Y237, M1-Y236, M1-L235, M1-W234, M1-P233, M1-V232, M1-F231, M1-S230, M1-G229, M1-M228, M1-I227, M1-L226, M1-L225, M1-A224, M1-I223, M1-G222, M1-S221, M1-Y220, M1-D219, M1-L218, M1-K217, M1-S216, M1-F215, M1-L214, M1-R213, M1-S212, M1-V211, M1-G210, M1-E209, M1-S208, M1-H207, M1-C206, M1-Y205, M1-V204, M1-T203, M1-H202, M1-F201, M1-L200, M1-W199, M1-S198, M1-F197, M1-S196, M1-L195, M1-C194, M1-L193, M1-I192, M1-A191, M1-G190, M1-L189, M1-F188, M1-F187, M1-L186, M1-G185, M1-F184, M1-V183, M1-V182, M1-K181, M1-E180, M1-Q179, M1-L178, M1-P177, M1-A176, M1-V175, M1-F174, M1-S173, M1-I172, M1-N171, M1-P170, M1-R169, M1-F168, M1-M167, M1-Y166, M1-F165, M1-I164, M1-G163, M1-L162, M1-C161, M1-L160, M1-F159, M1-F158, M1-V157, M1-C156, M1-G155, M1-L154, M1-L153, M1-H152, M1-T151, M1-W150, M1-I149, M1-N148, M1-G147, M1-T146, M1-E145, M1-T144, M1-H143, M1-I142, M1-R141, M1-F140, M1-I139, M1-S138, M1-K137, M1-F136, M1-C135, M1-A134, M1-R133, M1-F132, M1-S131, M1-P130, M1-M129, M1-P128, M1-P127, M1-R126, M1-H125, M1-G124, M1-H123, M1-L122, M1-L121, M1-F120, M1-D119, M1-N118, M1-D117, M1-K116, M1-L115, M1-W114, M1-D113, M1-P112, M1-L111, M1-V110, M1-D109, M1-H108, M1-P107, M1-I106, M1-V105, M1-R104, M1-W103, M1-R102, M1-G101, M1-E100, M1-W99, M1-V98, M1-K97, M1-C96, M1-V95, M1-F94, M1-E93, M1-E92, M1-M91, M1-R90, M1-E89, M1-M88, M1-A87, M1-H86, M1-H85, M1-A84, M1-Q83, M1-L82, M1-L81, M1-P80, M1-S79, M1-M78, M1-G77, M1-M76, M1-F75, M1-G74, M1-E73, M1-D72, M1-E71, M1-Q70, M1-S69, M1-N68, M1-D67, M1-D66, M1-H65, M1-C64, M1-E63, M1-P62, M1-E61, M1-E60, M1-P59, M1-S58, M1-N57, M1-E56, M1-Y55, M1-Y54, M1-S53, M1-S52, M1-C51, M1-V50, M1-P49, M1-T48, M1-E47, M1-L46, M1-S45, M1-P44, M1-E43, M1-L42, M1-D41, M1-G40, M1-Q39, M1-Y38, M1-N37, M1-D36, M1-N35, M1-N34, M1-S33, M1-G32, M1-R31, M1-T30, M1-D29, M1-D28, M1-L27, M1-Q26, M1-H25, M1-G24, M1-K23, M1-R22, M1-L21, M1-R20, M1-I19, M1-D18, M1-P17, M1-E16, M1-P15, M1-T14, M1-R13, M1-T12, M1-C11, M1-G10, M1-L9, M1-R8, and/or M1-H7 of SEQ ID NO:4. Polynucleotide sequences encoding these polypeptides are also provided. The present invention also encompasses the use of these C-terminal mouse AdipoR2.v1 deletion polypeptides as immunogenic and/or antigenic epitopes as described elsewhere herein.

Alternatively, preferred polypeptides of the present invention may comprise polypeptide sequences corresponding to, for example, internal regions of the mouse AdipoR2v1 polypeptide (e.g., any combination of both N- and C-terminal mouse AdipoR2v1 polypeptide deletions) of SEQ ID NO:4. For example, internal regions could be defined by the equation: amino acid NX to amino acid CX, wherein NX refers to any N-terminal deletion polypeptide amino acid of mouse AdipoR2v1 (SEQ ID NO:4), and where CX refers to any C-terminal deletion polypeptide amino acid of mouse AdipoR2v1 (SEQ ID NO:4). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the mouse AdipoR2v1 polypeptide.

The mouse AdipoR2v1 polypeptide of the present invention was determined to comprise several phosphorylation sites based upon the Motif algorithm (Genetics Computer Group, Inc.). The phosphorylation of such sites may regulate some biological activity of the mouse AdipoR2v1 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the mouse AdipoR2v1 polypeptide to associate with other polypeptides, particularly the cognate ligand for mouse AdipoR2v1, such as adiponectin, or its ability to modulate certain cellular signally pathways such as AMPK, p38 MAPK, MAPK, and/or ACC.

The mouse AdipoR2v1 polypeptide was predicted to comprise one PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. 260: 12492-12499 (1985); which are hereby incorporated by reference herein.

In preferred embodiments, the following PKC phosphorylation site polypeptide is encompassed by the present invention: RPPMPSFRACFKS (SEQ ID NO:31), and/or RPP-MPSFRACFKS (SEQ ID NO:32). Polynucleotides encoding these polypeptides are also provided. The present invention also encompasses the use of the mouse AdipoR2v1 PKC phosphorylation site polypeptides as immunogenic and/or antigenic epitopes as described elsewhere herein.

The mouse AdipoR2v1 polypeptide was predicted to comprise seven casein kinase II phosphorylation sites using the Motif algorithm (Genetics Computer Group, Inc.). Casein kinase II (CK-2) is a protein serine/threonine kinase whose activity is independent of cyclic nucleotides and calcium. CK-2 phosphorylates many different proteins. The substrate specificity [1] of this enzyme can be summarized as follows: (1) Under comparable conditions Ser is favored over Thr.; (2) An acidic residue (either Asp or Glu) must be present three residues from the C-terminal of the phosphate acceptor site; (3) Additional acidic residues in positions +1, +2, +4, and +5 increase the phosphorylation rate. Most physiological substrates have at least one acidic residue in these positions; (4) Asp is preferred to Glu as the provider of acidic determinants; and (5) A basic residue at the N-terminal of the acceptor site decreases the phosphorylation rate, while an acidic one will increase it.

A consensus pattern for casein kinase II phosphorylations site is as follows: [ST]-x(2)-[DE], wherein 'x' represents any amino acid, and S or T is the phosphorylation site.

Additional information specific to casein kinase II phosphorylation site-II domains may be found in reference to the following publication: Pinna L. A., Biochim. Biophys. Acta 1054:267-284 (1990); which is hereby incorporated herein in its entirety.

In preferred embodiments, the following casein kinase II phosphorylation site polypeptide is encompassed by the present invention: DDTRGSNNDNYQGD (SEQ ID NO:32), TPVCSSYYENSPEE (SEQ ID NO:33), SYY-ENSPEEPECHD (SEQ ID NO:34), CHDDNSQEDEGFMG (SEQ ID NO:35), VSRLFSKLDYSGIA (SEQ ID NO:36), AAIIVSQWDMFATP (SEQ ID NO:37), and/or IGGGCT-EEDAL (SEQ ID NO:38). Polynucleotides encoding these polypeptides are also provided. The present invention also encompasses the use of this casein kinase II phosphorylation site polypeptide as an immunogenic and/or antigenic epitope as described elsewhere herein.

The mouse AdipoR2v1 polypeptide has been shown to comprise one glycosylation site according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine glycosylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673-702 (1972); Pless D. D., Lennarz W. J., Proc. Natl. Acad. Sci. U.S.A. 74:134-138 (1977); Bause E., Biochem. J. 209:331-336 (1983); Gavel Y., von Heijne G., Protein Eng. 3:433-442 (1990); and Miletich J. P., Broze G. J. Jr., J. Biol. Chem. 265:11397-11404 (1990).

In preferred embodiments, the following asparagine glycosylation site polypeptide is encompassed by the present invention: YMFRPNISFVAPLQ (SEQ ID NO:39). Polynucleotides encoding this polypeptide is also provided. The present invention also encompasses the use of this mouse AdipoR2v1 asparagine glycosylation site polypeptide as an immunogenic and/or antigenic epitope as described elsewhere herein.

The mouse AdipoR2v1 polypeptide was predicted to comprise seven N-myristoylation sites using the Motif algorithm (Genetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA: protein N-myristoyl transferase (NMT), has been derived from the sequence of known N-myristoylated proteins and from studies using synthetic peptides. The specificity seems to be the following: i.) The N-terminal residue must be glycine; ii.) In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-{EDRKHPFYW}-x(2)-[STAGCN]-{P}, wherein 'x' represents any amino acid, and G is the N-myristoylation site.

Additional information specific to N-myristoylation sites may be found in reference to the following publication: Towler D. A., Gordon J. I., Adams S. P., Glaser L., Annu. Rev. Biochem. 57:69-99 (1988); and Grand R. J. A., Biochem. J. 258:625-638 (1989); which is hereby incorporated herein in its entirety.

In preferred embodiments, the following N-myristoylation site polypeptides are encompassed by the present invention: IHTETGNIWTHLLGCV (SEQ ID NO:40), GLFFLGAIL-CLSFSWL (SEQ ID NO:41), TPQYRGVRAGVFVGLG (SEQ ID NO:42), RGVRAGVFVGLGLSGI (SEQ ID NO:43), AGVFVGLGLSGIIPTL (SEQ ID NO:44), GLGLS-GIIPTLHYVIS (SEQ ID NO:45), and/or FRFMIGGGCT-EEDAL (SEQ ID NO:46). Polynucleotides encoding these polypeptides are also provided. The present invention also encompasses the use of these N-myristoylation site polypeptides as immunogenic and/or antigenic epitopes as described elsewhere herein.

The present invention encompasses the identification of compounds and drugs which stimulate mouse AdipoR2v1 on the one hand (i.e., agonists) and which inhibit the function of mouse AdipoR2v1 on the other hand (i.e., antagonists). In general, such screening procedures involve providing appropriate cells which express the receptor polypeptide of the present invention on the surface thereof. Such cells may include, for example, cells from mammals, yeast, *Drosophila* or *E. coli*. In a preferred embodiment, a polynucleotide encoding the receptor of the present invention may be employed to transfect cells to thereby express the mouse AdipoR2v1 polypeptide. The expressed receptor may then be contacted with a test compound to observe binding, stimulation or inhibition of a functional response.

Many polynucleotide sequences, such as EST sequences, are publicly available and accessible through sequence databases. Some of these sequences are related to SEQ ID NO:3 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 3961 of SEQ ID NO:3, b is an integer between 15 to 3975, where both a and b correspond to the positions of nucleotide residues shown in SEQ ID NO:3, and where b is greater than or equal to a+14.

Features of the Polypeptide Encoded by Polynucleotide No:3

The polypeptide of this polynucleotide provided as SEQ ID NO:6 (FIG. 3), encoded by the polynucleotide sequence according to SEQ ID NO:5 (FIG. 3), and/or encoded by the polynucleotide contained within the deposited clone, AdipoR3, is believed to represent a new adiponectin receptor polypeptide.

An alignment of the human AdipoR3 polypeptide of the present invention with the human AdipoR1 protein (hAdipoR1; GenbankAccession No: gi|NM_015999; SEQ ID NO:7); and the human AdipoR2 protein (hAdipoR2; Genbank Accession No: gi|NM_024551; SEQ ID NO:9) is provided in FIG. 5.

As shown in the hydropathy plot alignments of FIG. 8, the human AdipoR3 receptor shares similar topology to other adiponectin receptors.

The human AdipoR3 polypeptide (SEQ ID NO:6) of the present invention was originally described in a published PCT patent application (International Publication No. WO02/98898) and described as a polypeptide involved in the p53 pathway. However, based upon the striking structural similarity between human AdipoR3 to the human and mouse AdipoR1 and AdipoR2 receptors, the inventors have ascribed human AdipoR3 as representing a novel adiponectin receptor. Likewise, the human AdipoR3 polypeptide of the present invention is expected to share at least some biological activity with the AdipoR1, AdipoR2, and/or AdipoR2v1 receptors.

Similarly, the human AdipoR3 polypeptide is expected to be able to bind adiponectin, to bind to globular adiponectin, to bind to full-length adiponectin, to activate AMPK phosphorylation, to activate ACC phosphorylation, to activate MAPK phosphorylation, and to activate p38 MAPK phosphorylation, among others.

The determined nucleotide sequence of the human AdipoR3 cDNA in FIG. 3 (SEQ ID NO:5) contains an open reading frame encoding a protein of about 288 amino acid residues, with a deduced molecular weight of about 33.4 kDa. The amino acid sequence of the predicted human AdipoR3 polypeptide is shown in FIG. 3 (SEQ ID NO:6). The human AdipoR3 polypeptide shown in FIG. 3 was determined to share significant identity and similarity to other adiponectin receptors, as shown in FIG. 5. The percent identity and similarity values between the human AdipoR3 polypeptide to these known adiponectin receptors is provided in FIG. 11.

The human AdipoR3 polypeptide was predicted to comprise six transmembrane domains (TM1 to TM6) located from about amino acid 131 to about amino acid 149 (TM1; SEQ ID NO:81); from about amino acid 157 to about amino acid 172 (TM2; SEQ ID NO:82); from about amino acid 179 to about amino acid 197 (TM3; SEQ ID NO:83); from about amino acid 204 to about amino acid 225 (TM4; SEQ ID NO:84); from about amino acid 240 to about amino acid 263 (TM5; SEQ ID NO:85); and/or from about amino acid 266 to about amino acid 288 (TM6; SEQ ID NO:86) of SEQ ID NO:6 (FIG. 3). In this context, the term "about" may be construed to mean 1, 2, 3, 4, 5, 6, 7, 8, 9, or 10 amino acids beyond the N-Terminus and/or C-terminus of the above referenced transmembrane domain polypeptides.

In preferred embodiments, the following transmembrane domain polypeptides are encompassed by the present invention: LLGFVLFLFLEILTMLRPN (SEQ ID NO:81), QEKVIWRIFLLEKVSR (SEQ ID NO:82), YSGIAPLLIRS-FVPWLCYS (SEQ ID NO:83), PRLIYFSIIYVLGISAI-IVTWD (SEQ ID NO:84), LLGLGLSGIVPTMHFPIAEG-FVKA (SEQ ID NO:85), and/or VGQMGWFFLVAVMYITRAGLYAA (SEQ ID NO:86). Polynucleotides encoding these polypeptides are also provided. The present invention also encompasses the use of these human AdipoR3 transmembrane domain polypeptides as immunogenic and/or antigenic epitopes as described elsewhere herein.

The present invention also encompasses the polypeptide sequences that intervene between each of the predicted human AdipoR3 transmembrane domains. Since these regions are solvent accessible either extracellularly or intracellularly, they are particularly useful for designing antibodies specific to each region. Such antibodies may be useful as antagonists or agonists of the human AdipoR3 full-length polypeptide and may modulate its activity.

In preferred embodiments, the following inter-transmembrane domain polypeptides are encompassed by the present invention: MYFTAPL (SEQ ID NO:96), TFSKLY (SEQ ID NO:97), FYCSPQ (SEQ ID NO:98), and/or RFVTP-KHRQTRAGV (SEQ ID NO:99). The present invention also encompasses the use of these human AdipoR3 intratransmembrane domain polypeptides as immunogenic and/or antigenic epitopes as described elsewhere herein.

In preferred embodiments, the present invention encompasses the use of N-terminal deletions, C-terminal deletions, or any combination of N-terminal and C-terminal deletions of any one or more of the human AdipoR3 TM1 thru TM7 transmembrane domain polypeptides as antigenic and/or immunogenic epitopes.

In preferred embodiments, the present invention also encompasses the use of N-terminal deletions, C-terminal deletions, or any combination of N-terminal and C-terminal deletions of any one or more of the amino acids intervening (i.e., extracellular or intracellular loops) the human AdipoR3 TM1 thru TM7 transmembrane domain polypeptides as antigenic and/or immunogenic epitopes.

Although the human AdipoR3 receptor has seven transmembrane domains, it is believed to be structurally, topologically, and functionally distinct from G-protein coupled receptors. For example, Yamauchi et al demonstrated that the N-terminus of AdipoR1 and AdipoR2 is intracellular, as opposed to GPCRs which typically have their N-terminus extracellular. In addition, AdipoR1 and AdipoR2 do not appear to couple to G-proteins, but rather activate unique sets of signalling molecules such as PPAR-alpha, AMPK, and p38 MAPK. The same is thought to be true for the human AdipoR3 polypeptide of the present invention.

Alternatively, the human AdipoR3 receptor of the present invention may share at least some biological function with GPCRs.

The human AdipoR3 polypeptide was also determined to comprise several conserved cysteines which are denoted by dark shading, in addition to other identical residues, as shown in FIG. 5. Conservation of cysteines at key amino acid residues is indicative of conserved structural features, which may correlate with conservation of protein function and/or activity.

The human AdipoR3 polynucleotides and polypeptides of the present invention, including modulators and/or fragments thereof, have uses that include detecting, prognosing, treating, preventing, and/or ameliorating the following diseases and/or disorders: metabolic disorders, inflammatory disorders, cardiovascular disorders, obesity, diabetes, type I diabetes, type II diabetes, gestational diabetes, early onset diabetes, insulin resistance, disorders in which glucose-lowering would be beneficial, disorders in which amelioration of insulin resistance would be beneficial, disorders in which suppressed FA influx into liver would be beneficial, disorders in which reduced serum TG would be beneficial, myocardial infarction, heart failure, atherosclerosis, arteriosclerosis, disorders disclosed herein in the "Cardiovascular Disorders" section, disorders in which adiponectin levels are below normal, disorders that would benefit from increased adiponectin levels, disorders associated with aberrant vascular smooth muscle proliferation, disorders associated with aberrant foam cell formation, disorders in which inhibition of macrophage phagocytosis would be beneficial, disorders in which inhibition of TNF-alpha production would be beneficial, dyslipidemia, diabetic dyslipidemia, mixed dyslipidemia, hypercholesteremia, hypertriglyceridemia, hyperlipidemia, and anorexia nervosa.

The human AdipoR3 polynucleotides and polypeptides of the present invention, including modulators and/or fragments thereof, have uses that include detecting, prognosing, treating, preventing, and/or ameliorating the following inflammatory diseases and/or disorders: arthritis, rheumatoid arthritis, osteoarthritis, prosthetic joint failure, ulcerative colitis, Crohn's disease, inflammatory bowel and gastrointestinal diseases, gastritis, mucosal inflammation resulting from infection, enteropathy provoked by non-steroidal anti-inflammatory drugs, adult respiratory distress syndrome, asthma, cystic fibrosis, chronic obstructive pulmonary disease, myocarditis, multiple sclerosis, inflammation associated with diabetes melitus, glomerulonephritis, dermatitis, psoriasis, eczema, urticaria, burn injury, glaucoma, organ rejection, multi-organ diseases, systemic lupus erythematosis, sepsis, inflammatory sequelae of viral or bacterial infections, inflammatory conditions associated with atherosclerosis following hypoxic or ischaemic insults (with or without reperfusion, particularly in the brain or in ischaemic heart disease.

The human AdipoR3 polynucleotides and polypeptides of the present invention, including modulators and/or fragments thereof, have uses that include modulating signal transduction activity, in various cells, tissues, and organisms, and particularly in mammalian liver.

Human AdipoR3 polynucleotides and polypeptides of the present invention, including modulators and/or fragments thereof, have uses that include detecting, prognosing, treating, preventing, and/or ameliorating the following additional cardiovascular disorders: congestive heart failure, arrthymias, cardiomyopathy, microvascular disease, embolism, thrombosis, pulmonary edema, palpitation, dyspnea, angina, hypotension, syncope, heart murmur, aberrant ECG, hypertrophic cardiomyopathy, the Marfan syndrome, sudden death, prolonged QT syndrome, congenital defects, cardiac viral infections, valvular heart disease, and hypertension.

Similarly, human AdipoR3 polynucleotides and polypeptides may be useful for ameliorating cardiovascular diseases and symptoms which result indirectly from various non-cardiovascular effects, which include, but are not limited to, the following, obesity, smoking, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, have uses which include, directly or indirectly, treating, preventing, diagnosing, and/or prognosing the following, non-limiting, cardiovascular infections: blood stream invasion, bacteremia, sepsis, *Streptococcus pneumoniae* infection, group a streptococci infection, group b streptococci infection, *Enterococcus* infection, nonenterococcal group D streptococci infection, nonenterococcal group C streptococci infection, nonenterococcal group G streptococci infection, *Streptococcus viridans* infection, *Staphylococcus aureus* infection, coagulase-negative staphylococci infection, gram-negative Bacilli infection, Enterobacteriaceae infection, *Pseudomonas* spp. Infection, *Acinobacter* spp. Infection, *Flavobacterium meningosepticum* infection, *Aeromonas* spp. Infection, *Stenotrophomonas maltophilia* infection, gram-negative coccobacilli infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous *Mycobacteria* infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

Human AdipoR3 polypeptides and polynucleotides have additional uses which include diagnosing diseases related to the over and/or under expression of human AdipoR3 by identifying mutations in the human AdipoR3 gene by using human AdipoR3 sequences as probes or by determining human AdipoR3 protein or mRNA expression levels. human AdipoR3 polypeptides, may be useful for screening compounds that affect the activity of the protein. Human AdipoR3 peptides can also be used for the generation of specific antibodies and as bait in yeast two hybrid screens to find proteins that specifically interact with human AdipoR3 (described elsewhere herein).

In preferred embodiments, the following N-terminal human AdipoR3 deletion polypeptides are encompassed by the present invention: M1-A288, I2-A288, L3-A288, L4-A288, E5-A288, G6-A288, F7-A288, E8-A288, E9-A288, N10-A288, G11-A288, C12-A288, E13-A288, F14-A288, M15-A288, I16-A288, A17-A288, E18-A288, K19-A288, G20-A288, K21-A288, W22-A288, V23-A288, I24-A288, T25-A288, N26-A288, P27-A288, N28-A288, K29-A288, A30-A288, E31-A288, E32-A288, E33-A288, Q34-A288, T35-A288, C36-A288, P37-A288, V38-A288, P39-A288, Q40-A288, E41-A288, E42-A288, E43-A288, E44-A288, E45-A288, V46-A288, W47-A288, V48-A288, L49-A288, T50-A288, L51-A288, P52-A288, L53-A288, Q54-A288, A55-A288, H56-A288, H57-A288, T58-A288, M59-A288, E60-A288, K61-A288, M62-A288, E63-A288, E64-A288, F65-A288, V66-A288, Y67-A288, K68-A288, P69-A288, Q70-A288, L71-A288, Q72-A288, T73-A288, S74-A288, C75-A288, C76-A288, H77-A288, H78-A288, Q79-A288, Y80-A288, D81-A288, G82-A288, L83-A288, P84-A288, D85-A288, W86-A288, L87-A288, K88-A288, D89-A288, N90-A288, D91-A288, C92-A288, L93-A288, Q94-A288, D95-A288, N96-A288, D97-A288, C98-A288, L99-A288, L100-A288, Y101-A288, G102-A288, H103-A288, R104-A288, Q105-A288, P106-A288, M107-A288, S108-A288, S109-A288, F110-A288, W111-A288, A112-A288, C113-A288, F114-A288, K115-A288, S116-A288, I117-A288, F118-A288, Y119-A288, I120-A288, H121-A288, T122-A288, E123-A288, T124-A288, G125-A288, S126-A288, S127-A288, R128-A288, T129-A288, H130-A288, L131-A288, L132-A288, G133-A288, F134-A288, V135-A288, L136-A288, F137-A288, L138-A288, F139-A288, L140-A288, E141-A288, I142-A288, L143-A288, T144-A288, M145-A288, L146-A288, R147-A288, P148-A288, N149-A288, M150-A288, Y151-A288, F152-A288, T153-A288, A154-A288, P155-A288, L156-A288, Q157-A288, E158-A288, K159-A288, V160-A288, I161-A288, W162-A288, R163-A288, I164-A288, F165-A288, L166-A288, L167-A288, E168-A288, K169-A288, V170-A288, S171-A288, R172-A288, T173-A288, F174-A288, S175-A288, K176-A288, L177-A288, Y178-A288, Y179-A288, S180-A288, G181-A288, I182-A288, A183-A288, P184-A288, L185-A288, L186-A288, I187-A288, R188-A288, S189-A288, F190-A288, V191-A288, P192-A288, W193-A288, L194-A288, C195-A288, Y196-A288, S197-A288, F198-A288, Y199-A288, C200-A288, S201-A288, P202-A288, Q203-A288, P204-A288, R205-A288, L206-A288, I207-A288, Y208-A288, F209-A288, S210-A288, I211-A288, I212-A288, Y213-A288, V214-A288, L215-A288, G216-A288, I217-A288, S218-A288, A219-A288, I220-A288, I221-A288, V222-A288, T223-A288, W224-A288, D225-A288, R226-A288, F227-A288, V228-A288, T229-A288, P230-A288, K231-A288, H232-A288, R233-A288, Q234-A288, T235-A288, R236-A288, A237-A288, G238-A288, V239-A288, L240-A288, L241-A288, G242-A288, L243-A288, G244-A288, L245-A288, S246-A288, G247-A288, I248-A288, V249-A288, P250-A288, T251-A288, M252-A288, H253-A288, F254-A288, P255-A288, I256-A288, A257-A288, E258-A288, G259-A288, F260-A288, V261-A288, K262-A288, A263-A288, T264-A288, T265-A288, V266-A288, G267-A288, Q268-A288, M269-A288, G270-A288, W271-A288, F272-A288, F273-A288, L274-A288, V275-A288, A276-A288, V277-A288, M278-A288, Y279-A288, I280-A288, T281-A288, and/or R282-A288 of SEQ ID NO:6. Polynucleotide sequences encoding these polypeptides are also provided. The present invention also encompasses the use of these N-terminal human AdipoR3 deletion polypeptides as immunogenic and/or antigenic epitopes as described elsewhere herein.

In preferred embodiments, the following C-terminal human AdipoR3 deletion polypeptides are encompassed by the present invention: M1-A288, M1-A287, M1-Y286, M1-L285, M1-G284, M1-A283, M1-R282, M1-T281, M1-I280, M1-Y279, M1-M278, M1-V277, M1-A276, M1-V275, M1-L274, M1-F273, M1-F272, M1-W271, M1-G270, M1-M269, M1-Q268, M1-G267, M1-V266, M1-T265, M1-T264, M1-A263, M1-K262, M1-V261, M1-F260, M1-G259, M1-E258, M1-A257, M1-I256, M1-P255, M1-F254, M1-H253, M1-M252, M1-T251, M1-P250, M1-V249, M1-I248, M1-G247, M1-S246, M1-L245, M1-G244, M1-L243, M1-G242, M1-L241, M1-L240, M1-V239, M1-G238, M1-A237, M1-R236, M1-T235, M1-Q234, M1-R233, M1-H232, M1-K231, M1-P230, M1-T229, M1-V228, M1-F227, M1-R226, M1-D225, M1-W224, M1-T223, M1-V222, M1-I221, M1-I220, M1-A219, M1-S218, M1-I217, M1-G216, M1-L215, M1-V214, M1-Y213, M1-I212, M1-I211, M1-S210, M1-F209, M1-Y208, M1-I207, M1-L206, M1-R205, M1-P204, M1-Q203, M1-P202, M1-S201, M1-C200, M1-Y199, M1-F198, M1-S197, M1-Y196, M1-C195, M1-L194, M1-W193, M1-P192, M1-V191, M1-F190, M1-S189, M1-R188, M1-I187, M1-L186, M1-L185, M1-P184, M1-A183, M1-I182, M1-G181, M1-S180, M1-Y179, M1-Y178, M1-L177, M1-K176, M1-S175, M1-F174, M1-T173, M1-R172, M1-S171, M1-V170, M1-K169, M1-E168, M1-L167, M1-L166, M1-F165, M1-I164, M1-R163, M1-W162, M1-I161, M1-V160, M1-K159, M1-E158, M1-Q157, M1-L156, M1-P155, M1-A154, M1-T153, M1-F152, M1-Y151, M1-M150, M1-N149, M1-P148, M1-R147, M1-L146, M1-M145, M1-T144, M1-L143, M1-I142, M1-E141, M1-L140, M1-F139, M1-L138, M1-F137, M1-L136, M1-V135, M1-F134, M1-G133, M1-L132, M1-L131, M1-H130, M1-T129, M1-R128, M1-S127, M1-S126, M1-G125, M1-T124, M1-E123, M1-T122, M1-H121, M1-I120, M1-Y119, M1-F118, M1-I117, M1-S116, M1-K115, M1-F114, M1-C113, M1-A112, M1-W111, M1-F110, M1-S109, M1-S108, M1-M107, M1-P106, M1-Q105, M1-R104, M1-H103, M1-G102, M1-Y101, M1-L100, M1-L99, M1-C98, M1-D97, M1-N96, M1-D95, M1-Q94, M1-L93, M1-C92, M1-D91, M1-N90, M1-D89, M1-K88, M1-L87, M1-W86, M1-D85, M1-P84, M1-L83, M1-G82, M1-D81, M1-Y80, M1-Q79, M1-H78, M1-H77, M1-C76, M1-C75, M1-S74, M1-T73, M1-Q72, M1-L71, M1-Q70, M1-P69, M1-K68, M1-Y67, M1-V66, M1-F65, M1-E64, M1-E63, M1-M62, M1-K61, M1-E60, M1-M59, M1-T58, M1-H57, M1-H56, M1-A55, M1-Q54, M1-L53, M1-P52, M1-L51, M1-T50, M1-L49, M1-V48, M1-W47, M1-V46, M1-E45, M1-E44, M1-E43, M1-E42, M1-E41, M1-Q40, M1-P39, M1-V38, M1-P37, M1-C36, M1-T35, M1-Q34, M1-E33, M1-E32, M1-E31, M1-A30, M1-K29, M1-N28, M1-P27, M1-N26, M1-T25, M1-I24, M1-V23, M1-W22, M1-K21, M1-G20, M1-K19, M1-E18, M1-A17, M1-I16, M1-M15, M1-F14, M1-E13, M1-C12, M1-G11, M1-N10, M1-E9, M1-E8, and/or M1-F7 of SEQ ID NO:6. Polynucleotide sequences encoding these polypeptides are also provided. The present invention also encompasses the use of these C-terminal human AdipoR3 deletion polypeptides as immunogenic and/or antigenic epitopes as described elsewhere herein.

Alternatively, preferred polypeptides of the present invention may comprise polypeptide sequences corresponding to, for example, internal regions of the human AdipoR3 polypeptide (e.g., any combination of both N- and C-terminal human AdipoR3 polypeptide deletions) of SEQ ID NO:6. For example, internal regions could be defined by the equation: amino acid NX to amino acid CX, wherein NX refers to any N-terminal deletion polypeptide amino acid of human AdipoR3 (SEQ ID NO:6), and where CX refers to any C-terminal deletion polypeptide amino acid of human AdipoR3 (SEQ ID NO:6). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the human AdipoR3 polypeptide.

The human AdipoR3 polypeptide of the present invention was determined to comprise several phosphorylation sites based upon the Motif algorithm (Genetics Computer Group, Inc.). The phosphorylation of such sites may regulate some biological activity of the human AdipoR3 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the human AdipoR3 polypeptide to associate with other polypeptides, particularly the cognate ligand for human AdipoR3, such as adiponectin, or its ability to modulate certain cellular signally pathways such as AMPK, p38 MAPK, MAPK, and/or ACC.

Specifically, the human AdipoR3 polypeptide was predicted to comprise one tyrosine phosphorylation site using the Motif algorithm (Genetics Computer Group, Inc.). Such sites are phosphorylated at the tyrosine amino acid residue. The consensus pattern for tyrosine phosphorylation sites are as follows: [RK]-x(2)-[DE]-x(3)-Y, or or [RK]-x(3)-[DE]-x(2)-Y, where Y represents the phosphorylation site and 'x' represents an intervening amino acid residue. Additional information specific to tyrosine phosphorylation sites can be found in Patschinsky T., Hunter T., Esch F. S., Cooper J. A., Sefton B. M., Proc. Natl. Acad. Sci. U.S.A. 79:973-977 (1982); Hunter T., J. Biol. Chem. 257:4843-4848 (1982), and Cooper J. A., Esch F. S., Taylor S. S., Hunter T., J. Biol. Chem. 259:7835-7841 (1984), which are hereby incorporated herein by reference.

In preferred embodiments, the following tyrosine phosphorylation site polypeptides are encompassed by the present invention: Y HHTMEKMEEFVYKPQLQ (SEQ ID NO:47). Polynucleotides encoding these polypeptides are also provided. The present invention also encompasses the use of these human AdipoR3 tyrosine phosphorylation site polypeptides as immunogenic and/or antigenic epitopes as described elsewhere herein.

The human AdipoR3 polypeptide was predicted to comprise two PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. 260: 12492-12499 (1985); which are hereby incorporated by reference herein.

In preferred embodiments, the following PKC phosphorylation site polypeptide is encompassed by the present invention: HTETGSSRTHLLG (SEQ ID NO:48), and/or WDRFVTPKHRQTR (SEQ ID NO:49). Polynucleotides encoding these polypeptides are also provided. The present invention also encompasses the use of the human AdipoR3 PKC phosphorylation site polypeptides as immunogenic and/or antigenic epitopes as described elsewhere herein.

The human AdipoR3 polypeptide was predicted to comprise four N-myristoylation sites using the Motif algorithm (Genetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA: protein N-myristoyl transferase (NMT), has been derived from the sequence of known N-myristoylated proteins and from studies using synthetic peptides. The specificity seems to be the following: i.) The N-terminal residue must be glycine; ii.) In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-{EDRKHPFYW}-x(2)-[STAGCN]-{P}, wherein 'x' represents any amino acid, and G is the N-myristoylation site.

Additional information specific to N-myristoylation sites may be found in reference to the following publication: Towler D. A., Gordon J. I., Adams S. P., Glaser L., Annu. Rev. Biochem. 57:69-99 (1988); and Grand R. J. A., Biochem. J. 258:625-638 (1989); which is hereby incorporated herein in its entirety.

In preferred embodiments, the following N-myristoylation site polypeptides are encompassed by the present invention: IHTETGSSRTHLLGFV (SEQ ID NO:50), RQTRAGVLLGLGLSGI (SEQ ID NO:51), AGVLLGLGLSGIVPTM (SEQ ID NO:52), and/or GLGLSGIVPTMHFPIA (SEQ ID NO:53). Polynucleotides encoding these polypeptides are also provided. The present invention also encompasses the use of these N-myristoylation site polypeptides as immunogenic and/or antigenic epitopes as described elsewhere herein.

The present invention encompasses the identification of compounds and drugs which stimulate human AdipoR3 on the one hand (i.e., agonists) and which inhibit the function of human AdipoR3 on the other hand (i.e., antagonists). In general, such screening procedures involve providing appropriate cells which express the receptor polypeptide of the present invention on the surface thereof. Such cells may include, for example, cells from mammals, yeast, *Drosophila* or *E. coli*. In a preferred embodiment, a polynucleotide encoding the receptor of the present invention may be employed to transfect cells to thereby express the human AdipoR3 polypeptide. The expressed receptor may then be contacted with a test compound to observe binding, stimulation or inhibition of a functional response.

Many polynucleotide sequences, such as EST sequences, are publicly available and accessible through sequence databases. Some of these sequences are related to SEQ ID NO:5 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 853 of SEQ ID NO:5, b is an integer between 15 to 867, where both a and b correspond to the positions of nucleotide residues shown in SEQ ID NO:5, and where b is greater than or equal to a+14.

Features of the Polypeptide Encoded by Polynucleotide No:4

The polypeptide of this polynucleotide provided as SEQ ID NO:102 (FIGS. 12A-B), encoded by the polynucleotide sequence according to SEQ ID NO:101 (FIGS. 12A-B), and/or encoded by the polynucleotide contained within the deposited clone, AdipoR3v1, is believed to represent a novel variant of the AdipoR3 (FIG. 3; SEQ ID NO:6) adiponectin receptor polypeptide of the present invention.

An alignment of the AdipoR3v1 polypeptide of the present invention (SEQ ID NO:102) with the human AdipoR1 protein (hAdipoR1; GenbankAccession No: gi|NM_015999; SEQ ID NO:7); and the human AdipoR3 protein (AdipoR3; SEQ ID NO:9) is provided in FIG. 14.

As shown in the alignment, the AdipoR3v1 receptor shares significantly more identity with the human AdipoR1 polypeptide than the AdipoR3 polypeptide—sharing significant portions of both the N- and C-terminus of AdipoR1.

Based upon the striking structural similarity between AdipoR3v1 to the human AdipoR1 receptor, the inventors have ascribed AdipoR3v1 as representing another novel adiponectin receptor. Likewise, the AdipoR3v1 polypeptide of the present invention is expected to share at least some biological activity with the human AdipoR1, AdipoR2, AdipoR2v1, and/or AdipoR2v2 receptors.

Similarly, the AdipoR3v1 polypeptide is expected to be able to bind adiponectin, to bind to globular adiponectin, to bind to full-length adiponectin, to activate AMPK phosphorylation, to activate ACC phosphorylation, to activate MAPK phosphorylation, and to activate p38 MAPK phosphorylation, among others.

The determined nucleotide sequence of the AdipoR3v1 cDNA in FIGS. 12A-B (SEQ ID NO:101) contains an open reading frame encoding a protein of about 381 amino acid residues, with a deduced molecular weight of about 43.8 kDa. The amino acid sequence of the predicted AdipoR3v1 polypeptide is shown in FIGS. 12A-B (SEQ ID NO:102). The AdipoR3v1 polypeptide shown in FIGS. 12A-B was determined to share significant identity and similarity to other adiponectin receptors, as shown in FIG. 14. The percent identity and similarity values between the AdipoR3v1 polypeptide to these known adiponectin receptors is provided in FIG. 11.

Like AdipoR3, the AdipoR3v1 receptor has seven transmembrane domains. Despite the presence of these transmembrane domains, it is believed to be structurally, topologically, and functionally distinct from G-protein coupled receptors. For example, Yamauchi et al demonstrated that the N-terminus of AdipoR1 and AdipoR2 is intracellular, as opposed to GPCRs which typically have their N-terminus extracellular. In addition, AdipoR1 and AdipoR2 do not appear to couple to G-proteins, but rather activate unique sets of signalling molecules such as PPAR-alpha, AMPK, and p38 MAPK. The same is thought to be true for the human AdipoR3v1 polypeptide of the present invention.

Alternatively, the AdipoR3v1 receptor of the present invention may share at least some biological function with GPCRs.

The AdipoR3v1 polypeptide was also determined to comprise several conserved cysteines which are denoted by dark shading, in addition to other identical residues, as shown in FIG. 14. Conservation of cysteines at key amino acid residues is indicative of conserved structural features, which may correlate with conservation of protein function and/or activity.

The AdipoR3v1 polynucleotides and polypeptides of the present invention, including modulators and/or fragments thereof, have uses that include detecting, prognosing, treating, preventing, and/or ameliorating the following diseases and/or disorders: metabolic disorders, inflammatory disorders, cardiovascular disorders, obesity, diabetes, type I diabetes, type II diabetes, gestational diabetes, early onset diabetes, insulin resistance, disorders in which glucose-lowering would be beneficial, disorders in which amelioration of insulin resistance would be beneficial, disorders in which suppressed FA influx into liver would be beneficial, disorders in which reduced serum TG would be beneficial, myocardial infarction, heart failure, atherosclerosis, arteriosclerosis, disorders disclosed herein in the "Cardiovascular Disorders" section, disorders in which adiponectin levels are below normal, disorders that would benefit from increased adiponectin levels, disorders associated with aberrant vascular smooth muscle proliferation, disorders associated with aberrant foam cell formation, disorders in which inhibition of macrophage phagocytosis would be beneficial, disorders in which inhibition of TNF-alpha production would be beneficial, dyslipidemia, diabetic dyslipidemia, mixed dyslipidemia, hypercholesteremia, hypertriglyceridemia, hyperlipidemia, and anorexia nervosa.

The AdipoR3v1 polynucleotides and polypeptides of the present invention, including modulators and/or fragments thereof, have uses that include detecting, prognosing, treating, preventing, and/or ameliorating the following inflammatory diseases and/or disorders: arthritis, rheumatoid arthritis, osteoarthritis, prosthetic joint failure, ulcerative colitis, Crohn's disease, inflammatory bowel and gastrointestinal diseases, gastritis, mucosal inflammation resulting from infection, enteropathy provoked by non-steroidal anti-inflammatory drugs, adult respiratory distress syndrome, asthma, cystic fibrosis, chronic obstructive pulmonary disease, myocarditis, multiple sclerosis, inflammation associated with diabetes melitus, glomerulonephritis, dermatitis, psoriasis, eczema, urticaria, burn injury, glaucoma, organ rejection, multi-organ diseases, systemic lupus erythematosis, sepsis, inflammatory sequelae of viral or bacterial infections, inflammatory conditions associated with atherosclerosis following hypoxic or ischaemic insults (with or without reperfusion, particularly in the brain or in ischaemic heart disease.

The AdipoR3v1 polynucleotides and polypeptides of the present invention, including modulators and/or fragments thereof, have uses that include modulating signal transduction activity, in various cells, tissues, and organisms, and particularly in mammalian liver.

AdipoR3v1 polynucleotides and polypeptides of the present invention, including modulators and/or fragments thereof, have uses that include detecting, prognosing, treating, preventing, and/or ameliorating the following additional cardiovascular disorders: congestive heart failure, arrthymias, cardiomyopathy, microvascular disease, embolism, thrombosis, pulmonary edema, palpitation, dyspnea, angina, hypotension, syncope, heart murmur, aberrant ECG, hypertrophic cardiomyopathy, the Marfan syndrome, sudden death, prolonged QT syndrome, congenital defects, cardiac viral infections, valvular heart disease, and hypertension.

Similarly, AdipoR3v1 polynucleotides and polypeptides may be useful for ameliorating cardiovascular diseases and symptoms which result indirectly from various non-cardiovascular effects, which include, but are not limited to, the following, obesity, smoking, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, have uses which include, directly or indirectly, treating, preventing, diagnosing, and/or prognosing the following, non-limiting, cardiovascular infections: blood stream invasion, bacteremia, sepsis, *Streptococcus pneumoniae* infection, group a streptococci infection, group b streptococci infection, *Enterococcus* infection, nonenterococcal group D streptococci infection, nonenterococcal group C streptococci infection, nonenterococcal group G streptococci infection, *Streptococcus viridans* infection, *Staphylococcus aureus* infection, coagulase-negative staphylococci infection, gram-negative Bacilli infection, Enterobacteriaceae infection, *Pseudomonas* spp. Infection, *Acinobacter* spp. Infection, *Flavobacterium meningosepticum* infection, *Aeromonas* spp. Infection, *Stenotrophomonas maltophilia* infection, gram-negative coccobacilli infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous *Mycobacteria* infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

AdipoR3v1 polypeptides and polynucleotides have additional uses which include diagnosing diseases related to the over and/or under expression of AdipoR3v1 by identifying mutations in the AdipoR3v1 gene by using AdipoR3v1 sequences as probes or by determining AdipoR3v1 protein or mRNA expression levels. AdipoR3v1 polypeptides, may be useful for screening compounds that affect the activity of the protein. Human AdipoR3v1 peptides can also be used for the generation of specific antibodies and as bait in yeast two hybrid screens to find proteins that specifically interact with AdipoR3v1 (described elsewhere herein).

In preferred embodiments, the following N-terminal AdipoR3v1 deletion polypeptides are encompassed by the present invention: M1-L381, S2-L381, S3-L381, H4-L381, K5-L381, G6-L381, S7-L381, V8-L381, V9-L381, A10-L381, R11-L381, N12-L381, G13-L381, A14-L381, P15-L381, A16-L381, S17-L381, N18-L381, R19-L381, E20-L381, T21-L381, D22-L381, M23-L381, V24-L381, E25-L381, L26-L381, A27-L381, E28-L381, S29-L381, E30-L381, L31-L381, S32-L381, P33-L381, L34-L381, L35-L381, Q36-L381, E37-L381, K38-L381, G39-L381, K40-L381, W41-L381, V42-L381, I43-L381, T44-L381, N45-L381, P46-L381, N47-L381, K48-L381, A49-L381, E50-L381, E51-L381, E52-L381, Q53-L381, T54-L381, C55-L381, P56-L381, V57-L381, P58-L381, Q59-L381, E60-L381, E61-L381, E62-L381, E63-L381, E64-L381, V65-L381, W66-L381, V67-L381, L68-L381, T69-L381, L70-L381, P71-L381, L72-L381, Q73-L381, A74-L381, H75-L381, H76-L381, T77-L381, M78-L381, E79-L381, K80-L381, M81-L381, E82-L381, E83-L381, F84-L381, V85-L381, Y86-L381, K87-L381, L88-L381, Q89-L381, T90-L381, S91-L381, C92-L381, C93-L381, H94-L381, H95-L381, Q96-L381, Y97-L381, D98-L381, G99-L381, L100-L381, P101-L381, D102-L381, W103-L381, L104-L381, K105-L381, D106-L381, N107-L381, D108-L381, C109-L381, L110-L381, Q111-L381, D112-L381, N113-L381, D114-L381, C115-L381, L116-L381, L117-L381, Y118-L381, G119-L381, H120-L381, R121-L381, Q122-L381, P123-L381, M124-L381, S125-L381, S126-L381, F127-L381, W128-L381, A129-L381, C130-L381, F131-L381, K132-L381, S133-L381, I134-L381, F135-L381, Y136-L381, I137-L381, H138-L381, T139-L381, E140-L381, T141-L381, G142-L381, S143-L381, S144-L381, R145-L381, L381, T146-L381, H147-L381, L148-L381, L149-L381, G150-L381, F151-L381, V152-L381, L153-L381, F154-L381, L155-L381, F156-L381, L157-L381, E158-L381, I159-L381, L160-L381, T161-L381, M162-L381, L163-L381, R164-L381, P165-L381, N166-L381, M167-L381, Y168-L381, F169-L381, T170-L381, A171-L381, P172-L381, L173-L381, Q174-L381, E175-L381, K176-L381, V177-L381, I178-L381, W179-L381, R180-L381, I181-L381, F182-L381, L183-L381, L184-L381, G185-L381, A186-L381, V187-L381, L188-L381, S189-L381, L190-L381, S191-L381, F192-L381, S193-L381, W194-L381, L195-L381, V196-L381, R197-L381, T198-L381, V199-L381, Y200-L381, C201-L381, H202-L381, S203-L381, E204-L381, K205-L381, V206-L381, S207-L381, R208-L381, T209-L381, F210-L381, S211-L381, K212-L381, L213-L381, Y214-L381, Y215-L381, S216-L381, G217-L381, I218-L381, A219-L381, P220-L381, L221-L381, L222-L381, I223-L381, R224-L381, S225-L381, F226-L381, V227-L381, P228-L381, W229-L381, L230-L381, C231-L381, Y232-L381, S233-L381, F234-L381, Y235-L381, C236-L381, S237-L381, P238-L381, Q239-L381, P240-L381, R241-L381, L242-L381, I243-L381, Y244-L381, F245-L381, S246-L381, I247-L381, I248-L381, Y249-L381, V250-L381, L251-L381, G252-L381, I253-L381, S254-L381, A255-L381, I256-L381, I257-L381, V258-L381, D259-L381, Q260-L381, W261-L381, D262-L381, R263-L381, F264-L381, V265-L381, T266-L381, P267-L381, K268-L381, H269-L381, R270-L381, Q271-L381, T272-L381, R273-L381, A274-L381, G275-L381, V276-L381, L277-L381, L278-L381, G279-L381, L280-L381, G281-L381, L282-L381, S283-L381, G284-L381, I285-L381, V286-L381, P287-L381, T288-L381, M289-L381, H290-L381, F291-L381, P292-L381, I293-L381, A294-L381, E295-L381, G296-L381, F297-L381, V298-L381, K299-L381, A300-L381, T301-L381, T302-L381, V303-L381, G304-L381, Q305-L381, M306-L381, G307-L381, W308-L381, F309-L381, F310-L381, L311-L381, V312-L381, A313-L381, V314-L381, M315-L381, Y316-L381, I317-L381, T318-L381, R319-L381, A320-L381, G321-L381, L322-L381, Y323-L381, A324-L381, A325-L381, L326-L381, I327-L381, P328-L381, E329-L381, R330-L381, F331-L381, F332-L381, P333-L381, G334-L381, K335-L381, L336-L381, D337-L381, I338-L381, W339-L381, F340-L381, Q341-L381, S342-L381, Q343-L381, Q344-L381, I345-L381, F346-L381, H347-L381, V348-L381, L349-L381, M350-L381, V351-L381, T352-L381, V353-L381, A354-L381, F355-L381, V356-L381, H357-L381, F358-L381, C359-L381, G360-L381, V361-L381, S362-L381, N363-L381, L364-L381, Q365-L381, E366-L381, F367-L381, H368-L381, Y369-L381, S370-L381, R371-L381, E372-L381, G373-L381, D374-L381, and/or C375-L381 of SEQ ID NO:102. Polynucleotide sequences encoding these polypeptides are also provided. The present invention also encompasses the use of these N-terminal AdipoR3v1 deletion polypeptides as immunogenic and/or antigenic epitopes as described elsewhere herein.

In preferred embodiments, the following C-terminal AdipoR3v1 deletion polypeptides are encompassed by the present invention: M1-L381, M1-L380, M1-S379, M1-D378, M1-D377, M1-T376, M1-C375, M1-D374, M1-G373, M1-E372, M1-R371, M1-S370, M1-Y369, M1-H368, M1-F367, M1-E366, M1-Q365, M1-L364, M1-N363, M1-S362, M1-V361, M1-G360, M1-C359, M1-F358, M1-H357, M1-V356, M1-F355, M1-A354, M1-V353, M1-T352, M1-V351, M1-M350, M1-L349, M1-V348, M1-H347, M1-F346, M1-I345, M1-Q344, M1-Q343, M1-S342, M1-Q341, M1-F340, M1-W339, M1-I338, M1-D337, M1-L336, M1-K335, M1-G334, M1-P333, M1-F332, M1-F331, M1-R330, M1-E329, M1-P328, M1-I327, M1-L326, M1-A325, M1-A324, M1-Y323, M1-L322, M1-G321, M1-A320, M1-R319, M1-T318, M1-I317, M1-Y316, M1-M315, M1-V314, M1-A313, M1-V312, M1-L311, M1-F310, M1-F309, M1-W308, M1-G307, M1-M306, M1-Q305, M1-G304, M1-V303, M1-T302, M1-T301, M1-A300, M1-K299, M1-V298, M1-F297, M1-G296, M1-E295, M1-A294, M1-I293, M1-P292, M1-F291, M1-H290, M1-M289, M1-T288, M1-P287, M1-V286, M1-I285, M1-G284, M1-S283, M1-L282, M1-G281, M1-L280, M1-G279, M1-L278, M1-L277, M1-V276, M1-G275, M1-A274, M1-R273, M1-T272, M1-Q271, M1-R270, M1-H269, M1-K268, M1-P267, M1-T266, M1-V265, M1-F264, M1-R263, M1-D262, M1-W261, M1-Q260, M1-D259, M1-V258, M1-I257, M1-I256, M1-A255, M1-S254, M1-I253, M1-G252, M1-L251, M1-V250, M1-Y249, M1-I248, M1-I247, M1-S246, M1-F245, M1-Y244, M1-I243, M1-L242, M1-R241, M1-P240, M1-Q239, M1-P238, M1-S237, M1-C236, M1-Y235, M1-F234, M1-S233, M1-Y232, M1-C231, M1-L230, M1-W229, M1-P228, M1-V227, M1-F226, M1-S225, M1-R224, M1-I223, M1-L222, M1-L221, M1-P220, M1-A219, M1-I218, M1-G217, M1-S216, M1-Y215, M1-Y214, M1-L213, M1-K212, M1-S211, M1-F210, M1-T209, M1-R208, M1-S207, M1-V206, M1-K205, M1-E204, M1-S203, M1-H202, M1-C201, M1-Y200, M1-V199, M1-T198, M1-R197, M1-V196, M1-L195, M1-W194, M1-S193, M1-F192, M1-S191, M1-L190, M1-S189, M1-L188, M1-V187, M1-A186, M1-G185, M1-L184, M1-L183, M1-F182, M1-I181, M1-R180, M1-W179, M1-I178, M1-V177, M1-K176, M1-E175, M1-Q174, M1-L173, M1-P172, M1-A171, M1-T170, M1-F169, M1-Y168, M1-M167, M1-N166, M1-P165, M1-R164, M1-L163, M1-M162, M1-T161, M1-L160, M1-I159, M1-E158, M1-L157, M1-F156, M1-L155, M1-F154, M1-L153, M1-V152, M1-F151, M1-G150, M1-L149, M1-L148, M1-H147, M1-T146, M1-R145, M1-S144, M1-S143, M1-G142, M1-T141, M1-E140, M1-T139, M1-H138, M1-I137, M1-Y136, M1-F135, M1-I134, M1-S133, M1-K132, M1-F131, M1-C130, M1-A129, M1-W128, M1-F127, M1-S126, M1-S125, M1-M124, M1-P123, M1-Q122, M1-R121, M1-H120, M1-G119, M1-Y118, M1-L117, M1-L116, M1-C115, M1-D114, M1-N113, M1-D112, M1-Q111, M1-L110, M1-C109, M1-D108, M1-N107, M1-D106, M1-K105, M1-L104, M1-W103, M1-D102, M1-P101, ML-L100, M1-G99, M1-D98, M1-Y97, M1-Q96, M1-H95, M1-H94, M1-C93, M1-C92, M1-S91, M1-T90, M1-Q89, M1-L88, M1-K87, M1-Y86, M1-V85, M1-F84, M1-E83, M1-E82, M1-M81, M1-K80, M1-E79, M1-M78, M1-T77, M1-H76, M1-H75, M1-A74, M1-Q73, M1-L72, M1-P71, M1-L70, M1-T69, M1-L68, M1-V67, M1-W66, M1-V65, M1-E64, M1-E63, M1-E62, M1-E61, M1-E60, M1-Q59, M1-P58, M1-V57, M1-P56, M1-C55, M1-T54, M1-Q53, M1-E52, M1-E51, M1-E50, M1-A49, M1-K48, M1-N47, M1-P46, M1-N45, M1-T44, M1-I43, M1-V42, M1-W41, M1-K40, M1-G39, M1-K38, M1-E37, M1-Q36, M1-L35, M1-L34, M1-P33, M1-S32, M1-L31, M1-E30, M1-S29, M1-E28, M1-A27, M1-L26, M1-E25, M1-V24, M1-M23, M1-D22, M1-T21, M1-E20, M1-R19, M1-N18, M1-S17, M1-A16, M1-P15, M1-A14, M1-G13, M1-N12, M1-R11, M1-A10, M1-V9, M1-V8, and/or M1-S7 of SEQ ID NO:102. Polynucleotide sequences encoding these polypeptides are also provided. The present invention also encompasses the use of these C-terminal AdipoR3v1 deletion polypeptides as immunogenic and/or antigenic epitopes as described elsewhere herein.

Alternatively, preferred polypeptides of the present invention may comprise polypeptide sequences corresponding to, for example, internal regions of the AdipoR3v1 polypeptide (e.g., any combination of both N- and C-terminal AdipoR3v1 polypeptide deletions) of SEQ ID NO:102. For example, internal regions could be defined by the equation: amino acid NX to amino acid CX, wherein NX refers to any N-terminal deletion polypeptide amino acid of AdipoR3v1 (SEQ ID NO:102), and where CX refers to any C-terminal deletion polypeptide amino acid of AdipoR3v1 (SEQ ID NO:102). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the AdipoR3v1 polypeptide.

The AdipoR3v1 polypeptide of the present invention was determined to comprise several phosphorylation sites based upon the Motif algorithm (Genetics Computer Group, Inc.). The phosphorylation of such sites may regulate some biological activity of the AdipoR3v1 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the AdipoR3v1 polypeptide to associate with other polypeptides, particularly the cognate ligand for AdipoR3v1, such as adiponectin, or its ability to modulate certain cellular signally pathways such as AMPK, p38 MAPK, MAPK, and/or ACC.

Specifically, the human AdipoR3v1 polypeptide was predicted to comprise one tyrosine phosphorylation site using the Motif algorithm (Genetics Computer Group, Inc.). Such sites are phosphorylated at the tyrosine amino acid residue. The consensus pattern for tyrosine phosphorylation sites are as follows: [RK]-x(2)-[DE]-x(3)-Y, or [RK]-x(3)-[DE]-x(2)-Y, where Y represents the phosphorylation site and 'x' represents an intervening amino acid residue. Additional information specific to tyrosine phosphorylation sites can be found in Patschinsky T., Hunter T., Esch F. S., Cooper J. A., Sefton B. M., Proc. Natl. Acad. Sci. U.S.A. 79:973-977 (1982); Hunter T., J. Biol. Chem. 257:4843-4848 (1982), and Cooper J. A., Esch F. S., Taylor S. S., Hunter T., J. Biol. Chem. 259:7835-7841 (1984), which are hereby incorporated herein by reference.

In preferred embodiments, the following tyrosine phosphorylation site polypeptides are encompassed by the present invention: YHHTMEKMEEFVYKLQTS (SEQ ID NO:105). Polynucleotides encoding these polypeptides are also provided. The present invention also encompasses the use of these human AdipoR3v1 tyrosine phosphorylation site polypeptides as immunogenic and/or antigenic epitopes as described elsewhere herein.

The AdipoR3v1 polypeptide was predicted to comprise five PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. 260: 12492-12499 (1985); which are hereby incorporated by reference herein.

In preferred embodiments, the following PKC phosphorylation site polypeptide is encompassed by the present invention: MSSHKGSVVA (SEQ ID NO:106), NGAPASNRETDMV (SEQ ID NO:107), HTETGSSRTHLLG (SEQ ID NO:108), TVYCHSEKVSRTF (SEQ ID NO:109), and/or WDRFVTPKHRQTR (SEQ ID NO:110). Polynucleotides encoding these polypeptides are also provided. The present invention also encompasses the use of the AdipoR3v1 PKC phosphorylation site polypeptides as immunogenic and/or antigenic epitopes as described elsewhere herein.

The AdipoR3v1 polypeptide was predicted to comprise one casein kinase II phosphorylation site using the Motif algorithm (Genetics Computer Group, Inc.). Casein kinase II (CK-2) is a protein serine/threonine kinase whose activity is independent of cyclic nucleotides and calcium. CK-2 phosphorylates many different proteins. The substrate specificity [1] of this enzyme can be summarized as follows: (1) Under comparable conditions Ser is favored over Thr.; (2) An acidic residue (either Asp or Glu) must be present three residues from the C-terminal of the phosphate acceptor site; (3) Additional acidic residues in positions +1, +2, +4, and +5 increase the phosphorylation rate. Most physiological substrates have at least one acidic residue in these positions; (4) Asp is preferred to Glu as the provider of acidic determinants; and (5) A basic residue at the N-terminal of the acceptor site decreases the phosphorylation rate, while an acidic one will increase it.

A consensus pattern for casein kinase II phosphorylations site is as follows: [ST]-x(2)-[DE], wherein 'x' represents any amino acid, and S or T is the phosphorylation site.

Additional information specific to casein kinase II phosphorylation sites may be found in reference to the following publication: Pinna L. A., Biochim. Biophys. Acta 1054:267-284 (1990); which is hereby incorporated herein in its entirety.

In preferred embodiments, the following casein kinase II phosphorylation site polypeptide is encompassed by the present invention: NGAPASNRETDMVE (SEQ ID NO:111). Polynucleotides encoding these polypeptides are also provided. The present invention also encompasses the use of this casein kinase II phosphorylation site polypeptide as an immunogenic and/or antigenic epitope as described elsewhere herein.

The AdipoR3v1 polypeptide was predicted to comprise eight N-myristoylation sites using the Motif algorithm (Genetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA: protein N-myristoyl transferase (NMT), has been derived from the sequence of known N-myristoylated proteins and from studies using synthetic peptides. The specificity seems to be the following: i.) The N-terminal residue must be glycine; ii.) In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-{EDRKHPFYW}-x(2)-[STAGCN]-{P}, wherein 'x' represents any amino acid, and G is the N-myristoylation site.

Additional information specific to N-myristoylation sites may be found in reference to the following publication: Towler D. A., Gordon J. I., Adams S. P., Glaser L., Annu. Rev. Biochem. 57:69-99 (1988); and Grand R. J. A., Biochem. J. 258:625-638 (1989); which is hereby incorporated herein in its entirety.

In preferred embodiments, the following N-myristoylation site polypeptides are encompassed by the present invention:

MSSHKGSVVARNGAPA (SEQ ID NO:112), VVARNGA-PASNRETDM (SEQ ID NO:113), IHTETGSSRTHLLGFV (SEQ ID NO:114), RIFLLGAVLSLSFSWL (SEQ ID NO:115), RQTRAGVLLGLGLSGI (SEQ ID NO:116), AGVLLGLGLSGIVPTM (SEQ ID NO:117), GLGLS-GIVPTMHFPIA (SEQ ID NO:118), and/or YITRAG-LYAALIPERF (SEQ ID NO:119). Polynucleotides encoding these polypeptides are also provided. The present invention also encompasses the use of these N-myristoylation site polypeptides as immunogenic and/or antigenic epitopes as described elsewhere herein.

The present invention encompasses the identification of compounds and drugs which stimulate AdipoR3v1 on the one hand (i.e., agonists) and which inhibit the function of AdipoR3v1 on the other hand (i.e., antagonists). In general, such screening procedures involve providing appropriate cells which express the receptor polypeptide of the present invention on the surface thereof. Such cells may include, for example, cells from mammals, yeast, *Drosophila* or *E. coli*. In a preferred embodiment, a polynucleotide encoding the receptor of the present invention may be employed to transfect cells to thereby express the AdipoR3v1 polypeptide. The expressed receptor may then be contacted with a test compound to observe binding, stimulation or inhibition of a functional response.

Many polynucleotide sequences, such as EST sequences, are publicly available and accessible through sequence databases. Some of these sequences are related to SEQ ID NO:101 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 1132 of SEQ ID NO:101, b is an integer between 15 to 1146, where both a and b correspond to the positions of nucleotide residues shown in SEQ ID NO:101, and where b is greater than or equal to a+14.

Features of the Polypeptide Encoded by Polynucleotide No:5

The polypeptide of this polynucleotide provided as SEQ ID NO:104 (FIGS. 13A-B), encoded by the polynucleotide sequence according to SEQ ID NO:103 (FIGS. 13A-B), and/or encoded by the polynucleotide contained within the deposited clone, human AdipoR2v2 (also referred to as hAdipoR2v2), is believed to represent the physiologically relevant form of the human AdipoR2 polypeptide.

An alignment of the human AdipoR2v2 polypeptide of the present invention with the human AdipoR1 protein (hAdipoR1; GenbankAccession No: gi|NM_015999; SEQ ID NO:7); the human AdipoR2v1 protein of the present invention (hAdipoR2v1; SEQ ID NO:2); and the mouse AdipoR2v1 protein of the present invention (mAdipoR2v1; SEQ ID NO:4) is provided in FIG. 15.

An additional schematic representation of the human AdipoR2v2 polypeptide sequence compared to the human AdipoR1, human AdipoR2, and human AdipoR2v1 polypeptides is provided in FIG. 27. In particular, it is noted that the human AdipoR2v2 contains a novel hydrophobic region inbetween two of the adjacent transmembrane domain containing regions of the protein.

The human AdipoR2v2 polypeptide (SEQ ID NO:104) of the present invention is believed to represent a novel splice variant form of the human AdipoR2v1 polypeptide of the present invention (SEQ ID NO:2). Likewise, the AdipoR2v2 polypeptide is expected to share the same or similar biological activity as the reported AdipoR2 sequence, and/or the same or similar biological activity as the human AdipoR2v1 polypeptide of the present invention. Preferably, the AdipoR2v2 polypeptide is expected to have increased biological activity relative to the reported AdipoR2 sequence. Such increased biological function may be in the form of increased binding affinity for adiponectin, increased binding affinity for globular adiponectin, increased binding affinity for full-length adiponectin, increased association rate constant for adiponectin, increased association rate constant for globular adiponectin, increased association rate constant for full-length adiponectin, decreased dissociation rate constant for adiponectin, decreased dissociation rate constant for globular adiponectin, decreased dissociation rate constant for full-length adiponectin, increased ability to regulate AMPK phosphorylation, increased ability to regulate ACC phosphorylation, increased ability to regulate MAPK phosphorylation, increased ability to regulate p38 MAPK phosphorylation, among others.

Alternatively, the ability of the AdipoR2v2 sequence of the present invention to bind to adiponectin may be less than the reported AdipoR2 sequence. Thus, the AdipoR2v2 polypeptide may have increased biological activity relative to the reported AdipoR2 sequence. Such increased biological function may be in the form of decreased binding affinity for adiponectin, decreased binding affinity for globular adiponectin, decreased binding affinity for full-length adiponectin, decreased association rate constant for adiponectin, decreased association rate constant for globular adiponectin, decreased association rate constant for full-length adiponectin, increased dissociation rate constant for adiponectin, increased dissociation rate constant for globular adiponectin, increased dissociation rate constant for full-length adiponectin, decreased ability to regulate AMPK phosphorylation, decreased ability to regulate ACC phosphorylation, decreased ability to regulate MAPK phosphorylation, decreased ability to regulate p38 MAPK phosphorylation, among others.

The determined nucleotide sequence of the human AdipoR2v2 cDNA in FIGS. 13A-B (SEQ ID NO:103) contains an open reading frame encoding a protein of about 421 amino acid residues, with a deduced molecular weight of about 47.3 kDa. The amino acid sequence of the predicted human AdipoR2v2 polypeptide is shown in FIGS. 13A-B (SEQ ID NO:104). By virtue of the human AdipoR2v2 protein representing a splice variant form of the human AdipoR2v1 polypeptide, the human AdipoR2v2 polypeptide shown in FIGS. 13A-B was determined to share significant identity and similarity to other adiponectin receptors, as shown in FIG. 15. The percent identity and similarity values between the human AdipoR2v2 polypeptide to these known adiponectin receptors is provided in FIG. 18.

Consistent with the inventors description of the human AdipoR2v2 polypeptide representing another physiologically relevant form of the AdipoR2 polypeptide, the inventors determined that overexpressed forms of the human AdipoR2 protein are inherently unstable when expressed in COS-7 mammalian cell lines compared to the human AdipoR2v1 and AdipoR2v2 polypeptides, as shown in FIG. 28B and described in Example 6. Specifically, pcDNA3 expression constructs were created for human AdipoR1, human AdipoR2, human AdipoR2v1, and human AdipoR2v2. Two constructs were created for each Adipo receptor with one construct containing the encoding region of the FLAG tag epitope at the N-terminus of each receptor, and the other construct containing the coding region of the influenza hemagluttin (HA) epitope tag at the C-terminus. The plasmids were transfected into COS-7 cell lines, overexpressed, and the extracts run out on a SDS-PAGE gel. Each gel was transferred to nylon membrane and probes with anti-FLAG and/or anti-HA antibody. As shown in FIG. 28B, regardless of whether the epitope was tagged at either the N- or C-terminus, the level of human AdipoR2 receptor detected was consistently at very low levels. By comparison, the level of human AdipoR1, human AdipoR2v1, and human AdipoR2v2 polypeptides detected was very high. Accordingly, it is believed that the human AdipoR2 polypeptide is significantly less stable than the human AdipoR2v1 and human AdipoR2v2 receptors, particularly considering the only difference between each receptor construct was the sequence of each receptor itself since the promoter and context of expression for each AdipoR2 isoform were the same. These results support the notion that the human AdipoR2 polypeptide described by Yamauchi is an artifact and that the human AdipoR2v1 and human AdipoR2v2 are the physiologically relevant forms of this receptor. This analysis is also consistent with the human AdipoR1 receptor described by Yamauchi as being physiologically relevant.

The human AdipoR2v2 polypeptide was predicted to comprise eight transmembrane domains (TM1 to TM8) located from about amino acid 150 to about amino acid 174 (TM1; SEQ ID NO:121); from about amino acid 176 to about amino acid 208 (TM2; SEQ ID NO:122); from about amino acid 217 to about amino acid 237 (TM3; SEQ ID NO:123); from about amino acid 243 to about amino acid 268 (TM4; SEQ ID NO:124); from about amino acid 282 to about amino acid 304 (TM5; SEQ ID NO:125); from about amino acid 308 to about amino acid 336 (TM6; SEQ ID NO:126); from about amino acid 337 to about amino acid 365 (TM7; SEQ ID NO:127); and/or from about amino acid 382 to about amino acid 400 (TM8; SEQ ID NO:128) of SEQ ID NO:104 (FIGS. 13A-B). In this context, the term "about" may be construed to mean 1, 2, 3, 4, 5, 6, 7, 8, 9, or 10 amino acids beyond the N-Terminus and/or C-terminus of the above referenced transmembrane domain polypeptides.

In preferred embodiments, the following transmembrane domain polypeptides are encompassed by the present invention: WTHLLGCVFFLCLGIFYMFRPNISF (SEQ ID NO:120), APLQEKVVFGLFFLGAILCLSFSWLF-HTVYCHS (SEQ ID NO:121), KLDYSGIALLIMGSFVP-WLYY (SEQ ID NO:122), PQPCFIYLIVICVLGIAAI-IVSQWDM (SEQ ID NO:123), VLLCSPGWSAVVPSWLLTSSDLP (SEQ ID NO:124), SQSAGITGVFLGLGLSGIIPTLHYVISEG (SEQ ID NO:125), FLKAATIGQIGWLMLMASLYITGAALYAA (SEQ ID NO:126), and/or SHQLFHIFVVAGAFVHFHG (SEQ ID NO:127). Polynucleotides encoding these polypeptides are also provided. The present invention also encompasses the use of these human AdipoR2v2 transmembrane domain polypeptides as immunogenic and/or antigenic epitopes as described elsewhere herein.

The present invention also encompasses the polypeptide sequences that intervene between each of the predicted human AdipoR2v2 transmembrane domains. Since these regions are solvent accessible either extracellularly or intracellularly, they are particularly useful for designing antibodies specific to each region. Such antibodies may be useful as antagonists or agonists of the human AdipoR2v2 full-length polypeptide and may modulate its activity.

In preferred embodiments, the following inter-transmembrane domain polypeptides are encompassed by the present invention: EGVSRLFS (SEQ ID NO:128), SFYCN (SEQ ID NO:129), FATPQYRGVRADG (SEQ ID NO:130), and/or RIPERFFPGKCDIWFH (SEQ ID NO:131). Polynucleotides encoding these polypeptides are also provided. The present invention also encompasses the use of these human AdipoR2v2 intratransmembrane domain polypeptides as immunogenic and/or antigenic epitopes as described elsewhere herein.

In preferred embodiments, the present invention encompasses the use of N-terminal deletions, C-terminal deletions, or any combination of N-terminal and C-terminal deletions of any one or more of the human AdipoR2v2 TM1 thru TM8 transmembrane domain polypeptides as antigenic and/or immunogenic epitopes.

In preferred embodiments, the present invention also encompasses the use of N-terminal deletions, C-terminal deletions, or any combination of N-terminal and C-terminal deletions of any one or more of the amino acids intervening (i.e., extracellular or intracellular loops) the human AdipoR2v2 TM1 thru TM8 transmembrane domain polypeptides as antigenic and/or immunogenic epitopes.

Although the human AdipoR2v2 receptor has seven transmembrane domains, it is believed to be structurally, topologically, and functionally distinct from G-protein coupled receptors. Yamauchi et al demonstrated that the N-terminus of AdipoR2 is intracellular, as opposed to GPCRs which typically have their N-terminus extracellular. In addition, AdipoR2 does not appear to couple to G-proteins, but rather activate unique sets of signalling molecules such as PPAR-alpha, AMPK, and p38 MAPK.

Likewise, the human AdipoR2v2 receptor of the present invention is also thought to be structurally, topologically, and functionally distinct from G-protein coupled receptors. Alternatively, the human AdipoR2v2 receptor of the present invention may share at least some biological function with GPCRs.

The human AdipoR2v2 polypeptide was also determined to comprise several conserved cysteines which are denoted by dark shading, in addition to other identical residues, as shown in FIG. 15. Conservation of cysteines at key amino acid residues is indicative of conserved structural features, which may correlate with conservation of protein function and/or activity.

The present invention also encompasses polynucleotides encoding at least 316 consecutive amino acids of the human AdipoR2v2 polypeptide of the present invention (SEQ ID NO:104). Preferably the polynucleotides encode a polypeptide having at least some adiponectin receptor activity. The present invention also encompasses polynucleotides having at least 948 consecutive nucleotides of SEQ ID NO:103, wherein said polynucleotides preferably encode a polypeptide having at least some adiponectin receptor activity.

The present invention also is directed to the novel human AdipoR2v2 receptor polypeptide fragment located from amino acid 280 to amino acid 315 of SEQ ID NO:104. The present invention also is directed to the novel human AdipoR2v2 receptor polynucleotide from nucleotide 1044 to nucleotide 1151 of SEQ ID NO:103.

The present invention also is directed to the carboxy terminus of the novel human AdipoR2v2 receptor polypeptide fragment located from amino acid 401 to amino 421 of SEQ ID NO:104. The present invention also is directed to the novel human AdipoR2v2 receptor polynucleotide from nucleotide 1407 to nucleotide 1469 of SEQ ID NO:103. The present invention also encompasses the use of this carboxy terminal fragment polypeptide as an antigenic and/or immunogenic epitope. Antibodies to this particular carboxy terminal epitope of AdipoR2v2 would be useful therapeutically to modulate the activity of the AdipoR2v2 polypeptide.

Since the human AdipoR2v2 polypeptide represents a variant form of the human AdipoR2 protein (hAdipoR2; Genbank Accession No: gi|NM_024551; SEQ ID NO:9), it is expected that the expression pattern of the human AdipoR2v2 polypeptide of the present invention is the same or similar to the expression pattern of the human AdipoR2 protein.

The human AdipoR2 protein was determined to be expressed predominately in liver (Yamauchi et al., 2003). Likewise, the expression pattern of the human AdipoR2v2 polypeptide is also expected to be expressed predominately in liver.

The human AdipoR2v2 polynucleotides and polypeptides of the present invention, including modulators and/or fragments thereof, have uses that include detecting, prognosing, treating, preventing, and/or ameliorating the following diseases and/or disorders: metabolic disorders, inflammatory disorders, cardiovascular disorders, obesity, diabetes, type I diabetes, type II diabetes, gestational diabetes, early onset diabetes, insulin resistance, disorders in which glucose-lowering would be beneficial, disorders in which amelioration of insulin resistance would be beneficial, disorders in which suppressed FA influx into liver would be beneficial, disorders in which reduced serum TG would be beneficial, myocardial infarction, heart failure, atherosclerosis, arteriosclerosis, disorders disclosed herein in the "Cardiovascular Disorders" section, disorders in which adiponectin levels are below normal, disorders that would benefit from increased adiponectin levels, disorders associated with aberrant vascular smooth muscle proliferation, disorders associated with aberrant foam cell formation, disorders in which inhibition of macrophage phagocytosis would be beneficial, disorders in which inhibition of TNF-alpha production would be beneficial, dyslipidemia, diabetic dyslipidemia, mixed dyslipidemia, hypercholesteremia, hypertriglyceridemia, hyperlipidemia, and anorexia nervosa.

The human AdipoR2v2 polynucleotides and polypeptides of the present invention, including modulators and/or fragments thereof, have uses that include detecting, prognosing, treating, preventing, and/or ameliorating the following inflammatory diseases and/or disorders: arthritis, rheumatoid arthritis, osteoarthritis, prosthetic joint failure, ulcerative colitis, Crohn's disease, inflammatory bowel and gastrointestinal diseases, gastritis, mucosal inflammation resulting from infection, enteropathy provoked by non-steroidal anti-inflammatory drugs, adult respiratory distress syndrome, asthma, cystic fibrosis, chronic obstructive pulmonary disease, myocarditis, multiple sclerosis, inflammation associated with diabetes melitus, glomerulonephritis, dermatitis, psoriasis, eczema, urticaria, burn injury, glaucoma, organ rejection, multi-organ diseases, systemic lupus erythematosis, sepsis, inflammatory sequelae of viral or bacterial infections, inflammatory conditions associated with atherosclerosis following hypoxic or ischaemic insults (with or without reperfusion, particularly in the brain or in ischaemic heart disease.

The human AdipoR2v2 polynucleotides and polypeptides of the present invention, including modulators and/or fragments thereof, have uses that include modulating signal transduction activity, in various cells, tissues, and organisms, and particularly in mammalian liver.

Human AdipoR2v2 polynucleotides and polypeptides of the present invention, including modulators and/or fragments thereof, have uses that include detecting, prognosing, treating, preventing, and/or ameliorating the following additional cardiovascular disorders: congestive heart failure, arrthymias, cardiomyopathy, microvascular disease, embolism, thromobosis, pulmonary edema, palpitation, dyspnea, angina, hypotension, syncope, heart murmur, aberrant ECG, hypertrophic cardiomyopathy, the Marfan syndrome, sudden death, prolonged QT syndrome, congenital defects, cardiac viral infections, valvular heart disease, and hypertension.

Similarly, human AdipoR2v2 polynucleotides and polypeptides may be useful for ameliorating cardiovascular diseases and symptoms which result indirectly from various non-cardiovascular effects, which include, but are not limited to, the following, obesity, smoking, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, have uses which include, directly or indirectly, treating, preventing, diagnosing, and/or prognosing the following, non-limiting, cardiovascular infections: blood stream invasion, bacteremia, sepsis, *Streptococcus pneumoniae* infection, group a streptococci infection, group b streptococci infection, *Enterococcus* infection, nonenterococcal group D streptococci infection, nonenterococcal group C streptococci infection, nonenterococcal group G streptococci infection, *Streptococcus viridans* infection, *Staphylococcus aureus* infection, coagulase-negative staphylococci infection, gram-negative Bacilli infection, Enterobacteriaceae infection, *Pseudomonas* spp. Infection, *Acinobacter* spp. Infection, *Flavobacterium meningosepticum* infection, *Aeromonas* spp. Infection, *Stenotrophomonas maltophilia* infection, gram-negative coccobacilli infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous *Mycobacteria* infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

Human AdipoR2v2 polypeptides and polynucleotides have additional uses which include diagnosing diseases related to the over and/or under expression of human AdipoR2v2 by identifying mutations in the human AdipoR2v2 gene by using human AdipoR2v2 sequences as probes or by determining human AdipoR2v2 protein or mRNA expression levels. human AdipoR2v2 polypeptides, may be useful for screening compounds that affect the activity of the protein. Human AdipoR2v2 peptides can also be used for the generation of specific antibodies and as bait in yeast two hybrid screens to find proteins that specifically interact with human AdipoR2v2 (described elsewhere herein).

In preferred embodiments, the following N-terminal AdipoR2v2 deletion polypeptides are encompassed by the present invention: M1-L421, N2-L421, E3-L421, P4-L421, T5-L421, E6-L421, N7-L421, R8-L421, L9-L421, G10-L421, C11-L421, S12-L421, R13-L421, T14-L421, P15-L421, E16-L421, P17-L421, D18-L421, I19-L421, R20-L421, L21-L421, R22-L421, K23-L421, G24-L421, H25-L421, Q26-L421, L27-L421, D28-L421, G29-L421, T30-L421, R31-L421, R32-L421, G33-L421, D34-L421, N35-L421, D36-L421, S37-L421, H38-L421, Q39-L421, G40-L421, D41-L421, L42-L421, E43-L421, P44-L421, I45-L421, L46-L421, E47-L421, A48-L421, S49-L421, V50-L421, L51-L421, S52-L421, S53-L421, H54-L421, H55-L421, K56-L421, K57-L421, S58-L421, S59-L421, E60-L421, E61-L421, H62-L421, E63-L421, Y64-L421, S65-L421, D66-L421, E67-L421, A68-L421, P69-L421, Q70-L421, E71-L421, D72-L421, E73-L421, G74-L421, F75-L421, M76-L421, G77-L421, M78-L421, S79-L421, P80-L421, L81-L421, L82-L421, Q83-L421, A84-L421, H85-L421, H86-L421, A87-L421, M88-L421, E89-L421, K90-L421, M91-L421, E92-L421, E93-L421, F94-L421, V95-L421, C96-L421, K97-L421, V98-L421, W99-L421, E100-L421, G101-L421, R102-L421, W103-L421, R104-L421, V105-L421, I106-L421, P107-L421, H108-L421, D109-L421, V110-L421, L111-L421, P112-L421, D113-L421, W114-L421, L115-L421, K116-L421, D117-L421, N118-L421, D119-L421, F120-L421, L121-L421, L122-L421, H123-L421, G124-L421, H125-L421, R126-L421, P127-L421, P128-L421, M129-L421, P130-L421, S131-L421, F132-L421, R133-L421, A134-L421, C135-L421, F136-L421, K137-L421, S138-L421, I139-L421, F140-L421, R141-L421, I142-L421, H143-L421, T144-L421, E145-L421, T146-L421, G147-L421, N148-L421, I149-L421, W150-L421, T151-L421, H152-L421, L153-L421, L154-L421, G155-L421, C156-L421, V157-L421, F158-L421, F159-L421, L160-L421, C161-L421, L162-L421, G163-L421, I164-L421, F165-L421, Y166-L421, M167-L421, F168-L421, R169-L421, P170-L421, N171-L421, I172-L421, S173-L421, F174-L421, V175-L421, A176-L421, P177-L421, L178-L421, Q179-L421, E180-L421, K181-L421, V182-L421, V183-L421, F184-L421, G185-L421, L186-L421, F187-L421, F188-L421, L189-L421, G190-L421, A191-L421, I192-L421, L193-L421, C194-L421, L195-L421, S196-L421, F197-L421, S198-L421, W199-L421, L200-L421, F201-L421, H202-L421, T203-L421, V204-L421, Y205-L421, C206-L421, H207-L421, S208-L421, E209-L421, G210-L421, V211-L421, S212-L421, R213-L421, L214-L421, F215-L421, S216-L421, K217-L421, L218-L421, D219-L421, Y220-L421, S221-L421, G222-L421, I223-L421, A224-L421, L225-L421, L226-L421, I227-L421, M228-L421, G229-L421, S230-L421, F231-L421, V232-L421, P233-L421, W234-L421, L235-L421, Y236-L421, Y237-L421, S238-L421, F239-L421, Y240-L421, C241-L421, N242-L421, P243-L421, Q244-L421, P245-L421, C246-L421, F247-L421, I248-L421, Y249-L421, L250-L421, I251-L421, V252-L421, I253-L421, C254-L421, V255-L421, L256-L421, G257-L421, I258-L421, A259-L421, A260-L421, I261-L421, I262-L421, V263-L421, S264-L421, Q265-L421, W266-L421, D267-L421, M268-L421, F269-L421, A270-L421, T271-L421, P272-L421, Q273-L421, Y274-L421, R275-L421, G276-L421, V277-L421, R278-L421, A279-L421, D280-L421, G281-L421, V282-L421, L283-L421, L284-L421, C285-L421, S286-L421, P287-L421, G288-L421, W289-L421, S290-L421, A291-L421, V292-L421, V293-L421, P294-L421, S295-L421, W296-L421, L297-L421, L298-L421, T299-L421, S300-L421, S301-L421, D302-L421, L303-L421, P304-L421, A305-L421, S306-L421, A307-L421, S308-L421, Q309-L421, S310-L421, A311-L421, G312-L421, I313-L421, T314-L421, G315-L421, V316-L421, F317-L421, L318-L421, G319-L421, L320-L421, G321-L421, L322-L421, S323-L421, G324-L421, I325-L421, I326-L421, P327-L421, T328-L421, L329-L421, H330-L421, Y331-L421, V332-L421, I333-L421, S334-L421, E335-L421, G336-L421, F337-L421, L338-L421, K339-L421, A340-L421, A341-L421, T342-L421, I343-L421, G344-L421, Q345-L421, I346-L421, G347-L421, W348-L421, L349-L421, M350-L421, L351-L421, M352-L421, A353-L421, S354-L421, L355-L421, Y356-L421, I357-L421, T358-L421, G359-L421, A360-L421, A361-L421, L362-L421, Y363-L421, A364-L421, A365-L421, R366-L421, I367-L421, P368-L421, E369-L421, R370-L421, F371-L421, F372-L421, P373-L421, G374-L421, K375-L421, C376-L421, D377-L421, I378-L421, W379-L421, F380-L421, H381-L421, S382-L421, H383-L421, Q384-L421, L385-L421, F386-L421, H387-L421, I388-L421, F389-L421, V390-L421, V391-L421, A392-L421, G393-L421, A394-L421, F395-L421, V396-L421, H397-L421, F398-L421, H399-L421, G400-L421, V401-L421, S402-L421, N403-L421, L404-L421, Q405-L421, E406-L421, F407-L421, R408-L421, F409-L421, M410-L421, I411-L421, G412-L421, G413-L421, G414-L421, and/or C415-L421 of SEQ ID NO:104. Polynucleotide sequences encoding these polypeptides are also provided. The present invention also encompasses the use of these N-terminal AdipoR2v2 deletion polypeptides as immunogenic and/or antigenic epitopes as described elsewhere herein.

In preferred embodiments, the following C-terminal AdipoR2v2 deletion polypeptides are encompassed by the present invention: M1-L421, M1-A420, M1-D419, M1-E418, M1-E417, M1-S416, M1-C415, M1-G414, M1-G413, M1-G412, M1-I411, M1-M410, M1-F409, M1-R408, M1-F407, M1-E406, M1-Q405, M1-L404, M1-N403, M1-S402, M1-V401, M1-G400, M1-H399, M1-F398, M1-H397, M1-V396, M1-F395, M1-A394, M1-G393, M1-A392, M1-V391, M1-V390, M1-F389, M1-I388, M1-H387, M1-F386, M1-L385, M1-Q384, M1-H383, M1-S382, M1-H381, M1-F380, M1-W379, M1-I378, M1-D377, M1-C376, M1-K375, M1-G374, M1-P373, M1-F372, M1-F371, M1-R370, M1-E369, M1-P368, M1-I367, M1-R366, M1-A365, M1-A364, M1-Y363, M1-L362, M1-A361, M1-A360, M1-G359, M1-T358, M1-I357, M1-Y356, M1-L355, M1-S354, M1-A353, M1-M352, M1-L351, M1-M350, M1-L349, M1-W348, M1-G347, M1-I346, M1-Q345, M1-G344, M1-I343, M1-T342, M1-A341, M1-A340, M1-K339, M1-L338, M1-F337, M1-G336, M1-E335, M1-S334, M1-I333, M1-V332, M1-Y331, M1-H330, M1-L329, M1-T328, M1-P327, M1-I326, M1-I325, M1-G324, M1-S323, M1-L322, M1-G321, M1-L320, M1-G319, M1-L318, M1-F317, M1-V316, M1-G315, M1-T314, M1-I313, M1-G312, M1-A311, M1-S310, M1-Q309, M1-S308, M1-A307, M1-S306, M1-A305, M1-P304, M1-L303, M1-D302, M1-S301, M1-S300, M1-T299, M1-L298, M1-L297, M1-W296, M1-S295, M1-P294, M1-V293, M1-V292, M1-A291, M1-S290, M1-W289, M1-G288, M1-P287, M1-S286, M1-C285, M1-L284, M1-L283, M1-V282, M1-G281, M1-D280, M1-A279, M1-R278, M1-V277, M1-G276, M1-R275, M1-Y274, M1-Q273, M1-P272, M1-T271, M1-A270, M1-F269, M1-M268, M1-D267, M1-W266, M1-Q265, M1-S264, M1-V263, M1-I262, M1-I261, M1-A260, M1-A259, M1-I258, M1-G257, M1-L256, M1-V255, M1-C254, M1-I253, M1-V252, M1-I251, M1-L250, M1-Y249, M1-I248, M1-F247, M1-C246, M1-P245, M1-Q244, M1-P243, M1-N242, M1-C241, M1-Y240, M1-F239, M1-S238, M1-Y237, M1-Y236, M1-L235, M1-W234, M1-P233, M1-V232, M1-F231, M1-S230, M1-G229, M1-M228, M1-I227, M1-L226, M1-L225, M1-A224, M1-I223, M1-G222, M1-S221, M1-Y220, M1-D219, M1-L218, M1-K217, M1-S216, M1-F215, M1-L214, M1-R213, M1-S212, M1-V211, M1-G210, M1-E209, M1-S208, M1-H207, M1-C206, M1-Y205, M1-V204, M1-T203, M1-H202, M1-F201, M1-L200, M1-W199, M1-S198, M1-F197, M1-S196, M1-L195, M1-C194, M1-L193, M1-I192, M1-A191, M1-G190, M1-L189, M1-F188, M1-F187, M1-L186, M1-G185, M1-F184, M1-V183, M1-V182, M1-K181, M1-E180, M1-Q179, M1-L178, M1-P177, M1-A176, M1-V175, M1-F174, M1-S173, M1-I172, M1-N171, M1-P170, M1-R169, M1-F168, M1-M167, M1-Y166, M1-F165, M1-I164, M1-G163, M1-L162, M1-C161, M1-L160, M1-F159, M1-F158, M1-V157, M1-C156, M1-G155, M1-L154, M1-L153, M1-H152, M1-T151, M1-W150, M1-I149, M1-N148, M1-G147, M1-T146, M1-E145, M1-T144, M1-H143, M1-I142, M1-R141, M1-F140, M1-I139, M1-S138, M1-K137, M1-F136, M1-C135, M1-A134, M1-R133, M1-F132, M1-S131, M1-P130, M1-M129, M1-P128, M1-P127, M1-R126, M1-H125, M1-G124, M1-H123, M1-L122, M1-L121, M1-F120, M1-D119, M1-N118, M1-D117, M1-K116, M1-L115, M1-W114, M1-D113, M1-P112, M1-L111, M1-V110, M1-D109, M1-H108, M1-P107, M1-I106, M1-V105, M1-R104, M1-W103, M1-R102, M1-G101, M1-E100, M1-W99, M1-V98, M1-K97, M1-C96, M1-V95, M1-F94, M1-E93, M1-E92, M1-M91, M1-K90, M1-E89, M1-M88, M1-A87, M1-H86, M1-H85, M1-A84, M1-Q83, M1-L82, M1-L81, M1-P80, M1-S79, M1-M78, M1-G77, M1-M76, M1-F75, M1-G74, M1-E73, M1-D72, M1-E71, M1-Q70, M1-P69, M1-A68, M1-E67, M1-D66, M1-S65, M1-Y64, M1-E63, M1-H62, M1-E61, M1-E60, M1-S59, M1-S58, M1-K57, M1-K56, M1-H55, M1-H54, M1-S53, M1-S52, M1-L51, M1-V50, M1-S49, M1-A48, M1-E47, M1-L46, M1-I45, M1-P44, M1-E43, M1-L42, M1-D41, M1-G40, M1-Q39, M1-H38, M1-S37, M1-D36, M1-N35, M1-D34, M1-G33, M1-R32, M1-R31, M1-T30, M1-G29, M1-D28, M1-L27, M1-Q26, M1-H25, M1-G24, M1-K23, M1-R22, M1-L21, M1-R20, M1-I19, M1-D18, M1-P17, M1-E16, M1-P15, M1-T14, M1-R13, M1-S12, M1-C11, M1-G10, M1-L9, M1-R8, and/or M1-N7 of SEQ ID NO:104. Polynucleotide sequences encoding these polypeptides are also provided. The present invention also encompasses the use of these C-terminal AdipoR2v2 deletion polypeptides as immunogenic and/or antigenic epitopes as described elsewhere herein.

Alternatively, preferred polypeptides of the present invention may comprise polypeptide sequences corresponding to, for example, internal regions of the human AdipoR2v2 polypeptide (e.g., any combination of both N- and C-terminal human AdipoR2v2 polypeptide deletions) of SEQ ID NO:104. For example, internal regions could be defined by the equation: amino acid NX to amino acid CX, wherein NX refers to any N-terminal deletion polypeptide amino acid of human AdipoR2v2 (SEQ ID NO:104), and where CX refers to any C-terminal deletion polypeptide amino acid of human AdipoR2v2 (SEQ ID NO:104). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the human AdipoR2v2 polypeptide.

The human AdipoR2v2 polypeptide of the present invention was determined to comprise several phosphorylation sites based upon the Motif algorithm (Genetics Computer Group, Inc.). The phosphorylation of such sites may regulate some biological activity of the human AdipoR2v2 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the human AdipoR2v2 polypeptide to associate with other polypeptides, particularly the cognate ligand for human AdipoR2v2, such as adiponectin, or its ability to modulate certain cellular signally pathways such as AMPK, p38 MAPK, MAPK, and/or ACC.

Specifically, the human AdipoR2v2 polypeptide was predicted to comprise two tyrosine phosphorylation site using the Motif algorithm (Genetics Computer Group, Inc.). Such sites are phosphorylated at the tyrosine amino acid residue. The consensus pattern for tyrosine phosphorylation sites are as follows: [RK]-x(2)-[DE]-x(3)-Y, or [RK]-x(3)-[DE]-x(2)-Y, where Y represents the phosphorylation site and 'x' represents an intervening amino acid residue. Additional information specific to tyrosine phosphorylation sites can be found in Patschinsky T., Hunter T., Esch F. S., Cooper J. A., Sefton B. M., Proc. Natl. Acad. Sci. U.S.A. 79:973-977 (1982); Hunter T., J. Biol. Chem. 257:4843-4848 (1982), and Cooper J. A., Esch F. S., Taylor S. S., Hunter T., J. Biol. Chem. 259:7835-7841 (1984), which are hereby incorporated herein by reference.

In preferred embodiments, the following tyrosine phosphorylation site polypeptides are encompassed by the present invention: Y LSSHHKKSSEEHEYSDEAP (SEQ ID NO:132), and/or Y SSHHKKSSEEHEYSDEAP (SEQ ID NO:133). Polynucleotides encoding these polypeptides are also provided. The present invention also encompasses the use of these human AdipoR2v2 tyrosine phosphorylation site polypeptides as immunogenic and/or antigenic epitopes as described elsewhere herein.

The human AdipoR2v2 polypeptide was predicted to comprise two PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. 260: 12492-12499 (1985); which are hereby incorporated by reference herein.

In preferred embodiments, the following PKC phosphorylation site polypeptides are encompassed by the present invention: HQLDGTRRGDNDS (SEQ ID NO:134), and/or RPPMPSFRACFKS (SEQ ID NO:135). Polynucleotides encoding these polypeptides are also provided. The present invention also encompasses the use of the human AdipoR2v2

PKC phosphorylation site polypeptides as immunogenic and/or antigenic epitopes as described elsewhere herein.

The human AdipoR2v2 polypeptide was predicted to comprise five casein kinase II phosphorylation sites using the Motif algorithm (Genetics Computer Group, Inc.). Casein kinase II (CK-2) is a protein serine/threonine kinase whose activity is independent of cyclic nucleotides and calcium. CK-2 phosphorylates many different proteins. The substrate specificity [1] of this enzyme can be summarized as follows: (1) Under comparable conditions Ser is favored over Thr.; (2) An acidic residue (either Asp or Glu) must be present three residues from the C-terminal of the phosphate acceptor site; (3) Additional acidic residues in positions +1, +2, +4, and +5 increase the phosphorylation rate. Most physiological substrates have at least one acidic residue in these positions; (4) Asp is preferred to Glu as the provider of acidic determinants; and (5) A basic residue at the N-terminal of the acceptor site decreases the phosphorylation rate, while an acidic one will increase it.

A consensus pattern for casein kinase II phosphorylations site is as follows: [ST]-x(2)-[DE], wherein 'x' represents any amino acid, and S or T is the phosphorylation site.

Additional information specific to casein kinase II phosphorylation site-II domains may be found in reference to the following publication: Pinna L. A., Biochim. Biophys. Acta 1054:267-284 (1990); which is hereby incorporated herein in its entirety.

In preferred embodiments, the following casein kinase II phosphorylation site polypeptide is encompassed by the present invention: SHHKKSSEEHEYSD (SEQ ID NO:136), VSRLFSKLDYSGIA (SEQ ID NO:137), AAIIVSQWDMFATP (SEQ ID NO:138), PSWLLTSSDLPASA (SEQ ID NO:139), and/or IGGGCSEEDAL (SEQ ID NO:140). Polynucleotides encoding these polypeptides are also provided. The present invention also encompasses the use of this casein kinase II phosphorylation site polypeptide as an immunogenic and/or antigenic epitope as described elsewhere herein.

The human AdipoR2v2 polypeptide was predicted to comprise one cAMP- and cGMP-dependent protein kinase phosphorylation site using the Motif algorithm (Genetics Computer Group, Inc.). There has been a number of studies relative to the specificity of cAMP- and cGMP-dependent protein kinases. Both types of kinases appear to share a preference for the phosphorylation of serine or threonine residues found close to at least two consecutive N-terminal basic residues.

A consensus pattern for cAMP- and cGMP-dependent protein kinase phosphorylation sites is as follows: [RK](2)-x-[ST], wherein "x" represents any amino acid, and S or T is the phosphorylation site.

Additional information specific to cAMP- and cGMP-dependent protein kinase phosphorylation sites may be found in reference to the following publication: Fremisco J. R., Glass D. B., Krebs E. G, J. Biol. Chem. 255:4240-4245 (1980); Glass D. B., Smith S. B., J. Biol. Chem. 258:14797-14803 (1983); and Glass D. B., El-Maghrabi M. R., Pilkis S. J., J. Biol. Chem. 261:2987-2993 (1986); which is hereby incorporated herein in its entirety.

In preferred embodiments, the following cAMP- and cGMP-dependent protein kinase phosphorylation site polypeptide is encompassed by the present invention: LSSHHKKSSEEHEY (SEQ ID NO:141). Polynucleotides encoding this polypeptide are also provided. The present invention also encompasses the use of this cAMP- and cGMP-dependent protein kinase phosphorylation site polypeptide as an immunogenic and/or antigenic epitope as described elsewhere herein.

The human AdipoR2v2 polypeptide has been shown to comprise two glycosylation site according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine glycosylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673-702 (1972); Pless D. D., Lennarz W. J., Proc. Natl. Acad. Sci. U.S.A. 74:134-138 (1977); Bause E., Biochem. J. 209:331-336 (1983); Gavel Y., von Heijne G., Protein Eng. 3:433-442 (1990); and Miletich J. P., Broze G. J. Jr., J. Biol. Chem. 265:11397-11404 (1990).

In preferred embodiments, the following asparagine glycosylation site polypeptides are encompassed by the present invention: TRRGDNDSHQGDLE (SEQ ID NO:142), and/or YMFRPNISFVAPLQ (SEQ ID NO:143). Polynucleotides encoding these polypeptides are also provided. The present invention also encompasses the use of these human AdipoR2v2 asparagine glycosylation site polypeptides as immunogenic and/or antigenic epitopes as described elsewhere herein.

The human AdipoR2v2 polypeptide was predicted to comprise eight N-myristoylation sites using the Motif algorithm (Genetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA: protein N-myristoyl transferase (NMT), has been derived from the sequence of known N-myristoylated proteins and from studies using synthetic peptides. The specificity seems to be the following: i.) The N-terminal residue must be glycine; ii.) In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-{EDRKHPFYW}-x(2)-[STAGCN]-{P}, wherein 'x' represents any amino acid, and G is the N-myristoylation site.

Additional information specific to N-myristoylation sites may be found in reference to the following publication: Towler D. A., Gordon J. I., Adams S. P., Glaser L., Annu. Rev. Biochem. 57:69-99 (1988); and Grand R. J. A., Biochem. J. 258:625-638 (1989); which is hereby incorporated herein in its entirety.

In preferred embodiments, the following N-myristoylation site polypeptides are encompassed by the present invention:

GHQLDGTRRGDNDSHQ (SEQ ID NO:144), IHTETGNIWTHLLGCV (SEQ ID NO:145), GLFFLGAILCLSFSWL (SEQ ID NO:146), GVRADGVLLCSPGWSA (SEQ ID NO:147), SAGITGVFLGLGLSGI (SEQ ID NO:148), TGVFLGLGLSGIIPTL (SEQ ID NO:149), GLGLSGIIPTLHYVIS (SEQ ID NO:150), and/or FRFMIGGGCSEEDAL (SEQ ID NO:151). Polynucleotides encoding these polypeptides are also provided. The present invention also encompasses the use of these N-myristoylation site polypeptides as immunogenic and/or antigenic epitopes as described elsewhere herein.

The human AdipoR2v2 polypeptide has been shown to comprise one RGD cell attachment site domain according to the Motif algorithm (Genetics Computer Group, Inc.). The sequence Arg-Gly-Asp, found in fibronectin, is crucial for its interaction with its cell surface receptor, an integrin. What has been called the 'RGD' tripeptide is also found in the sequences of a number of other proteins, where it has been shown to play a role in cell adhesion. Non-limiting examples of these proteins are the following: some forms of collagens, fibrinogen, vitronectin, von Willebrand factor (VWF), snake disintegrins, and slime mold discoidins. The 'RGD' tripeptide is also found in other proteins where it may serve the same purpose. A consensus pattern for RGD cell attachment sites is the following: R-G-D. Additional information relating to RGD cell attachment site domains may be found in reference to the following publications, which are hereby incorporated by reference herein: Ruoslahti E., Pierschbacher M. D., Cell 44:517-518 (1986); and d'Souza S. E., Ginsberg M. H., Plow E. F., Trends Biochem. Sci. 16:246-250 (1991).

In preferred embodiments, the following RGD cell attachment site domain polypeptide is encompassed by the present invention: LDGTRRGDNDSHQ (SEQ ID NO:42). Polynucleotides encoding these polypeptides are also provided. The present invention also encompasses the use of this RGD cell attachment site domain polypeptide as an immunogenic and/or antigenic epitope as described elsewhere herein.

The present invention encompasses the identification of compounds and drugs which stimulate human AdipoR2v2 on the one hand (i.e., agonists) and which inhibit the function of human AdipoR2v2 on the other hand (i.e., antagonists). In general, such screening procedures involve providing appropriate cells which express the receptor polypeptide of the present invention on the surface thereof. Such cells may include, for example, cells from mammals, yeast, Drosophila or E. coli. In a preferred embodiment, a polynucleotide encoding the receptor of the present invention may be employed to transfect cells to thereby express the human AdipoR2v2 polypeptide. The expressed receptor may then be contacted with a test compound to observe binding, stimulation or inhibition of a functional response.

Many polynucleotide sequences, such as EST sequences, are publicly available and accessible through sequence databases. Some of these sequences are related to SEQ ID NO:103 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 1724 of SEQ ID NO:103, b is an integer between 15 to 1738, where both a and b correspond to the positions of nucleotide residues shown in SEQ ID NO:103, and where b is greater than or equal to a+14.

Features of the Polypeptide Encoded by Polynucleotide No:6

The polypeptide of this polynucleotide provided as SEQ ID NO:165 (FIGS. 20A-B), encoded by the polynucleotide sequence according to SEQ ID NO:164 (FIGS. 20A-B), and/or encoded by the polynucleotide contained within the deposited clone, rat AdipoR1 (also referred to as rAdipoR1), is believed to represent the physiologically relevant form of the rat AdipoR1 polypeptide.

An alignment of the rat AdipoR1 polypeptide of the present invention with the human AdipoR1 protein (hAdipoR1; GenbankAccession No: gi|NM_015999; SEQ ID NO:7); and the mouse AdipoR1 protein (mAdipoR1; Genbank Accession No: gi|BCO14875; SEQ ID NO:8) is provided in FIG. 22.

The inventors believe that the rat AdipoR1 polypeptide of the present invention is the physiologically relevant form of this protein. Likewise, the rat AdipoR1 polypeptide is expected to share the same or similar biological activity as the reported activity for the mouse and human AdipoR1 sequence. Preferably, the rat AdipoR1 polypeptide is expected to bind to adiponectin, bind to globular adiponectin, bind full-length adiponectin, ability to regulate AMPK phosphorylation, ability to regulate ACC phosphorylation, ability to regulate MAPK phosphorylation, ability to regulate p38 MAPK phosphorylation, among others.

The determined nucleotide sequence of the rat AdipoR1 cDNA in FIGS. 20A-B (SEQ ID NO:164) contains an open reading frame encoding a protein of about 375 amino acid residues, with a deduced molecular weight of about 42.5 kDa. The amino acid sequence of the predicted rat AdipoR1 polypeptide is shown in FIGS. 20A-B (SEQ ID NO:165). By virtue of the rat AdipoR1 protein representing an ortholog of the human and mouse AdipoR1 polypeptides, the rat AdipoR1 polypeptide shown in FIGS. 20A-B shares significant identity and similarity to other adiponectin receptors, as shown in FIG. 22. The percent identity and similarity values between the rat AdipoR1 polypeptide to these known adiponectin receptors is provided in FIG. 26.

The rat AdipoR1 polypeptide was predicted to comprise seven transmembrane domains (TM1 to TM7) located from about amino acid 137 to about amino acid 162 (TM1; SEQ ID NO:168); from about amino acid 167 to about amino acid 192 (TM2; SEQ ID NO:169); from about amino acid 208 to about amino acid 227 (TM3; SEQ ID NO:170); from about amino acid 234 to about amino acid 255 (TM4; SEQ ID NO:171); from about amino acid 270 to about amino acid 292 (TM5; SEQ ID NO:172); from about amino acid 298 to about amino acid 320 (TM6; SEQ ID NO:173); and/or from about amino acid 337 to about amino acid 354 (TM7; SEQ ID NO:174) of SEQ ID NO:165 (FIGS. 20A-B). In this context, the term "about" may be construed to mean 1, 2, 3, 4, 5, 6, 7, 8, 9, or 10 amino acids beyond the N-Terminus and/or C-terminus of the above referenced transmembrane domain polypeptides.

In preferred embodiments, the following transmembrane domain polypeptides are encompassed by the present invention: NIWTHLLGFVLFLFLGILTMLRPNMY (SEQ ID NO:168), LQEKVVFGMFFLGAVLCLSFSWLFHT (SEQ ID NO:169), DYSGIALLIMGSFVPWLYYS (SEQ ID NO:170), PRLIYLSIVCVLGISAIIVAQW (SEQ ID NO:171), VFLGLGLSGVVPTMHFTIAEGFV (SEQ ID NO:172), GQMGWFFLMAVMYITGAGLYAAR (SEQ ID NO:173), and/or HQIFHVLVVAAAFVHFYG (SEQ ID NO:174). Polynucleotides encoding these polypeptides are also provided. The present invention also encompasses the use of these rat AdipoR1 transmembrane domain polypeptides as immunogenic and/or antigenic epitopes as described elsewhere herein.

The present invention also encompasses the polypeptide sequences that intervene between each of the predicted rat AdipoR1 transmembrane domains. Since these regions are solvent accessible either extracellularly or intracellularly, they are particularly useful for designing antibodies specific to each region. Such antibodies may be useful as antagonists or agonists of the rat AdipoR1 full-length polypeptide and may modulate its activity.

In preferred embodiments, the following inter-transmembrane domain polypeptides are encompassed by the present invention: VYCHSEKVSRTFSKL (SEQ ID NO:182), FYCSPQ (SEQ ID NO:183), DRFATPKHRQTRAG (SEQ ID NO:184), KATTV (SEQ ID NO:185), and/or IPERFFPGKFDIWFQS (SEQ ID NO:186). Polynucleotides encoding these polypeptides are also provided. The present invention also encompasses the use of these rat AdipoR1 transmembrane domain polypeptides as immunogenic and/or antigenic epitopes as described elsewhere herein.

In preferred embodiments, the present invention encompasses the use of N-terminal deletions, C-terminal deletions, or any combination of N-terminal and C-terminal deletions of any one or more of the rat AdipoR1 TM1 thru TM7 transmembrane domain polypeptides as antigenic and/or immunogenic epitopes.

In preferred embodiments, the present invention also encompasses the use of N-terminal deletions, C-terminal deletions, or any combination of N-terminal and C-terminal deletions of any one or more of the amino acids intervening (i.e., extracellular or intracellular loops) the rat AdipoR1 TM1 thru TM7 transmembrane domain polypeptides as antigenic and/or immunogenic epitopes.

Although the rat AdipoR1 receptor has seven transmembrane domains, it is believed to be structurally, topologically, and functionally distinct from G-protein coupled receptors. Yamauchi et al demonstrated that the N-terminus of human AdipoR2 is intracellular, as opposed to GPCRs which typically have their N-terminus extracellular. In addition, the human AdipoR2 does not appear to couple to G-proteins, but rather activate unique sets of signalling molecules such as PPAR-alpha, AMPK, and p38 MAPK. The same is thought to be true for AdipoR1.

Likewise, the rat AdipoR1 receptor of the present invention is also thought to be structurally, topologically, and functionally distinct from G-protein coupled receptors. Alternatively, the rat AdipoR1 receptor of the present invention may share at least some biological function with GPCRs.

The rat AdipoR1 polypeptide was also determined to comprise several conserved cysteines which are denoted by dark shading, in addition to other identical residues, as shown in FIGS. 20A-B. Conservation of cysteines at key amino acid residues is indicative of conserved structural features, which may correlate with conservation of protein function and/or activity.

The present invention also encompasses polynucleotides encoding at least 326 consecutive amino acids of the rat AdipoR1 polypeptide of the present invention (SEQ ID NO:165). Preferably the polynucleotides encode a polypeptide having at least some adiponectin receptor activity. The present invention also encompasses polynucleotides having at least 978 consecutive nucleotides of SEQ ID NO:164, wherein said polynucleotides preferably encode a polypeptide having at least some adiponectin receptor activity.

The present invention also is directed to the carboxy terminus of the novel rat AdipoR1 receptor polypeptide fragment located from amino acid 355 to amino acid 375 of SEQ ID NO:165. The present invention also is directed to the novel rat AdipoR1 receptor polynucleotide from nucleotide 1287 to nucleotide 1249 of SEQ ID NO:164. The present invention also encompasses the use of this carboxy terminal fragment polypeptide as an antigenic and/or immunogenic epitope. Antibodies to this particular carboxy terminal epitope of rat AdipoR1 would be useful therapeutically to modulate the activity of the rat AdipoR1 polypeptide.

The human AdipoR2 protein was determined to be expressed predominately in liver (Yamauchi et al., 2003). Likewise, the expression pattern of the rat AdipoR1 polypeptide is also expected to be expressed predominately in liver.

The rat AdipoR1 polynucleotides and polypeptides of the present invention, including modulators and/or fragments thereof, are useful tools for investigating the relationship between adiponectin signaling and glucose homeostasis when rat diabetic models are used for studies. Likewise, rat AdipoR1 is useful for the creation of transgenic knock-out mice. The rat AdipoR1 polynucleotides and polypeptides of the present invention are also useful for exploring the roles of adiponectin signaling in adipogenesis and lipid metabolism.

The rat AdipoR1 polynucleotides and polypeptides of the present invention, including modulators and/or fragments thereof, have uses that include detecting, prognosing, treating, preventing, and/or ameliorating the following diseases and/or disorders: metabolic disorders, inflammatory disorders, cardiovascular disorders, obesity, diabetes, type I diabetes, type II diabetes, gestational diabetes, early onset diabetes, insulin resistance, disorders in which glucose-lowering would be beneficial, disorders in which amelioration of insulin resistance would be beneficial, disorders in which suppressed FA influx into liver would be beneficial, disorders in which reduced serum TG would be beneficial, myocardial infarction, heart failure, atherosclerosis, arteriosclerosis, disorders disclosed herein in the "Cardiovascular Disorders" section, disorders in which adiponectin levels are below normal, disorders that would benefit from increased adiponectin levels, disorders associated with aberrant vascular smooth muscle proliferation, disorders associated with aberrant foam cell formation, disorders in which inhibition of macrophage phagocytosis would be beneficial, disorders in which inhibition of TNF-alpha production would be beneficial, dyslipidemia, diabetic dyslipidemia, mixed dyslipidemia, hypercholesteremia, hypertriglyceridemia, hyperlipidemia, and anorexia nervosa.

The rat AdipoR1 polynucleotides and polypeptides of the present invention, including modulators and/or fragments thereof, have uses that include detecting, prognosing, treating, preventing, and/or ameliorating the following inflammatory diseases and/or disorders: arthritis, rheumatoid arthritis, osteoarthritis, prosthetic joint failure, ulcerative colitis, Crohn's disease, inflammatory bowel and gastrointestinal diseases, gastritis, mucosal inflammation resulting from infection, enteropathy provoked by non-steroidal anti-inflammatory drugs, adult respiratory distress syndrome, asthma, cystic fibrosis, chronic obstructive pulmonary disease, myocarditis, multiple sclerosis, inflammation associated with diabetes melitus, glomerulonephritis, dermatitis, psoriasis, eczema, urticaria, burn injury, glaucoma, organ rejection, multi-organ diseases, systemic lupus erythematosis, sepsis, inflammatory sequelae of viral or bacterial infections, inflammatory conditions associated with atherosclerosis following hypoxic or ischaemic insults (with or without reperfusion, particularly in the brain or in ischaemic heart disease.

The rat AdipoR1 polynucleotides and polypeptides of the present invention, including modulators and/or fragments thereof, have uses that include modulating signal transduction activity, in various cells, tissues, and organisms, and particularly in mammalian liver.

Rat AdipoR1 polynucleotides and polypeptides of the present invention, including modulators and/or fragments thereof, have uses that include detecting, prognosing, treating, preventing, and/or ameliorating the following additional cardiovascular disorders: congestive heart failure, arrthymias, cardiomyopathy, microvascular disease, embolism, thromobosis, pulmonary edema, palpitation, dyspnea, angina, hypotension, syncope, heart murmur, aberrant ECG, hypertrophic cardiomyopathy, the Marfan syndrome, sudden death, prolonged QT syndrome, congenital defects, cardiac viral infections, valvular heart disease, and hypertension.

Similarly, rat AdipoR1 polynucleotides and polypeptides may be useful for ameliorating cardiovascular diseases and symptoms which result indirectly from various non-cardiovascular effects, which include, but are not limited to, the following, obesity, smoking, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, have uses which include, directly or indirectly, treating, preventing, diagnosing, and/or prognosing the following, non-limiting, cardiovascular infections: blood stream invasion, bacteremia, sepsis, *Streptococcus pneumoniae* infection, group a streptococci infection, group b streptococci infection, *Enterococcus* infection, nonenterococcal group D streptococci infection, nonenterococcal group C streptococci infection, nonenterococcal group G streptococci infection, *Streptococcus viridans* infection, *Staphylococcus aureus* infection, coagulase-negative staphylococci infection, gram-negative Bacilli infection, Enterobacteriaceae infection, *Pseudomonas* spp. Infection, *Acinobacter* spp. Infection, *Flavobacterium meningosepticum* infection, *Aeromonas* spp. Infection, *Stenotrophomonas maltophilia* infection, gram-negative coccobacilli infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous *Mycobacteria infection, Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

Rat AdipoR1 polypeptides and polynucleotides have additional uses which include diagnosing diseases related to the over and/or under expression of rat AdipoR1 by identifying mutations in the rat AdipoR1 gene by using rat AdipoR1 sequences as probes or by determining rat AdipoR1 protein or mRNA expression levels. rat AdipoR1 polypeptides, may be useful for screening compounds that affect the activity of the protein. Rat AdipoR1 peptides can also be used for the generation of specific antibodies and as bait in yeast two hybrid screens to find proteins that specifically interact with rat AdipoR1 (described elsewhere herein).

Rat AdipoR1 polynucleotides and polypeptides are particularly useful for the generation of rat AdipoR1 modulators. Such modulators may also have utility in modulating other adiponectin receptors either specifically (e.g., human and mouse orthologs of AdipoR1), or generally (e.g., AdipoR2 receptors known in the art and/or disclosed herein). Rat AdipoR1 polynucleotides and polypeptides are also useful for the generation of rat knock-out mice that lack the Adipo R1 gene, and/or in the generation of other species that have the rat AdipoR1 gene knocked-in. Such recombinant mice are useful for assessing biological function and characteristics of the rat AdipoR1 receptor, and would also be useful as model organisms for assessing the same.

In preferred embodiments, the following N-terminal rat AdipoR1 deletion polypeptides are encompassed by the present invention: M1-L375, S2-L375, S3-L375, H4-L375, K5-L375, G6-L375, S7-L375, A8-L375, V9-L375, A10-L375, Q11-L375, G12-L375, N13-L375, G14-L375, A15-L375, P16-L375, S17-L375, S18-L375, N19-L375, R20-L375, E21-L375, A22-L375, D23-L375, T24-L375, V25-L375, E26-L375, L27-L375, A28-L375, E29-L375, L30-L375, G31-L375, P32-L375, L33-L375, L34-L375, E35-L375, E36-L375, K37-L375, G38-L375, K39-L375, R40-L375, A41-L375, A42-L375, T43-L375, S44-L375, P45-L375, A46-L375, K47-L375, A48-L375, E49-L375, E50-L375, E51-L375, Q52-L375, A53-L375, C54-L375, P55-L375, V56-L375, P57-L375, Q58-L375, E59-L375, E60-L375, E61-L375, E62-L375, E63-L375, V64-L375, R65-L375, V66-L375, L67-L375, T68-L375, L69-L375, P70-L375, L71-L375, Q72-L375, A73-L375, H74-L375, H75-L375, A76-L375, M77-L375, E78-L375, K79-L375, M80-L375, E81-L375, E82-L375, F83-L375, V84-L375, Y85-L375, K86-L375, V87-L375, W88-L375, E89-L375, G90-L375, R91-L375, W92-L375, R93-L375, V94-L375, I95-L375, P96-L375, Y97-L375, D98-L375, V99-L375, L100-L375, P101-L375, D102-L375, W103-L375, L104-L375, K105-L375, D106-L375, N107-L375, D108-L375, Y109-L375, L110-L375, L111-L375, H112-L375, G113-L375, H114-L375, R115-L375, P116-L375, P117-L375, M118-L375, P119-L375, S120-L375, F121-L375, R122-L375, A123-L375, C124-L375, F125-L375, K126-L375, S127-L375, I128-L375, F129-L375, R130-L375, I131-L375, H132-L375, T133-L375, E134-L375, T135-L375, G136-L375, N137-L375, I138-L375, W139-L375, T140-L375, H141-L375, L142-L375, L143-L375, G144-L375, F145-L375, V146-L375, L147-L375, F148-L375, L149-L375, F150-L375, L151-L375, G152-L375, I153-L375, L154-L375, T155-L375, M156-L375, L157-L375, R158-L375, P159-L375, N160-L375, M161-L375, Y162-L375, F163-L375, M164-L375, A165-L375, P166-L375, L167-L375, Q168-L375, E169-L375, K170-L375, V171-L375, V172-L375, F173-L375, G174-L375, M175-L375, F176-L375, F177-L375, L178-L375, G179-L375, A180-L375, V181-L375, L182-L375, C183-L375, L184-L375, S185-L375, F186-L375, S187-L375, W188-L375, L189-L375, F190-L375, H191-L375, T192-L375, V193-L375, Y194-L375, C195-L375, H196-L375, S197-L375, E198-L375, K199-L375, V200-L375, S201-L375, R202-L375, T203-L375, F204-L375, S205-L375, K206-L375, L207-L375, D208-L375, Y209-L375, S210-L375, G211-L375, I212-L375, A213-L375, L214-L375, L215-L375, I216-L375, M217-L375, G218-L375, S219-L375, F220-L375, V221-L375, P222-L375, W223-L375, L224-L375, Y225-L375, Y226-L375, S227-L375, F228-L375, Y229-L375, C230-L375, S231-L375, P232-L375, Q233-L375, P234-L375, R235-L375, L236-L375, I237-L375, Y238-L375, L239-L375, S240-L375, I241-L375, V242-L375, C243-L375, V244-L375, L245-L375, G246-L375, I247-L375, S248-L375, A249-L375, I250-L375, I251-L375, V252-L375, A253-L375, Q254-L375, W255-L375, D256-L375, R257-L375, F258-L375, A259-L375, T260-L375, P261-L375, K262-L375, H263-L375, R264-L375, Q265-L375, T266-L375, R267-L375, A268-L375, G269-L375, V270-L375, F271-L375, L272-L375, G273-L375, L274-L375, G275-L375, L276-L375, S277-L375, G278-L375, V279-L375, V280-L375, P281-L375, T282-L375, M283-L375, H284-L375, F285-L375, T286-L375, I287-L375, A288-L375, E289-L375, G290-L375, F291-L375, V292-L375, K293-L375, A294-L375, T295-L375, T296-L375, V297-L375, G298-L375, Q299-L375, M300-L375, G301-L375, W302-L375, F303-L375, F304-L375, L305-L375, M306-L375, A307-L375, V308-L375, M309-L375, Y310-L375, I311-L375, T312-L375, G313-L375, A314-L375, G315-L375, L316-L375, Y317-L375, A318-L375, A319-L375, R320-L375, I321-L375, P322-L375, E323-L375, R324-L375, F325-L375, F326-L375, P327-L375, G328-L375, K329-L375, F330-L375, D331-L375, I332-L375, W333-L375, F334-L375, Q335-L375, S336-L375, H337-L375, Q338-L375, I339-L375, F340-L375, H341-L375, V342-L375, L343-L375, V344-L375, V345-L375, A346-L375, A347-L375, A348-L375, F349-L375, V350-L375, H351-L375, F352-L375, Y353-L375, G354-L375, V355-L375, S356-L375, N357-L375, L358-L375, Q359-L375, E360-L375, F361-L375, R362-L375, Y363-L375, G364-L375, L365-L375, E366-L375, G367-L375, G368-L375, and/or C369-L375 of SEQ ID NO:165. Polynucleotide sequences encoding these polypeptides are also provided. The present invention also encompasses the use of these N-terminal rat AdipoR1 deletion polypeptides as immunogenic and/or antigenic epitopes as described elsewhere herein.

In preferred embodiments, the following C-terminal rat AdipoR1 deletion polypeptides are encompassed by the present invention: M1-L375, M1-L374, M1-S373, M1-D372, M1-D371, M1-T370, M1-C369, M1-G368, M1-G367, M1-E366, M1-L365, M1-G364, M1-Y363, M1-R362, M1-F361, M1-E360, M1-Q359, M1-L358, M1-N357, M1-S356, M1-V355, M1-G354, M1-Y353, M1-F352, M1-H351, M1-V350, M1-F349, M1-A348, M1-A347, M1-A346, M1-V345, M1-V344, M1-L343, M1-V342, M1-H341, M1-F340, M1-I339, M1-Q338, M1-H337, M1-S336, M1-Q335, M1-F334, M1-W333, M1-I332, M1-D331, M1-F330, M1-K329, M1-G328, M1-P327, M1-F326, M1-F325, M1-R324, M1-E323, M1-P322, M1-I321, M1-R320, M1-A319, M1-A318, M1-Y317, M1-L316, M1-G315, M1-A314, M1-G313, M1-T312, M1-I311, M1-Y310, M1-M309, M1-V308, M1-A307, M1-M306, M1-L305, M1-F304, M1-F303, M1-W302, M1-G301, M1-M300, M1-Q299, M1-G298, M1-V297, M1-T296, M1-T295, M1-A294, M1-K293, M1-V292, M1-F291, M1-G290, M1-E289, M1-A288, M1-I287, M1-T286, M1-F285, M1-H284, M1-M283, M1-T282, M1-P281, M1-V280, M1-V279, M1-G278, M1-S277, M1-L276, M1-G275, M1-L274, M1-G273, M1-L272, M1-F271, M1-V270, M1-G269, M1-A268, M1-R267, M1-T266, M1-Q265, M1-R264, M1-H263, M1-K262, M1-P261, M1-T260, M1-A259, M1-F258, M1-R257, M1-D256, M1-W255, M1-Q254, M1-A253, M1-V252, M1-I251, M1-I250, M1-A249, M1-S248, M1-I247, M1-G246, M1-L245, M1-V244, M1-C243, M1-V242, M1-I241, M1-S240, M1-L239, M1-Y238, M1-I237, M1-L236, M1-R235, M1-P234, M1-Q233, M1-P232, M1-S231, M1-C230, M1-Y229, M1-F228, M1-S227, M1-Y226, M1-Y225, M1-L224, M1-W223, M1-P222, M1-V221, M1-F220, M1-S219, M1-G218, M1-M217, M1-I216, M1-L215, M1-L214, M1-A213, M1-I212, M1-G211, M1-S210, M1-Y209, M1-D208, M1-L207, M1-K206, M1-S205, M1-F204, M1-T203, M1-R202, M1-S201, M1-V200, M1-K199, M1-E198, M1-S197, M1-H196, M1-C195, M1-Y194, M1-V193, M1-T192, M1-H191, M1-F190, M1-L189, M1-W188, M1-S187, M1-F186, M1-S185, M1-L184, M1-C183, M1-L182, M1-V181, M1-A180, M1-G179, M1-L178, M1-F177, M1-F176, M1-M175, M1-G174, M1-F173, M1-V172, M1-V171, M1-K170, M1-E169, M1-Q168, M1-L167, M1-P166, M1-A165, M1-M164, M1-F163, M1-Y162, M1-M161, M1-N160, M1-P159, M1-R158, M1-L157, M1-M156, M1-T155, M1-L154, M1-I153, M1-G152, M1-L151, M1-F150, M1-L149, M1-F148, M1-L147, M1-V146, M1-F145, M1-G144, M1-L143, M1-L142, M1-H141, M1-T140, M1-W139, M1-I138, M1-N137, M1-G136, M1-T135, M1-E134, M1-T133, M1-H132, M1-I131, M1-R130, M1-F129, M1-I128, M1-S127, M1-K126, M1-F125, M1-C124, M1-A123, M1-R122, M1-F121, M1-S120, M1-P119, M1-M118, M1-P117, M1-P116, M1-R115, M1-H114, M1-G113, M1-H112, M1-L111, M1-L110, M1-Y109, M1-D108, M1-N107, M1-D106, M1-K105, M1-L104, M1-W103, M1-D102, M1-P101, M1-L100, M1-V99, M1-D98, M1-Y97, M1-P96, M1-I95, M1-V94, M1-R93, M1-W92, M1-R91, M1-G90, M1-E89, M1-W88, M1-V87, M1-K86, M1-Y85, M1-V84, M1-F83, M1-E82, M1-E81, M1-M80, M1-K79, M1-E78, M1-M77, M1-A76, M1-H75, M1-H74, M1-A73, M1-Q72, M1-L71, M1-P70, M1-L69, M1-T68, M1-L67, M1-V66, M1-R65, M1-V64, M1-E63, M1-E62, M1-E61, M1-E60, M1-E59, M1-Q58, M1-P57, M1-V56, M1-P55, M1-C54, M1-A53, M1-Q52, M1-E51, M1-E50, M1-E49, M1-A48, M1-K47, M1-A46, M1-P45, M1-S44, M1-T43, M1-A42, M1-A41, M1-R40, M1-K39, M1-G38, M1-K37, M1-E36, M1-E35, M1-L34, M1-L33, M1-P32, M1-G31, M1-L30, M1-E29, M1-A28, M1-L27, M1-E26, M1-V25, M1-T24, M1-D23, M1-A22, M1-E21, M1-R20, M1-N19, M1-S18, M1-S17, M1-P16, M1-A15, M1-G14, M1-N13, M1-G12, M1-Q11, M1-A10, M1-V9, M1-A8, and/or M1-S7 of SEQ ID NO:165. Polynucleotide sequences encoding these polypeptides are also provided. The present invention also encompasses the use of these C-terminal rat AdipoR1 deletion polypeptides as immunogenic and/or antigenic epitopes as described elsewhere herein.

Alternatively, preferred polypeptides of the present invention may comprise polypeptide sequences corresponding to, for example, internal regions of the rat AdipoR1 polypeptide (e.g., any combination of both N- and C-terminal rat AdipoR1 polypeptide deletions) of SEQ ID NO:165. For example, internal regions could be defined by the equation: amino acid NX to amino acid CX, wherein NX refers to any N-terminal deletion polypeptide amino acid of rat AdipoR1 (SEQ ID NO:165), and where CX refers to any C-terminal deletion polypeptide amino acid of rat AdipoR1 (SEQ ID NO:165). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the rat AdipoR1 polypeptide.

The rat AdipoR1 polypeptide of the present invention was determined to comprise several phosphorylation sites based upon the Motif algorithm (Genetics Computer Group, Inc.). The phosphorylation of such sites may regulate some biological activity of the rat AdipoR1 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the rat AdipoR1 polypeptide to associate with other polypeptides, particularly the cognate ligand for rat AdipoR1, such as adiponectin, or its ability to modulate certain cellular signally pathways such as AMPK, p38 MAPK, MAPK, and/or ACC.

The rat AdipoR1 polypeptide was predicted to comprise five PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. 260: 12492-12499 (1985); which are hereby incorporated by reference herein.

In preferred embodiments, the following PKC phosphorylation site polypeptide is encompassed by the present invention: MSSHKGSAVA (SEQ ID NO:188), NGAPSSNREADTV (SEQ ID NO:189), RPPMPSFRACFKS (SEQ ID NO:190), TVYCHSEKVSRTF (SEQ ID NO:191), and/or WDRFATPKHRQTR (SEQ ID NO:192). Polynucleotides encoding these polypeptides are also provided. The present invention also encompasses the use of the rat AdipoR1 PKC phosphorylation site polypeptides as immunogenic and/or antigenic epitopes as described elsewhere herein.

The rat AdipoR1 polypeptide was predicted to comprise three casein kinase II phosphorylation sites using the Motif algorithm (Genetics Computer Group, Inc.). Casein kinase II (CK-2) is a protein serine/threonine kinase whose activity is independent of cyclic nucleotides and calcium. CK-2 phosphorylates many different proteins. The substrate specificity [1] of this enzyme can be summarized as follows: (1) Under comparable conditions Ser is favored over Thr.; (2) An acidic residue (either Asp or Glu) must be present three residues from the C-terminal of the phosphate acceptor site; (3) Additional acidic residues in positions +1, +2, +4, and +5 increase the phosphorylation rate. Most physiological substrates have at least one acidic residue in these positions; (4) Asp is preferred to Glu as the provider of acidic determinants; and (5) A basic residue at the N-terminal of the acceptor site decreases the phosphorylation rate, while an acidic one will increase it.

A consensus pattern for casein kinase II phosphorylations site is as follows: [ST]-x(2)-[DE], wherein 'x' represents any amino acid, and S or T is the phosphorylation site.

Additional information specific to casein kinase II phosphorylation site-II domains may be found in reference to the following publication: Pinna L. A., Biochim. Biophys. Acta 1054:267-284 (1990); which is hereby incorporated herein in its entirety.

In preferred embodiments, the following casein kinase II phosphorylation site polypeptide is encompassed by the present invention: NGAPSSNREADTVE (SEQ ID NO:193), VSRTFSKLDYSGIA (SEQ ID NO:194), and/or PTMHFTIAEGFVKA (SEQ ID NO:195). Polynucleotides encoding these polypeptides are also provided. The present invention also encompasses the use of this casein kinase II phosphorylation site polypeptide as an immunogenic and/or antigenic epitope as described elsewhere herein.

The rat AdipoR1 polypeptide was predicted to comprise one tyrosine phosphorylation site using the Motif algorithm (Genetics Computer Group, Inc.). Such sites are phosphorylated at the tyrosine amino acid residue. The consensus pattern for tyrosine phosphorylation sites are as follows: [RK]-x(2)-[DE]-x(3)-Y, or or [RK]-x(3)-[DE]-x(2)-Y, where Y represents the phosphorylation site and 'x' represents an intervening amino acid residue. Additional information specific to tyrosine phosphorylation sites can be found in Patschinsky T., Hunter T., Esch F. S., Cooper J. A., Sefton B. M., Proc. Natl. Acad. Sci. U.S.A. 79:973-977 (1982); Hunter T., J. Biol. Chem. 257:4843-4848 (1982), and Cooper J. A., Esch F. S., Taylor S. S., Hunter T., J. Biol. Chem. 259:7835-7841 (1984), which are hereby incorporated herein by reference.

In preferred embodiments, the following tyrosine phosphorylation site polypeptides are encompassed by the present invention: HHAMEKMEEFVYKVWEG (SEQ ID NO:196). Polynucleotides encoding these polypeptides are also provided. The present invention also encompasses the use of these rat AdipoR1 tyrosine phosphorylation site polypeptides as immunogenic and/or antigenic epitopes as described elsewhere herein.

The rat AdipoR1 polypeptide was predicted to comprise nine N-myristoylation sites using the Motif algorithm (Genetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA: protein N-myristoyl transferase (NMT), has been derived from the sequence of known N-myristoylated proteins and from studies using synthetic peptides. The specificity seems to be the following: i.) The N-terminal residue must be glycine; ii.) In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-{EDRKHPFYW}-x(2)-[STAGCN]-{P}, wherein 'x' represents any amino acid, and G is the N-myristoylation site.

Additional information specific to N-myristoylation sites may be found in reference to the following publication: Towler D. A., Gordon J. I., Adams S. P., Glaser L., Annu. Rev. Biochem. 57:69-99 (1988); and Grand R. J. A., Biochem. J. 258:625-638 (1989); which is hereby incorporated herein in its entirety.

In preferred embodiments, the following N-myristoylation site polypeptides are encompassed by the present invention: MSSHKGSAVAQGNGAP (SEQ ID NO:197), VAQGNGAPSSNREADT (SEQ ID NO:198), IHTETGNIWTHLLGFV (SEQ ID NO:199), GMFFLGAVLCLSFSWL (SEQ ID NO:200), RQTRAGVFLGLGLSGV (SEQ ID NO:201), AGVFLGLGLSGVVPTM (SEQ ID NO:202), GLGLSGVVPTMHFTIA (SEQ ID NO:203), YITGAGLYAARIPERF (SEQ ID NO:204), and/or QEFRYGLEGGCTDDSL (SEQ ID NO:205). Polynucleotides encoding these polypeptides are also provided. The present invention also encompasses the use of these N-myristoylation site polypeptides as immunogenic and/or antigenic epitopes as described elsewhere herein.

The rat AdipoR1 polypeptide has been shown to comprise one amidation site according to the Motif algorithm (Genetics Computer Group, Inc.). The precursor of hormones and other active peptides which are C-terminally amidated is always directly followed by a glycine residue which provides the amide group, and most often by at least two consecutive basic residues (Arg or Lys) which generally function as an active peptide precursor cleavage site. Although all amino acids can be amidated, neutral hydrophobic residues such as Val or Phe are good substrates, while charged residues such as Asp or Arg are much less reactive. A consensus pattern for amidation sites is the following: x-G-[RK]-[RK], wherein "X" represents the amidation site. Additional information relating to asparagine glycosylation may be found in reference to the following publications, which are hereby incorporated by reference herein: Kreil G., Meth. Enzymol. 106:218-223 (1984); and Bradbury A. F., Smyth D. G., Biosci. Rep. 7:907-916 (1987).

In preferred embodiments, the following amidation site polypeptide is encompassed by the present invention: PLLEEKGKRAATSP (SEQ ID NO:206). Polynucleotides encoding these polypeptides are also provided. The present invention also encompasses the use of this rat AdipoR1 amidation site polypeptide as an immunogenic and/or antigenic epitope as described elsewhere herein.

The present invention encompasses the identification of compounds and drugs which stimulate rat AdipoR1 on the one hand (i.e., agonists) and which inhibit the function of rat AdipoR1 on the other hand (i.e., antagonists). In general, such screening procedures involve providing appropriate cells which express the receptor polypeptide of the present invention on the surface thereof. Such cells may include, for example, cells from mammals, yeast, *Drosophila* or *E. coli*. In a preferred embodiment, a polynucleotide encoding the receptor of the present invention may be employed to transfect cells to thereby express the rat AdipoR1 polypeptide. The expressed receptor may then be contacted with a test compound to observe binding, stimulation or inhibition of a functional response.

Many polynucleotide sequences, such as EST sequences, are publicly available and accessible through sequence databases. Some of these sequences are related to SEQ ID NO:164 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 1428 of SEQ ID NO:164, b is an integer between 15 to 1442, where both a and b correspond to the positions of nucleotide residues shown in SEQ ID NO:164, and where b is greater than or equal to a+14.

Features of the Polypeptide Encoded by Polynucleotide No:7

The polypeptide of this polynucleotide provided as SEQ ID NO:167 (FIGS. 21A-B), encoded by the polynucleotide sequence according to SEQ ID NO:166 (FIGS. 21A-B), and/or encoded by the polynucleotide contained within the deposited clone, rat AdipoR2 (also referred to as rAdipoR1), is believed to represent the physiologically relevant form of the rat AdipoR2 polypeptide.

An alignment of the rat AdipoR2 polypeptide of the present invention with the human AdipoR2v2 polypeptide of the present invention (SEQ ID NO:104); the human AdipoR2v1 protein of the present invention (hAdipoR2v1; SEQ ID NO:2); and the mouse AdipoR2v1 protein of the present invention (mAdipoR2v1; SEQ ID NO:4) is provided in FIG. 24.

The inventors believe that the rat AdipoR2 polypeptide of the present invention is the physiologically relevant form of this protein. Likewise, the rat AdipoR2 polypeptide is expected to share the same or similar biological activity as the reported activity for the mouse and human AdipoR2 sequence, in addition to the human AdipoR2v1 and human AdipoR2v2 polypeptides of the present invention. Preferably, the rat AdipoR2 polypeptide is expected to bind to adiponectin, bind to globular adiponectin, bind full-length adiponectin, ability to regulate AMPK phosphorylation, ability to regulate ACC phosphorylation, ability to regulate MAPK phosphorylation, ability to regulate p38 MAPK phosphorylation, among others.

The determined nucleotide sequence of the rat AdipoR2 cDNA in FIGS. 21A-B (SEQ ID NO:166) contains an open reading frame encoding a protein of about 386 amino acid residues, with a deduced molecular weight of about 44.1 kDa. The amino acid sequence of the predicted rat AdipoR2 polypeptide is shown in FIGS. 21A-B (SEQ ID NO:167). By virtue of the rat AdipoR2 protein representing an ortholog of the human and mouse AdipoR2 polypeptides, and particularly the human AdipoR1v1 of the present invention, the rat AdipoR2 polypeptide shown in FIGS. 21A-B shares significant identity and similarity to other adiponectin receptors, as shown in FIG. 24. The percent identity and similarity values between the rat AdipoR2 polypeptide to these known adiponectin receptors is provided in FIG. 26.

The rat AdipoR2 polypeptide was predicted to comprise seven transmembrane domains (TM1 to TM7) located from about amino acid 151 to about amino acid 172 (TM1; SEQ ID NO:175); from about amino acid 177 to about amino acid 201 (TM2; SEQ ID NO:176); from about amino acid 217 to about amino acid 235 (TM3; SEQ ID NO:177); from about amino acid 243 to about amino acid 266 (TM4; SEQ ID NO:178); from about amino acid 279 to about amino acid 303 (TM5; SEQ ID NO:179); from about amino acid 307 to about amino acid 327 (TM6; SEQ ID NO:180); and/or from about amino acid 348 to about amino acid 364 (TM7; SEQ ID NO:181) of SEQ ID NO:167 (FIGS. 21A-B). In this context, the term "about" may be construed to mean 1, 2, 3, 4, 5, 6, 7, 8, 9, or 10 amino acids beyond the N-Terminus and/or C-terminus of the above referenced transmembrane domain polypeptides.

In preferred embodiments, the following transmembrane domain polypeptides are encompassed by the present invention: THLLGCVFFLCLGIFYMFRPNI (SEQ ID NO:175), LQEKVVFGLFFLGAILCLSFSWLF (SEQ ID NO:176), KLDYSGIALLIMGSFVPWL (SEQ ID NO:177), PQPCFIYLIVICVLGIAAIIVSQW (SEQ ID NO:178), AGVFVGLGLSGIIPTLHYVISEGFL (SEQ ID NO:179), TIRQIGWLMLMASLYITGAAL (SEQ ID NO:180), and/or HQLFHIFVVAGAFVHFH (SEQ ID NO:181). Polynucleotides encoding these polypeptides are also provided. The present invention also encompasses the use of these rat AdipoR2 transmembrane domain polypeptides as immunogenic and/or antigenic epitopes as described elsewhere herein.

The present invention also encompasses the polypeptide sequences that intervene between each of the predicted rat AdipoR2 transmembrane domains. Since these regions are solvent accessible either extracellularly or intracellularly, they are particularly useful for designing antibodies specific to each region. Such antibodies may be useful as antagonists or agonists of the rat AdipoR2 full-length polypeptide and may modulate its activity.

In preferred embodiments, the following inter-transmembrane domain polypeptides are encompassed by the present invention: SFVA (SEQ ID NO:207), HTVYCHSEGVSRLFS (SEQ ID NO:208), YYSFYCN (SEQ ID NO:209), DMFATPQYRGVR (SEQ ID NO:210), and/or YAARIPERFFPGKCDIWFHS (SEQ ID NO:211). Polynucleotides encoding these polypeptides are also provided. The present invention also encompasses the use of these rat AdipoR2 transmembrane domain polypeptides as immunogenic and/or antigenic epitopes as described elsewhere herein.

In preferred embodiments, the present invention encompasses the use of N-terminal deletions, C-terminal deletions, or any combination of N-terminal and C-terminal deletions of any one or more of the rat AdipoR2 TM1 thru TM7 transmembrane domain polypeptides as antigenic and/or immunogenic epitopes.

In preferred embodiments, the present invention also encompasses the use of N-terminal deletions, C-terminal deletions, or any combination of N-terminal and C-terminal deletions of any one or more of the amino acids intervening (i.e., extracellular or intracellular loops) the rat AdipoR2 TM1 thru TM7 transmembrane domain polypeptides as antigenic and/or immunogenic epitopes.

Although the rat AdipoR2 receptor has seven transmembrane domains, it is believed to be structurally, topologically, and functionally distinct from G-protein coupled receptors. Yamauchi et al demonstrated that the N-terminus of human AdipoR2 is intracellular, as opposed to GPCRs which typically have their N-terminus extracellular. In addition, the human AdipoR2 does not appear to couple to G-proteins, but rather activate unique sets of signalling molecules such as PPAR-alpha, AMPK, and p38 MAPK. The same is thought to be true for AdipoR1.

Likewise, the rat AdipoR2 receptor of the present invention is also thought to be structurally, topologically, and functionally distinct from G-protein coupled receptors. Alternatively, the rat AdipoR2 receptor of the present invention may share at least some biological function with GPCRs.

The rat AdipoR2 polypeptide was also determined to comprise several conserved cysteines which are denoted by dark shading, in addition to other identical residues, as shown in FIGS. 21A-B. Conservation of cysteines at key amino acid residues is indicative of conserved structural features, which may correlate with conservation of protein function and/or activity.

The present invention also encompasses polynucleotides encoding at least 235 consecutive amino acids of the rat AdipoR2 polypeptide of the present invention (SEQ ID NO:167). Preferably the polynucleotides encode a polypeptide having at least some adiponectin receptor activity. The present invention also encompasses polynucleotides having at least 705 consecutive nucleotides of SEQ ID NO:166, wherein said polynucleotides preferably encode a polypeptide having at least some adiponectin receptor activity.

The present invention also is directed to the novel rat AdipoR2 receptor polypeptide fragment located from amino acid 1 to amino 87 of SEQ ID NO:167. The present invention also is directed to the novel rat AdipoR2 receptor polynucleotide from nucleotide 1 to nucleotide 390 of SEQ ID NO:166.

The present invention also is directed to the carboxy terminus of the novel rat AdipoR2 receptor polypeptide fragment located from amino acid 365 to amino acid 386 of SEQ ID NO:167. The present invention also is directed to the novel rat AdipoR2 receptor polynucleotide from nucleotide 1222 to nucleotide 1287 of SEQ ID NO:166. The present invention also encompasses the use of this carboxy terminal fragment polypeptide as an antigenic and/or immunogenic epitope. Antibodies to this particular carboxy terminal epitope of rat AdipoR2 would be useful therapeutically to modulate the activity of the rat AdipoR2 polypeptide.

The human AdipoR2 protein was determined to be expressed predominately in liver (Yamauchi et al., 2003). Likewise, the expression pattern of the rat AdipoR2 polypeptide is also expected to be expressed predominately in liver.

The rat AdipoR2 polynucleotides and polypeptides of the present invention, including modulators and/or fragments thereof, are useful tools for investigating the relationship between adiponectin signaling and glucose homeostasis when rat diabetic models are used for studies. Likewise, rat AdipoR2 is useful for the creation of transgenic knock-out mice. The rat AdipoR2 polynucleotides and polypeptides of the present invention are also useful for exploring the roles of adiponectin signaling in adipogenesis and lipid metabolism.

The rat AdipoR2 polynucleotides and polypeptides of the present invention, including modulators and/or fragments thereof, have uses that include detecting, prognosing, treating, preventing, and/or ameliorating the following diseases and/or disorders: metabolic disorders, inflammatory disorders, cardiovascular disorders, obesity, diabetes, type I diabetes, type II diabetes, gestational diabetes, early onset diabetes, insulin resistance, disorders in which glucose-lowering would be beneficial, disorders in which amelioration of insulin resistance would be beneficial, disorders in which suppressed FA influx into liver would be beneficial, disorders in which reduced serum TG would be beneficial, myocardial infarction, heart failure, atherosclerosis, arteriosclerosis, disorders disclosed herein in the "Cardiovascular Disorders" section, disorders in which adiponectin levels are below normal, disorders that would benefit from increased adiponectin levels, disorders associated with aberrant vascular smooth muscle proliferation, disorders associated with aberrant foam cell formation, disorders in which inhibition of macrophage phagocytosis would be beneficial, disorders in which inhibition of TNF-alpha production would be beneficial, dyslipidemia, diabetic dyslipidemia, mixed dyslipidemia, hypercholesteremia, hypertriglyceridemia, hyperlipidemia, and anorexia nervosa.

The rat AdipoR2 polynucleotides and polypeptides of the present invention, including modulators and/or fragments thereof, have uses that include detecting, prognosing, treating, preventing, and/or ameliorating the following inflammatory diseases and/or disorders: arthritis, rheumatoid arthritis, osteoarthritis, prosthetic joint failure, ulcerative colitis, Crohn's disease, inflammatory bowel and gastrointestinal diseases, gastritis, mucosal inflammation resulting from infection, enteropathy provoked by non-steroidal anti-inflammatory drugs, adult respiratory distress syndrome, asthma, cystic fibrosis, chronic obstructive pulmonary disease, myocarditis, multiple sclerosis, inflammation associated with diabetes melitus, glomerulonephritis, dermatitis, psoriasis, eczema, urticaria, burn injury, glaucoma, organ rejection, multi-organ diseases, systemic lupus erythematosis, sepsis, inflammatory sequelae of viral or bacterial infections, inflammatory conditions associated with atherosclerosis following hypoxic or ischaemic insults (with or without reperfusion, particularly in the brain or in ischaemic heart disease.

The rat AdipoR2 polynucleotides and polypeptides of the present invention, including modulators and/or fragments thereof, have uses that include modulating signal transduction activity, in various cells, tissues, and organisms, and particularly in mammalian liver.

Rat AdipoR2 polynucleotides and polypeptides of the present invention, including modulators and/or fragments thereof, have uses that include detecting, prognosing, treating, preventing, and/or ameliorating the following additional cardiovascular disorders: congestive heart failure, arrthymias, cardiomyopathy, microvascular disease, embolism, thrombosis, pulmonary edema, palpitation, dyspnea, angina, hypotension, syncope, heart murmur, aberrant ECG, hypertrophic cardiomyopathy, the Marfan syndrome, sudden death, prolonged QT syndrome, congenital defects, cardiac viral infections, valvular heart disease, and hypertension.

Similarly, rat AdipoR2 polynucleotides and polypeptides may be useful for ameliorating cardiovascular diseases and symptoms which result indirectly from various non-cardiovascular effects, which include, but are not limited to, the following, obesity, smoking, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, have uses which include, directly or indirectly, treating, preventing, diagnosing, and/or prognosing the following, non-limiting, cardiovascular infections: blood stream invasion, bacteremia, sepsis, *Streptococcus pneumoniae* infection, group a streptococci infection, group b streptococci infection, *Enterococcus* infection, nonenterococcal group D streptococci infection, nonenterococcal group C streptococci infection, nonenterococcal group G streptococci infection, *Streptococcus viridans* infection, *Staphylococcus aureus* infection, coagulase-negative staphylococci infection, gram-negative Bacilli infection, Enterobacteriaceae infection, *Pseudomonas* spp. Infection, *Acinobacter* spp. Infection, *Flavobacterium meningosepticum* infection, *Aeromonas* spp. Infection, *Stenotrophomonas maltophilia* infection, gram-negative coccobacilli infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous *Mycobacteria* infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

Rat AdipoR2 polypeptides and polynucleotides have additional uses which include diagnosing diseases related to the over and/or under expression of rat AdipoR2 by identifying mutations in the rat AdipoR2 gene by using rat AdipoR2 sequences as probes or by determining rat AdipoR2 protein or mRNA expression levels. rat AdipoR2 polypeptides, may be useful for screening compounds that affect the activity of the protein. Rat AdipoR1 peptides can also be used for the generation of specific antibodies and as bait in yeast two hybrid screens to find proteins that specifically interact with rat AdipoR2 (described elsewhere herein).

Rat AdipoR2 polynucleotides and polypeptides are particularly useful for the generation of rat AdipoR2 modulators. Such modulators may also have utility in modulating other adiponectin receptors either specifically (e.g., human and mouse orthologs of AdipoR2, particularly the human AdipoR2v1 polypeptide of the present invention), or generally (e.g., AdipoR1 receptors known in the art and/or disclosed herein). Rat AdipoR2 polynucleotides and polypeptides are also useful for the generation of rat knock-out mice that lack the Adipo R2 gene, and/or in the generation of other species that have the rat AdipoR2 gene knocked-in. Such recombinant mice are useful for assessing biological function and characteristics of the rat AdipoR2 receptor, and would also be useful as model organisms for assessing the same.

In preferred embodiments, the following N-terminal rat AdipoR2 deletion polypeptides are encompassed by the present invention: M1-L386, N2-L386, E3-L386, P4-L386, T5-L386, E6-L386, H7-L386, R8-L386, L9-L386, G10-L386, C11-L386, T12-L386, R13-L386, T14-L386, P15-L386, E16-L386, P17-L386, D18-L386, I19-L386, R20-L386, L21-L386, R22-L386, K23-L386, G24-L386, H25-L386, Q26-L386, L27-L386, D28-L386, D29-L386, T30-L386, R31-L386, G32-L386, G33-L386, N34-L386, N35-L386, D36-L386, N37-L386, H38-L386, H39-L386, G40-L386, D41-L386, L42-L386, E43-L386, P44-L386, S45-L386, L46-L386, E47-L386, T48-L386, P49-L386, V50-L386, C51-L386, S52-L386, S53-L386, Y54-L386, Y55-L386, E56-L386, N57-L386, S58-L386, P59-L386, E60-L386, E61-L386, L62-L386, E63-L386, C64-L386, H65-L386, D66-L386, D67-L386, N68-L386, S69-L386, Q70-L386, E71-L386, D72-L386, E73-L386, G74-L386, F75-L386, M76-L386, G77-L386, M78-L386, S79-L386, P80-L386, L81-L386, L82-L386, Q83-L386, A84-L386, H85-L386, H86-L386, A87-L386, M88-L386, E89-L386, R90-L386, M91-L386, E92-L386, E93-L386, F94-L386, V95-L386, C96-L386, K97-L386, V98-L386, W99-L386, E100-L386, G101-L386, R102-L386, W103-L386, R104-L386, V105-L386, I106-L386, P107-L386, H108-L386, D109-L386, V110-L386, L111-L386, P112-L386, D113-L386, W114-L386, L115-L386, K116-L386, D117-L386, N118-L386, D119-L386, F120-L386, L121-L386, L122-L386, H123-L386, G124-L386, H125-L386, R126-L386, P127-L386, P128-L386, M129-L386, P130-L386, S131-L386, F132-L386, R133-L386, A134-L386, C135-L386, F136-

L386, K137-L386, S138-L386, I139-L386, F140-L386, R141-L386, I142-L386, H143-L386, T144-L386, E145-L386, T146-L386, G147-L386, N148-L386, I149-L386, W150-L386, T151-L386, H152-L386, L153-L386, L154-L386, G155-L386, C156-L386, V157-L386, F158-L386, F159-L386, L160-L386, C161-L386, L162-L386, G163-L386, I164-L386, F165-L386, Y166-L386, M167-L386, F168-L386, R169-L386, P170-L386, N171-L386, I172-L386, S173-L386, F174-L386, V175-L386, A176-L386, P177-L386, L178-L386, Q179-L386, E180-L386, K181-L386, V182-L386, V183-L386, F184-L386, G185-L386, L186-L386, F187-L386, F188-L386, L189-L386, G190-L386, A191-L386, I192-L386, L193-L386, C194-L386, L195-L386, S196-L386, F197-L386, S198-L386, W199-L386, L200-L386, F201-L386, H202-L386, T203-L386, V204-L386, Y205-L386, C206-L386, H207-L386, S208-L386, E209-L386, G210-L386, V211-L386, S212-L386, R213-L386, L214-L386, F215-L386, S216-L386, K217-L386, L218-L386, D219-L386, Y220-L386, S221-L386, G222-L386, I223-L386, A224-L386, L225-L386, L226-L386, I227-L386, M228-L386, G229-L386, S230-L386, F231-L386, V232-L386, P233-L386, W234-L386, L235-L386, Y236-L386, Y237-L386, S238-L386, F239-L386, Y240-L386, C241-L386, N242-L386, P243-L386, Q244-L386, P245-L386, C246-L386, F247-L386, I248-L386, Y249-L386, L250-L386, I251-L386, V252-L386, I253-L386, C254-L386, V255-L386, L256-L386, G257-L386, I258-L386, A259-L386, A260-L386, I261-L386, I262-L386, V263-L386, S264-L386, Q265-L386, W266-L386, D267-L386, M268-L386, F269-L386, A270-L386, T271-L386, P272-L386, Q273-L386, Y274-L386, R275-L386, G276-L386, V277-L386, R278-L386, A279-L386, G280-L386, V281-L386, F282-L386, V283-L386, G284-L386, L285-L386, G286-L386, L287-L386, S288-L386, G289-L386, I290-L386, I291-L386, P292-L386, T293-L386, L294-L386, H295-L386, Y296-L386, V297-L386, I298-L386, S299-L386, E300-L386, G301-L386, F302-L386, L303-L386, K304-L386, A305-L386, A306-L386, T307-L386, I308-L386, R309-L386, Q310-L386, I311-L386, G312-L386, W313-L386, L314-L386, M315-L386, L316-L386, M317-L386, A318-L386, S319-L386, L320-L386, Y321-L386, I322-L386, T323-L386, G324-L386, A325-L386, A326-L386, L327-L386, Y328-L386, A329-L386, A330-L386, R331-L386, I332-L386, P333-L386, E334-L386, R335-L386, F336-L386, F337-L386, P338-L386, G339-L386, K340-L386, C341-L386, D342-L386, I343-L386, W344-L386, F345-L386, H346-L386, S347-L386, H348-L386, Q349-L386, L350-L386, F351-L386, H352-L386, I353-L386, F354-L386, V355-L386, V356-L386, A357-L386, G358-L386, A359-L386, F360-L386, V361-L386, H362-L386, F363-L386, H364-L386, G365-L386, V366-L386, S367-L386, N368-L386, L369-L386, Q370-L386, E371-L386, F372-L386, R373-L386, F374-L386, M375-L386, I376-L386, G377-L386, G378-L386, G379-L386, and/or C380-L386 of SEQ ID NO:167. Polynucleotide sequences encoding these polypeptides are also provided. The present invention also encompasses the use of these N-terminal rat AdipoR2 deletion polypeptides as immunogenic and/or antigenic epitopes as described elsewhere herein.

In preferred embodiments, the following C-terminal rat AdipoR2 deletion polypeptides are encompassed by the present invention: M1-L386, M1-A385, M1-D384, M1-K383, M1-E382, M1-T381, M1-C380, M1-G379, M1-G378, M1-G377, M1-I376, M1-M375, M1-F374, M1-R373, M1-F372, M1-E371, M1-Q370, M1-L369, M1-N368, M1-S367, M1-V366, M1-G365, M1-H364, M1-F363, M1-H362, M1-V361, M1-F360, M1-A359, M1-G358, M1-A357, M1-V356, M1-V355, M1-F354, M1-I353, M1-H352, M1-F351, M1-L350, M1-Q349, M1-H348, M1-S347, M1-H346, M1-F345, M1-W344, M1-I343, M1-D342, M1-C341, M1-K340, M1-G339, M1-P338, M1-F337, M1-F336, M1-R335, M1-E334, M1-P333, M1-I332, M1-R331, M1-A330, M1-A329, M1-Y328, M1-L327, M1-A326, M1-A325, M1-G324, M1-T323, M1-I322, M1-Y321, M1-L320, M1-S319, M1-A318, M1-M317, M1-L316, M1-M315, M1-L314, M1-W313, M1-G312, M1-I311, M1-Q310, M1-R309, M1-I308, M1-T307, M1-A306, M1-A305, M1-K304, M1-L303, M1-F302, M1-G301, M1-E300, M1-S299, M1-I298, M1-V297, M1-Y296, M1-H295, M1-L294, M1-T293, M1-P292, M1-I291, M1-I290, M1-G289, M1-S288, M1-L287, M1-G286, M1-L285, M1-G284, M1-V283, M1-F282, M1-V281, M1-G280, M1-A279, M1-R278, M1-V277, M1-G276, M1-R275, M1-Y274, M1-Q273, M1-P272, M1-T271, M1-A270, M1-F269, M1-M268, M1-D267, M1-W266, M1-Q265, M1-S264, M1-V263, M1-I262, M1-I261, M1-A260, M1-A259, M1-I258, M1-G257, M1-L256, M1-V255, M1-C254, M1-I253, M1-V252, M1-I251, M1-L250, M1-Y249, M1-I248, M1-F247, M1-C246, M1-P245, M1-Q244, M1-P243, M1-N242, M1-C241, M1-Y240, M1-F239, M1-S238, M1-Y237, M1-Y236, M1-L235, M1-W234, M1-P233, M1-V232, M1-F231, M1-S230, M1-G229, M1-M228, M1-I227, M1-L226, M1-L225, M1-A224, M1-I223, M1-G222, M1-S221, M1-Y220, M1-D219, M1-L218, M1-K217, M1-S216, M1-F215, M1-L214, M1-R213, M1-S212, M1-V211, M1-G210, M1-E209, M1-S208, M1-H207, M1-C206, M1-Y205, M1-V204, M1-T203, M1-H202, M1-F201, M1-L200, M1-W199, M1-S198, M1-F197, M1-S196, M1-L195, M1-C194, M1-L193, M1-I192, M1-A191, M1-G190, M1-L189, M1-F188, M1-F187, M1-L186, M1-G185, M1-F184, M1-V183, M1-V182, M1-K181, M1-E180, M1-Q179, M1-L178, M1-P177, M1-A176, M1-V175, M1-F174, M1-S173, M1-I172, M1-N171, M1-P170, M1-R169, M1-F168, M1-M167, M1-Y166, M1-F165, M1-I164, M1-G163, M1-L162, M1-C161, M1-L160, M1-F159, M1-F158, M1-V157, M1-C156, M1-G155, M1-L154, M1-L153, M1-H152, M1-T151, M1-W150, M1-I149, M1-N148, M1-G147, M1-T146, M1-E145, M1-T144, M1-H143, M1-I142, M1-R141, M1-F140, M1-I139, M1-S138, M1-K137, M1-F136, M1-C135, M1-A134, M1-R133, M1-F132, M1-S131, M1-P130, M1-M129, M1-P128, M1-P127, M1-R126, M1-H125, M1-G124, M1-H123, M1-L122, M1-L121, M1-F120, M1-D119, M1-N118, M1-D117, M1-K116, M1-L115, M1-W114, M1-D113, M1-P112, M1-L111, M1-V110, M1-D109, M1-H108, M1-P107, M1-I106, M1-V105, M1-R104, M1-W103, M1-R102, M1-G101, M1-E100, M1-W99, M1-V98, M1-K97, M1-C96, M1-V95, M1-F94, M1-E93, M1-E92, M1-M91, M1-R90, M1-E89, M1-M88, M1-A87, M1-H86, M1-H85, M1-A84, M1-Q83, M1-L82, M1-L81, M1-P80, M1-S79, M1-M78, M1-G77, M1-M76, M1-F75, M1-G74, M1-E73, M1-D72, M1-E71, M1-Q70, M1-S69, M1-N68, M1-D67, M1-D66, M1-H65, M1-C64, M1-E63, M1-L62, M1-E61, M1-E60, M1-P59, M1-S58, M1-N57, M1-E56, M1-Y55, M1-Y54, M1-S53, M1-S52, M1-C51, M1-V50, M1-P49, M1-T48, M1-E47, M1-L46, M1-S45, M1-P44, M1-E43, M1-L42, M1-D41, M1-G40, M1-H39, M1-H38, M1-N37, M1-D36, M1-N35, M1-N34, M1-G33, M1-G32, M1-R31, M1-T30, M1-D29, M1-D28, M1-L27, M1-Q26, M1-H25, M1-G24, M1-K23, M1-R22, M1-L21, M1-R20, M1-I19, M1-D18, M1-P17, M1-E16, M1-P15, M1-T14, M1-R13, M1-T12, M1-C11, M1-G10, M1-L9, M1-R8, and/or M1-H7 of SEQ ID NO:167. Polynucleotide sequences encoding these polypeptides are also provided. The present invention also encompasses the use of these C-terminal rat AdipoR2 deletion polypeptides as immunogenic and/or antigenic epitopes as described elsewhere herein.

Alternatively, preferred polypeptides of the present invention may comprise polypeptide sequences corresponding to, for example, internal regions of the rat AdipoR2 polypeptide (e.g., any combination of both N- and C-terminal rat AdipoR2 polypeptide deletions) of SEQ ID NO:167. For example, internal regions could be defined by the equation: amino acid NX to amino acid CX, wherein NX refers to any N-terminal deletion polypeptide amino acid of rat AdipoR2 (SEQ ID NO:167), and where CX refers to any C-terminal deletion polypeptide amino acid of rat AdipoR2 (SEQ ID NO:167). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the rat AdipoR2 polypeptide.

The rat AdipoR2 polypeptide of the present invention was determined to comprise several phosphorylation sites based upon the Motif algorithm (Genetics Computer Group, Inc.). The phosphorylation of such sites may regulate some biological activity of the rat AdipoR2 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the rat AdipoR2 polypeptide to associate with other polypeptides, particularly the cognate ligand for rat AdipoR2, such as adiponectin, or its ability to modulate certain cellular signally pathways such as AMPK, p38 MAPK, MAPK, and/or ACC.

The rat AdipoR2 polypeptide was predicted to comprise three PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184 (1986), and Kishimoto A., Nishiyama K., Nakanishi H., Uratsuji Y., Nomura H., Takeyama Y., Nishizuka Y., J. Biol. Chem. 260: 12492-12499 (1985); which are hereby incorporated by reference herein.

In preferred embodiments, the following PKC phosphorylation site polypeptide is encompassed by the present invention: RPPMPSFRACFKS (SEQ ID NO:212), FLKAATIRQIGWL (SEQ ID NO:213), and/or IGGGCTEKDAL (SEQ ID NO:214). Polynucleotides encoding these polypeptides are also provided. The present invention also encompasses the use of the rat AdipoR2 PKC phosphorylation site polypeptides as immunogenic and/or antigenic epitopes as described elsewhere herein.

The rat AdipoR2 polypeptide was predicted to comprise six casein kinase II phosphorylation sites using the Motif algorithm (Genetics Computer Group, Inc.). Casein kinase II (CK-2) is a protein serine/threonine kinase whose activity is independent of cyclic nucleotides and calcium. CK-2 phosphorylates many different proteins. The substrate specificity [1] of this enzyme can be summarized as follows: (1) Under comparable conditions Ser is favored over Thr.; (2) An acidic residue (either Asp or Glu) must be present three residues from the C-terminal of the phosphate acceptor site; (3) Additional acidic residues in positions +1, +2, +4, and +5 increase the phosphorylation rate. Most physiological substrates have at least one acidic residue in these positions; (4) Asp is preferred to Glu as the provider of acidic determinants; and (5) A basic residue at the N-terminal of the acceptor site decreases the phosphorylation rate, while an acidic one will increase it.

A consensus pattern for casein kinase II phosphorylations site is as follows: [ST]-x(2)-[DE], wherein 'x' represents any amino acid, and S or T is the phosphorylation site.

Additional information specific to casein kinase II phosphorylation site-II domains may be found in reference to the following publication: Pinna L. A., Biochim. Biophys. Acta 1054:267-284 (1990); which is hereby incorporated herein in its entirety.

In preferred embodiments, the following casein kinase II phosphorylation site polypeptide is encompassed by the present invention: TPVCSSYYENSPEE (SEQ ID NO:215), SYYENSPEELECHD (SEQ ID NO:216), CHDDNSQEDEGFMG (SEQ ID NO:217), VSRLFSKLDYSGIA (SEQ ID NO:218), AAIIVSQWDMFATP (SEQ ID NO:219), and/or IGGGCTEKDAL (SEQ ID NO:220). Polynucleotides encoding these polypeptides are also provided. The present invention also encompasses the use of this casein kinase II phosphorylation site polypeptide as an immunogenic and/or antigenic epitope as described elsewhere herein.

The rat AdipoR2 polypeptide was predicted to comprise eight N-myristoylation sites using the Motif algorithm (Genetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA: protein N-myristoyl transferase (NMT), has been derived from the sequence of known N-myristoylated proteins and from studies using synthetic peptides. The specificity seems to be the following: i.) The N-terminal residue must be glycine; ii.) In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-{EDRKHPFYW}-x(2)-[STAGCN]-{P}, wherein 'x' represents any amino acid, and G is the N-myristoylation site.

Additional information specific to N-myristoylation sites may be found in reference to the following publication: Towler D. A., Gordon J. I., Adams S. P., Glaser L., Annu. Rev. Biochem. 57:69-99 (1988); and Grand R. J. A., Biochem. J. 258:625-638 (1989); which is hereby incorporated herein in its entirety.

In preferred embodiments, the following N-myristoylation site polypeptides are encompassed by the present invention: DDTRGGNNDNHHGDLE (SEQ ID NO:221), IHTETGNIWTHLLGCV (SEQ ID NO:222), GLFFLGAILCLSFSWL (SEQ ID NO:223), TPQYRGVRAGVFVGLG (SEQ ID NO:224), RGVRAGVFVGLGLSGI (SEQ ID NO:225), AGVFVGLGLSGIIPTL (SEQ ID NO:226), GLGLSGIIPTLHYVIS (SEQ ID NO:227), and/or FRFMIGGGCTEKDAL (SEQ ID NO:228). Polynucleotides encoding these polypeptides are also provided. The present invention also encompasses the use of these N-myristoylation site polypeptides as immunogenic and/or antigenic epitopes as described elsewhere herein.

The rat AdipoR2 polypeptide has been shown to comprise one glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine glycosylation sites have the following consensus pattern, N-{P}-[ST]-{P}, wherein N represents the glycosylation site. However, it is well known that that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation may be found in reference to the following publications, which are hereby incorporated by reference herein: Marshall R. D., Annu. Rev. Biochem. 41:673-702 (1972); Pless D. D., Lennarz W. J., Proc. Natl. Acad. Sci. U.S.A. 74:134-138 (1977); Bause E., Biochem. J. 209:331-336 (1983); Gavel Y., von Heijne G., Protein Eng. 3:433-442 (1990); and Miletich J. P., Broze G. J. Jr., J. Biol. Chem. 265:11397-11404 (1990).

In preferred embodiments, the following asparagine glycosylation site polypeptide is encompassed by the present invention: YMFRPNISFVAPLQ (SEQ ID NO:187). Polynucleotides encoding this polypeptide are also provided. The present invention also encompasses the use of this rat AdipoR2 asparagine glycosylation site polypeptide as an immunogenic and/or antigenic epitope as described elsewhere herein.

The present invention encompasses the identification of compounds and drugs which stimulate rat AdipoR2 on the one hand (i.e., agonists) and which inhibit the function of rat AdipoR2 on the other hand (i.e., antagonists). In general, such screening procedures involve providing appropriate cells which express the receptor polypeptide of the present invention on the surface thereof. Such cells may include, for example, cells from mammals, yeast, *Drosophila* or *E. coli*. In a preferred embodiment, a polynucleotide encoding the receptor of the present invention may be employed to transfect cells to thereby express the rat AdipoR2 polypeptide. The expressed receptor may then be contacted with a test compound to observe binding, stimulation or inhibition of a functional response.

Many polynucleotide sequences, such as EST sequences, are publicly available and accessible through sequence databases. Some of these sequences are related to SEQ ID NO:166 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 1355 of SEQ ID NO:166, b is an integer between 15 to 1369, where both a and b correspond to the positions of nucleotide residues shown in SEQ ID NO:166, and where b is greater than or equal to a+14.

TABLE I

| Polynucleotide No. | CDNA CloneID | ATCC Deposit No. Z and Date | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| 1 | Human AdipoR2v1, (also referred to as hAdipoR2v1) | PTA-6088 Jun. 18, 2004 | N/A | 1 | 1585 | 210 | 1367 | 2 | 386 |
| 2 | Mouse AdipoR2v1 (also referred to as mAdipoR2v1) | N/A | N/A | 3 | 3975 | 153 | 1310 | 4 | 386 |
| 3 | Human AdipoR3 | N/A | N/A | 5 | 867 | 1 | 864 | 6 | 288 |
| 4 | Human AdipoR3v1 | N/A | N/A | 101 | 1146 | 1 | 1143 | 102 | 381 |
| 5 | Human AdipoR2v2 | N/A Jun. 18, 2004 | N/A | 103 | 1738 | 207 | 1469 | 104 | 421 |
| 6 | Rat AdipoR1 | N/A Xx/Xx/Xx | N/A | 164 | 1442 | 225 | 1349 | 165 | 375 |
| 7 | Rat AdipoR2 | N/A Xx/Xx/Xx | N/A | 166 | 1369 | 130 | 1287 | 167 | 386 |

Table I summarizes the information corresponding to each "Polynucleotide No." described above. The nucleotide sequence identified as "NT SEQ ID NO:X" was assembled from partially homologous ("overlapping") sequences obtained from the "cDNA clone ID" identified in Table I and, in some cases, from additional related DNA clones. The overlapping sequences were assembled into a single contiguous sequence of high redundancy (usually several overlapping sequences at each nucleotide position), resulting in a final sequence identified as SEQ ID NO:X.

The cDNA Clone ID was deposited on the date and given the corresponding deposit number listed in "ATCC Deposit No:Z and Date." "Vector" refers to the type of vector contained in the cDNA Clone ID.

"Total NT Seq. Of Clone" refers to the total number of nucleotides in the clone contig identified by "Polynucleotide No." The deposited clone may contain all or most of the sequence of SEQ ID NO:X. The nucleotide position of SEQ ID NO:X of the putative start codon (methionine) is identified as "5' NT of Start Codon of ORF."

The translated amino acid sequence, beginning with the methionine, is identified as "AA SEQ ID NO:Y" although other reading frames can also be easily translated using known molecular biology techniques. The polypeptides produced by these alternative open reading frames are specifically contemplated by the present invention.

The total number of amino acids within the open reading frame of SEQ ID NO:Y is identified as "Total AA of ORF".

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further herein. For instance, SEQ ID NO:1, 3, 5, 101, 103, 164, or 166 is useful for designing nucleic acid hybridization probes that will detect nucleic acid sequences contained in SEQ ID NO:1, 3, 5, 101, 103, 164, or 166 or the cDNA contained in the deposited clone. These probes will also hybridize to nucleic acid molecules in biological samples, thereby enabling a variety of forensic and diagnostic methods of the invention. Similarly, polypeptides identified from SEQ ID NO:2, 4, 6, 102, 104, 165, or 167 may be used, for example, to generate antibodies which bind specifically to proteins containing the polypeptides and the proteins encoded by the cDNA clones identified in Table I.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:1, 3, 5, 101, 103, 164, or 166 and the predicted translated amino acid sequence identified as SEQ ID NO:2, 4, 6, 102, 104, 165, or 167, but also a sample of plasmid DNA containing a cDNA of the invention deposited with the ATCC, as set forth in Table I. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited cDNA, collecting the protein, and determining its sequence.

The present invention also relates to the polynucleotides corresponding to SEQ ID NO:1, 3, 5, 101, 103, 164, or 166, SEQ ID NO:2, 4, 6, 102, 104, 165, or 167, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length polynucleotides (including, but not limited to the full-length coding region), allelic variants, splice variants, orthologs, and/or species homologues of polynucleotides corresponding to SEQ ID NO:1, 3, 5, 101, 103, 164, or 166, SEQ ID NO:2, 4, 6, 102, 104, 165, or 167, or a deposited clone, relying on the sequence from the sequences disclosed herein or the clones deposited with the ATCC. For example, allelic variants and/or species homologues may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, can be substantially purified using techniques described herein or otherwise known in the art, such as, for example, by the one-step method described in Smith and Johnson, Gene 67:31-40 (1988). Polypeptides of the invention also can be purified from natural, synthetic or recombinant sources using protocols described herein or otherwise known in the art, such as, for example, antibodies of the invention raised against the full-length form of the protein.

The present invention provides a polynucleotide comprising, or alternatively consisting of, the sequence identified as SEQ ID NO:1, 3, 5, 101, 103, 164, or 166, and/or a cDNA provided in ATCC Deposit No. PTA-6088. The present invention also provides a polypeptide comprising, or alternatively consisting of, the sequence identified as SEQ ID NO:2, 4, 6, 102, 104, 165, or 167, and/or a polypeptide encoded by the cDNA provided in ATCC Deposit NO:Z. The present invention also provides polynucleotides encoding a polypeptide comprising, or alternatively consisting of the polypeptide sequence of SEQ ID NO:2, 4, 6, 102, 104, 165, or 167, and/or a polypeptide sequence encoded by the cDNA contained in ATCC Deposit No:PTA-6088.

Preferably, the present invention is directed to a polynucleotide comprising, or alternatively consisting of, the sequence identified as SEQ ID NO:1, 3, 5, 101, 103, 164, or 166, and/or a cDNA provided in ATCC Deposit No.:PTA-6088 that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:1, 3, 5, 101, 103, 164, or 166, the sequence contained in a deposit, and/or the nucleic acid sequence encoding the sequence disclosed as SEQ ID NO:2, 4, 6, 102, 104, 165, or 167.

The present invention also encompasses polynucleotides capable of hybridizing, preferably under reduced stringency conditions, more preferably under stringent conditions, and most preferably under highly stringent conditions, to polynucleotides described herein. Examples of stringency conditions are shown in Table II below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE II

| Stringency Condition | Polynucleotide Hybrid± | Hybrid Length (bp) ‡ | Hybridization Temperature and Buffer† | Wash Temperature and Buffer† |
|---|---|---|---|---|
| A | DNA:DNA | > or equal to 50 | 65° C.; 1xSSC -or- 42° C.; 1xSSC, 50% formamide | 65° C.; 0.3xSSC |
| B | DNA:DNA | <50 | Tb*; 1xSSC | Tb*; 1xSSC |
| C | DNA:RNA | > or equal to 50 | 67° C.; 1xSSC -or- 45° C.; 1xSSC, 50% formamide | 67° C.; 0.3xSSC |
| D | DNA:RNA | <50 | Td*; 1xSSC | Td*; 1xSSC |
| E | RNA:RNA | > or equal to 50 | 70° C.; 1xSSC -or- 50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC -or- 45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC -or- 45° C.; 4xSSC, 50% formamide | 67° C.; 1xSSC |
| J | DNA:RNA | <50 | Tj*; 4xSSC | Tj*; 4xSSC |
| K | RNA:RNA | > or equal to 50 | 70° C.; 4xSSC -or- 40° C.; 6xSSC, 50% formamide | 67° C.; 1xSSC |
| L | RNA:RNA | <50 | Tl*; 2xSSC | Tl*; 2xSSC |
| M | DNA:DNA | > or equal to 50 | 50° C.; 4xSSC -or- 40° C. 6xSSC, 50% formamide | 50° C.; 2xSSC |
| N | DNA:DNA | <50 | Tn*; 6xSSC | Tn*; 6xSSC |
| O | DNA:RNA | > or equal to 50 | 55° C.; 4xSSC -or- 42° C.; 6xSSC, 50% formamide | 55° C.; 2xSSC |
| P | DNA:RNA | <50 | Tp*; 6xSSC | Tp*; 6xSSC |
| Q | RNA:RNA | > or equal to 50 | 60° C.; 4xSSC -or- 45° C.; 6xSSC, 50% formamide | 60° C.; 2xSSC |
| R | RNA:RNA | <50 | Tr*; 4xSSC | Tr*; 4xSSC |

‡ The "hybrid length" is the anticipated length for the hybridized region(s) of the hybridizing polynucleotides. When hybridizing a polynucleotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., MegAlign program of the DNA*Star suite of programs, etc).
†SSPE (1xSSPE is 0.15M NaCl, 10 mM NaH2PO4, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete. The hydridizations and washes may additionally include 5X Denhardt's reagent, .5-1.0% SDS, 100 ug/ml denatured, fragmented salmon sperm DNA, 0.5% sodium pyrophosphate, and up to 50% formamide.
*Tb-Tr: The hybridization temperature for hybrids anticipated to be less than 50 base pairs in length should be 5-10° C. less than the melting temperature Tm of the hybrids there Tm is determined according to the following equations. For hybrids less than 18 base pairs in length, Tm(° C.) = 2(# of A + T bases) + 4(# of G + C bases). For hybrids between 18 and 49 base pairs in length, Tm(° C.) = 81.5 + 16.6($\log_{10}$[Na+]) + 0.41(% G + C) − (600/N), where N is the number of bases in the hybrid, and [Na+] is the concentration of sodium ions in the hybridization buffer ([NA+] for 1xSSC = .165 M).
±The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3-6.4, which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

The invention encompasses the application of PCR methodology to the polynucleotide sequences of the present invention, the clone deposited with the ATCC, and/or the cDNA encoding the polypeptides of the present invention. PCR techniques for the amplification of nucleic acids are described in U.S. Pat. No. 4,683,195 and Saiki et al., Science, 239:487-491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, NY, 1989; Ehrlich et al., Science, 252:1643-1650, (1991); and "PCR Protocols, A Guide to Methods and Applications", Eds., Innis et al., Academic Press, New York, (1990).

Polynucleotide and Polypeptide Variants

The present invention also encompasses variants (e.g., allelic variants, orthologs, etc.) of the polynucleotide sequence disclosed herein in SEQ ID NO:1, 3, 5, 101, 103, 164, or 166, the complementary strand thereto, and/or the cDNA sequence contained in the deposited clone.

The present invention also encompasses variants of the polypeptide sequence, and/or fragments therein, disclosed in SEQ ID NO:2, 4, 6, 102, 104, 165, or 167, a polypeptide encoded by the polynucleotide sequence in SEQ ID NO:1, 3, 5, 101, 103, 164, or 166, and/or a polypeptide encoded by a cDNA in the deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence encoding a human AdipoR2v1, mouse AdipoR2v1, human AdipoR3, human AdipoR2v2, human AdipoR3v, rat AdipoR1, and/or rat AdipoR2 related polypeptide having an amino acid sequence as shown in the sequence listing and described in SEQ ID NO:1, 3, 5, 101, 103, 164, or 166 or the cDNA contained in ATCC deposit No:PTA-6088; (b) a nucleotide sequence encoding a mature human AdipoR2v1, mouse AdipoR2v1, human AdipoR3, human AdipoR2v2, human AdipoR3v, rat AdipoR1, and/or rat AdipoR2 related polypeptide having the amino acid sequence as shown in the sequence listing and described in SEQ ID NO:1, 3, 5, 101, 103, 164, or 166 or the cDNA contained in ATCC deposit No: PTA-6088; (c) a nucleotide sequence encoding a biologically active fragment of a human AdipoR2v1, mouse AdipoR2v1, human AdipoR3, human AdipoR2v2, human AdipoR3v, rat AdipoR1, and/or rat AdipoR2 related polypeptide having an amino acid sequence shown in the sequence listing and described in SEQ ID NO:1, 3, 5, 101, 103, 164, or 166 or the cDNA contained in ATCC deposit No: PTA-6088; (d) a nucleotide sequence encoding an antigenic fragment of a human AdipoR2v1, mouse AdipoR2v1, human AdipoR3, human AdipoR2v2, human AdipoR3v, rat AdipoR1, and/or rat AdipoR2 related polypeptide having an amino acid sequence sown in the sequence listing and described in SEQ ID NO:1, 3, 5, 101, 103, 164, or 166 or the cDNA contained in ATCC deposit No: PTA-6088; (e) a nucleotide sequence encoding a human AdipoR2v1, mouse AdipoR2v1, human AdipoR3, human AdipoR2v2, human AdipoR3v, rat AdipoR1, and/or rat AdipoR2 related polypeptide comprising the complete amino acid sequence encoded by a human cDNA plasmid contained in SEQ ID NO:1, 3, 5, 101, 103, 164, or 166 or the cDNA contained in ATCC deposit No: PTA-6088; (f) a nucleotide sequence encoding a mature human AdipoR2v1, mouse AdipoR2v1, human AdipoR3, human AdipoR2v2, human AdipoR3v, rat AdipoR1, and/or rat AdipoR2 related polypeptide having an amino acid sequence encoded by a human cDNA plasmid contained in SEQ ID NO:1, 3, 5, 101, 103, 164, or 166 or the cDNA contained in ATCC deposit No: PTA-6088; (g) a nucleotide sequence encoding a biologically active fragment of a human AdipoR2v1, mouse AdipoR2v1, human AdipoR3, human AdipoR2v2, human AdipoR3v, rat AdipoR1, and/or rat AdipoR2 related polypeptide having an amino acid sequence encoded by a human cDNA plasmid contained in SEQ ID NO:1, 3, 5, 101, 103, 164, or 166 or the cDNA contained in ATCC deposit No: PTA-6088; (h) a nucleotide sequence encoding an antigenic fragment of a human AdipoR2v1, mouse AdipoR2v1, human AdipoR3, human AdipoR2v2, human AdipoR3v, rat AdipoR1, and/or rat AdipoR2 related polypeptide having an amino acid sequence encoded by a human cDNA plasmid contained in SEQ ID NO:1, 3, 5, 101, 103, 164, or 166 or the cDNA contained in ATCC deposit No: PTA-6088; (i) a nucleotide sequence complimentary to any of the nucleotide sequences in (a), (b), (c), (d), (e), (f), (g), or (h), above.

The present invention is also directed to polynucleotide sequences which comprise, or alternatively consist of, a polynucleotide sequence which is at least about 80%, 85%, 90%, 91%, 92%, 93%, 93.6%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

Another aspect of the invention provides an isolated nucleic acid molecule comprising, or alternatively, consisting of, a polynucleotide having a nucleotide sequence selected from the group consisting of: (a) a nucleotide sequence encoding a human AdipoR2v1, mouse AdipoR2v1, human AdipoR3, human AdipoR2v2, human AdipoR3v, rat AdipoR1, and/or rat AdipoR2 related polypeptide having an amino acid sequence as shown in the sequence listing and descried in Table I; (b) a nucleotide sequence encoding a mature human AdipoR2v1, mouse AdipoR2v1, human AdipoR3, human AdipoR2v2, human AdipoR3v, rat AdipoR1, and/or rat AdipoR2 related polypeptide having the amino acid sequence as shown in the sequence listing and descried in Table I; (c) a nucleotide sequence encoding a biologically active fragment of a human AdipoR2v1, mouse AdipoR2v1, human AdipoR3, human AdipoR2v2, human AdipoR3v, rat AdipoR1, and/or rat AdipoR2 related polypeptide having an amino acid sequence as shown in the sequence listing and descried in Table I; (d) a nucleotide sequence encoding an antigenic fragment of a human AdipoR2v1, mouse AdipoR2v1, human AdipoR3, human AdipoR2v2, human AdipoR3v, rat AdipoR1, and/or rat AdipoR2 related polypeptide having an amino acid sequence as shown in the sequence listing and descried in Table I; (e) a nucleotide sequence encoding a human AdipoR2v1, mouse AdipoR2v1, human AdipoR3, human AdipoR2v2, human AdipoR3v, rat AdipoR1, and/or rat AdipoR2 related polypeptide comprising the complete amino acid sequence encoded by a human cDNA in a cDNA plasmid contained in the ATCC Deposit and described in Table I; (f) a nucleotide sequence encoding a mature human AdipoR2v1, mouse AdipoR2v1, human AdipoR3, human AdipoR2v2, human AdipoR3v, rat AdipoR1, and/or rat AdipoR2 related polypeptide having an amino acid sequence encoded by a human cDNA in a cDNA plasmid contained in the ATCC Deposit and described in Table I: (g) a nucleotide sequence encoding a biologically active fragment of a human AdipoR2v1, mouse AdipoR2v1, human AdipoR3, human AdipoR2v2, human AdipoR3v, rat AdipoR1, and/or rat AdipoR2 related polypeptide having an amino acid sequence encoded by a human cDNA in a cDNA plasmid contained in the ATCC Deposit and described in Table I; (h) a nucleotide sequence encoding an antigenic fragment of a human AdipoR2v1, mouse AdipoR2v1, human AdipoR3, human AdipoR2v2, human AdipoR3v, rat AdipoR1, and/or rat AdipoR2 related polypeptide having an amino acid sequence encoded by a human cDNA in a cDNA plasmid contained in the ATCC deposit and described in Table I; (i) a nucleotide sequence complimentary to any of the nucleotide sequences in (a), (b), (c), (d), (e), (f), (g), or (h) above.

The present invention is also directed to nucleic acid molecules which comprise, or alternatively, consist of, a nucleotide sequence which is at least about 80%, 85%, 90%, 91%, 92%, 93%, 93.6%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above.

The present invention encompasses polypeptide sequences which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, the following non-limited examples, the polypeptide sequence identified as SEQ ID NO:2, 4, 6, 102, 104, 165, or 167, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, the polypeptide sequence shown in SEQ ID NO:2, 4, 6, 102, 104, 165, or 167, a polypeptide sequence encoded by the nucleotide sequence in SEQ ID NO:1, 3, 5, 101, 103, 164, or 166, a polypeptide sequence encoded by the cDNA in cDNA plasmid:Z, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in Table I, the ORF (open reading frame), or any fragment specified as described herein.

As a practical matter, whether any particular nucleic acid molecule or polypeptide is at least about 80%, 85%, 90%, 91%, 92%, 93%, 93.6%, 94%, 95%, 96%, 97%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps: Off; Hydrophilic Residue Gap=Off; and Transition Weighting=0. The pairwise and multiple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modified CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as E. coli).

Naturally occurring variants are called "allelic variants" and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutapolynucleotidesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem. 268: 2984-2988 (1993), reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein (Dobeli et al., J. Biotechnology 7:199-216 (1988)).

Moreover, ample evidence demonstrates that variants often retain a biological activity similar to that of the naturally occurring protein. For example, Gayle and coworkers (J. Biol. Chem. 268:22105-22111 (1993)) conducted extensive mutational analysis of human cytokine IL-1a. They used random mutapolynucleotidesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

Thus, the invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutapolynucleotidesis or alanine-scanning mutapolynucleotidesis (introduction of single alanine mutations at every residue in the molecule) can be used. (Cunningham and Wells, Science 244:1081-1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306-1310 (1990).

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306-1310 (1990).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table III below.

TABLE III

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple polynucleotides with related function and assessing the relative penalty of each substitution to proper gene function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino acid substitution.

Besides conservative amino acid substitution, variants of the present invention include, but are not limited to, the following: (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

Moreover, the invention further includes polypeptide variants created through the application of molecular evolution ("DNA Shuffling") methodology to the polynucleotide disclosed as SEQ ID NO:1, 3, 5, 101, 103, 164, or 166, the sequence of the clone submitted in a deposit, and/or the cDNA encoding the polypeptide disclosed as SEQ ID NO:2, 4, 6, 102, 104, 165, or 167. Such DNA Shuffling technology is known in the art and more particularly described elsewhere herein (e.g., WPC, Stemmer, PNAS, 91:10747, (1994)), and in the Examples provided herein).

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1-5, 5-10, 5-25, 5-50, 10-50 or 50-150, conservative amino acid substitutions are preferable.

Polynucleotide and Polypeptide Fragments

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:1, 3, 5, 101, 103, 164, or 166 or the complementary strand thereto, or is a portion of a polynucleotide sequence encoding the polypeptide of SEQ ID NO:2, 4, 6, 102, 104, 165, or 167. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length" for example, is intended to include 20 or more contiguous bases from the cDNA sequence contained in a deposited clone or the nucleotide sequence shown in SEQ ID NO:1, 3, 5, 101, 103, 164, or 166. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, or 2001 to the end of SEQ ID NO:1, 3, 5, 101, 103, 164, or 166, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NO:2, 4, 6, 102, 104, 165, or 167 or encoded by the cDNA contained in a deposited clone. Protein (polypeptide) fragments may be "free-standing" or comprised within a larger polypeptide of which the fragment forms a part or region, most preferably as a single continuous region. Representative examples of polypeptide fragments of the invention, include, for example, fragments comprising, or alternatively consisting of, from about amino acid number 1-20, 21-40, 41-60, 61-80, 81-100, 102-120, 121-140, 141-160, 161-180, 181-200, 201-220, 221-240, 241-260, 261-280, 281-300, 301-320, 321-340, 341-360, 361-380, 381-400, or 400 to the end of the coding region. Moreover, polypeptide fragments can be about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 amino acids in length. In this context "about" includes the particularly recited ranges or values, and ranges or values larger or smaller by several (10, 9, 8, 7, 6, 5, 4, 3, 2, or 1) amino acids, at either extreme or at both extremes. Polynucleotides encoding these polypeptides are also encompassed by the invention.

Preferred polypeptide fragments include the full-length protein. Further preferred polypeptide fragments include the full-length protein having a continuous series of deleted residues from the amino or the carboxy terminus, or both. For example, any number of amino acids, ranging from 1-60, can be deleted from the amino terminus of the full-length polypeptide. Similarly, any number of amino acids, ranging from 1-30, can be deleted from the carboxy terminus of the full-length protein. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2, 4, 6, 102, 104, 165, or 167 falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at lease one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

The present invention encompasses polypeptides comprising, or alternatively consisting of, an epitope of the polypeptide having an amino acid sequence of SEQ ID NO:2, 4, 6, 102, 104, 165, or 167, or an epitope of the polypeptide sequence encoded by a polynucleotide sequence contained in ATCC deposit No. PTA-6088 or encoded by a polynucleotide that hybridizes to the complement of the sequence of SEQ ID NO:1, 3, 5, 101, 103, 164, or 166 or contained in ATCC deposit No. PTA-6088 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1, 3, 5, 101, 103, 164, or 166), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes" as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope" as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope" as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length, or longer. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394, 827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811, 238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:1, 3, 5, 101, 103, 164, or 166 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutapolynucleotidesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:2, 4, 6, 102, 104, 165, or 167, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. 24:316-325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4): 1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988); and Current Protocols, Chapter 2; which are hereby incorporated herein by reference in its entirety). In a preferred method, a preparation of the human AdipoR2v1, mouse AdipoR2v1, human AdipoR3, human AdipoR2v2, human AdipoR3v, rat AdipoR1, and/or rat AdipoR2 protein is prepared and purified to render it substantially free of natural contaminants. Such a preparation is then introduced into an animal in order to produce polyclonal antisera of greater specific activity. For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivatizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, 2nd ed. (1988), by Hammerling, et al., Monoclonal Antibodies and T-Cell Hybridomas (Elsevier, N.Y., pp. 563-681 (1981); Köhler et al., Eur. J. Immunol. 6:511 (1976); Köhler et al., Eur. J. Immunol. 6:292 (1976), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Preferably, the immunizing agent consists of an human AdipoR2v1, mouse AdipoR2v1, human AdipoR3, human AdipoR2v2, human AdipoR3v, rat AdipoR1, and/or rat AdipoR2 polypeptide or, more preferably, with a human AdipoR2v1, mouse AdipoR2v1, human AdipoR3, human AdipoR2v2, human AdipoR3v, rat AdipoR1, and/or rat AdipoR2 polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. More preferred are the parent myeloma cell line (SP2O) as provided by the ATCC. As inferred throughout the specification, human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoabsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra, and/or according to Wands et al. (Gastroenterology 80:225-232 (1981)). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to polynucleotides encoding the heavy and light chains of murine antibodies, or such chains from human, humanized, or other sources). The hydridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples described herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403, 484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240: 1038-1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; Cabilly et al., Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985); U.S. Pat. Nos. 5,807, 715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522-525 (1986); Reichmann et al., Nature, 332:323-327 (1988); Verhoeyen et al., Science, 239: 1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature 332:323-329 (1988)1 and Presta, Curr. Op. Struct. Biol., 2:593-596 (1992).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of cole et al., and Boerder et al., are also available for the preparation of human monoclonal antibodies (cole et al., Monoclonal Antibodies and Cancer Therapy, Alan R. Riss, (1985); and Boerner et al., J. Immunol., 147(1):86-95, (1991)).

Human antibodies can also be produced using transgenic mice which are incapable of expressing functional endogenous immunoglobulins, but which can express human immunoglobulin polynucleotides. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain polynucleotides. The mouse heavy and light chain immunoglobulin polynucleotides may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transpolynucleotides harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633, 425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin polynucleotides have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., Biotechnol., 10:779-783 (1992); Lonberg et al., Nature 368:856-859 (1994); Fishwild et al., Nature Biotechnol., 14:845-51 (1996); Neuberger, Nature Biotechnol., 14:826 (1996); Lonberg and Huszer, Intern. Rev. Immunol., 13:65-93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Such anti-idiotypic antibodies capable of binding to the human AdipoR2v1, mouse AdipoR2v1, human AdipoR3, human AdipoR2v2, human AdipoR3v, rat AdipoR1, and/or rat AdipoR2 polypeptide can be produced in a two-step procedure. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

The antibodies of the present invention may be bispecific antibodies. Bispecific antibodies are monoclonal, Preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2, 4, 6, 102, 104, 165, or 167.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutapolynucleotidesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing polynucleotides from a mouse antibody molecule of appropriate antigen specificity together with polynucleotides from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)).

More preferably, a clone encoding an antibody of the present invention may be obtained according to the method described in the Example section herein.

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign polynucleotides. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) polynucleotides can be employed in tk-, hgprt- or aprt- cells, respectively. Also, antimetabolite resistance can be used as the basis of selection for the following polynucleotides: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5):155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned polynucleotides in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties).

As discussed, supra, the polypeptides corresponding to a polypeptide, polypeptide fragment, or a variant of SEQ ID NO:2, 4, 6, 102, 104, 165, or 167 may be fused or conjugated to the above antibody portions to increase the in vivo half life of the polypeptides or for use in immunoassays using methods known in the art. Further, the polypeptides corresponding to SEQ ID NO:2, 4, 6, 102, 104, 165, or 167 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270: 3958-3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270:9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

The present invention also encompasses the creation of synthetic antibodies directed against the polypeptides of the present invention. One example of synthetic antibodies is described in Radrizzani, M., et al., Medicina, (Aires), 59(6): 753-8, (1999)). Recently, a new class of synthetic antibodies has been described and are referred to as molecularly imprinted polymers (MIPs) (Semorex, Inc.). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins' with equal or greater potency than that of natural antibodies. These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent 'super' MIPs can be coated onto beads or wells for use in highly sensitive separations or assays, or for use in high throughput screening of proteins.

Moreover, MIPs based upon the structure of the polypeptide(s) of the present invention may be useful in screening for compounds that bind to the polypeptide(s) of the invention. Such a MIP would serve the role of a synthetic "receptor" by mimicking the native architecture of the polypeptide. In fact, the ability of a MIP to serve the role of a synthetic receptor has already been demonstrated for the estrogen receptor (Ye, L., Yu, Y., Mosbach, K, Analyst., 126(6):760-5, (2001); Dickert, F, L., Hayden, O., Halikias, K, P, Analyst., 126(6):766-71, (2001)). A synthetic receptor may either be mimicked in its entirety (e.g., as the entire protein), or mimicked as a series of short peptides corresponding to the protein (Rachkov, A., Minoura, N, Biochim, Biophys, Acta., 1544(1-2):255-66, (2001)). Such a synthetic receptor MIPs may be employed in any one or more of the screening methods described elsewhere herein.

MIPs have also been shown to be useful in "sensing" the presence of its mimicked molecule (Cheng, Z., Wang, E., Yang, X, Biosens, Bioelectron., 16(3):179-85, (2001); Jenkins, A, L., Yin, R., Jensen, J. L, Analyst., 126(6):798-802, (2001); Jenkins, A, L., Yin, R., Jensen, J. L, Analyst., 126(6): 798-802, (2001)). For example, a MIP designed using a polypeptide of the present invention may be used in assays designed to identify, and potentially quantitate, the level of said polypeptide in a sample. Such a MIP may be used as a substitute for any component described in the assays, or kits, provided herein (e.g., ELISA, etc.).

A number of methods may be employed to create MIPs to a specific receptor, ligand, polypeptide, peptide, organic molecule. Several preferred methods are described by Esteban et al in J. Anal, Chem., 370(7):795-802, (2001), which is hereby incorporated herein by reference in its entirety in addition to any references cited therein. Additional methods are known in the art and are encompassed by the present invention, such as for example, Hart, B, R., Shea, K, J. J. Am. Chem., Soc., 123(9):2072-3, (2001); and Quaglia, M., Chenon, K., Hall, A, J., De, Lorenzi, E., Sellergren, B, J. Am. Chem., Soc., 123 (10):2146-54, (2001); which are hereby incorporated by reference in their entirety herein.

Uses for Antibodies Directed Against Polypeptides of the Invention

The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278(2):123-131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147-158). The antibodies used in the diagnostic assays can be labeled with a detectable moiety. The detectable moiety should be capable of producing, either directly or indirectly, a detectable signal. For example, the detectable moiety may be a radioisotope, such as 2H, 14C, 32P, or 125I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219 (1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a Sephadex resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses of Antibodies

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, and $10^{-15}$ M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one could envision cloning the gene encoding an antibody directed against a polypeptide of the present invention, said polypeptide having the potential to elicit an allergic and/or immune response in an organism, and transforming the organism with said antibody gene such that it is expressed (e.g., constitutively, inducibly, etc.) in the organism. Thus, the organism would effectively become resistant to an allergic response resulting from the ingestion or presence of such an immune/allergic reactive polypeptide. Moreover, such a use of the antibodies of the present invention may have particular utility in preventing and/or ameliorating autoimmune diseases and/or disorders, as such conditions are typically a result of antibodies being directed against endogenous proteins. For example, in the instance where the polypeptide of the present invention is responsible for modulating the immune response to auto-antigens, transforming the organism and/or individual with a construct comprising any of the promoters disclosed herein or otherwise known in the art, in addition, to a polynucleotide encoding the antibody directed against the polypeptide of the present invention could effective inhibit the organisms immune system from eliciting an immune response to the auto-antigen(s). Detailed descriptions of therapeutic and/or gene therapy applications of the present invention are provided elsewhere herein.

Alternatively, antibodies of the present invention could be produced in a plant (e.g., cloning the gene of the antibody directed against a polypeptide of the present invention, and transforming a plant with a suitable vector comprising said gene for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting gene expression of a particular gene, or polynucleotides, in a human, mammal, and/or other organism. See, for example, International Publication Number WO 00/05391, published Feb. 3, 2000, to Dow Agrosciences LLC. The application of such methods for the antibodies of the present invention are known in the art, and are more particularly described elsewhere herein.

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

Antibody-Based Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering polynucleotides to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer polynucleotides to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign polynucleotides into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Compositions

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging with Antibodies

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced in-between such peptide moieties, which could additionally be subjected to protease activity to remove said peptide(s) from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958-3964 (1995).)

Similarly, EP-A-O 464 533 (Canadian counterpart 2045869) discloses fusion proteins comprising various portions of the constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995).)

Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984)).

The skilled artisan would acknowledge the existence of other "tags" which could be readily substituted for the tags referred to supra for purification and/or identification of polypeptides of the present invention (Jones C., et al., J Chromatogr A. 707(1):3-22 (1995)). For example, the c-myc tag and the 8F9, 3C7, 6E10, G4m B7 and 9E10 antibodies thereto (Evan et al., Molecular and Cellular Biology 5:3610-3616 (1985)); the Herpes Simplex virus glycoprotein D (gD) tag and its antibody (Paborsky et al., Protein Engineering, 3(6): 547-553 (1990), the Flag-peptide—i.e., the octapeptide sequence DYKDDDDK (SEQ ID NO:66), (Hopp et al., Biotech. 6:1204-1210 (1988); the KT3 epitope peptide (Martin et al., Science, 255:192-194 (1992)); a-tubulin epitope peptide (Skinner et al., J. Biol. Chem., 266:15136-15166, (1991)); the T7 gene 10 protein peptide tag (Lutz-Freyermuth et al., Proc. Natl. Sci. USA, 87:6363-6397 (1990)), the FITC epitope (Zymed, Inc.), the GFP epitope (Zymed, Inc.), and the Rhodamine epitope (Zymed, Inc.).

The present invention also encompasses the attachment of up to nine codons encoding a repeating series of up to nine arginine amino acids to the coding region of a polynucleotide of the present invention. The invention also encompasses chemically derivatizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender, P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivatized to attach hapten molecules (e.g., DNP, (Zymed, Inc.)). Due to the availability of monoclonal antibodies specific to such haptens, the protein could be readily purified using immunoprecipitation, for example.

Polypeptides of the present invention, including fragments and/or variants thereof, in addition to, antibodies directed against such polypeptides, fragments, and/or variants, may be fused to any of a number of known, and yet to be determined, toxins, such as ricin, saporin (Mashiba H, et al., Ann. N.Y. Acad. Sci. 1999; 886:233-5), or HC toxin (Tonukari N J, et al., Plant Cell. 2000 February; 12(2):237-248), for example. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell, to specific tissues, and/or to specific species. Such bifunctional antibodies are known in the art, though a review describing additional advantageous fusions, including citations for methods of production, can be found in P. J. Hudson, Curr. Opp. In. Imm. 11:548-557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. In view of the present disclosure, one skilled in the art could determine whether any particular "toxin" could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance polynucleotides for culturing in E. coli and other bacteria. Representative examples of appropriate hosts include, but are not limited to, bacterial cells, such as E. coli, Streptomyces and Salmonella typhimurium cells; fungal cells, such as yeast cells (e.g., Saccharomyces cerevisiae or Pichia pastoris (ATCC Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia-Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for O2. Consequently, in a growth medium depending on methanol as a main carbon source, the promoter region of one of the two alcohol oxidase polynucleotides (AOX1) is highly active. In the presence of methanol, alcohol oxidase produced from the AOX1 gene comprises up to approximately 30% of the total soluble protein in *Pichia pastoris*. See, Ellis, S. B., et al., Mol. Cell. Biol. 5:1111-21 (1985); Koutz, P. J, et al., Yeast 5:167-77 (1989); Tschopp, J. F., et al., Nucl. Acids Res. 15:3859-76 (1987). Thus, a heterologous coding sequence, such as, for example, a polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a polypeptide of the invention, as set forth herein, in a Pichea yeast system essentially as described in "Pichia Protocols: Methods in Molecular Biology" D. R. Higgins and J. Cregg, eds. The Humana Press, Totowa, N.J., 1998. This expression vector allows expression and secretion of a protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijlstra et al., Nature 342:435-438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., Nature, 310:105-111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The invention further encompasses chemical derivitization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above, etc.) stabilizing agents.

The invention encompasses derivitization of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics®, commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2, 4, 6, 102, 104, 165, or 167 or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in mammals. Further, the trans-acting transcription factors of such "artificial" promoters could also be "artificial" or chimeric in design themselves and could act as activators or repressors to said "artificial" promoter.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15-25 bp) from the sequences shown in SEQ ID NO:1, 3, 5, 101, 103, 164, or 166. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:1, 3, 5, 101, 103, 164, or 166 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flowsorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000-4,000 bp are preferred. For a review of this technique, see Verma et al., "Human Chromosomes: a Manual of Basic Techniques" Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. Assuming 1 megabase mapping resolution and one gene per 20 kb, a cDNA precisely localized to a chromosomal region associated with the disease could be one of 50-500 potential causative polynucleotides.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Furthermore, increased or decreased expression of the gene in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The US patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point ($T_m$) by 8°-20° C., vs. 4°-16° C. for the DNA/DNA 15-mer duplex. Also, the absence of charge groups in PNA means that hybridization can be done at low ionic strengths and reduce possible interference by salt during the analysis.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention. See, for example, G. Cutrona, et al., Nat. Biotech., 18:300-303, (2000); which is hereby incorporated herein by reference.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., Nat. Biotech, 18:615-622 (2000), which is hereby incorporated by reference herein in its entirety). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see EP 1007712, which is hereby incorporated by reference herein in its entirety).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organisms genome. These sequences can be used to prepare PCR primers for amplifying and isolating such selected DNA, which can then be sequenced. Using this technique, organisms can be identified because each organism will have a unique set of DNA sequences. Once an unique ID database is established for an organism, positive identification of that organism, living or dead, can be made from extremely small tissue samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976-985 (1985); Jalkanen, M., et al., J. Cell. Biol. 105:3087-3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207-216 (1993); Ferrantini et al., Cancer Research, 53:107-1112 (1993); Ferrantini et al., J. Immunology 153: 4604-4615 (1994); Kaido, T., et al., Int. J. Cancer 60: 221-229 (1995); Ogura et al., Cancer Research 50: 5102-5106 (1990); Santodonato, et al., Human Gene Therapy 7:1-10 (1996); Santodonato, et al., Gene Therapy 4:1246-1255 (1997); and Zhang, et al., Cancer Gene Therapy 3: 31-38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589, 466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413-7416 (1987), which is herein incorporated by reference); mRNA (Malone et al., Proc. Natl. Acad. Sci. USA, 86:6077-6081 (1989), which is herein incorporated by reference); and purified transcription factors (Debs et al., J. Biol. Chem., 265:10189-10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl. Acad. Sci. USA, 84:7413-7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413-7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512-527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include Ca2+-EDTA chelation (Papahadjopoulos et al., Biochim. Biophys. Acta, 394:483 (1975); Wilson et al., Cell, 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA, 76:145 (1979)); and reverse-phase evaporation (REV) (Fraley et al., J. Biol. Chem., 255:10431 (1980); Szoka et al., Proc. Natl. Acad. Sci. USA, 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy, 1:5-14 (1990), which is incorporated herein by reference in its entirety. The vector may transduce the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutapolynucleotidesis. Furthermore, adenoviruses have been used as live enteric vaccines for many years with an excellent safety profile (Schwartz et al., Am. Rev. Respir. Dis., 109:233-238 (1974)). Finally, adenovirus mediated gene transfer has been demonstrated in a number of instances including transfer of alpha-1-antitrypsin and CFTR to the lungs of cotton rats (Rosenfeld et al., Science, 252:431-434 (1991); Rosenfeld et al., Cell, 68:143-155 (1992)). Furthermore, extensive studies to attempt to establish adenovirus as a causative agent in human cancer were uniformly negative (Green et al. Proc. Natl. Acad. Sci. USA, 76:6606 (1979)).

Suitable adenoviral vectors useful in the present invention are described, for example, in Kozarsky and Wilson, Curr. Opin. Genet. Devel., 3:499-503 (1993); Rosenfeld et al., Cell, 68:143-155 (1992); Engelhardt et al., Human Genet. Ther., 4:759-769 (1993); Yang et al., Nature Genet., 7:362-369 (1994); Wilson et al., Nature, 365:691-692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the polynucleotides deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following polynucleotides: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932-8935 (1989); and Zijlstra et al., Nature, 342:435-438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding angiogenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189: 11277-11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention may be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions of hematopoietic cells. A polynucleotides or polypeptides, or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat or prevent blood coagulation diseases, disorders, and/or conditions (e.g., afibrinogenemia, factor deficiencies, arterial thrombosis, venous thrombosis, etc.), blood platelet diseases, disorders, and/or conditions (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting. Polynucleotides or polypeptides, or agonists or antagonists of the present invention are may also be useful for the detection, prognosis, treatment, and/or prevention of heart attacks (infarction), strokes, scarring, fibrinolysis, uncontrolled bleeding, uncontrolled coagulation, uncontrolled complement fixation, and/or inflammation.

A polynucleotides or polypeptides, or agonists or antagonists of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide or agonists or antagonist may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more preferably an adenoviral vector (See G J. Nabel, et. al., PNAS 1999 96: 324-326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic polynucleotides or antigens. By "repressing expression of the oncogenic polynucleotides" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell. Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus polynucleotides needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Moreover, polypeptides of the present invention may be useful in inhibiting the angiopolynucleotidesis of proliferative cells or tissues, either alone, as a protein fusion, or in combination with other polypeptides directly or indirectly, as described elsewhere herein. In a most preferred embodiment, said anti-angiopolynucleotidesis effect may be achieved indirectly, for example, through the inhibition of hematopoietic, tumor-specific cells, such as tumor-associated macrophages (See Joseph I B, et al. J Natl Cancer Inst, 90(21):1648-53 (1998), which is hereby incorporated by reference). Antibodies directed to polypeptides or polynucleotides of the present invention may also result in inhibition of angiopolynucleotidesis directly, or indirectly (See Witte L, et al., Cancer Metastasis Rev. 17(2):155-61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et al., Eur J Biochem 254(3):439-59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuvants, such as apoptonin, galectins, thioredoxins, antiinflammatory proteins (See for example, Mutat. Res. 400(1-2):447-55 (1998), Med. Hypotheses. 50(5):423-33 (1998), Chem. Biol. Interact. April 24; 111-112:23-34 (1998), J Mol Med. 76(6):402-12 (1998), Int. J. Tissue React. 20(1):3-15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998; 231: 125-41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the invention may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, criss-cross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a Therapeutic, described in more detail below. Methods of delivering polynucleotides of the invention are described in more detail herein.

Anti-Angiopolynucleotidesis Activity

The naturally occurring balance between endogenous stimulators and inhibitors of angiopolynucleotidesis is one in which inhibitory influences predominate. Rastinejad et al., Cell 56:345-355 (1989). In those rare instances in which neovascularization occurs under normal physiological conditions, such as wound healing, organ regeneration, embryonic development, and female reproductive processes, angiopolynucleotidesis is stringently regulated and spatially and temporally delimited. Under conditions of pathological angiopolynucleotidesis such as that characterizing solid tumor growth, these regulatory controls fail. Unregulated angiopolynucleotidesis becomes pathologic and sustains progression of many neoplastic and non-neoplastic diseases. A number of serious diseases are dominated by abnormal neovascularization including solid tumor growth and metastases, arthritis, some types of eye diseases, disorders, and/or conditions, and psoriasis. See, e.g., reviews by Moses et al., Biotech. 9:630-634 (1991); Folkman et al., N. Engl. J. Med., 333:1757-1763 (1995); Auerbach et al., J. Microvasc. Res. 29:401-411 (1985); Folkman, Advances in Cancer Research, eds. Klein and Weinhouse, Academic Press, New York, pp. 175-203 (1985); Patz, Am. J. Opthalmol. 94:715-743 (1982); and Folkman et al., Science 221:719-725 (1983). In a number of pathological conditions, the process of angiopolynucleotidesis contributes to the disease state. For example, significant data have accumulated which suggest that the growth of solid tumors is dependent on angiopolynucleotidesis. Folkman and Klagsbrun, Science 235:442-447 (1987).

The present invention provides for treatment of diseases, disorders, and/or conditions associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)). Thus, the present invention provides a method of treating, preventing, and/or diagnosing an angiopolynucleotidesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat or prevent a cancer or tumor. Cancers which may be treated, prevented, and/or diagnosed with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat or prevent cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating, preventing, and/or diagnosing other diseases, disorders, and/or conditions, besides cancers, which involve angiopolynucleotidesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculopolynucleotidesis; granulations; hypertrophic scars (keloids); nonunion fractures; scleroderma; trachoma; vascular adhesions; myocardial angiopolynucleotidesis; coronary collaterals; cerebral collaterals; arteriovenous malformations; ischemic limb angiopolynucleotidesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating, preventing, and/or diagnosing hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating, preventing, and/or diagnosing neovascular diseases of the eye, including for example, corneal neovascularization, neovascular glaucoma, proliferative diabetic retinopathy, retrolental fibroplasia and macular degeneration.

Moreover, Ocular diseases, disorders, and/or conditions associated with neovascularization which can be treated, prevented, and/or diagnosed with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., Am. J. Ophthal. 85:704-710 (1978) and Gartner et al., Surv. Ophthal. 22:291-312 (1978).

Thus, within one aspect of the present invention methods are provided for treating or preventing neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of diseases, disorders, and/or conditions can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2-3 times per year. A steroid could also be added to the injection solution to reduce inflammation resulting from the injection itself.

Within another aspect of the present invention, methods are provided for treating or preventing neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat or prevent early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating or preventing proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating or preventing retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, diseases, disorders, and/or conditions which can be treated, prevented, and/or diagnosed with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, diseases, disorders, and/or conditions and/or states, which can be treated, prevented, and/or diagnosed with the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluopolynucleotidesis, granulations, hypertrophic scars (keloids), nonunion fractures, scleroderma, trachoma, vascular adhesions, myocardial angiopolynucleotidesis, coronary collaterals, cerebral collaterals, arteriovenous malformations, ischemic limb angiopolynucleotidesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiopolynucleotidesis as a pathologic consequence such as cat scratch disease (*Rochele minalia quintosa*), ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiopolynucleotidesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-17326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312-316, 1992); Thalidomide; Angostatic steroid; AGM-1470; carboxynaminoimidazole; and metalloproteinase inhibitors such as BB94.

Diseases at the Cellular Level

Diseases associated with increased cell survival or the inhibition of apoptosis that could be treated, prevented, and/or diagnosed by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metastasis of cancers, in particular those listed above.

Additional diseases or conditions associated with increased cell survival that could be treated, prevented or diagnosed by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by the polynucleotides or polypeptides, and/or agonists or antagonists of the invention, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss.

The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepidermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intestine, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and duodenal ulcers and help heal by scar formation of the mucosal lining and regeneration of glandular mucosa and duodenal mucosal lining more rapidly. Inflammatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and bronchiolar epithelium to prevent or treat acute or chronic lung damage. For example, emphysema, which results in the progressive loss of alveoli, and inhalation injuries, i.e., resulting from smoke inhalation and burns, that cause necrosis of the bronchiolar epithelium and alveoli could be effectively treated, prevented, and/or diagnosed using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Neurological Diseases

Nervous system diseases, disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the polypeptides, polynucleotides, or agonists or antagonists of the invention are used to protect neural cells from the damaging effects of cerebral hypoxia. According to this embodiment, the compositions of the invention are used to treat, prevent, and/or diagnose neural cell injury associated with cerebral hypoxia. In one aspect of this embodiment, the polypeptides, polynucleotides, or agonists or antagonists of the invention are used to treat, prevent, and/or diagnose neural cell injury associated with cerebral ischemia. In another aspect of this embodiment, the polypeptides, polynucleotides, or agonists or antagonists of the invention are used to treat, prevent, and/or diagnose neural cell injury associated with cerebral infarction. In another aspect of this embodiment, the polypeptides, polynucleotides, or agonists or antagonists of the invention are used to treat, prevent, and/or diagnose or prevent neural cell injury associated with a stroke. In a further aspect of this embodiment, the polypeptides, polynucleotides, or agonists or antagonists of the invention are used to treat, prevent, and/or diagnose neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507-3515 (1990)); increased sprouting of neurons may be detected by methods known in the art, such as, for example, the methods set forth in Pestronk et al. (Exp. Neurol. 70:65-82 (1980)) or Brown et al. (Ann. Rev. Neurosci. 4:17-42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiolitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia, polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., *Corynebacterium, Mycobacterium, Norcardia*), *Cryptococcus neoformans*, Aspergillosis, Bacillaceae (e.g., Anthrax, *Clostridium*), Bacteroidaceae, Blastomycosis, *Bordetella, Borrelia* (e.g., *Borrelia burgdorferi*), Brucellosis, Candidiasis, *Campylobacter*, Coccidioidomycosis, Cryptococcosis, Dermatocyceses, *E. coli* (e.g., Enterotoxigenic *E. coli* and Enterohemorrhagic *E. coli*), Enterobacteriaceae (*Klebsiella, Salmonella* (e.g., *Salmonella typhi*, and *Salmonella paratyphi*), *Serratia, Yersinia*), *Erysipelothrix, Helicobacter*, Legionellosis, Leptospirosis, *Listeria, Mycoplasmatales, Mycobacterium leprae, Vibrio cholerae*, Neisseriaceae (e.g., *Acinetobacter*, Gonorrhea, Menigococcal), *Meisseria meningitidis*, Pasteurellacea Infections (e.g., *Actinobacillus, Heamophilus* (e.g., *Heamophilus influenza* type B), *Pasteurella*), *Pseudomonas*, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis, polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59-87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiopolynucleotidesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Chemotaxis

A polynucleotide or polypeptide and/or agonist or antagonist of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that a polynucleotide or polypeptide and/or agonist or antagonist of the present invention may inhibit chemotactic activity. These molecules could also be used to treat, prevent, and/or diagnose diseases, disorders, and/or conditions. Thus, a polynucleotide or polypeptide and/or agonist or antagonist of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2): Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or E. coli. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the polynucleotides encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724-33 (1997); Harayama, S. Trends Biotechnol. 16(2):76-82 (1998); Hansson, L. O., et al., J. Mol. Biol. 287:265-76 (1999); and Lorenzo, M. M. and Blasco, R. Biotechniques 24(2):308-13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutapolynucleotidesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic (dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (c) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

The human AdipoR2v1, mouse AdipoR2v1, human AdipoR3, human AdipoR2v2, human AdipoR3v, rat AdipoR1, and/or rat AdipoR2 and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a human AdipoR2v1, mouse AdipoR2v1, human AdipoR3, human AdipoR2v2, human AdipoR3v, rat AdipoR1, and/or rat AdipoR2 polypeptide, or a bindable peptide fragment, of this invention, comprising providing a plurality of compounds, combining the human AdipoR2v1, mouse AdipoR2v1, human AdipoR3, human AdipoR2v2, human AdipoR3v, rat AdipoR1, and/or rat AdipoR2 polypeptide, or a bindable peptide fragment, with each of a plurality of compounds for a time sufficient to allow binding under suitable conditions and detecting binding of the human AdipoR2v1, mouse AdipoR2v1, human AdipoR3, human AdipoR2v2, human AdipoR3v, rat AdipoR1, and/or rat AdipoR2 polypeptide or peptide to each of the plurality of test compounds, thereby identifying the compounds that specifically bind to the human AdipoR2v1, mouse AdipoR2v1, human AdipoR3, human AdipoR2v2, human AdipoR3v, rat AdipoR1, and/or rat AdipoR2 polypeptide or peptide.

Methods of identifying compounds that modulate the activity of the novel human AdipoR2v1, mouse AdipoR2v1, human AdipoR3, human AdipoR2v2, human AdipoR3v, rat AdipoR1, and/or rat AdipoR2 and/or peptides are provided by the present invention and comprise combining a potential or candidate compound or drug modulator of calpain biological activity with an human AdipoR2v1, mouse AdipoR2v1, human AdipoR3, human AdipoR2v2, human AdipoR3v, rat AdipoR1, and/or rat AdipoR2 polypeptide or peptide, for example, the human AdipoR2v1, mouse AdipoR2v1, human AdipoR3, human AdipoR2v2, human AdipoR3v, rat AdipoR1, and/or rat AdipoR2 amino acid sequence as set forth in SEQ ID NO:2, 4, 6, 102, 104, 165, or 167, and measuring an effect of the candidate compound or drug modulator on the biological activity of the human AdipoR2v1, mouse AdipoR2v1, human AdipoR3, human AdipoR2v2, human AdipoR3v, rat AdipoR1, and/or rat AdipoR2 polypeptide or peptide. Such measurable effects include, for example, physical binding interaction; the ability to cleave a suitable calpain substrate; effects on native and cloned human AdipoR2v, mouse AdipoR2v1, human AdipoR3, human AdipoR2v2, human AdipoR3v, rat AdipoR1, and/or rat AdipoR2-expressing cell line; and effects of modulators or other calpain-mediated physiological measures.

Another method of identifying compounds that modulate the biological activity of the novel AdipoR2v1, mouse AdipoR2v1, human AdipoR3, human AdipoR2v2, human AdipoR3v1, rat AdipoR1, and/or rat AdipoR2 of the present invention comprises combining a potential or candidate compound or drug modulator of a calpain biological activity with a host cell that expresses the human AdipoR2v1, mouse AdipoR2v1, human AdipoR3, human AdipoR2v2, human AdipoR3v, rat AdipoR1, and/or rat AdipoR2 polypeptide and measuring an effect of the candidate compound or drug modulator on the biological activity of the human AdipoR2v1, mouse AdipoR2v1, human AdipoR3, human AdipoR2v2, human AdipoR3v, rat AdipoR1, and/or rat AdipoR2 polypeptide. The host cell can also be capable of being induced to express the human AdipoR2v1, mouse AdipoR2v1, human AdipoR3, human AdipoR2v2, human AdipoR3v, rat AdipoR1, and/or rat AdipoR2 polypeptide, e.g., via inducible expression. Physiological effects of a given modulator candidate on the human AdipoR2v1, mouse AdipoR2v1, human AdipoR3, human AdipoR2v2, human AdipoR3v, rat AdipoR1, and/or rat AdipoR2 polypeptide can also be measured. Thus, cellular assays for particular calpain modulators may be either direct measurement or quantification of the physical biological activity of the human AdipoR2v1, mouse AdipoR2v1, human AdipoR3, human AdipoR2v2, human AdipoR3v, rat AdipoR1, and/or rat AdipoR2 polypeptide, or they may be measurement or quantification of a physiological effect. Such methods preferably employ a human AdipoR2v1, mouse AdipoR2v1, human AdipoR3, human AdipoR2v2, human AdipoR3v, rat AdipoR1, and/or rat AdipoR2 polypeptide as described herein, or an overexpressed recombinant human AdipoR2v1, mouse AdipoR2v1, human AdipoR3, human AdipoR2v2, human AdipoR3v, rat AdipoR1, and/or rat AdipoR2 polypeptide in suitable host cells containing an expression vector as described herein, wherein the human AdipoR2v1, mouse AdipoR2v1, human AdipoR3, human AdipoR2v2, human AdipoR3v, rat AdipoR1, and/or rat AdipoR2 polypeptide is expressed, overexpressed, or undergoes upregulated expression.

Another aspect of the present invention embraces a method of screening for a compound that is capable of modulating the biological activity of a human AdipoR2v1, mouse AdipoR2v1, human AdipoR3, human AdipoR2v2, human AdipoR3v, rat AdipoR1, and/or rat AdipoR2 polypeptide, comprising providing a host cell containing an expression vector harboring a nucleic acid sequence encoding a human AdipoR2v1, mouse AdipoR2v1, human AdipoR3, human AdipoR2v2, human AdipoR3v, rat AdipoR1, and/or rat AdipoR2 polypeptide, or a functional peptide or portion thereof (e.g., SEQ ID NO:2, 4, 6, 102, 104, 165, or 167); determining the biological activity of the expressed human AdipoR2v1, mouse AdipoR2v1, human AdipoR3, human AdipoR2v2, human AdipoR3v, rat AdipoR1, and/or rat AdipoR2 polypeptide in the absence of a modulator compound; contacting the cell with the modulator compound and determining the biological activity of the expressed human AdipoR2v1, mouse AdipoR2v1, human AdipoR3, human AdipoR2v2, human AdipoR3v, rat AdipoR1, and/or rat AdipoR2 polypeptide in the presence of the modulator compound. In such a method, a difference between the activity of the human AdipoR2v1, mouse AdipoR2v1, human AdipoR3, human AdipoR2v2, human AdipoR3v, rat AdipoR1, and/or rat AdipoR2 polypeptide in the presence of the modulator compound and in the absence of the modulator compound indicates a modulating effect of the compound.

Essentially any chemical compound can be employed as a potential modulator or ligand in the assays according to the present invention. Compounds tested as calpain modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel human AdipoR2v1, mouse AdipoR2v1, human AdipoR3, human AdipoR2v2, human AdipoR3v, rat AdipoR1, and/or rat AdipoR2 polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.*, 37:487-493; and Houghton et al., 1991, *Nature*, 354:84-88). Other chemistries for generating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA*, 90:6909-6913), vinylogous polypeptides (Hagihara et al., 1992, *J. Amer. Chem. Soc.*, 114:6568), non-peptidal peptidomimetics with glucose scaffolding (Hirschmann et al., 1992, *J. Amer. Chem. Soc.*, 114:9217-9218), analogous organic synthesis of small compound libraries (Chen et al., 1994, *J. Amer. Chem. Soc.*, 116:2661), oligocarbamates (Cho et al., 1993, *Science*, 261:1303), and/or peptidyl phosphonates (Campbell et al., 1994, *J. Org. Chem.*, 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology*, 14(3):309-314) and PCT/US96/10287), carbohydrate libraries (e.g., Liang et al., 1996, *Science*, 274-1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000-20,000 different compounds are possible using the described integrated systems.

In another of its aspects, the present invention encompasses screening and small molecule (e.g., drug) detection assays which involve the detection or identification of small molecules that can bind to a given protein, i.e., a human AdipoR2v1, mouse AdipoR2v1, human AdipoR3, human AdipoR2v2, human AdipoR3v, rat AdipoR1, and/or rat AdipoR2 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, *Gen. Eng. News*, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a human AdipoR2v1, mouse AdipoR2v1, human AdipoR3, human AdipoR2v2, human AdipoR3v, rat AdipoR1, and/or rat AdipoR2 polypeptide or peptide to measure a biological binding or ligand binding activity, the source may be a whole cell lysate that can be prepared by successive freeze-thaw cycles (e.g., one to three) in the presence of standard protease inhibitors. The human AdipoR2v1, mouse AdipoR2v1, human AdipoR3, human AdipoR2v2, human AdipoR3v, rat AdipoR1, and/or rat AdipoR2 polypeptide may be partially or completely purified by standard protein purification methods, e.g., affinity chromatography using specific antibody described infra, or by ligands specific for an epitope tag engineered into the recombinant human AdipoR2v1, mouse AdipoR2v1, human AdipoR3, human AdipoR2v2, human AdipoR3v, rat AdipoR1, and/or rat AdipoR2 polypeptide molecule, also as described herein. Binding activity can then be measured as described.

Compounds which are identified according to the methods provided herein, and which modulate or regulate the biological activity or physiology of the AdipoR2v1, mouse AdipoR2v1, human AdipoR3, human AdipoR2v2, human AdipoR3v1, rat AdipoR1, and/or rat AdipoR2 according to the present invention are a preferred embodiment of this invention. It is contemplated that such modulatory compounds may be employed in treatment and therapeutic methods for treating a condition that is mediated by the novel AdipoR2v1, mouse AdipoR2v1, human AdipoR3, human AdipoR2v2, human AdipoR3v1, rat AdipoR1, and/or rat AdipoR2 by administering to an individual in need of such treatment a therapeutically effective amount of the compound identified by the methods described herein.

In addition, the present invention provides methods for treating an individual in need of such treatment for a disease, disorder, or condition that is mediated by the AdipoR2v1, mouse AdipoR2v1, human AdipoR3, human AdipoR2v2, human AdipoR3v1, rat AdipoR1, and/or rat AdipoR2 of the invention, comprising administering to the individual a therapeutically effective amount of the human AdipoR2v1, mouse AdipoR2v1, human AdipoR3, human AdipoR2v2, human AdipoR3v, rat AdipoR1, and/or rat AdipoR2-modulating compound identified by a method provided herein.

Antisense and Ribozyme (Antagonists)

In specific embodiments, antagonists according to the present invention are nucleic acids corresponding to the sequences contained in SEQ ID NO:1, 3, 5, 101, 103, 164, or 166, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10 mM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature, 29:304-310 (1981), the promoter contained in the 3' long terminal repeat of Rous sarcoma virus (Yamamoto et al., Cell, 22:787-797 (1980), the herpes thymidine promoter (Wagner et al., Proc. Natl. Acad. Sci. U.S.A., 78:1441-1445 (1981), the regulatory sequences of the metallothionein gene (Brinster et al., Nature, 296:39-42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA" referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372:333-335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553-6556 (1989); Lemaitre et al., Proc. Natl. Acad. Sci., 84:648-652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958-976 (1988)) or intercalating agents. (See, e.g., Zon, Pharm. Res., 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625-6641 (1987)). The oligonucleotide is a 2-O-methylribonucleotide (Inoue et al., Nucl. Acids Res., 15:6131-6148 (1987)), or a chimeric RNA-DNA analogue (Inoue et al., FEBS Lett. 215:327-330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448-7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222-1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585-591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiopolynucleotidesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Biotic Associations

A polynucleotide or polypeptide and/or agonist or antagonist of the present invention may increase the organisms ability, either directly or indirectly, to initiate and/or maintain biotic associations with other organisms. Such associations may be symbiotic, nonsymbiotic, endosymbiotic, macrosymbiotic, and/or microsymbiotic in nature. In general, a polynucleotide or polypeptide and/or agonist or antagonist of the present invention may increase the organisms ability to form biotic associations with any member of the fungal, bacterial, lichen, mycorrhizal, cyanobacterial, dinoflaggellate, and/or algal, kingdom, phylums, families, classes, genuses, and/or species.

The mechanism by which a polynucleotide or polypeptide and/or agonist or antagonist of the present invention may increase the host organisms ability, either directly or indirectly, to initiate and/or maintain biotic associations is variable, though may include, modulating osmolarity to desirable levels for the symbiont, modulating pH to desirable levels for the symbiont, modulating secretions of organic acids, modulating the secretion of specific proteins, phenolic compounds, nutrients, or the increased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

In an alternative embodiment, a polynucleotide or polypeptide and/or agonist or antagonist of the present invention may decrease the host organisms ability to form biotic associations with another organism, either directly or indirectly. The mechanism by which a polynucleotide or polypeptide and/or agonist or antagonist of the present invention may decrease the host organisms ability, either directly or indirectly, to initiate and/or maintain biotic associations with another organism is variable, though may include, modulating osmolarity to undesirable levels, modulating pH to undesirable levels, modulating secretions of organic acids, modulating the secretion of specific proteins, phenolic compounds, nutrients, or the decreased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

The hosts ability to maintain biotic associations with a particular pathogen has significant implications for the overall health and fitness of the host. For example, human hosts have symbiosis with enteric bacteria in their gastrointestinal tracts, particularly in the small and large intestine. In fact, bacteria counts in feces of the distal colon often approach $10^{12}$ per milliliter of feces. Examples of bowel flora in the gastrointestinal tract are members of the Enterobacteriaceae, Bacteriodes, in addition to a-hemolytic streptococci, *E. coli*, Bifobacteria, Anaerobic cocci, Eubacteria, Costridia, lactobacilli, and yeasts. Such bacteria, among other things, assist the host in the assimilation of nutrients by breaking down food stuffs not typically broken down by the hosts digestive system, particularly in the hosts bowel. Therefore, increasing the hosts ability to maintain such a biotic association would help assure proper nutrition for the host.

Aberrations in the enteric bacterial population of mammals, particularly humans, has been associated with the following disorders: diarrhea, ileus, chronic inflammatory disease, bowel obstruction, duodenal diverticula, biliary calculous disease, and malnutrition. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant enteric flora population.

The composition of the intestinal flora, for example, is based upon a variety of factors, which include, but are not limited to, the age, race, diet, malnutrition, gastric acidity, bile salt excretion, gut motility, and immune mechanisms. As a result, the polynucleotides and polypeptides, including agonists, antagonists, and fragments thereof, may modulate the ability of a host to form biotic associations by affecting, directly or indirectly, at least one or more of these factors.

Although the predominate intestinal flora comprises anaerobic organisms, an underlying percentage represents aerobes (e.g., *E. coli*). This is significant as such aerobes rapidly become the predominate organisms in intraabdominal infections—effectively becoming opportunistic early in infection pathopolynucleotidesis. As a result, there is an intrinsic need to control aerobe populations, particularly for immune compromised individuals.

In a preferred embodiment, a polynucleotides and polypeptides, including agonists, antagonists, and fragments thereof, are useful for inhibiting biotic associations with specific enteric symbiont organisms in an effort to control the population of such organisms.

Biotic associations occur not only in the gastrointestinal tract, but also on an in the integument. As opposed to the gastrointestinal flora, the cutaneous flora is comprised almost equally with aerobic and anaerobic organisms. Examples of cutaneous flora are members of the gram-positive cocci (e.g., *S. aureus*, coagulase-negative staphylococci, micrococcus, *M. sedentarius*), gram-positive bacilli (e.g., *Corynebacterium* species, *C. minutissimum*, *Brevibacterium* species, *Propoionibacterium* species, *P. acnes*), gram-negative bacilli (e.g., *Acinebacter* species), and fungi (*Pityrosporum orbiculare*). The relatively low number of flora associated with the integument is based upon the inability of many organisms to adhere to the skin. The organisms referenced above have acquired this unique ability. Therefore, the polynucleotides and polypeptides of the present invention may have uses which include modulating the population of the cutaneous flora, either directly or indirectly.

Aberrations in the cutaneous flora are associated with a number of significant diseases and/or disorders, which include, but are not limited to the following: impetigo, ecthyma, blistering distal dactulitis, pustules, folliculitis, cutaneous abscesses, pitted keratolysis, trichomycosis axcillaris, dermatophytosis complex, axillary odor, erthyrasma, cheesy foot odor, acne, tinea versicolor, seborrheic dermititis, and *Pityrosporum folliculitis*, to name a few. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant cutaneous flora population.

Additional biotic associations, including diseases and disorders associated with the aberrant growth of such associations, are known in the art and are encompassed by the invention. See, for example, "Infectious Disease", Second Edition, Eds., S. L., Gorbach, J. G., Bartlett, and N. R., Blacklow, W.B. Saunders Company, Philadelphia, (1998); which is hereby incorporated herein by reference).

Pheromones

In another embodiment, a polynucleotide or polypeptide and/or agonist or antagonist of the present invention may increase the organisms ability to synthesize and/or release a pheromone. Such a pheromone may, for example, alter the organisms behavior and/or metabolism.

A polynucleotide or polypeptide and/or agonist or antagonist of the present invention may modulate the biosynthesis and/or release of pheromones, the organisms ability to respond to pheromones (e.g., behaviorally, and/or metabolically), and/or the organisms ability to detect pheromones. Preferably, any of the pheromones, and/or volatiles released from the organism, or induced, by a polynucleotide or polypeptide and/or agonist or antagonist of the invention have behavioral effects the organism.

Other Activities

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiopolynucleotidesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, prevent, and/or diagnose neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptides of the present invention may be employed to stimulate growth and differentiation of hematopoietic cells and bone marrow cells when used in combination with other cytokines.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used to prepare individuals for extraterrestrial travel, low gravity environments, prolonged exposure to extraterrestrial radiation levels, low oxygen levels, reduction of metabolic activity, exposure to extraterrestrial pathogens, etc. Such a use may be administered either prior to an extraterrestrial event, during an extraterrestrial event, or both. Moreover, such a use may result in a number of beneficial changes in the recipient, such as, for example, any one of the following, non-limiting, effects: an increased level of hematopoietic cells, particularly red blood cells which would aid the recipient in coping with low oxygen levels; an increased level of B-cells, T-cells, antigen presenting cells, and/or macrophages, which would aid the recipient in coping with exposure to extraterrestrial pathogens, for example; a temporary (i.e., reversible) inhibition of hematopoietic cell production which would aid the recipient in coping with exposure to extraterrestrial radiation levels; increase and/or stability of bone mass which would aid the recipient in coping with low gravity environments; and/or decreased metabolism which would effectively facilitate the recipients ability to prolong their extraterrestrial travel by any one of the following, non-limiting means: (i) aid the recipient by decreasing their basal daily energy requirements; (ii) effectively lower the level of oxidative and/or metabolic stress in recipient (i.e., to enable recipient to cope with increased extraterrestial radiation levels by decreasing the level of internal oxidative/metabolic damage acquired during normal basal energy requirements; and/or (iii) enabling recipient to subsist at a lower metabolic temperature (i.e., cryogenic, and/or sub-cryogenic environment).

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein).

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Also preferred is a method of treatment of an individual in need of an increased level of a protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

REFERENCES

Yamauchi, T. et al. Cloning of adiponectin receptors that mediate antidiabetic metabolic effects. Nature 2003 423: p 762-769.

Kyte, J. and Doolitle, R. F. A simple method for displaying the hydropathic character of a protein. J. Mol. Biol., 1982. 157(1): p 105-32.

Altschul S F; Gish W; Miller W; Myers E W; Lipman D J Basic local alignment search tool. J. Mol. Biol. 1990 215: p 403-10.

Tsao T S, Lodish H F, Fruebis J. ACRP30, a new hormone controlling fat and glucose metabolism. Eur J Pharmacol. 2002 Apr. 12; 440(2-3):213-21.

Shapiro L, Scherer P E. Crystal structure of a complement-1q family protein suggests an evolutionary link to tumor necrosis factor. Curr Biol. 1998 Mar. 12; 8(6):335-8.

Diez J J, Iglesias P. The role of the novel adipocyte-derived hormone adiponectin in human disease. Eur J Endocrinol. 2003 March; 148(3):293-300.

Fruebis J, Tsao T S, Javorschi S, Ebbets-Reed D, Erickson M R, Yen F T, Bihain B E, Lodish H F. Proteolytic cleavage product of 30-kDa adipocyte complement-related protein increases fatty acid oxidation in muscle and causes weight loss in mice. Proc Natl Acad Sci USA. 2001 Feb. 13; 98(4):2005-10.

Tomas E, Tsao T S, Saha A K, Murrey H E, Zhang Cc C, Itani S I, Lodish H F, Ruderman N B. Enhanced muscle fat oxidation and glucose transport by ACRP30 globular domain: acetyl-CoA carboxylase inhibition and AMP-activated protein kinase activation. Proc Natl Acad Sci USA. 2002 Dec. 10; 99(25):16309-13

Yamauchi T, Kamon J, Minokoshi Y, Ito Y, Waki H, Uchida S, Yamashita S, Noda M, Kita S, Ueki K, Eto K, Akanuma Y, Froguel P, Foufelle F, Ferre P, Carling D, Kimura S, Nagai R, Kahn B B, Kadowaki T. Adiponectin stimulates glucose utilization and fatty-acid oxidation by activating AMP-activated protein kinase. Nat Med. 2002 November; 8(11): 1288-95.

Kubota N, Terauchi Y, Yamauchi T, Kubota T, Moroi M, Matsui J, Eto K, Yamashita T, Kamon J, Satoh H, Yano W, Froguel P, Nagai R, Kimura S, Kadowaki T, Noda T. Disruption of adiponectin causes insulin resistance and neointimal formation. J Biol Chem. 2002 Jul. 19; 277(29):25863-6

Maeda N, Shimomura I, Kishida K, Nishizawa H, Matsuda M, Nagaretani H, Furuyama N, Kondo H, Takahashi M, Arita Y, Komuro R, Ouchi N, Kihara S, Tochino Y, Okutomi K, Horie M, Takeda S, Aoyama T, Funahashi T, Matsuzawa Y. Diet-induced insulin resistance in mice lacking adiponectin/ACRP30. Nat Med. 2002 July; 8(7):731-7.

Yamauchi T, Kamon J, Waki H, Imai Y, Shimozawa N, Hioki K, Uchida S, Ito Y, Takakuwa K, Matsui J, Takata M, Eto K, Terauchi Y, Komeda K, Tsunoda M, Murakami K, Ohnishi Y, Naitoh T, Yamamura K, Ueyama Y, Froguel P, Kimura S, Nagai R, Kadowaki T. Globular adiponectin protected ob/ob mice from diabetes and ApoE-deficient mice from atherosclerosis. J Biol Chem. 2003 Jan. 24; 278(4):2461-8.

EXAMPLES

Description of the Preferred Embodiments

Example 1

Bioinformatics Analysis

Identification of the Full Length cDNA Sequences for Human AdipoR2v1, Human AdipoR2v2, Mouse AdipoR2v1, Human AdipoR3, Human AdipoR3v1, Rat AdipoR1 and Rat AdipoR2 by Bioinformatics The published human AdipoR2 receptor DNA sequence (Genbank Accession No. gi|NM_015999) was searched against both human and mouse EST databases (parsed versions of the NCBI Public EST database) using the BLASTN program. Human EST sequence BC051858 and mouse EST sequence BC024094 were found to contain additional 5' coding sequences for AdipoR2 receptors. The longer sequences of AdipoR2 were verified by multiple EST sequences from different human and mouse cDNA libraries. Additional evidence that the reported mouse and human AdipoR2 receptors were incomplete is demonstrated by FIG. 10 which illustrates the exons of the human AdipoR2v1 of the present invention into the corresponding genomic sequence on the human genome (NCBI human genome version 30).

The putative full length cDNA sequences of the human and mouse AdipoR2 receptors, referred to herein as human AdipoR2v1 and mouse AdipoR2v1, respectively, are shown in FIGS. 1A-B (SEQ ID NO:1) and 2A-D (SEQ ID NO:3). The full length human AdipoR2v1 and mouse AdipoR2v1 cDNAs encode proteins that are 386 amino acids in length, compared to the originally reported length of 299 and 311 amino acids respectively by Yamauchi et al.

For mapping of human AdipoR2, AdipoR3 chromosome localizations, the AdipoR2 and AdipoR3 cDNA sequence was mapped to the human genome (NCBI human genome version 30) using Mega-Blast/Sim4 method in the Biotique Local Integration System (BLIS) program.

The complete protein sequence of human AdipoR2v1, mouse AdipoR2v1, and human AdipoR3 was analyzed for potential transmembrane domains. TMPRED program was used for transmembrane prediction. The program predicted seven transmembrane domains and the predicted domains match with the predicted transmembrane domains of related adiponectin receptors at the sequence level. The identified transmembrane domains for human AdipoR2v1, mouse AdipoR2v1, and human AdipoR3 are illustrated in FIGS. 1A-B, FIGS. 2A-D, and FIG. 3 and discussed herein.

The full length cDNA clone of the human adiponectin receptor AdipoR2v2 was identified by sequencing the entire insert of EST clone gi|BQ439997 (IMAGE:6155544) from a uterus cDNA library. The full length cDNA sequence obtained is named AdipoR2v2 (SEQ ID NO:103, FIGS. 13A-B). The translated amino acid sequence of AdipoR2v2 is shown in FIGS. 13A-B (SEQ ID NO:104).

Figure 6:
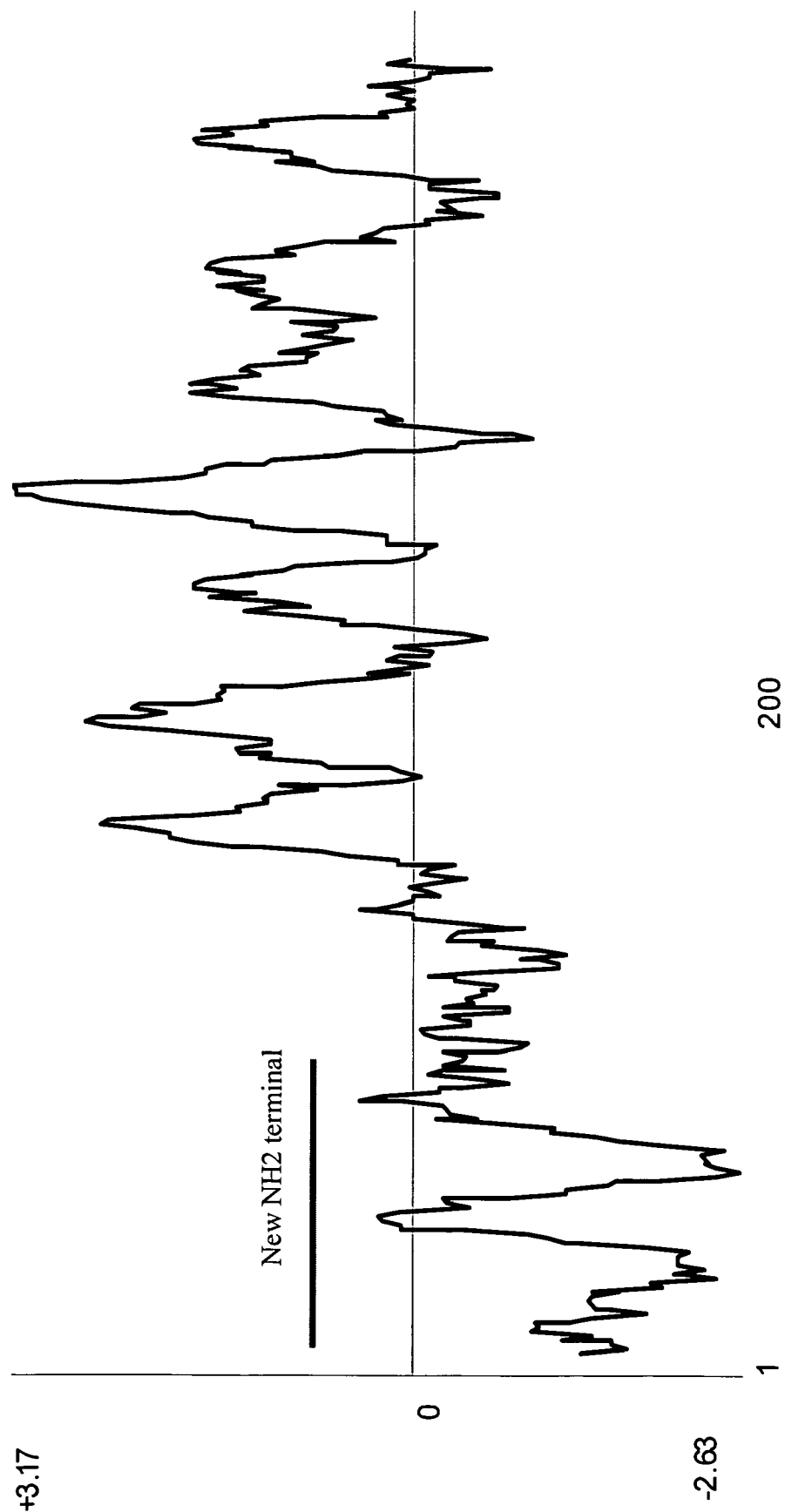
FIG. 6 shows a hydrophobicity plot of the human AdipoR2.v1 polypeptide of the present invention (SEQ ID NO:2) according to the BioPlot Hydrophobicity algorithm of Vector NTI (version 5.5). The seven hydrophilic peaks are consistent with the human AdipoR2.v1 polypeptide being an adiponectin receptor.
Figure 7:
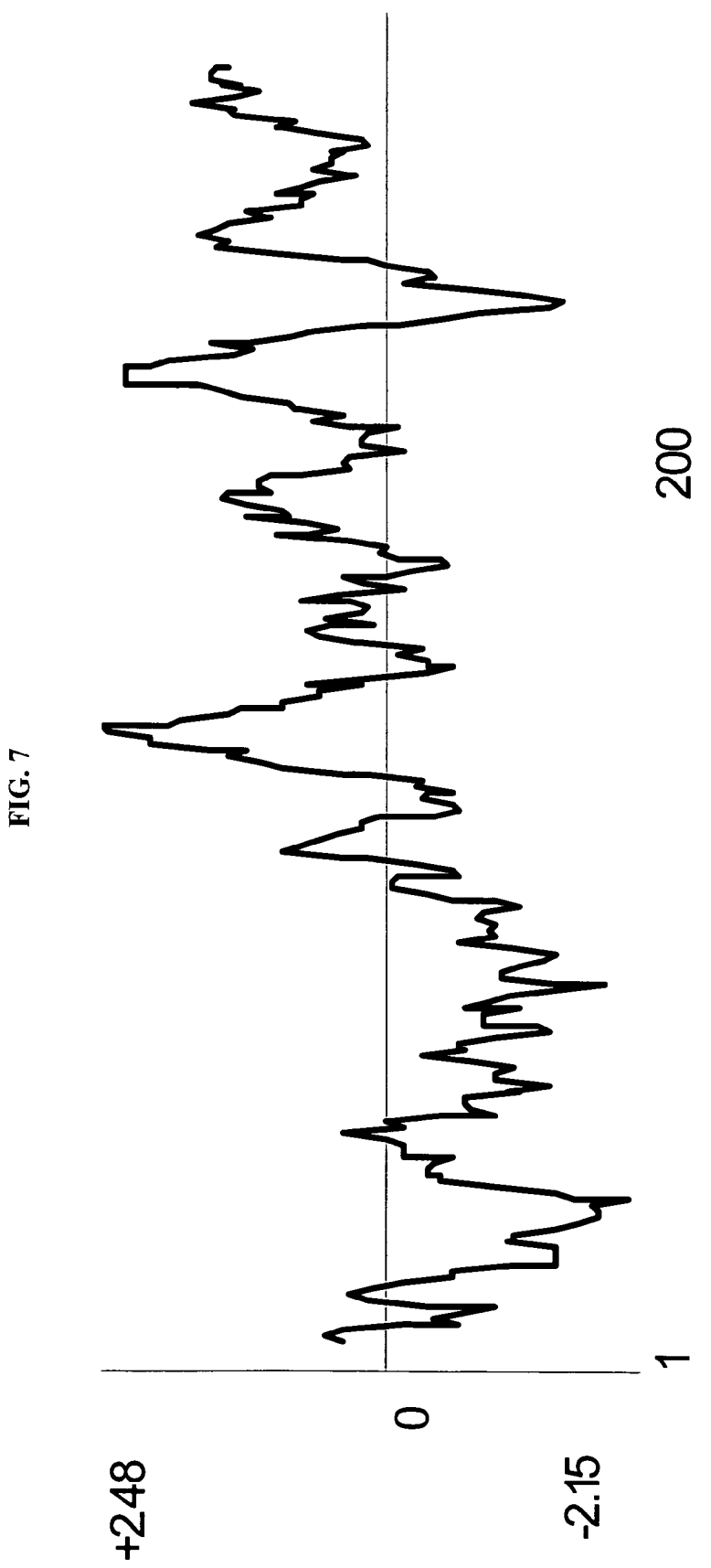
FIG. 7 shows a hydrophobicity plot of the human AdipoR3 polypeptide according to the BioPlot Hydrophobicity algorithm of Vector NTI (version 5.5). The seven hydrophilic peaks are consistent with the human AdipoR3 polypeptide being an adiponectin receptor.

As shown in the multiple sequence alignment of the cDNA sequences of human AdipoR2, AdipoR2v1 and AdipoR2v2 is shown in FIGS. 4A-B and FIG. 15. Both AdipoR2v1 and AdipoR2v2 have the extra 261 bp coding sequence 5' upstream of the cDNA of AdipoR2. There is an in-frame stop upstream of the new starting codon ATG in AdipoR2v1 and AdipoR2v, suggesting that this new ATG is the most 5' starting codon for AdipoR2. The addition of 261 bp at 5' upstream of the cDNA sequence of AdipoR2 adds 87 amino acids to NH2 terminal of the protein sequence of AdipoR2. According to Yamauchi et al., the NH2 terminal of the AdipoR2 molecule is located in the cytoplasmic side of the plasma membrane. Hydrophobicity plot of the protein sequences of AdipoR2v1 and AdipoR2v2 (FIGS. 6 and 16) suggests that these extra 87 amino acids form a long cytoplasmic domain. These additional amino acids could be important signal transduction molecule binding sites and may carry important signal transduction functions for the adiponectin receptor.

There is a single nucleotide polymorphism (SNP) detected on the cDNA sequences of AdipoR2v1 and AdipoR2v2. The C->T nucleotide substitution results in a change of amino acid from Ser->Phe. As shown in FIG. 16, this SNP is located in the first transmembrane domain. The existence of this SNP may have significant impact on receptor dimerization/oligomerization, ligand binding and signal transduction of the receptor. This non-synonymous C->T SNP may affect the biological function of adiponectin receptor 2 on obesity, diabetes and atherosclerosis.

The human AdipoR2v2 cDNA sequence also contains an insertion of 105 bp in the middle of the molecule, resulting in additional 35 amino acids for the protein sequence of AdipoR2v2 (see FIG. 15). These additional 35 amino acids are located between the 4$^{th}$ and 5$^{th}$ transmembrane domain of the receptor, in the cytoplasmic side of the plasma membrane. They could be important docking sites for intracellular signal transduction molecules. Alternatively, the additional 35 amino acids could function as an additional transmembrane domain. This potential new transmembrane domain would have significant impact on the ligand-receptor interaction between adiponectin and adiponectin receptor AdipoR2v2. The potential transmembrane domains of human AdipoR2v2 are illustrated in FIGS. 13A-B.

An alignment of the human AdipoR2v2 amino acid sequence to the human genomic DNA sequence from chromosome 12 using Genewise program is shown in FIG. 17. All the sequence features discussed above regarding AdipoR2v2 could be found in the genomic DNA sequence.

In the case of the rat AdipoR1 sequence, the human adiponectin receptor 1 (hAdipoR1) of the present invention was used as a template to search the rat EST database with TBLASTN. Four ESTs (CA339744, CB771587, CB801151 and BQ208259) were found to cover different parts of the rAdipoR1 coding region. Using the GCG Assembly program, these four ESTs were assembled into a consensus sequence shown to arrive at the final rat AdipoR1 sequence shown in FIGS. 20A-B (SEQ ID NO:164). The nucleotide sequence from 225 bp to 1349 bp of SEQ ID NO:164 encodes a putative rAdipoR1 protein (see FIGS. 20A-B, SEQ ID NO:165).

In the case of the rat AdipoR2 sequence, the human adiponectin receptor 2 (hAdipoR2v1) of the present invention was used as a template to search the rat EST database with TBLASTN. Similarly, there were four rat ESTs found to cover different parts of the rAdipoR2 coding region. These four ESTs were then assembled into a consensus sequence by the GCG Assembly program to arrive at the final sequence shown on FIGS. 21A-B (SEQ ID NO:166). Nucleotides 130 bp and 1287 bp encode the rat AdipoR2 polypeptide sequence (FIGS. 20A-B; SEQ ID NO:167).

The location of the putative transmembrane domains of the rAdipoR1 and rAdipoR2 were predicted by using the Vector NTI Bioplot program and are illustrated by the hydrophobicity plots provided in FIG. 23 and FIG. 25, respectively. Both the rat AdipoR1 and rat AdipoR2 receptors are predicted to contain seven transmembrane domains.

Both rAdipoR1 and rAdipoR2 share high homology with their corresponding orthologs in human and mouse species as shown in FIGS. 22 and 24, respectively. The significantly conserved homology of these receptors through evolution indicates that these receptors play key roles in biology.

Example 2

Method of Constructing a Size Fractionated Brain and Testis cDNA Library

Poly A$^+$ RNA from Clontech is treated with DNase I to remove genomic DNA contamination. The RNA is converted into double stranded cDNA using the SuperScript™ Plasmid System for cDNA Synthesis and Plasmid Cloning (Life Technologies). The cDNA is size fractionated on a TransGenomics HPLC size exclusion column (TosoHass) with dimensions of 7.8 mm×30 cm and a particle size of 10 µm. Tris buffered saline is used as the mobile phase, and the column is run at a flow rate of 0.5 ml/min. The system is calibrated using a 1 kb ladder to determine which fractions are to be pooled to obtain the largest cDNA library. Generally, fractions that eluted in the range of 12 to 15 minutes are used. The cDNA is precipitated, concentrated and then ligated into the Sal I/Not I sites in pSPORT. Following electroporation of the cDNA into DH12S, DNA from the resulting colonies is prepared and subjected to Sal I/Not I restriction enzyme digestion. Generally, the average insert size of libraries made by this procedure is greater than 3.5 Kb and the overall complexity of the library is greater than 10$^7$ independent clones. The library is amplified in semi-solid agar for 2 days at 30 C. An aliquot (200 microliters) of the amplified library is inoculated into a 200 ml culture for single-stranded DNA isolation by super-infection with a fi helper phage. The single-stranded circular DNA is concentrated by ethanol precipitation, resuspended at a concentration of one microgram per microliter and used for the cDNA capture experiments.

Example 3

Method of Converting Double Stranded cDNA Libraries into Single Strand Circular Forms Preparation of Culture LB medium (200 mL+400 ul carb) is inoculated with 0.2 to 1 ml of thawed cDNA library. The culture is incubated, shaking at 250 rpm at 37° C. for 45 min. The optical density of the culture is measured. The OD600 is preferably between 0.025 and 0.040. One mL M13K07 helper phage is added to the culture and grown for 2 hours. At that time, 500 uL Kanamycin (30 mg/mL) is added and incubation continued for 15-18 hours.

Preparation of Cells for Precipitation

Cultures are poured into six 50 mL tubes. Cells are centrifuged at 10000 rpm in an HB-6 rotor for 15 minutes at 4° C. The supernatant is retrieved and cells discarded. The supernatant is filtered through a 0.2 um filter. DNase I (12000 units from Gibco) is added and incubated at room temperature for 90 minutes.

PEG Precipitation of DNA

Fifty mL of ice-cold 40% PEG 8000, 2.5 M NaCl, 10 mM $MgSO_4$ is added to the cell pellets. The solution is mixed and distributed into 6 centrifuge tubes and covered with parafilm. The tubes are incubated on wet ice for 1 hour (or at 4° C. overnight).

Phage are pelleted at 10000 rpm in an HB-6 rotor for 20 minutes at 4° C. The supernatant is discarded and the sides of the tubes wiped dry. The pellets are resuspended in 1 mL TE, pH 8.

The resuspended pellets are placed in a 14 mL Sarstedt tube (6 mL total). SDS is added to 0.1% (60 uL of stock 10% SDS). Proteinase K (60 uL of 20 mg/mL) is then added and incubated at 42 C for 1 hour.

DNA is extracted with phenol/chloroform by first adding 1 mL of 5M NaCl followed by an equal volume of phenol/chloroform (6 mL). The mixture is vortexed and centrifuged at 5K in an HB-6 rotor for 5 minutes at 4° C. The aqueous (top) phase is transferred to a new Sarstedt tube. Extractions are repeated until no interface is visible.

The DNA is precipitated in ethanol by adding 2 volumes of 100% ethanol and precipitating overnight at −20° C. The DNA is centrifuged at 10000 rpm in HB-6 rotor for 20 minutes at 4° C. The ethanol is discarded and the pellets resuspended in 700 uL 70% ethanol. The resuspended pellets are centrifuged at 14000 rpm for 10 minutes at 4° C. The ethanol is discarded and the pellets dried by vacuum.

Oligosaccharides are then removed by resuspending the pellet in 50 uL TE, pH 8. The solutions are frozen on dry ice for 10 minutes and centrifuged at 14000 rpm for 15 minutes at 4° C. The supernatant is transferred to a new tube and the volume recorded.

The concentration of DNA is determined by measuring absorbance at 260/280. DNA is diluted 1:100 in a quartz cuvette (3 uL DNA+297 uL TE). The following equation is used to calculate DNA concentration:

(32 ug/mL*OD)(mL/100 uL)(100)(OD260)=DNA concentration

The preferred purity ratio is 1.7-2.0.

The DNA is diluted to 1 ug/uL with TB, pH 8 and stored at 4° C.

To test the quality of single-stranded DNA (ssDNA) the following reaction mixtures are prepared:
1. DNA mix per reaction
  a. 1 uL of 5 ng/uL ssDNA (1:200 dilution of VI.D.2 above)
  b. 11 uL dH2O
  c. 1.5 uL 10 uM T7 SPORT primer (fresh dilution of stock)
  d. 1.5 uL 10× Precision-Taq buffer 2. Repair mix per reaction
  a. 4 uL 5 mM dNTPs (1.25 mM each)
  b. 1.5 uL 10× Precision-Taq buffer
  c. 9.25 uL dH2O
  d. 0.25 uL Precision-Taq polymerase
  e. Preheat cocktail at 70° C. until middle of thermal cycle The DNA mixes are aliquoted into PCR tubes and thermal cycle carried out as follows:
  1. 95° C., 20 sec
  2. 59° C., 1 min; add 15 uL repair mix
  3. 73° C., 23 min Ethanol precipitation of the ssDNA is performed by adding 15 ug glycogen, 16 uL 7.5 M $NH_4OAc$, 125 uL 100% ethanol. The sample is centrifuged at 14000 rpm for 30 minutes at 4° C. and the pellet washed with 125 uL 70% ethanol. The ethanol is discarded and pellet dried by vacuum. The pellet is resuspended in 10 uL TB, pH 8.

The DNA is electroporated into DH10B or DH12S cells. A DNA mixture consisting of:
  1. 2 uL repaired library (=1.0×10−3 ug)
  2. 1 uL 1 ng/uL unrepaired library (=1.0×10−3 ug)
  3. 1 uL 0.01 ug/uL pUC19 positive control DNA (=1×10−5 ug)

is aliquoted to Eppendorf tubes. Cells are thawed on ice-water. Forty uL of cells are added to each DNA aliquot by pipetting into a chilled cuvette placed between metal plates. Electroporation is carried out at 1.8 kV. Immediately following electroporation, 1 mL SOC (SOB+glucose+$Mg^{++}$) media is added to the cuvette, then transferred to a 15 mL tube. Cells are allowed to recover for 1 hr at 37° C. with shaking (225 rpm). Cells are then plated according to the following dilution scheme:

A. Dilutions of Culture
  1. Serial dilutions of culture in 1:10 increments (20 uL into 180 uL LB broth)
  2. Repaired dilutions
    a. 1:100
    b. 1:1K
    c. 1:10K
  3. Unrepaired dilutions
    a. 1:10
    b. 1:100
  4. Positive control dilutions
    a. 1:10
    b. 1:100

100 uL of each dilution is plated on small LB+carb plates and incubated at 37° C. overnight. Colonies are counted to calculate titer as follows:
  1. use smallest countable dilution
  2. (# of colonies)(dilution factor)(200 uL/100 uL)(1000 uL/20 uL)=CFUs
  3. CFUs/ug DNA used=CFU/ug %Background=(unrepaired CFU/ug/repaired CFU/ug)×100%

Example 4

Method of Cloning the Novel Human AdipoR2v1, Mouse AdipoR2v1, Human AdipoR3, Human AdipoR2v2, Human AdipoR3v, Rat AdipoR1, and/or Rat AdipoR2 Receptors of the Present Invention One microliter of anti-sense biotinylated oligos (or sense oligos when annealing to single stranded DNA from pSPORT2 vector), containing one hundred and fifty nanograms of 1 to 50 different 80mer oligo probes, is added to six microliters (six micrograms) of a mixture of up to 15 single-stranded covalently closed circular cDNA libraries and seven microliters of 100% formamide in a 0.5 ml PCR tube. The sequence of the 80mer oligos used for each of the adiponectin receptors of the present invention are as follows:

```
GPCR Clone80mer Cloning Oligo Sequence human      gatcttttatatgtttcgcccaaatatctcctttgtggccc
AdipoR2v1  ctctgcaagagaaggtggtctttggattattttcttag
           (SEQ ID NO: 54)

mouse      ggcccctctgcaagagaaagtggtctttggcttgttcttct
AdipoR2v1  tgggagccattctctgcctttccttttcatggctcttcc
           (SEQ ID NO: 55)

human      ggacacatctgcttggtttcgtgctgtttctcttttggaa
AdipoR3    atcttgaccatgctcagaccaaatatgtacttcacggcc
           (SEQ ID NO: 56)
```

The same primer used for cloning the human AdipoR2v1 polynucleotide could be used to clone the human AdipoR2v2 polynucleotide.

The human AdipoR3v1 polynucleotide could be cloned by performing separate PCR amplifications with Primer Sets A, B, C, D, and E using human genomic DNA as a template. Representative PCR conditions for the same are provided below. The locations of each of these primers relative to the human AdipoR3v1 encoding polynucleotide sequence, in addition to the genomic sequence in which the human AdipoR3v1 coding resides, is provided in FIGS. 19A-B. The sequences for each Primer Set are provided below.

```
                                                      SEQ ID
Primer Name  Sequence                                  NO:

Primer Set   ATGTCTTCTCACAAAGGGTCTGTGGTGGCAA           154
A - Forward

Primer Set   TCAGAGTTCAGCCAGTTCCACCATG                 155
A - Reverse

Primer Set   CTGGCTGAATCTGAATTGTCACCCCTGC              156
B - Forward

Primer Set   GCTTGTCTGGAGCTTGTACACAAACTCCT             157
B - Reverse

Primer Set   AGGAGTTTGTGTACAAGCTCCAGACAAGCTGC          158
C - Forward

Primer Set   GAGCACTGCACCCAAAAGGAATATCCT               159
C - Reverse

Primer Set   TTTGGGTGCAGTGCTCAGCCTCAGC                 160
D - Forward

Primer Set   TCACAATGATGGCAGAGATGCCCAGGAC              161
D - Reverse

Primer Set   CATCTCTGCCATCATTGTGGACCAGTGGGAC           162
E - Forward

Primer Set   TCAGAGAAGGGAGTCATCAGTGCA                  163
E - Reverse
```

Once the PCR amplifications using PCR Primer Sets A, B, C, D, and E are completed, the PCR products obtained therefrom are isolated. The isolated PCR products from Primer Sets A, B, C, D, and E are all added together and subjected to a second round of PCR amplification using the below amplification conditions. The product from this second round of amplification is then subjected to a third round of PCR amplification using the forward primer from Primer Set A (SEQ ID NO:154) and the reverse primer from Primer Set E (SEQ ID NO:163). The product of the final amplification should be approximately 1.1 kb in size. This product can then be subcloned into an appropriate vector using methods well known in the art (e.g., a pTA cloning kit from Invitrogen). The skilled artisan would appreciate that both the second round and third round of amplification could be combined for efficiency. The skilled artisan would also appreciate that slight differences in the actual PCR conditions may be required to optimize this cloning strategy.

The rat AdipoR1 and rat AdipoR2 receptors can be cloned by PCR amplifying total cDNA of rat white adipose tissue using the following PCR primers:

```
                                          SEQ ID
Primer Name         Sequence               NO:

Rat AdipoR1 - Forward  TCATCACTGGGAGATCTC      229

Rat AdipoR1 - Reverse  CCTCCACCAACCCTCAGGTG    230

Rat AdipoR2 - Forward  GTCGGAAGGAGGGTCAACTC    231

Rat AdipoR2 - Reverse  CTCAGGGTCAAAGTCCCTG     232
```

General PCR conditions for most of the reactions discussed above are as follows: the mixture is heated in a thermal cycler to 95° C. for 2 min. Fourteen microliters of 2× hybridization buffer (50% formamide, 1.5 M NaCl, 0.04 M NaPO$_4$, pH 7.2, 5 min EDTA, 0.2% SDS) is added to the heated probe/cDNA library mixture and incubated at 42° C. for 26 hours. Hybrids between the biotinylated oligo and the circular cDNA are isolated by diluting the hybridization mixture to 220 microliters solution containing 1 M NaCl, 10 mm Tris-HCl pH 7.5, 1 mM EDTA, pH 8.0 and adding 125 microliters of streptavidin magnetic beads. This solution is incubated at 42° C. for 60 min, and mixed every 5 min to re-suspend the beads. The beads are separated from the solution with a magnet and washed three times in 200 microliters of 0.1×SSPE, 0.1% SDS at 45° C.

The single stranded cDNA is released from the biotinylated oligo/streptavidin magnetic bead complex by adding 50 microliters of 0.1 N NaOH and incubating at room temperature for 10 min. Six microliters of 3 M sodium acetate is added along with 15 micrograms of glycogen and the solution ethanol precipitated with 120 microliters of 100% ethanol. The precipitated DNA is resuspended in 12 microliters of TB (10 min Tris-HCl, pH 8.0), 1 mM EDTA, pH 8.0). The single-stranded cDNA is converted into double-stranded DNA in a thermal cycler by mixing 5 microliters of the captured DNA with 1.5 microliters of 10 micromolar standard SP6 primer for libraries in pSPORT 1 and 2 and 17 primer for libraries in pCMVSPORT and 1.5 microliters of 10×PCR buffer.

Sequences of primers used to repair single-stranded circular DNA isolated from the primary selection are as follows:

T7Sport 5'-TAATACGACTCACTATAGGG-3' (SEQ ID NO: 57)

SP6Sport 5'-ATTTAGGTGACACTATAG-3' (SEQ ID NO: 58)

The mixture is heated to 95° C. for 20 seconds and the temperature gradually brought down to 59° C. Fifteen microliters of a repair mix, that was preheated to 70° C. is added to the DNA (repair mix contains 4 microliters of 5 mM dNTPs (1.25 mM each), 1.5 microliters of 10×PCR buffer, 9.25 microliters of water, and 0.25 microliters of Taq polymerase). The solution incubation temperature is raised back to 73° C. and incubated for 23 mm. The repaired DNA is ethanol precipitated and resuspended in 10 microliters of TB. Electroporation is carried out using two microliters DNA per 40 microliters of E. coli DH12S cells. Three hundred and thirty three microliters are plated onto one 150-mm plate of LB agar plus 100 micrograms/milliliter of ampicillin. After overnight incubation at 37° C., the colonies from all plates are harvested by scraping into 10 ml of LB medium+50 micrograms/milliliter of ampicillin and 2 ml of sterile glycerol.

The second round of selection is initiated by making single-stranded circular DNA from the primary selected library using the method listed above. The purified single-stranded circular DNA is then assayed with gene-specific primers for each of the targeted sequences using standard PCR conditions.

The sequences of the Gene-Specific-Primer ("GSP") pairs used to identify the various targeted cDNAs in the primary selected single stranded cDNA libraries are as follows:

| GPCR Clone | GSP Oligo Sequence |
|---|---|
| human AdipoR2v1-s, | gtattcttcctgtgcctggg (SEQ ID NO: 59) |
| human AdipoR2v1-a | agaaaggcagagaatggctc (SEQ ID NO: 60) |
| Mouse AdipoR2v1-s, | cgcccaaatatatcttttg (SEQ ID NO: 61) |
| mouse AdipoR2v1-a | ctgagtggcagtacaccgtg (SEQ ID NO: 62) |
| human AdipoR3-s, | ccatacagaaaccggcagcagcc (SEQ ID NO: 63) |
| human AdipoR3-a | ccaaatcactttctcctgtagagg (SEQ ID NO: 64) |

The same primer pairs used for the human AdipoR2v1 polynucleotide could be used to confirm the human AdipoR2v2 polynucleotide.

The secondary hybridization is carried out using only those 80mer biotinylated probes whose targeted sequences were positive with the GSPs. The resulting single-stranded circular DNA is converted to double strands using the antisense oligo for each target sequence as the repair primer (the sense primer is used for material captured from pSPORT2 libraries. The resulting double stranded DNA is electroporated into DH10B and the resulting colonies inoculated into 96 deep well blocks. Following overnight growth, DNA is prepared and sequentially screened for each of the targeted sequences using the GSPs. The DNA is also cut with Sal I and Not I and the inserts sized by agarose gel electrophoresis.

Those cDNA clones that were positive by PCR had the inserts sized and two clones were chosen for DNA sequencing for each gene. All of the clones had identical sequence for each respective gene.

The full-length nucleotide sequence and the encoded polypeptide for human AdipoR2v1, mouse AdipoR2v1, human AdipoR3, human AdipoR2v2, human AdipoR3v, rat AdipoR1, and/or rat AdipoR2 are shown in FIGS. 1A-B.

Example 5

Expression Profiling of the Novel Human AdipoR2v1, Mouse AdipoR2v1, Human AdipoR3, Human AdipoR2v2, Human AdipoR3v, Rat AdipoR1, and/or Rat AdipoR2 Receptors The PCR primer pairs described in Example 4 may be used to measure the steady state levels of human AdipoR2v1, mouse AdipoR2v1, human AdipoR3, human AdipoR2v2, human AdipoR3v, rat AdipoR1, and/or rat AdipoR2 mRNA by quantitative PCR:

Briefly, first strand cDNA may be made from commercially available mRNA. The relative amount of cDNA used in each assay can be determined by performing a parallel experiment using a primer pair for a gene expressed in equal amounts in all tissues, cyclophilin. The cyclophilin primer pair would ideally detect small variations in the amount of cDNA in each sample and these data can then be used for normalization of the data obtained with the primer pair for this gene. The PCR data may be converted into a relative assessment of the difference in transcript abundance amongst the tissues tested.

Example 6

Method of Creating Epitope Tagged AdipoR Receptor and Assessing Expression Level of the Same in Overexpressed Cell Lines Materials Monoclonal anti-FLAG® M2 antibody was obtained from Sigma; rabbit polyclonal anti-HA IgG from Upstate, Inc.; goat anti-mouse and goat anti-rabbit horseradish peroxidase (HRP)-conjugated antibodies from BioRad; Complete® protease inhibitor cocktail tablets and FuGene 6 transfection reagent from Roche Molecular Biochemicals; oligonucleotide primers from Sigma-Genosys; LA-PCR kit and ligation kit from Panvera Corporation; QuikChange™ site-directed mutagenesis kit from Stratagene; African green monkey kidney cell line COS-7 cells from ATCC.

Construction of Plasmids

All AdipoR expression constructs were cloned into pcDNA3 under the control of CMV promoter/enhancer. For NH2-FLAG epitope tagging, the fusion proteins consisted of an initiation methionine, a novel amino acid G, one copy of FLAG epitope (DYKDDDD—SEQ ID NO:233) and various adiponectin receptor (designated AdipoR here after) isoforms in-frame beginning from their second amino acid codons of each respective predicted open reading frame. For COOH-HA tagging, the fusion proteins consisted of the full length predicted amino acid coding sequence fused in-frame with one copy of HA epitope (YPYDVPDYA—SEQ ID NO:234) appended at each respective COOH-terminus. A schematic representation of the location of the FLAG and HA tags is provided in FIG. 28A.

For human AdipoR1 expression plasmid pcDNA3-AdipoR1, polymerase chain reaction (PCR) was conducted using Image Clone 3878067 (Open Biosystems) as template and the following set of primers:

1) for FLAG epitope tagging at the NH2-end: (forward primer) 5'-GGCCGAAGCCGGATCCGCCACCATGGGC-GATTATAAAGATGACGATGACGGCTCT-TCCCACAAAGGATCTGTG-3' (SEQ ID NO:235), and (reverse primer) 5'-GGCCGAAGCCCTCGAGGGCTCA-GAGAAGGGTGTCATCAGTACAGCC-3' (SEQ ID NO:236);

2) for HA epitope tagging at the COOH-end: (forward primer) 5'-GGCCGAAGCCGGATCCGCCACCATGTCT-TCCCACAAAGGATCTGTG-3' (SEQ ID NO:237), and (reverse primer) 5'-GGCCGAAGCCCTCGAGGGCT-CAAGCGTAATCTGGAACATCGTATGGGTAGAGAA GGGTGTCATCAGTACAGCC-3' (SEQ ID NO:238), respectively.

The resultant ~1.1 kb fragments were digested with BamH I and Xho I, and ligated with the 5.4 kb pcDNA3 BamH I-Xho I digestion product.

To construct the human AdipoR2 expression plasmid, pcDNA-AdipoR2, the following PCRs were conducted:

1) For NH2-FLAG tagged version, using pcDNA-AdipoR2V1 as template, 5'-GGCCGAAGCCGAATTCGC-CACCATGGGCGATTATAAAGATGACGAT-GACGGCGAAAAAATGGAAGAATTTG-3' (SEQ ID NO:239), and 5'-GGCCGAAGCCCTCGAGGGCTCA-CAGTGCATCCTCTTCACTGCAGCCCCC-3' (SEQ ID NO:240) as primers;

2) For COOH-HA tagged version, using pcDNA-AdipoR2V1 as template, 5'-GGCCGAAGCCGAATTCGC-CACCATGGAAAAAATGGAAGAATTTG-3' (SEQ ID NO:241), and 5'-GGCCGAAGCCCTCGAGGGCT-CAAGCGTAATCTGGAACATCGTATGGG-TACAGTGCATCCTCTTCACTGCAGCCCCC-3' (SEQ ID NO:242) as primers. The PCR amplification products were digested with EcoR I and Xho I, and ligated into pcDNA3 as described above.

To construct AdipoR2V1 expression plasmid, pcDNA-AdipoR2V1, site directed mutagenesis was conducted using the pcDNA-AdipoR2V2 as the template (described below), in addition to the following primers: 5'-CGGGGAGTAA-GAGCAGGAGTGTTTTTGGGACTAGGCCTG-3' (SEQ ID NO:243), and 5'-CAGGCCTAGTCCCAAAAACACTC-CTGCTCTTACTCCCCG-3' (SEQ ID NO:244), using QuickChange XL Site-Directed Mutagenesis kit (Stratagene) according to the manufacturer's instructions.

For human AdipoR2V2 expression plasmid pcDNA3-AdipoR2V2, PCR was conducted using Image Clone 6155544 as the template, and the following sets of primers:

1) for FLAG epitope tagging at the NH2-end: (forward primer) 5'-GGCCGAAGCCGAATTCGCCACCATGGGC-GATTATAAAGATGACGATGACGGCAAC-GAGCCAACAGAAAACCGATTGGGG-3' (SEQ ID NO:245), (reverse primer) 5'-GGCCGAAGCCCTC-GAGGGCTCACAGTGCATCCTCTTCACTG-CAGCCCC-3' (SEQ ID NO:246);

2) for HA epitope tagging at the COOH-end: (forward primer) 5'-GGCCGAAGCCGAATTCGCCACCATGAAC-GAGCCAACAGAAAACCGATTGGGG-3' (SEQ ID NO:247), (reverse primer) 5'-GGCCGAAGCCCTC-GAGGGCTCAAGCGTAATCTGGAACATCG-TATGGGTACAGTGCATCCTCTTCACTGCAGCCCCC-3' (SEQ ID NO:248), respectively. The resultant ~1.2 kb fragments were digested with EcoR I and Xho I, ligated with ~5.4 kb digestion product of pcDNA3 by EcoR I and Xho I.

The sequence of all of the expression plasmids was verified. The predicted amino acid sequences were identical to those described for AdipoR2V1 (SEQ ID NO:1), and AdipoR2V2 (SEQ ID NO:103), respectively, or to the encoding sequence described in Yamauchi et al for the AdipoR1 polypeptide (SEQ ID NO:7) and AdipoR2 polypeptide (SEQ ID NO:8).

Transfection of COS-7 and Immunoblot Analyses

Monolayers of COS-7 cells were maintained in 5% $CO_2$ at 37° C. in Medium A (Dulbecco's modified Eagle's medium containing 10% fetal calf serum, 2 mM L-Glutamine, 100 units/ml penicillin and 100 □g/ml streptomycin sulfate). For transfection, on day 0, cells were seeded at $1.5 \times 10^6$ cells/10 cm plate in Medium A. On day 3, cells were re-fed with 10 ml of fresh medium A. For each transfection, 10 μg of each one of the AdipoR expression plasmids was mixed with 30 μl of Fugene reagent in 0.2 ml of prewarmed Dulbecco's modified Eagle's medium (without antibiotics) for 30 min. The mixture was then added to each plate. On day 4, the transfected cells were harvested and washed with cold PBS.

The cells were then lysed by passing through 25 gauge needles in 1 ml of ice cold Buffer A (10 mM Tris, pH 7.5, 250 mM sucrose, 1× Complete protease inhibitor cocktail) for 15 times. The cell-lysates were centrifuged for 1000×g for 10 min. The resultant supernatants were centrifuged for 30 min at 100,000×g in TLA100.2 rotor at 4° C. The pellets (membrane fraction) were suspended in 1×SDS loading buffer (1 plate of cells/50 μl). Aliquots of 17 μl of membrane fraction (derived from ~⅓ of plate) was loaded in each lane for SDS-PAGE. Blots were probed with anti-FLAG monoclonal antibody and anti-HA polyclonal IgG. The signals were detected with goat anti-mouse and goat anti-rabbit antibody conjugated with HRP reacted with SuperSignal® West Pico Chemiluminescent Substrate (Pierce). The results are shown in FIG. 28B.

Example 7

Method of Assessing Whether the Novel Human AdipoR2v1, Mouse AdipoR2v1, Human AdipoR3, Human AdipoR2v2, Human AdipoR3v, Rat AdipoR1, and/or Rat AdipoR2 Receptors of the Present Invention have Adiponectin Activity As described herein, the human AdipoR2v1 and mouse AdipoR2v1 adiponectin receptors represent longer physiologically relevant forms of the previously reported human and mouse AdipoR2 receptors. Therefore, the human AdipoR2v1 and mouse AdipoR2v1 adiponectin receptors are expected to have either the same or more adiponectin activity compared to the reported human and mouse AdipoR2 receptors.

A number of methods may be employed to confirm the adiponectin activity of the human AdipoR2v1 and mouse AdipoR2v1 adiponectin receptors of the present invention. Specifically, the methods described and referenced for the human and mouse AdipoR2 receptors by Yamauchi et al could be utilized. The methods described and referenced by Yamauchi et al (Nature 434:762-769 (2003)) are hereby incorporated herein by reference in their entirety.

The adiponectin activity of the human and mouse AdipoR2v1 receptors of the present invention may be tested by assessing their ability to bind radiolabelled adiponectin. Briefly, recombinant globular or full-length adiponectin is biotinylated with NHS-LC-biotin (Pierce). Synthetic adiponectin is labelled with 125I at Tyr by IODO beads (Pierce) in the presence of Na[125I] (2,000 Ci mmol-1, Amersham Pharmacia Biotech) according to the manufacturer's protocol. Cells are seeded at a density of 4.1 104 cells per well.

After an overnight culture, the cells are incubated at 4° C. for 1 h with binding buffer (ice-cold phosphate-buffered saline (PBS), 0.1% bovine serum albumin) containing designated concentrations of 125I-labelled adiponectin (5,000 counts per min per ng protein) plus unlabelled competitors. The binding equilibrium is found to be established when the binding assay is conducted at 4° C. after 1 h. The cells are then washed three times with ice-cold PBS, lysed in 0.1 M NaOH, 0.1% SDS, and the cell-bound radioactivity is determined using a-counter (Nature Med. 8, 1288-1295 (2002); Nature 387, 620-624). Nonspecific binding is determined using a 200-fold excess of unlabelled adiponectin. Specific binding is calculated by subtracting nonspecific binding from the total binding.

In addition, the adiponectin activity of the human AdipoR2v1 and mouse AdipoR2v1 adiponectin receptors of the present invention may be assessed by measuring the level of intracellular $Ca^{2+}$ concentration and cAMP and cGMP contents (Nature 387, 620-624), the level of phosphorylation of AMPK, ACC (Nature Med. 8, 1288-1295 (2002)), p38 MAPK, and MAPK (J. Biol. Chem. 276:44495-44501 (2001); Mol. Cell 8:971-982 (2001); and Proc. Natl. Acad. Sci. USA 98:3820-3825 (2001)), the level of PPAR-alpha ligand activity (J. Biol. Chem. 278:2461-2468 (2003)), $[^{14}C]$ $CO_2$ production from $[1-^{14}C]$palmitic acid, and glucose uptake (Nature Med. 7:941-946 (2001); and Nature Med. 8:1288-1295 (2002)).

Example 8

Method of Assessing Whether the Novel Human AdipoR2v1, Mouse AdipoR2v1, Human AdipoR3, Human AdipoR2v2, Human AdipoR3v, Rat AdipoR1, and/or Rat AdipoR2 Receptors of the Present Invention have GPCR Coupling Activity The use of mammalian cell reporter assays to demonstrate functional coupling of known GPCRs (G Protein Coupled Receptors) has been well documented in the literature (Gilman, 1987, Boss et al., 1996; Alam & Cook, 1990; George et al., 1997; Selbie & Hill, 1998; Rees et al., 1999). In fact, reporter assays have been successfully used for identifying novel small molecule agonists or antagonists against GPCRs as a class of drug targets (Zlokarnik et al., 1998; George et al., 1997; Boss et al., 1996; Rees et al, 2001). In such reporter assays, a promoter is regulated as a direct consequence of activation of specific signal transduction cascades following agonist binding to a GPCR (Alam & Cook 1990; Selbie & Hill, 1998; Boss et al., 1996; George et al., 1997; Gilman, 1987).

A number of response element-based reporter systems have been developed that enable the study of GPCR function. These include cAMP response element (CRE)-based reporter polynucleotides for G alpha i/o, G alpha s-coupled GPCRs, Nuclear Factor Activator of Transcription (NFAT)-based reporters for G alpha q/11-coupled receptors and MAP kinase reporter polynucleotides for use in G alpha i/o coupled receptors (Selbie & Hill, 1998; Boss et al., 1996; George et al., 1997; Gilman, 1987; Rees et al., 2001). Transcriptional response elements that regulate the expression of Beta-Lactamase within a CHO K1 cell line (Cho/NFAT-CRE: Aurora Biosciences™) (Zlokarnik et al., 1998) have been implemented to characterize the function of the orphan AdipoR2v1, mouse AdipoR2v1, human AdipoR3, human AdipoR2v2, human AdipoR3v1, rat AdipoR1, and/or rat AdipoR2 of the present invention. The system enables demonstration of constitutive G-protein coupling to endogenous cellular signaling components upon intracellular overexpression of orphan receptors. Overexpression has been shown to represent a physiologically relevant event. For example, it has been shown that overexpression occurs in nature during metastatic carcinomas, wherein defective expression of the monocyte chemotactic protein 1 receptor, CCR2, in macrophages is associated with the incidence of human ovarian carcinoma (Sica, et al., 2000; Salcedo et al., 2000). Indeed, it has been shown that overproduction of the Beta 2 Adrenergic Receptor in transgenic mice leads to constitutive activation of the receptor signaling pathway such that these mice exhibit increased cardiac output (Kypson et al., 1999; Dorn et al., 1999). These are only a few of the many examples demonstrating constitutive activation of GPCRs whereby many of these receptors are likely to be in the active, R*, conformation (J. Wess 1997).

Materials and Methods

DNA Constructs

The putative GPCR human AdipoR2v1, mouse AdipoR2v1, human AdipoR3, human AdipoR2v2, human AdipoR3v, rat AdipoR1, and/or rat AdipoR2 cDNA may be PCR amplified using PFU™ (Stratagene). The primers used in the PCR reaction are specific to the human AdipoR2v1, mouse AdipoR2v1, human AdipoR3, human AdipoR2v2, human AdipoR3v, rat AdipoR1, and/or rat AdipoR2 polynucleotides. An appropriate 3 prime primer may be designed so as to add a Flag-tag epitope to the AdipoR2v1, mouse AdipoR2v1, human AdipoR3, human AdipoR2v2, human AdipoR3v1, rat AdipoR1, and/or rat AdipoR2 for immunocytochemistry. The product from the PCR reaction may be isolated from a 0.8% Agarose gel (Invitrogen) and purified using a Gel Extraction Kit™ from Qiagen.

The purified product may be then digested overnight along with the pcDNA3.1 Hygro™ mammalian expression vector from Invitrogen using the HindIII and BamHI restriction enzymes (New England Biolabs). These digested products are then purified using the Gel Extraction Kit™ from Qiagen and subsequently ligated to the pcDNA3.1 Hygro™ expression vector using a DNA molar ratio of 4 parts insert:1 vector. All DNA modification enzymes are purchased from NEB. The ligation may be incubated overnight at 16 degrees Celsius, after which time, one microliter of the mix may be used to transform DH5 alpha cloning efficiency competent *E. coli*™ (Gibco BRL). A detailed description of the pcDNA3.1 Hygro™ mammalian expression vector is available at the Invitrogen web site. The plasmid DNA from the ampicillin resistant clones are isolated using the Wizard DNA Miniprep System™ from Promega. Positive clones are then confirmed and scaled up for purification using the Qiagen Maxiprep™ plasmid DNA purification kit.

Cell Line Generation

The pcDNA3.1hygro vector containing the orphan human AdipoR2v1, mouse AdipoR2v1, human AdipoR3, human AdipoR2v2, human AdipoR3v, rat AdipoR1, and/or rat AdipoR2 cDNA are used to transfect Cho/NFAT-CRE (Aurora Biosciences) cells using Lipofectamine 2000™ according to the manufacturers specifications (Gibco BRL). Two days later, the cells are split 1:3 into selective media (DMEM 11056, 600 ug/ml Hygromycin, 200 ug/ml Zeocin, 10% FBS). All cell culture reagents are purchased from Gibco BRL-Invitrogen.

The Cho/NFAT-CRE cell lines, transiently or stably transfected with the orphan human AdipoR2v1, mouse AdipoR2v1, human AdipoR3, human AdipoR2v2, human AdipoR3v, rat AdipoR1, and/or rat AdipoR2 GPCR, are analyzed using the FACS Vantage SE™ (BD), fluorescence microscopy (Nikon), and the LJL Analyst™ (Molecular Devices). In this system, changes in real-time gene expression, as a consequence of constitutive G-protein coupling of the orphan human AdipoR2v1, mouse AdipoR2v1, human AdipoR3, human AdipoR2v2, human AdipoR3v, rat AdipoR1, and/or rat AdipoR2 GPCR, is examined by analyzing the fluorescence emission of the transformed cells at 447 nm and 518 nm. The changes in gene expression can be visualized using Beta-Lactamase as a reporter, that, when induced by the appropriate signaling cascade, hydrolyzes an intracellularly loaded, membrane-permeant ester, Cephalosporin-Coumarin-Fluorescein-2/Acetoxymethyl™ (CCF2/AM™ Aurora Biosciences; Zlokarnik, et al., 1998). The CCF2/AM™ substrate is a 7-hydroxycoumarin cephalosporin with a fluorescein attached through a stable thioether linkage. Induced expression of the Beta-Lactamase enzyme is readily apparent since each enzyme molecule produced is capable of changing the fluorescence of many CCF2/AM™ substrate molecules. A schematic of this cell based system is shown below.

Prior to analyzing the fluorescent emissions from the cell lines as described above, the cells are loaded with the CCF2/AM substrate. A 6×CCF2/AM loading buffer may be prepared whereby 1 mM CCF2/AM (Aurora Biosciences) may be dissolved in 100% DMSO (Sigma). 12 ul of this stock solution may be added to 60 ul of 100 mg/ml Pluronic F127 (Sigma) in DMSO containing 0.1% Acetic Acid (Sigma). This solution may be added while vortexing to 1 mL of Sort Buffer (PBS minus calcium and magnesium-Gibco-25 mM HEPES-Gibco-pH 7.4, 0.1% BSA). Cells are placed in serum-free media and the 6×CCF2/AM may be added to a final concentration of 1×. The cells are then loaded at room temperature for one to two hours, and then subjected to fluorescent emission analysis as described herein. Additional details relative to the cell loading methods and/or instrument settings may be found by reference to the following publications: see Zlokarnik, et al., 1998; Whitney et al., 1998; and BD Biosciences, 1999.

Immunocytochemistry

The cell lines transfected and selected for expression of Flag-epitope tagged orphan GPCRs are analyzed by immunocytochemistry. The cells are plated at 1×10^3 in each well of a glass slide (VWR). The cells are rinsed with PBS fol-

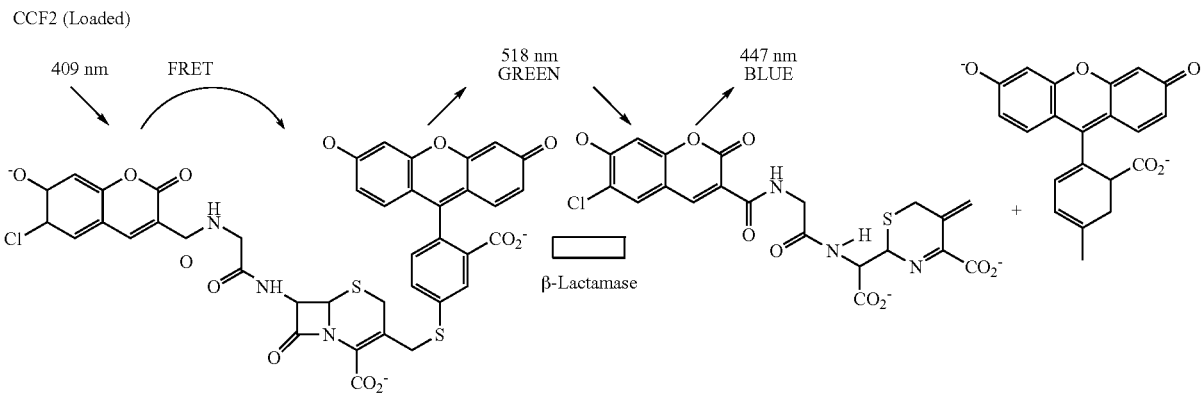

In summary, CCF2/AM™ is a membrane permeant, intracellularly-trapped, fluorescent substrate with a cephalosporin core that links a 7-hydroxycoumarin to a fluorescein. For the intact molecule, excitation of the coumarin at 409 nm results in Fluorescence Resonance Energy Transfer (FRET) to the fluorescein which emits green light at 518 nm. Production of active Beta-Lactamase results in cleavage of the Beta-Lactam ring, leading to disruption of FRET, and excitation of the coumarin only—thus giving rise to blue fluorescent emission at 447 nm.

Fluorescent emissions are detected using a Nikon-TE300 microscope equipped with an excitation filter (D405/10X-25), dichroic reflector (430DCLP), and a barrier filter for dual DAPI/FITC (510 nM) to visually capture changes in Beta-Lactamase expression. The FACS Vantage SE is equipped with a Coherent Enterprise II Argon Laser and a Coherent 302C Krypton laser. In flow cytometry, UV excitation at 351-364 nm from the Argon Laser or violet excitation at 407 nm from the Krypton laser are used. The optical filters on the FACS Vantage SE are HQ460/50m and HQ535/40m bandpass separated by a 490 dichroic mirror.

lowed by acid fixation for 30 minutes at room temperature using a mixture of 5% Glacial Acetic Acid/90% ETOH. The cells are then blocked in 2% BSA and 0.1% Triton in PBS, incubated for 2 h at room temperature or overnight at 4° C. A monoclonal anti-Flag FITC antibody may be diluted at 1:50 in blocking solution and incubated with the cells for 2 h at room temperature. Cells are then may behed three times with 0.1% Triton in PBS for five minutes. The slides are overlayed with mounting media dropwise with Biomedia-Gel Mount™ (Biomedia; Containing Anti-Quenching Agent). Cells are examined at 10× magnification using the Nikon TE300 equipped with FITC filter (535 nm).

Demonstration of Cell Surface Expression

Human AdipoR2v1, mouse AdipoR2v1, human AdipoR3, human AdipoR2v2, human AdipoR3v1, rat AdipoR1, and/or rat AdipoR2 may be tagged at the C-terminus using the Flag epitope and inserted into the pcDNA3.1 Hygro™ expression vector, as described herein. Immunocytochemistry of Cho Nfat-CRE cell lines transfected with the Flag-tagged human AdipoR2v1, mouse AdipoR2v1, human AdipoR3, human AdipoR2v2, human AdipoR3v, rat AdipoR1, and/or rat AdipoR2 construct with FITC conjugated Anti Flag monoclonal antibody demonstrated that human AdipoR2v1, mouse AdipoR2v1, human AdipoR3, human AdipoR2v2, human AdipoR3v, rat AdipoR1, and/or rat AdipoR2 is indeed a cell surface receptor. The immunocytochemistry also confirmed expression of the human AdipoR2v1, mouse AdipoR2v1, human AdipoR3, human AdipoR2v2, human AdipoR3v, rat AdipoR1, and/or rat AdipoR2 in the Cho Nfat-CRE cell lines. Briefly, Cho Nfat-CRE cell lines are transfected with pcDNA3.1 Hygro™/human AdipoR2v1, mouse AdipoR2v1, human AdipoR3, human AdipoR2v2, human AdipoR3v, rat AdipoR1, and/or rat AdipoR2-Flag vector, fixed with 70% methanol, and permeablized with 0.1% TritonX100. The cells are then blocked with 1% Serum and incubated with a FITC conjugated Anti Flag monoclonal antibody at 1:50 dilution in PBS-Triton. The cells are then may behed several times with PBS-Triton, overlayed with mounting solution, and fluorescent images are captured. The control cell line, non-transfected ChoNfat CRE cell line, exhibited no detectable background fluorescence. Plasma membrane localization would be consistent with human AdipoR2v1, mouse AdipoR2v1, human AdipoR3, human AdipoR2v2, human AdipoR3v, rat AdipoR1, and/or rat AdipoR2 representing a 7 transmembrane domain containing GPCR.

Screening Paradigm

The Aurora Beta-Lactamase technology provides a clear path for identifying agonists and antagonists of the AdipoR2v1, mouse AdipoR2v1, human AdipoR3, human AdipoR2v2, human AdipoR3v1, rat AdipoR1, and/or rat AdipoR2. Cell lines that exhibit a range of constitutive coupling activity may be identified by sorting through human AdipoR2v1, mouse AdipoR2v1, human AdipoR3, human AdipoR2v2, human AdipoR3v, rat AdipoR1, and/or rat AdipoR2 transfected cell lines using the FACS Vantage SE. For example, cell lines that exhibit an intermediate coupling response, using the LJL analyst, would provide the opportunity to screen, indirectly, for both agonists and antagonists of human AdipoR2v1, mouse AdipoR2v1, human AdipoR3, human AdipoR2v2, human AdipoR3v, rat AdipoR1, and/or rat AdipoR2 by looking for inhibitors that block the beta lactamase response, or agonists that increase the beta lactamase response. As described herein, modulating the expression level of beta lactamase directly correlates with the level of cleaved CCR2 substrate. For example, this screening paradigm has been shown to work for the identification of modulators of a known GPCR, 5HT6, that couples through Adenylate Cyclase, in addition to, the identification of modulators of the 5HT2c GPCR, that couples through changes in $[Ca^{2+}]i$. human AdipoR2v1, mouse AdipoR2v1, human AdipoR3, human AdipoR2v2, human AdipoR3v, rat AdipoR1, and/or rat AdipoR2 modulator screens may be carried out using a variety of high throughput methods known in the art, though preferably using the fully automated Aurora UHTSS system.

In preferred embodiments, the human AdipoR2v1, mouse AdipoR2v1, human AdipoR3, human AdipoR2v2, human AdipoR3v, rat AdipoR1, and/or rat AdipoR2 transfected Cho Nfat-CRE cell lines of the present invention are useful for the identification of agonists and antagonists of the AdipoR2v1, mouse AdipoR2v1, human AdipoR3, human AdipoR2v2, human AdipoR3v1, rat AdipoR1, and/or rat AdipoR2. Representative uses of these cell lines would be their inclusion in a method of identifying human AdipoR2v1, mouse AdipoR2v1, human AdipoR3, human AdipoR2v2, human AdipoR3v, rat AdipoR1, and/or rat AdipoR2 agonists and antagonists. Preferably, the cell lines are useful in a method for identifying a compound that modulates the biological activity of the AdipoR2v1, mouse AdipoR2v1, human AdipoR3, human AdipoR2v2, human AdipoR3v1, rat AdipoR1, and/or rat AdipoR2, comprising the steps of (a) combining a candidate modulator compound with a host cell expressing the AdipoR2v1, mouse AdipoR2v1, human AdipoR3, human AdipoR2v2, human AdipoR3v1, rat AdipoR1, and/or rat AdipoR2 having the sequence as set forth in SEQ ID NO:2, 4, 6, 102, 104, 165, or 167; and (b) measuring an effect of the candidate modulator compound on the activity of the expressed AdipoR2v1, mouse AdipoR2v1, human AdipoR3, human AdipoR2v2, human AdipoR3v1, rat AdipoR1, and/or rat AdipoR2. Representative vectors expressing the AdipoR2v1, mouse AdipoR2v1, human AdipoR3, human AdipoR2v2, human AdipoR3v1, rat AdipoR1, and/or rat AdipoR2 are referenced herein (e.g., pcDNA3.1 Hygro™) or otherwise known in the art.

The cell lines are also useful in a method of screening for a compound that is capable of modulating the biological activity of AdipoR2v1, mouse AdipoR2v1, human AdipoR3, human AdipoR2v2, human AdipoR3v1, rat AdipoR1, and/or rat AdipoR2, comprising the steps of: (a) determining the biological activity of the AdipoR2v1, mouse AdipoR2v1, human AdipoR3, human AdipoR2v2, human AdipoR3v1, rat AdipoR1, and/or rat AdipoR2 in the absence of a modulator compound; (b) contacting a host cell expression the AdipoR2v1, mouse AdipoR2v1, human AdipoR3, human AdipoR2v2, human AdipoR3v1, rat AdipoR1, and/or rat AdipoR2 with the modulator compound; and (c) determining the biological activity of the AdipoR2v1, mouse AdipoR2v1, human AdipoR3, human AdipoR2v2, human AdipoR3v1, rat AdipoR1, and/or rat AdipoR2 in the presence of the modulator compound; wherein a difference between the activity of the AdipoR2v1, mouse AdipoR2v1, human AdipoR3, human AdipoR2v2, human AdipoR3v1, rat AdipoR1, and/or rat AdipoR2 in the presence of the modulator compound and in the absence of the modulator compound indicates a modulating effect of the compound. Additional uses for these cell lines are described herein or otherwise known in the art.

1. Rees, S., Brown, S., Stables, J.: Reporter gene systems for the study of G Protein Coupled Receptor signalling in mammalian cells. In Milligan G. (ed.): Signal Transduction: A practical approach. Oxford: Oxford University Press, 1999: 171-221.
2. Alam, J., Cook, J. L.: Reporter Genes: Application to the study of mammalian gene transcription. Anal. Biochem. 1990; 188: 245-254.
3. Selbie, L. A. and Hill, S. J.: G protein-coupled receptor cross-talk: The fine-tuning of multiple receptor-signaling pathways. TiPs. 1998; 19: 87-93.
4. Boss, V., Talpade, D. J., and Murphy, T. J.: Induction of NFAT mediated transcription by Gq-coupled Receptors in lymphoid and non-lymphoid cells. JBC. 1996; 271: 10429-10432.
5. George, S. E., Bungay, B. J., and Naylor, L. H.: Functional coupling of endogenous serotonin (5-HT1B) and calcitonin (C1a) receptors in Cho cells to a cyclic AMP-responsive luciferase reporter gene. J. Neurochem. 1997; 69: 1278-1285.
6. Suto, C M, Igna D M: Selection of an optimal reporter for cell-based high throughput screening assays. J. Biomol. Screening. 1997; 2: 7-12.
7. Zlokarnik, G., Negulescu, P. A., Knapp, T. E., More, L., Burres, N., Feng, L., Whitney, M., Roemer, K., and Tsien, R. Y. Quantitation of transcription and clonal selection of single living cells with a B-Lactamase Reporter. Science. 1998; 279: 84-88.

8. S. Fiering et. al., Genes Dev. 4, 1823 (1990).
9. J. Karttunen and N. Shastri, PNAS 88, 3972 (1991).
10. Hawes, B. E., Luttrell. L. M., van Biesen, T., and Lefkowitz, R. J. (1996) JBC 271, 12133-12136.
11. Gilman, A. G. (1987) Annul. Rev. Biochem. 56, 615-649.
12. Maniatis et al.,
13. Salcedo, R., Ponce, M. L., Young, H. A., May beserman, K., Ward, J. M., Kleinman, H. K., Oppenheim, J. J., Murphy, W. J. Human endothelial cells express CCR2 and respond to MCP-1: direct role of MCP-1 in angiopolynucleotidesis and tumor progression. Blood. 2000; 96 (1): 34-40.
14. Sica, A., Saccani, A., Bottazzi, B., Bemasconi, S., Allavena, P., Gaetano, B., LaRossa, G., Scotton, C., Balkwill F., Mantovani, A. Defective expression of the monocyte chemotactic protein 1 receptor CCR2 in macrophages associated with human ovarian carcinoma. J. Immunology. 2000; 164: 733-8.
15. Kypson, A., Hendrickson, S., Akhter, S., Wilson, K., McDonald, P., Lilly, R., Dolber, P., Glower, D., Lefkowitz, R., Koch, W. Adenovirus-mediated gene transfer of the B2 AR to donor hearts enhances cardiac function. Gene Therapy. 1999; 6: 1298-304.
16. Dorn, G. W., Tepe, N. M., Lorenz, J. N., Kock, W. J., Ligget, S. B. Low and high level transgenic expression of B2AR differentially affect cardiac hypertrophy and function in Galpha q-overexpressing mice. PNAS. 1999; 96: 6400-5.
17. J. Wess. G protein coupled receptor: molecular mechanisms involved in receptor activation and selectivity of G-protein recognition.
18. Whitney, M, Rockenstein, E, Cantin, G., Knapp, T., Zlokarnik, G., Sanders, P., Durick, K., Craig, F. F., and Negulescu, P. A. A genome-wide functional assay of signal transduction in living mammalian cells. 1998. Nature Biotech. 16: 1329-1333.
19. BD Biosciences: FACS Vantage SE Training Manual. Part Number 11-11020-00 Rev. A. August 1999.
20. Chen, G., Jaywickreme, C., Way, J., Armour S., Queen K., Watson., C., Ignar, D., Chen, W. J., Kenakin, T. Constitutive Receptor systems for drug discovery. J. Pharmacol. Toxicol. Methods 1999; 42: 199-206.

Example 9

Alternative Method of Assessing the Ability of Human AdipoR2v1, Mouse AdipoR2v1, Human AdipoR3, Human AdipoR2v2, Human AdipoR3v, Rat AdipoR1, and/or Rat AdipoR2 Receptors to Serve as a GPCR Receptor The activity of the AdipoR2v1, mouse AdipoR2v1, human AdipoR3, human AdipoR2v2, human AdipoR3v1, rat AdipoR1, and/or rat AdipoR2 may be measured using an assay based upon the property of some known GPCRs to support proliferation in vitro of fibroblasts and tumor cells under serum-free conditions (Chiquet Ehrismann, R. et al. (1986) Cell 47: 131-139). Briefly, wells in 96 well cluster plates (Falcon, Fisher Scientific, Santa Clara Calif.) are coated with AdipoR2v1, mouse AdipoR2v1, human AdipoR3, human AdipoR2v2, human AdipoR3v1, rat AdipoR1, and/or rat AdipoR2 by incubation with solutions at 50-100 Rg/ml for 15 min at ambient temperature. The coating solution is aspirated, and the wells washed with Dulbecco's medium before cells are plated. Rat fibroblast cultures or rat mammary tumor cells are prepared as described and plated at a density of 104-105 cells/ml in Dulbecco's medium supplemented with 10% fetal calf serum (FCS).

After three days the media are removed, and the cells washed three times with phosphate buffered saline (PBS) before the addition of serum-free Dulbecco's medium containing 0.25 mg/ml bovine serum albumin (BSA, Fraction V, Sigma Chemical, St. Louis, Mo.). After 2 days the medium is aspirated, and 100 µl of [3H] thymidine (NEN) at 2 IlCi/ml in fresh Dulbecco's medium containing 0.25 mg/ml BSA added. Parallel plates are fixed and stained to determine cell numbers. After 16 hr, the medium is aspirated, the cell layer washed with PBS, and the 10% trichloroacetic acid-precipitable counts in the cell layer determined by liquid scintillation counting of radioisotope (normalized to relative cell numbers; Chiquet-Ehrismann, R. et al. (1986) supra). The rates of cell proliferation and [3H] thymidine uptake are proportional to the levels of GCRP in the sample.

Alternatively, the assay for human AdipoR2v1, mouse AdipoR2v1, human AdipoR3, human AdipoR2v2, human AdipoR3v, rat AdipoR1, and/or rat AdipoR2 polypeptide activity is based upon the property of CD97/Emrl GPCR family proteins to modulate G protein-activated second messenger signal transduction pathways (e.g., cAMP; Gaudin, P. et al. (1998) J. Biol. Chem. 273: 4990-4996). A plasmid encoding the full length human AdipoR2v1, mouse AdipoR2v1, human AdipoR3, human AdipoR2v2, human AdipoR3v, rat AdipoR1, and/or rat AdipoR2 polypeptide is transfected into a mammalian cell line (e.g., COS-7 or Chinese hamster ovary (CHO-K1) cell lines) using methods well-known in the art. Transfected cells are grown in 12-well trays in culture medium containing 2% FCS for 48 hours, the culture medium is discarded, then the attached cells are gently washed with PBS. The cells are then incubated in culture medium with 10% FCS or 2% FCS for 30 minutes, then the medium is removed and cells lysed by treatment with 1 M perchloric acid. The cAMP levels in the lysate are measured by radioimmunoassay using methods well-known in the art. Changes in the levels of cAMP in the lysate from 10% FCS-treated cells compared with those in 2% FCS-treated cells are proportional to the amount of the human AdipoR2v1, mouse AdipoR2v1, human AdipoR3, human AdipoR2v2, human AdipoR3v, rat AdipoR1, and/or rat AdipoR2 polypeptide present in the transfected cells.

Example 10

Method of Screening for Compounds that Interact with the Human AdipoR2v1, Mouse AdipoR2v1, Human AdipoR3, Human AdipoR2v2, Human AdipoR3v, Rat AdipoR1, and/or Rat AdipoR2 Receptors Polypeptide The following assays are designed to identify compounds that bind to the human AdipoR2v1, mouse AdipoR2v1, human AdipoR3, human AdipoR2v2, human AdipoR3v, rat AdipoR1, and/or rat AdipoR2 polypeptide, bind to other cellular proteins that interact with the human AdipoR2v1, mouse AdipoR2v1, human AdipoR3, human AdipoR2v2, human AdipoR3v, rat AdipoR1, and/or rat AdipoR2 polypeptide, and to compounds that interfere with the interaction of the human AdipoR2v1, mouse AdipoR2v1, human AdipoR3, human AdipoR2v2, human AdipoR3v, rat AdipoR1, and/or rat AdipoR2 polypeptide with other cellular proteins.

Such compounds can include, but are not limited to, other cellular proteins. Specifically, such compounds can include, but are not limited to, peptides, such as, for example, soluble peptides, including, but not limited to Ig-tailed fusion peptides, comprising extracellular portions of human AdipoR2v1, mouse AdipoR2v1, human AdipoR3, human AdipoR2v2, human AdipoR3v, rat AdipoR1, and/or rat AdipoR2 polypeptide transmembrane receptors, and members of random peptide libraries (see, e.g., Lam, K. S. et al., 1991, Nature 354:82-84; Houghton, R. et al., 1991, Nature 354:84-86), made of D- and/or L-configuration amino acids, phosphopeptides (including, but not limited to, members of random or partially degenerate phosphopeptide libraries; see, e.g., Songyang, Z., et al., 1993, Cell 72:767-778), antibodies (including, but not limited to, polyclonal, monoclonal, humanized, anti-idiotypic, chimeric or single chain antibodies, and FAb, F(ab').sub.2 and FAb expression library fragments, and epitope-binding fragments thereof), and small organic or inorganic molecules.

Compounds identified via assays such as those described herein can be useful, for example, in elaborating the biological function of the human AdipoR2v1, mouse AdipoR2v1, human AdipoR3, human AdipoR2v2, human AdipoR3v, rat AdipoR1, and/or rat AdipoR2 polypeptide, and for ameliorating symptoms of tumor progression, for example. In instances, for example, whereby a tumor progression state or disorder results from a lower overall level of human AdipoR2v1, mouse AdipoR2v1, human AdipoR3, human AdipoR2v2, human AdipoR3v, rat AdipoR1, and/or rat AdipoR2 expression, human AdipoR2v1, mouse AdipoR2v1, human AdipoR3, human AdipoR2v2, human AdipoR3v, rat AdipoR1, and/or rat AdipoR2 polypeptide, and/or human AdipoR2v1, mouse AdipoR2v1, human AdipoR3, human AdipoR2v2, human AdipoR3v, rat AdipoR1, and/or rat AdipoR2 polypeptide activity in a cell involved in the tumor progression state or disorder, compounds that interact with the human AdipoR2v1, mouse AdipoR2v1, human AdipoR3, human AdipoR2v2, human AdipoR3v, rat AdipoR1, and/or rat AdipoR2 polypeptide can include ones which accentuate or amplify the activity of the bound human AdipoR2v1, mouse AdipoR2v1, human AdipoR3, human AdipoR2v2, human AdipoR3v, rat AdipoR1, and/or rat AdipoR2 polypeptide. Such compounds would bring about an effective increase in the level of human AdipoR2v1, mouse AdipoR2v1, human AdipoR3, human AdipoR2v2, human AdipoR3v, rat AdipoR1, and/or rat AdipoR2 polypeptide activity, thus ameliorating symptoms of the tumor progression disorder or state. In instances whereby mutations within the human AdipoR2v1, mouse AdipoR2v1, human AdipoR3, human AdipoR2v2, human AdipoR3v, rat AdipoR1, and/or rat AdipoR2 polypeptide cause aberrant AdipoR2v1, mouse AdipoR2v1, human AdipoR3, human AdipoR2v2, human AdipoR3v1, rat AdipoR1, and/or rat AdipoR2 to be made which have a deleterious effect that leads to tumor progression, compounds that bind human AdipoR2v1, mouse AdipoR2v1, human AdipoR3, human AdipoR2v2, human AdipoR3v, rat AdipoR1, and/or rat AdipoR2 polypeptide can be identified that inhibit the activity of the bound human AdipoR2v1, mouse AdipoR2v1, human AdipoR3, human AdipoR2v2, human AdipoR3v, rat AdipoR1, and/or rat AdipoR2 polypeptide. Assays for testing the effectiveness of such compounds are known in the art and discussed, elsewhere herein.

Example 12

Method of Screening, In Vitro, Compounds that Bind to the Human AdipoR2v1, Mouse AdipoR2v1, Human AdipoR3, Human AdipoR2v2, Human AdipoR3v, Rat AdipoR1, and/or Rat AdipoR2 Receptors In vitro systems can be designed to identify compounds capable of binding the human AdipoR2v1, mouse AdipoR2v1, human AdipoR3, human AdipoR2v2, human AdipoR3v, rat AdipoR1, and/or rat AdipoR2 polypeptide of the invention. Compounds identified can be useful, for example, in modulating the activity of wild type and/or mutant human AdipoR2v1, mouse AdipoR2v1, human AdipoR3, human AdipoR2v2, human AdipoR3v, rat AdipoR1, and/or rat AdipoR2 polypeptide, preferably mutant human AdipoR2v1, mouse AdipoR2v1, human AdipoR3, human AdipoR2v2, human AdipoR3v, rat AdipoR1, and/or rat AdipoR2 polypeptide, can be useful in elaborating the biological function of the human AdipoR2v1, mouse AdipoR2v1, human AdipoR3, human AdipoR2v2, human AdipoR3v, rat AdipoR1, and/or rat AdipoR2 polypeptide, can be utilized in screens for identifying compounds that disrupt normal human AdipoR2v1, mouse AdipoR2v1, human AdipoR3, human AdipoR2v2, human AdipoR3v, rat AdipoR1, and/or rat AdipoR2 polypeptide interactions, or can in themselves disrupt such interactions.

The principle of the assays used to identify compounds that bind to the human AdipoR2v1, mouse AdipoR2v1, human AdipoR3, human AdipoR2v2, human AdipoR3v, rat AdipoR1, and/or rat AdipoR2 polypeptide involves preparing a reaction mixture of the human AdipoR2v1, mouse AdipoR2v1, human AdipoR3, human AdipoR2v2, human AdipoR3v, rat AdipoR1, and/or rat AdipoR2 polypeptide and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring human AdipoR2v1, mouse AdipoR2v1, human AdipoR3, human AdipoR2v2, human AdipoR3v, rat AdipoR1, and/or rat AdipoR2 polypeptide or the test substance onto a solid phase and detecting human AdipoR2v1, mouse AdipoR2v1, human AdipoR3, human AdipoR2v2, human AdipoR3v, rat AdipoR1, and/or rat AdipoR2 polypeptide/test compound complexes anchored on the solid phase at the end of the reaction. In one embodiment of such a method, the human AdipoR2v1, mouse AdipoR2v1, human AdipoR3, human AdipoR2v2, human AdipoR3v, rat AdipoR1, and/or rat AdipoR2 polypeptide can be anchored onto a solid surface, and the test compound, which is not anchored, can be labeled, either directly or indirectly.

In practice, microtitre plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for human AdipoR2v1, mouse AdipoR2v1, human AdipoR3, human AdipoR2v2, human AdipoR3v, rat AdipoR1, and/or rat AdipoR2 polypeptide or the test compound to anchor any complexes formed in solution, and a labeled antibody specific for the other component of the possible complex to detect anchored complexes.

Another example of a screening assay to identify compounds that bind to human AdipoR2v1, mouse AdipoR2v1, human AdipoR3, human AdipoR2v2, human AdipoR3v, rat AdipoR1, and/or rat AdipoR2, relates to the application of a cell membrane-based scintillation proximity assay ("SPA"). Such an assay would require the identification of a ligand for human AdipoR2v1, mouse AdipoR2v1, human AdipoR3, human AdipoR2v2, human AdipoR3v, rat AdipoR1, and/or rat AdipoR2 polypeptide. Once identified, unlabeled ligand is added to assay-ready plates that would serve as a positive control. The SPA beads and membranes are added next, and then $^{125}$I-labeled ligand is added. After an equilibration period of 2-4 hours at room temperature, the plates can be counted in a scintillation counting machine, and the percent inhibition or stimulation calculated. Such an SPA assay may be based upon a manual, automated, or semi-automated platform, and encompass 96, 384, 1536-well plates or more. Any number of SPA beads may be used as applicable to each assay. Examples of SPA beads include, for example, Leadseeker WGA PS (Amersham cat #RPNQ 0260), and SPA Beads (PVT-PEI-WGA-TypeA; Amersham cat #RPNQ0003). The utilized membranes may also be derived from a number of cell line and tissue sources depending upon the expression profile of the respective polypeptide and the adaptability of such a cell line or tissue source to the development of a SPA-based assay. Examples of membrane preparations include, for example, cell lines transformed to express the receptor to be assayed in CHO cells or HEK cells, for example. SPA-based assays are well known in the art and are encompassed by the present invention. One such assay is described in U.S. Pat. No. 4,568,649, which is incorporated herein by reference. The skilled artisan would acknowledge that certain modifications of known SPA assays may be required to adapt such assays to each respective polypeptide.

One such screening procedure involves the use of melanophores which are transfected to express the human AdipoR2v1, mouse AdipoR2v1, human AdipoR3, human AdipoR2v2, human AdipoR3v, rat AdipoR1, and/or rat AdipoR2 polypeptide of the present invention. Such a screening technique is described in PCT WO 92/01810, published Feb. 6, 1992. Such an assay may be employed to screen for a compound which inhibits activation of the receptor polypeptide of the present invention by contacting the melanophore cells which encode the receptor with both the receptor ligand, such as LPA, and a compound to be screened. Inhibition of the signal generated by the ligand indicates that a compound is a potential antagonist for the receptor, i.e., inhibits activation of the receptor.

The technique may also be employed for screening of compounds which activate the receptor by contacting such cells with compounds to be screened and determining whether such compound generates a signal, i.e., activates the receptor. Other screening techniques include the use of cells which express the human AdipoR2v1, mouse AdipoR2v1, human AdipoR3, human AdipoR2v2, human AdipoR3v, rat AdipoR1, and/or rat AdipoR2 polypeptide (for example, transfected CHO cells) in a system which measures extracellular pH changes caused by receptor activation. In this technique, compounds may be contacted with cells expressing the receptor polypeptide of the present invention. A second messenger response, e.g., signal transduction or pH changes, is then measured to determine whether the potential compound activates or inhibits the receptor.

Another screening technique involves expressing the human AdipoR2v1, mouse AdipoR2v1, human AdipoR3, human AdipoR2v2, human AdipoR3v, rat AdipoR1, and/or rat AdipoR2 polypeptide in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antagonists or agonists by determining inhibition of binding of labeled ligand, such as LPA, to cells which have the receptor on the surface thereof, or cell membranes containing the receptor. Such a method involves transfecting a cell (such as eukaryotic cell) with DNA encoding the human AdipoR2v1, mouse AdipoR2v1, human AdipoR3, human AdipoR2v2, human AdipoR3v, rat AdipoR1, and/or rat AdipoR2 polypeptide such that the cell expresses the receptor on its surface. The cell is then contacted with a potential antagonist or agonist in the presence of a labeled form of a ligand, such as LPA. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors. This method is called binding assay.

Another screening procedure involves the use of mammalian cells (CHO, HEK 293, *Xenopus* Oocytes, RBL-2H3, etc) which are transfected to express the receptor of interest. The cells are loaded with an indicator dye that produces a fluorescent signal when bound to calcium, and the cells are contacted with a test substance and a receptor agonist, such as LPA. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist or agonist for the receptor.

Another screening procedure involves use of mammalian cells (CHO, HEK293, *Xenopus* Oocytes, RBL-2H3, etc.) which are transfected to express the receptor of interest, and which are also transfected with a reporter gene construct that is coupled to activation of the receptor (for example, luciferase or beta-galactosidase behind an appropriate promoter). The cells are contacted with a test substance and the receptor agonist (ligand), such as LPA, and the signal produced by the reporter gene is measured after a defined period of time. The signal can be measured using a luminometer, spectrophotometer, fluorimeter, or other such instrument appropriate for the specific reporter construct used. Change of the signal generated by the ligand indicates that a compound is a potential antagonist or agonist for the receptor.

Another screening technique for antagonists or agonits involves introducing RNA encoding the human AdipoR2v1, mouse AdipoR2v1, human AdipoR3, human AdipoR2v2, human AdipoR3v, rat AdipoR1, and/or rat AdipoR2 polypeptide into *Xenopus* oocytes (or CHO, HEK 293, RBL-2H3, etc.) to transiently or stably express the receptor. The receptor oocytes are then contacted with the receptor ligand, such as LPA, and a compound to be screened. Inhibition or activation of the receptor is then determined by detection of a signal, such as, cAMP, calcium, proton, or other ions.

Another method involves screening for human AdipoR2v1, mouse AdipoR2v1, human AdipoR3, human AdipoR2v2, human AdipoR3v, rat AdipoR1, and/or rat AdipoR2 polypeptide inhibitors by determining inhibition or stimulation of human AdipoR2v1, mouse AdipoR2v1, human AdipoR3, human AdipoR2v2, human AdipoR3v, rat AdipoR1, and/or rat AdipoR2 polypeptide-mediated cAMP and/or adenylate cyclase accumulation or diminution. Such a method involves transiently or stably transfecting a eukaryotic cell with human AdipoR2v1, mouse AdipoR2v1, human AdipoR3, human AdipoR2v2, human AdipoR3v, rat AdipoR1, and/or rat AdipoR2 polypeptide receptor to express the receptor on the cell surface.

The cell is then exposed to potential antagonists or agonists in the presence of human AdipoR2v1, mouse AdipoR2v1, human AdipoR3, human AdipoR2v2, human AdipoR3v, rat AdipoR1, and/or rat AdipoR2 polypeptide ligand, such as LPA. The changes in levels of cAMP is then measured over a defined period of time, for example, by radio-immuno or protein binding assays (for example using Flashplates or a scintillation proximity assay). Changes in cAMP levels can also be determined by directly measuring the activity of the enzyme, adenylyl cyclase, in broken cell preparations. If the potential antagonist or agonist binds the receptor, and thus inhibits human AdipoR2v1, mouse AdipoR2v1, human AdipoR3, human AdipoR2v2, human AdipoR3v, rat AdipoR1, and/or rat AdipoR2 polypeptide-ligand binding, the levels of human AdipoR2v1, mouse AdipoR2v1, human AdipoR3, human AdipoR2v2, human AdipoR3v, rat AdipoR1, and/or rat AdipoR2 polypeptide-mediated cAMP, or adenylate cyclase activity, will be reduced or increased.

One preferred screening method involves co-transfecting HEK-293 cells with a mammalian expression plasmid encoding a G-protein coupled receptor (GPCR), such as human AdipoR2v1, mouse AdipoR2v1, human AdipoR3, human AdipoR2v2, human AdipoR3v, rat AdipoR1, and/or rat AdipoR2, along with a mixture comprised of mammalian expression plasmids cDNAs encoding GU15 (Wilkie T. M. et al Proc Natl Acad Sci USA 1991 88: 10049-10053), GU16 (Amatruda T. T. et al Proc Natl Acad Sci USA 1991 8: 5587-5591, and three chimeric G-proteins referred to as Gqi5, Gqs5, and Gqo5 (Conklin B R et al Nature 1993 363: 274-276, Conklin B. R. et al Mol Pharmacol 1996 50: 885-890). Following a 24 h incubation the transfected HEK-293 cells are plated into poly-D-lysine coated 96 well black/clear plates (Becton Dickinson, Bedford, Mass.).

The cells are assayed on FLIPR (Fluorescent Imaging Plate Reader, Molecular Devices, Sunnyvale, Calif.) for a calcium mobilization response following addition of test ligands. Upon identification of a ligand which stimulates calcium mobilization in HEK-293 cells expressing a given GPCR and the G-protein mixtures, subsequent experiments are performed to determine which, if any, G-protein is required for the functional response. HEK-293 cells are then transfected with the test GPCR, or co-transfected with the test GPCR and G015, GD16, GqiS, Gqs5, or Gqo5. If the GPCR requires the presence of one of the G-proteins for functional expression in HEK-293 cells, all subsequent experiments are performed with HEK-293 cell cotransfected with the GPCR and the G-protein which gives the best response. Alternatively, the receptor can be expressed in a different cell line, for example RBL-2H3, without additional Gproteins.

Another screening method for agonists and antagonists relies on the endogenous pheromone response pathway in the yeast, *Saccharomyces cerevisiae*. Heterothallic strains of yeast can exist in two mitotically stable haploid mating types, MATa and MATα. Each cell type secretes a small peptide hormone that binds to a G-protein coupled receptor on opposite mating type cells which triggers a MAP kinase cascade leading to G1 arrest as a prelude to cell fusion.

Genetic alteration of certain polynucleotides in the pheromone response pathway can alter the normal response to pheromone, and heterologous expression and coupling of human G-protein coupled receptors and humanized G-protein subunits in yeast cells devoid of endogenous pheromone receptors can be linked to downstream signaling pathways and reporter polynucleotides (e.g., U.S. Pat. Nos. 5,063,154; 5,482,835; 5,691,188). Such genetic alterations include, but are not limited to, (i) deletion of the STE2 or STE3 gene encoding the endogenous G-protein coupled pheromone receptors; (ii) deletion of the FAR1 gene encoding a protein that normally associates with cyclin dependent kinases leading to cell cycle arrest; and (iii) construction of reporter polynucleotides fused to the FUS1 gene promoter (where FUS1 encodes a membrane-anchored glycoprotein required for cell fusion). Downstream reporter polynucleotides can permit either a positive growth selection (e.g., histidine prototrophy using the FUS1-HIS3 reporter), or a colorimetric, fluorimetric or spectrophotometric readout, depending on the specific reporter construct used (e.g., b-galactosidase induction using a FUS1-LacZ reporter).

The yeast cells can be further engineered to express and secrete small peptides from random peptide libraries, some of which can permit autocrine activation of heterologously expressed human (or mammalian) G-protein coupled receptors (Broach, J. R. and Thorner, J., Nature 384: 14-16, 1996; Manfredi et al., Mol. Cell. Biol. 16: 4700-4709, 1996). This provides a rapid direct growth selection (e.g, using the FUS1-HIS3 reporter) for surrogate peptide agonists that activate characterized or orphan receptors. Alternatively, yeast cells that functionally express human (or mammalian) G-protein coupled receptors linked to a reporter gene readout (e.g., FUS1-LacZ) can be used as a platform for high-throughput screening of known ligands, fractions of biological extracts and libraries of chemical compounds for either natural or surrogate ligands.

Functional agonists of sufficient potency (whether natural or surrogate) can be used as screening tools in yeast cell-based assays for identifying G-protein coupled receptor antagonists. For example, agonists will promote growth of a cell with FUS-HIS3 reporter or give positive readout for a cell with FUSI-LacZ. However, a candidate compound which inhibits growth or negates the positive readout induced by an agonist is an antagonist. For this purpose, the yeast system offers advantages over mammalian expression systems due to its ease of utility and null receptor background (lack of endogenous G-protein coupled receptors) which often interferes with the ability to identify agonists or antagonists.

Example 12

Isolation of a Specific Clone from the Deposited Sample

The deposited material in the sample assigned the ATCC Deposit Number cited in Table I for any given cDNA clone also may contain one or more additional plasmids, each comprising a cDNA clone different from that given clone. Thus, deposits sharing the same ATCC Deposit Number contain at least a plasmid for each cDNA clone identified in Table I. Typically, each ATCC deposit sample cited in Table I comprises a mixture of approximately equal amounts (by weight) of about 1-10 plasmid DNAs, each containing a different cDNA clone and/or partial cDNA clone; but such a deposit sample may include plasmids for more or less than 2 cDNA clones.

Two approaches can be used to isolate a particular clone from the deposited sample of plasmid DNA(s) cited for that clone in Table I. First, a plasmid is directly isolated by screening the clones using a polynucleotide probe corresponding to SEQ ID NO:1, 3, 5, 101, 103, 164, or 166.

Particularly, a specific polynucleotide with 30-40 nucleotides is synthesized using an Applied Biosystems DNA synthesizer according to the sequence reported. The oligonucleotide is labeled, for instance, with 32P-(-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17-20 nucleotides derived from both ends of the SEQ ID NO:1, 3, 5, 101, 103, 164, or 166 (i.e., within the region of SEQ ID NO:1, 3, 5, 101, 103, 164, or 166 bounded by the 5' NT and the 3' NT of the clone defined in Table I) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5-5 mM MgCl2, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

The polynucleotide(s) of the present invention, the polynucleotide encoding the polypeptide of the present invention, or the polypeptide encoded by the deposited clone may represent partial, or incomplete versions of the complete coding region (i.e., full-length gene). Several methods are known in the art for the identification of the 5' or 3' non-coding and/or coding portions of a gene which may not be present in the deposited clone. The methods that follow are exemplary and should not be construed as limiting the scope of the invention. These methods include but are not limited to, filter probing, clone enrichment using specific probes, and protocols similar or identical to 5' and 3' "RACE" protocols that are well known in the art. For instance, a method similar to 5' RACE is available for generating the missing 5' end of a desired full-length transcript. (Fromont-Racine et al., Nucleic Acids Res. 21(7):1683-1684 (1993)).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full-length gene.

This above method starts with total RNA isolated from the desired source, although poly-A+ RNA can be used. The RNA preparation can then be treated with phosphatase if necessary to eliminate 5' phosphate groups on degraded or damaged RNA that may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene. Moreover, it may be advantageous to optimize the RACE protocol to increase the probability of isolating additional 5' or 3' coding or non-coding sequences. Various methods of optimizing a RACE protocol are known in the art, though a detailed description summarizing these methods can be found in B. C. Schaefer, Anal. Biochem., 227:255-273, (1995).

An alternative method for carrying out 5' or 3' RACE for the identification of coding or non-coding sequences is provided by Frohman, M. A., et al., Proc. Nat'l. Acad. Sci. USA, 85:8998-9002 (1988). Briefly, a cDNA clone missing either the 5' or 3' end can be reconstructed to include the absent base pairs extending to the translational start or stop codon, respectively. In some cases, cDNAs are missing the start of translation, therefor. The following briefly describes a modification of this original 5' RACE procedure. Poly A+ or total RNAs reverse transcribed with Superscript II (Gibco/BRL) and an antisense or I complementary primer specific to the cDNA sequence. The primer is removed from the reaction with a Microcon Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoIJ SaiI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (Promega), restriction digested with XhoI or SalI, and ligated to a plasmid such as pBluescript SKII (Stratagene) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are commercially available for purchase. Similar reagents and methods to those above are supplied in kit form from Gibco/BRL for both 5' and 3' RACE for recovery of full length polynucleotides. A second kit is available from Clontech which is a modification of a related technique, SLIC (single-stranded ligation to single-stranded cDNA), developed by Dumas et al., Nucleic Acids Res., 19:5227-32 (1991). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

RNA Ligase Protocol for Generating the 5' or 3' End Sequences to Obtain Full Length Genes Once a gene of interest is identified, several methods are available for the identification of the 5' or 3' portions of the gene which may not be present in the original cDNA plasmid. These methods include, but are not limited to, filter probing, clone enrichment using specific probes and protocols similar and identical to 5' and 3'RACE. While the full-length gene may be present in the library and can be identified by probing, a useful method for generating the 5' or 3' end is to use the existing sequence information from the original cDNA to generate the missing information. A method similar to 5'RACE is available for generating the missing 5' end of a desired full-length gene. (This method was published by Fromont-Racine et al., Nucleic Acids Res., 21(7): 1683-1684 (1993)). Briefly, a specific RNA oligonucleotide is ligated to the 5' ends of a population of RNA presumably 30 containing full-length gene RNA transcript and a primer set containing a primer specific to the ligated RNA oligonucleotide and a primer specific to a known sequence of the gene of interest, is used to PCR amplify the 5' portion of the desired full length gene which may then be sequenced and used to generate the full length gene. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a gene specific oligonucleotide. The first strand synthesis reaction can then be used as a template for PCR amplification of the desired 5' end using a primer specific to the ligated RNA oligonucleotide and a primer specific to the known sequence of the apoptosis related of interest. The resultant product is then sequenced and analyzed to confirm that the 5' end sequence belongs to the relevant apoptosis related.

Example 13

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described herein is labeled with p32 using the Rediprime™ DNA labeling system (Amersham Life Science), according to manufacturer's instructions. After labeling, the probe is purified using CHROMA SPIN0-100 column (Clontech Laboratories, Inc.) according to manufacturer's protocol number PT1200-1. The purified labeled probe is then used to examine various tissues for mRNA expression.

Tissue Northern blots containing the bound mRNA of various tissues are examined with the labeled probe using ExpressHyb™ hybridization solution (Clonetech according to manufacturers protocol number PT1190-1. Northern blots can be produced using various protocols well known in the art (e.g., Sambrook et al). Following hybridization and washing, the blots are mounted and exposed to film at −70 C overnight, and the films developed according to standard procedures.

Example 14

Chromosomal Mapping of the Polynucleotides

An oligonucleotide primer set is designed according to the sequence at the 5' end of SEQ ID NO:1, 3, 5, 101, 103, 164, or 166. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Mammalian DNA, preferably human DNA, is used as template in addition to a somatic cell hybrid panel containing individual chromosomes or chromosome fragments (Bios, Inc). The reactions are analyzed on either 8% polyacrylamide gels or 3.5% agarose gels. Chromosome mapping is determined by the presence of an approximately 100 bp PCR fragment in the particular somatic cell hybrid.

Example 15

Bacterial Expression of a Polypeptide

A polynucleotide encoding a polypeptide of the present invention is amplified using PCR oligonucleotide primers corresponding to the 5' and 3' ends of the DNA sequence, as outlined herein, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.600) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3-4 hours at 4 degree C. The cell debris is removed by centrifugation, and the supernatant containing the polypeptide is loaded onto a nickel-nitrilo-triacetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Example 16

Purification of a Polypeptide from an Inclusion Body

The following alternative method can be used to purify a polypeptide expressed in *E. coli* when it is present in the form of inclusion bodies. Unless otherwise specified, all of the following steps are conducted at 4-10 degree C.

Upon completion of the production phase of the *E. coli* fermentation, the cell culture is cooled to 4-10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2-4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perceptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perceptive Biosystems) and weak anion (Poros CM-20, Perceptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 ug of purified protein is loaded. The purified protein can also be tested

Example 17

Cloning and Expression of a Polypeptide in a Baculovirus Expression System

In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted polynucleotides are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

A polynucleotide encoding a polypeptide of the present invention is amplified using PCR oligonucleotide primers corresponding to the 5' and 3' ends of the DNA sequence, as outlined herein, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described in Example 12. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures" Texas Agricultural Experimental Station Bulletin No. 1555 (1987).

The amplified fragment is isolated from a 1% agarose gel using a commercially available kit ("Geneclean" BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413-7417 (1987). One ug of BaculoGold™ virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 18

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357-1370 (1978); Hamlin, J. L. and Ma, C., Biochem. et Biophys. Acta, 1097:107-143 (1990); Page, M. J. and Sydenham, M. A., Biotechnology 9:64-68 (1991).) Another useful selection marker is the enzyme glutamine synthase (GS) (Murphy et al., Biochem J. 227:277-279 (1991); Bebbington et al., Bio/Technology 10:169-175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("Geneclean" BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five µg of an expression plasmid is cotransformed with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100-200 uM. Expression of the desired gene product is analyzed, for instance, by SDS-PAGE and Western blot or by reversed phase HPLC analysis.

Example 19

Method of Creating N- and C-Terminal Deletion Mutants Corresponding to the Human AdipoR2v1, Mouse AdipoR2v1, Human AdipoR3, Human AdipoR2v2, Human AdipoR3v, Rat AdipoR1, and/or Rat AdipoR2 Polypeptide of the Present Invention As described elsewhere herein, the present invention encompasses the creation of N- and C-terminal deletion mutants, in addition to any combination of N- and C-terminal deletions thereof, corresponding to the human AdipoR2v1, mouse AdipoR2v1, human AdipoR3, human AdipoR2v2, human AdipoR3v, rat AdipoR1, and/or rat AdipoR2 polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length human AdipoR2v1, mouse AdipoR2v1, human AdipoR3, human AdipoR2v2, human AdipoR3v, rat AdipoR1, and/or rat AdipoR2 polypeptide sequence (as described in Example 12, for example), appropriate primers of about 15-25 nucleotides derived from the desired 5' and 3' positions of SEQ ID NO:1, 3, 5, 101, 103, 164, or 166 may be designed to PCR amplify, and subsequently clone, the intended N- and/or C-terminal deletion mutant. Such primers could comprise, for example, an initiation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

Representative PCR amplification conditions are provided below, although the skilled artisan would appreciate that other conditions may be required for efficient amplification. A 100 ul PCR reaction mixture may be prepared using 10 ng of the template DNA (cDNA clone of human AdipoR2v1, mouse AdipoR2v1, human AdipoR3, human AdipoR2v2, human AdipoR3v, rat AdipoR1, and/or rat AdipoR2), 200 uM 4dNTPs, 1 uM primers, 0.25 U Taq DNA polymerase (PE), and standard Taq DNA polymerase buffer. Typical PCR cycling condition are as follows:

20-25 cycles:
45 sec, 93 degrees
2 min, 50 degrees
2 min, 72 degrees
1 cycle:
10 min, 72 degrees After the final extension step of PCR, 5 U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent E. coli cells using methods provided herein and/or otherwise known in the art.

The 5' primer sequence for amplifying any additional N-terminal deletion mutants may be determined by reference to the following formula: (S+(X*3)) to ((S+(X*3))+25), wherein 'S' is equal to the nucleotide position of the initiating start codon of the human AdipoR2v1, mouse AdipoR2v1, human AdipoR3, human AdipoR2v2, human AdipoR3v, rat AdipoR1, and/or rat AdipoR2 gene (SEQ ID NO:1, 3, 5, 101, 103, 164, or 166), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1, 3, 5, 101, 103, 164, or 166. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula: (S+(X*3)) to ((S+(X*3))-25), wherein 'S' is equal to the nucleotide position of the initiating start codon of the human AdipoR2v1, mouse AdipoR2v1, human AdipoR3, human AdipoR2v2, human AdipoR3v, rat AdipoR1, and/or rat AdipoR2 gene (SEQ ID NO:1, 3, 5, 101, 103, 164, or 166), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1, 3, 5, 101, 103, 164, or 166. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

Example 20

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EP A 394,827; Traunecker, et al., Nature 331:84-86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

Human IgG Fc region (SEQ ID NO: 65)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCGACGGCCGCGACTCTAGAGGAT

Example 21

Production of an Antibody from a Polypeptide

The antibodies of the present invention can be prepared by a variety of methods. (See, Current Protocols, Chapter 2.) As one example of such methods, cells expressing a polypeptide of the present invention are administered to an animal to induce the production of sera containing polyclonal antibodies. In a preferred method, a preparation of the protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Kohler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563-681 (1981).) In general, such procedures involve immunizing an animal (preferably a mouse) with polypeptide or, more preferably, with a polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225-232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc.), and the subsequent secretion of such antibodies from the plant.

Example 22

Regulation of Protein Expression Via Controlled Aggregation in the Endoplasmic Reticulum As described more particularly herein, proteins regulate diverse cellular processes in higher organisms, ranging from rapid metabolic changes to growth and differentiation. Increased production of specific proteins could be used to prevent certain diseases and/or disease states. Thus, the ability to modulate the expression of specific proteins in an organism would provide significant benefits.

Numerous methods have been developed to date for introducing foreign polynucleotides, either under the control of an inducible, constitutively active, or endogenous promoter, into organisms. Of particular interest are the inducible promoters (see, M. Gossen, et al., Proc. Natl. Acad. Sci. USA., 89:5547 (1992); Y. Wang, et al., Proc. Natl. Acad. Sci. USA, 91:8180 (1994), D. No., et al., Proc. Natl. Acad. Sci. USA, 93:3346 (1996); and V. M. Rivera, et al., Nature Med, 2:1028 (1996); in addition to additional examples disclosed elsewhere herein). In one example, the gene for erthropoietin (Epo) was transferred into mice and primates under the control of a small molecule inducer for expression (e.g., tetracycline or rapamycin) (see, D. Bohl, et al., Blood, 92:1512, (1998); K. G. Rendahl, et al., Nat. Biotech, 16:757, (1998); V. M. Rivera, et al., Proc. Natl. Acad. Sci. USA, 96:8657 (1999); and X. Ye et al., Science, 283:88 (1999). Although such systems enable efficient induction of the gene of interest in the organism upon addition of the inducing agent (i.e., tetracycline, rapamycin, etc.), the levels of expression tend to peak at 24 hours and trail off to background levels after 4 to 14 days. Thus, controlled transient expression is virtually impossible using these systems, though such control would be desirable.

A new alternative method of controlling gene expression levels of a protein from a transgene (i.e., includes stable and transient transformants) has recently been elucidated (V. M. Rivera., et al., Science, 287:826-830, (2000)). This method does not control gene expression at the level of the mRNA like the aforementioned systems. Rather, the system controls the level of protein in an active secreted form. In the absence of the inducing agent, the protein aggregates in the ER and is not secreted. However, addition of the inducing agent results in dis-aggregation of the protein and the subsequent secretion from the ER. Such a system affords low basal secretion, rapid, high level secretion in the presence of the inducing agent, and rapid cessation of secretion upon removal of the inducing agent. In fact, protein secretion reached a maximum level within 30 minutes of induction, and a rapid cessation of secretion within 1 hour of removing the inducing agent. The method is also applicable for controlling the level of production for membrane proteins.

Detailed methods are presented in V. M. Rivera., et al., Science, 287:826-830, (2000)), briefly:

Fusion protein constructs are created using polynucleotide sequences of the present invention with one or more copies (preferably at least 2, 3, 4, or more) of a conditional aggregation domain (CAD) a domain that interacts with itself in a ligand-reversible manner (i.e., in the presence of an inducing agent) using molecular biology methods known in the art and discussed elsewhere herein. The CAD domain may be the mutant domain isolated from the human FKBP12 (Phe$^{36}$ to Met) protein (as disclosed in V. M. Rivera., et al., Science, 287:826-830, (2000), or alternatively other proteins having domains with similar ligand-reversible, self-aggregation properties. As a principle of design the fusion protein vector would contain a furin cleavage sequence operably linked between the polynucleotides of the present invention and the CAD domains. Such a cleavage site would enable the proteolytic cleavage of the CAD domains from the polypeptide of the present invention subsequent to secretion from the ER and upon entry into the trans-Golgi (J. B. Denault, et al., FEBS Lett., 379:113, (1996)). Alternatively, the skilled artisan would recognize that any proteolytic cleavage sequence could be substituted for the furin sequence provided the substituted sequence is cleavable either endogenously (e.g., the furin sequence) or exogenously (e.g., post secretion, post purification, post production, etc.). The preferred sequence of each feature of the fusion protein construct, from the 5' to 3' direction with each feature being operably linked to the other, would be a promoter, signal sequence, "X" number of (CAD)$_x$ domains, the furin sequence (or other proteolytic sequence), and the coding sequence of the polypeptide of the present invention. The artisan would appreciate that the promoter and signal sequence, independent from the other, could be either the endogenous promoter or signal sequence of a polypeptide of the present invention, or alternatively, could be a heterologous signal sequence and promoter.

The specific methods described herein for controlling protein secretion levels through controlled ER aggregation are not meant to be limiting are would be generally applicable to any of the polynucleotides and polypeptides of the present invention, including variants, homologues, orthologs, and fragments therein.

Example 23

Alteration of Protein Glycosylation Sites to Enhance Characteristics of Polypeptides of the Invention Many eukaryotic cell surface and proteins are post-translationally processed to incorporate N-linked and O-linked carbohydrates (Kornfeld and Kornfeld (1985) Annu. Rev. Biochem. 54:631-64; Rademacher et al., (1988) Annu. Rev. Biochem. 57:785-838). Protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion (Fieldler and Simons (1995) Cell, 81:309-312; Helenius (1994) Mol. Biol. Of the Cell 5:253-265; Olden et al., (1978) Cell, 13:461-473; Caton et al., (1982) Cell, 37:417-427; Alexamnder and Elder (1984), Science, 226:1328-1330; and Flack et al., (1994), J. Biol. Chem., 269:14015-14020). In higher organisms, the nature and extent of glycosylation can markedly affect the circulating half-life and bio-availability of proteins by mechanisms involving receptor mediated uptake and clearance (Ashwell and Morrell, (1974), Adv. Enzymol., 41:99-128; Ashwell and Harford (1982), Ann. Rev. Biochem., 51:531-54). Receptor systems have been identified that are thought to play a major role in the clearance of serum proteins through recognition of various carbohydrate structures on the glycoproteins (Stockert (1995), Physiol. Rev., 75:591-609; Kery et al., (1992), Arch. Biochem. Biophys., 298:49-55). Thus, production strategies resulting in incomplete attachment of terminal sialic acid residues might provide a means of shortening the bioavailability and half-life of glycoproteins. Conversely, expression strategies resulting in saturation of terminal sialic acid attachment sites might lengthen protein bioavailability and half-life.

In the development of recombinant glycoproteins for use as pharmaceutical products, for example, it has been speculated that the pharmacodynamics of recombinant proteins can be modulated by the addition or deletion of glycosylation sites from a glycoproteins primary structure (Berman and Lasky (1985a) Trends in Biotechnol., 3:51-53). However, studies have reported that the deletion of N-linked glycosylation sites often impairs intracellular transport and results in the intracellular accumulation of glycosylation site variants (Machamer and Rose (1988), J. Biol Chem., 263:5955-5960; Gallagher et al., (1992), J. Virology., 66:7136-7145; Collier et al., (1993), Biochem., 32:7818-7823; Claffey et al., (1995) Biochemica et Biophysica Acta, 1246:1-9; Dube et al., (1988), J. Biol. Chem. 263:17516-17521). While glycosylation site variants of proteins can be expressed intracellularly, it has proved difficult to recover useful quantities from growth conditioned cell culture medium.

Moreover, it is unclear to what extent a glycosylation site in one species will be recognized by another species glycosylation machinery. Due to the importance of glycosylation in protein metabolism, particularly the secretion and/or expression of the protein, whether a glycosylation signal is recognized may profoundly determine a proteins ability to be expressed, either endogenously or recombinately, in another organism (i.e., expressing a human protein in E. coli, yeast, or viral organisms; or an E. coli, yeast, or viral protein in human, etc.). Thus, it may be desirable to add, delete, or modify a glycosylation site, and possibly add a glycosylation site of one species to a protein of another species to improve the proteins functional, bioprocess purification, and/or structural characteristics (e.g., a polypeptide of the present invention).

A number of methods may be employed to identify the location of glycosylation sites within a protein. One preferred method is to run the translated protein sequence through the PROSITE computer program (Swiss Institute of Bioinformatics). Once identified, the sites could be systematically deleted, or impaired, at the level of the DNA using mutapolynucleotidesis methodology known in the art and available to the skilled artisan, Preferably using PCR-directed mutapolynucleotidesis (See Maniatis, Molecular Cloning: A Laboratory Manual, Cold Spring Harbor Press, Cold Spring, N.Y. (1982)). Similarly, glycosylation sites could be added, or modified at the level of the DNA using similar methods, preferably PCR methods (See, Maniatis, supra). The results of modifying the glycosylation sites for a particular protein (e.g., solubility, secretion potential, activity, aggregation, proteolytic resistance, etc.) could then be analyzed using methods know in the art.

The skilled artisan would acknowledge the existence of other computer algorithms capable of predicting the location of glycosylation sites within a protein. For example, the Motif computer program (Genetics Computer Group suite of programs) provides this function, as well.

Example 24

Method of Enhancing the Biological Activity/Functional Characteristics of Invention Through Molecular Evolution Although many of the most biologically active proteins known are highly effective for their specified function in an organism, they often possess characteristics that make them undesirable for transgenic, therapeutic, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased polynucleotides. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutapolynucleotidesis, "error-prone" PCR, chemical mutapolynucleotidesis, site-directed mutapolynucleotidesis, and other methods well known in the art (for a comprehensive listing of current mutapolynucleotidesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutapolynucleotidesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145-152, (1986), and Hill, D E, et al, Methods Enzymol., 55:559-568, (1987). Both approaches have limits to the level of mutapolynucleotidesis that can be obtained. However, either approach enables the investigator to effectively control the rate of mutapolynucleotidesis. This is particularly important considering the fact that mutations beneficial to the activity of the enzyme are fairly rare. In fact, using too high a level of mutapolynucleotidesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments—further diversifying the potential hybridization sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2-4 ug of the DNA substrate(s) would be digested with 0.0015 units of Dnase I (Sigma) per ul in 100 ul of 50 mM Tris-HCL, pH 7.4/1 mM MgCl2 for 10-20 min. at room temperature. The resulting fragments of 10-50 bp could then be purified by running them through a 2% low-melting point agarose gel by electrophoresis onto DE81 ion-exchange paper (Whatmann) or could be purified using Microcon concentrators (Amicon) of the appropriate molecular weight cutoff, or could use oligonucleotide purification columns (Qiagen), in addition to other methods known in the art. If using DE81 ion-exchange paper, the 10-50 bp fragments could be eluted from said paper using 1M NaCl, followed by ethanol precipitation.

The resulting purified fragments would then be subjected to a PCR assembly reaction by re-suspension in a PCR mixture containing: 2 mM of each dNTP, 2.2 mM MgCl2, 50 mM KCl, 10 mM Tris.HCL, pH 9.0, and 0.1% Triton X-100, at a final fragment concentration of 10-30 ng/ul. No primers are added at this point. Taq DNA polymerase (Promega) would be used at 2.5 units per 100 ul of reaction mixture. A PCR program of 94 C for 60 s; 94 C for 30 s, 50-55 C for 30 s, and 72 C for 30 s using 30-45 cycles, followed by 72 C for 5 min using an MJ Research (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C for 30 s, 50 C for 30 s, and 72 C for 30 s). The referred primers would be primers corresponding to the nucleic acid sequences of the polynucleotide(s) utilized in the shuffling reaction. Said primers could consist of modified nucleic acid base pairs using methods known in the art and referred to elsewhere herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutapolynucleotidesis using the methods described by Zhao, et al. (Nucl Acid Res., 25(6):1307-1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336-347, (1997), F. R., Cross, et al., Mol. Cell. Biol., 18:2923-2931, (1998), and A. Crameri., et al., Nat. Biotech., 15:436-438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutapolynucleotidesis. An effect of forcing DNA polymerase to synthesize full-length polynucleotides from the small fragment DNA pool is a background mutapolynucleotidesis rate. In combination with a stringent selection method, enzymatic activity has been evolved up to 16000 fold increase over the wild-type form of the enzyme. In essence, the background mutapolynucleotidesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference.

Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436-438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

Example 25

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1, 3, 5, 101, 103, 164, or 166. Suggested PCR conditions consist of 35 cycles at 95 degrees C. for 30 seconds; 60-120 seconds at 52-58 degrees C.; and 60-120 seconds at 70 degrees C., using buffer solutions described in Sidransky et al., Science 252: 706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products are cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to the methods described herein are nick-translated with digoxigenindeoxyuridine 5'-triphosphate (Boehringer Manheim), and FISH performed as described in Johnson et al., Methods Cell Biol. 35:73-99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 26

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described elsewhere herein. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25-400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 27

Formulation

The invention also provides methods of treatment and/or prevention diseases, disorders, and/or conditions (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention may also be suitably administered by sustained-release systems. Suitable examples of sustained-release Therapeutics include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547-556 (1983)), poly(2-hydroxyethyl methacrylate) (Langer et al., J. Biomed. Mater. Res. 15:167-277 (1981), and Langer, Chem. Tech. 12:98-105 (1982)), ethylene vinyl acetate (Langer et al., Id.) or poly-D-(-)-3-hydroxybutyric acid (EP 133,988).

Sustained-release Therapeutics also include liposomally entrapped Therapeutics of the invention (see, generally, Langer, Science 249:1527-1533 (1990); Treat et al., in Liposomes in the Therapy of Infectious Disease and Cancer, Lopez-Berestein and Fidler (eds.), Liss, New York, pp. 317-327 and 353-365 (1989)). Liposomes containing the Therapeutic are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527-1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The Therapeutic will typically be formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR (zidovudine/AZT), VIDEX (didanosine/ddI), HIVID (zalcitabine/ddC), ZERIT (stavudine/d4T), EPIVIR (lamivudine/3TC), and COMBIVIR (zidovudine/lamivudine). Non-nucleoside reverse transcriptase inhibitors that may be administered in combination with the Therapeutics of the invention, include, but are not limited to, VIRAMUNE (nevirapine), RESCRIPTOR (delavirdine), and SUSTIVA (efavirenz). Protease inhibitors that may be administered in combination with the Therapeutics of the invention, include, but are not limited to, CRIXIVAN (indinavir), NORVIR (ritonavir), INVIRASE (saquinavir), and VIRACEPT (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE, DAPSONE, PENTAMIDINE, ATOVAQUONE, ISONIAZID, RIFAMPIN, PYRAZINAMIDE, ETHAMBUTOL, RIFABUTIN, CLARITHROMYCIN, AZITHROMYCIN, GANCICLOVIR, FOSCARNET, CIDOFOVIR, FLUCONAZOLE, ITRACONAZOLE, KETOCONAZOLE, ACYCLOVIR, FAMCICOLVIR, PYRIMETHAMINE, LEUCOVORIN, NEUPOGEN (filgrastim/G-CSF), and LEUKINE (sargramostim/GM-CSF). In a specific embodiment, Therapeutics of the invention are used in any combination with TRIMETHOPRIM-SULFAMETHOXAZOLE, DAPSONE, PENTAMIDINE, and/or ATOVAQUONE to prophylactically treat or prevent an opportunistic *Pneumocystis carinii* pneumonia infection. In another specific embodiment, Therapeutics of the invention are used in any combination with ISONIAZID, RIFAMPIN, PYRAZINAMIDE, and/or ETHAMBUTOL to prophylactically treat or prevent an opportunistic *Mycobacterium avium* complex infection. In another specific embodiment, Therapeutics of the invention are used in any combination with RIFABUTIN, CLARITHROMYCIN, and/or AZITHROMYCIN to prophylactically treat or prevent an opportunistic *Mycobacterium tuberculosis* infection. In another specific embodiment, Therapeutics of the invention are used in any combination with GANCICLOVIR, FOSCARNET, and/or CIDOFOVIR to prophylactically treat or prevent an opportunistic cytomegalovirus infection. In another specific embodiment, Therapeutics of the invention are used in any combination with FLUCONAZOLE, ITRACONAZOLE, and/or KETOCONAZOLE to prophylactically treat or prevent an opportunistic fungal infection. In another specific embodiment, Therapeutics of the invention are used in any combination with ACYCLOVIR and/or FAMCICOLVIR to prophylactically treat or prevent an opportunistic herpes simplex virus type I and/or type II infection. In another specific embodiment, Therapeutics of the invention are used in any combination with PYRIMETHAMINE and/or LEUCOVORIN to prophylactically treat or prevent an opportunistic *Toxoplasma gondii* infection. In another specific embodiment, Therapeutics of the invention are used in any combination with LEUCOVORIN and/or NEUPOGEN to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE (OKT3), SANDIMMUNE/NEORAL/SANGDYA (cyclosporin), PROGRAF (tacrolimus), CELLCEPT (mycophenolate), Azathioprine, glucorticosteroids, and RAPAMUNE (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR, IVEEGAM, SANDOGLOBULIN, GAMMAGARD S/D, and GAMIMUNE. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Growth Factors, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE (SARGRAMOSTIM) and NEUPOGEN (FILGRASTIM).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In a specific embodiment, formulations of the present invention may further comprise antagonists of P-glycoprotein (also referred to as the multiresistance protein, or PGP), including antagonists of its encoding polynucleotides (e.g., antisense oligonucleotides, ribozymes, zinc-finger proteins, etc.). P-glycoprotein is well known for decreasing the efficacy of various drug administrations due to its ability to export intracellular levels of absorbed drug to the cell exterior. While this activity has been particularly pronounced in cancer cells in response to the administration of chemotherapy regimens, a variety of other cell types and the administration of other drug classes have been noted (e.g., T-cells and anti-HIV drugs). In fact, certain mutations in the PGP gene significantly reduces PGP function, making it less able to force drugs out of cells. People who have two versions of the mutated gene—one inherited from each parent—have more than four times less PGP than those with two normal versions of the gene. People may also have one normal gene and one mutated one. Certain ethnic populations have increased incidence of such PGP mutations. Among individuals from Ghana, Kenya, the Sudan, as well as African Americans, frequency of the normal gene ranged from 73% to 84%. In contrast, the frequency was 34% to 59% among British whites, Portuguese, Southwest Asian, Chinese, Filipino and Saudi populations. As a result, certain ethnic populations may require increased administration of PGP antagonist in the formulation of the present invention to arrive at the an efficacious dose of therapeutic (e.g., those from african descent). Conversly, certain ethnic populations, particularly those having increased frequency of the mutated PGP (e.g., of caucasian descent, or non-african descent) may require less pharmaceutical compositions in the formulation due to an effective increase in efficacy of such compositions as a result of the increased effective absorption (e.g., less PGP activity) of said composition.

In additional embodiments, the Therapeutics of the invention are administered in combination with other therapeutic or prophylactic regimens, such as, for example, radiation therapy.

Example 28

Method of Treating Decreased Levels of the Polypeptide

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1-100 ug/kg of the polypeptide for six consecutive days. Preferably, the polypeptide is in the secreted form. The exact details of the dosing scheme, based on administration and formulation, are provided herein.

Example 29

Method of Treating Increased Levels of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided herein.

Example 30

Method of Treatment Using Gene Therapy—Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 12 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 31

Gene Therapy Using Endogenous Genes Corresponding to Polynucleotides of the Invention Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932-8935 (1989); and Zijlstra et al., Nature, 342:435-438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2HPO4, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MBI Fermentas, Amherst, N.Y.) is digested with HindIII. The CMV promoter is amplified by PCR with an XbaI site on the 5' end and a BamHI site on the 3' end. Two non-coding sequences are amplified via PCR: one non-coding sequence (fragment 1) is amplified with a HindIII site at the 5' end and an Xba site at the 3' end; the other non-coding sequence (fragment 2) is amplified with a BamHI site at the 5' end and a HindIII site at the 3' end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately 1.5×106 cells) is then added to the cuvette, and the cell suspension and DNA solutions are gently mixed. Electroporation is performed with a Gene-Pulser apparatus (Bio-Rad). Capacitance and voltage are set at 960 µF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 32

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata et al., Cardiovasc. Res. 35(3):470-479 (1997); Chao et al., Pharmacol. Res. 35(6):517-522 (1997); Wolff, Neuromuscul. Disord. 7(5):314-318 (1997); Schwartz et al., Gene Ther. 3(5):405-411 (1996); Tsurumi et al., Circulation 94(12):3281-3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126-139 and Abdallah B. et al. (1995) Biol. Cell 85(1):1-7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 33

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retrovirus mediated gene transfer into germ lines (Van der Putten et al., Proc. Natl. Acad. Sci., USA 82:6148-6152 (1985)), blastocysts or embryos; gene targeting in embryonic stem cells (Thompson et al., Cell 56:313-321 (1989)); electroporation of cells or embryos (Lo, 1983, Mol Cell. Biol. 3:1803-1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717-723 (1989); etc. For a review of such techniques, see Gordon, "Transgenic Animals" Intl. Rev. Cytol. 115:171-229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64-66 (1996); Wilmut et al., Nature 385:810-813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265: 103-106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (RT-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 34

Knock-Out Animals

Endogenous gene expression can also be reduced by inactivating or "knocking out" the gene and/or its promoter using targeted homologous recombination. (E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 35

Method of Isolating Antibody Fragments Directed Against Human AdipoR2v1, Mouse AdipoR2v1, Human AdipoR3, Human AdipoR2v2, Human AdipoR3v, Rat AdipoR1, and/or Rat AdipoR2 Receptors from a Library of scFvs Naturally occurring V-polynucleotides isolated from human PBLs are constructed into a library of antibody fragments which contain reactivities against human AdipoR2v1, mouse AdipoR2v1, human AdipoR3, human AdipoR2v2, human AdipoR3v, rat AdipoR1, and/or rat AdipoR2 to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 E. coli harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to inoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 μg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphopolynucleotidesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 μg/ml or 10 μg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc.), and the subsequent secretion of such antibodies from the plant.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

SEQUENCE LISTING

```
<160> NUMBER OF SEQ ID NOS: 248

<210> SEQ ID NO 1
<211> LENGTH: 1585
<212> TYPE: DNA
<213> ORGANISM: Homo sapiens
<220> FEATURE:
<221> NAME/KEY: CDS
<222> LOCATION: (210)..(1367)

<400> SEQUENCE: 1
cggacgcgtg ggcgcggcgg cggcagcggc ggcggctaca ccgggcttgg cccctcct        60 cctccgttcc ccctcctcc ccctcccct cagcggtggc tcccaagaag tccgagacac      120
gcggatcaac tcactatcct gaaggtccat tctcccaaga agaggggaca gaaagacaga     180
tctatttgta agaaaggctt gggtatccc atg aac gag cca aca gaa aac cga     233
                                    Met Asn Glu Pro Thr Glu Asn Arg
                                     1               5 ttg ggg tgc agc agg act cca gag cca gat ata agg ctc aga aaa ggg     281
Leu Gly Cys Ser Arg Thr Pro Glu Pro Asp Ile Arg Leu Arg Lys Gly
         10                  15                  20 cac caa ctg gat ggt aca cga aga ggt gat aat gac agc cac caa gga     329
His Gln Leu Asp Gly Thr Arg Arg Gly Asp Asn Asp Ser His Gln Gly
 25                  30                  35                  40 gat ttg gag ccc att tta gag gca tct gtt cta tct tcc cat cat aaa     377
Asp Leu Glu Pro Ile Leu Glu Ala Ser Val Leu Ser Ser His His Lys
                 45                  50                  55 aaa agc tct gag gaa cat gaa tac agt gat gaa gct cct cag gaa gat     425
Lys Ser Ser Glu Glu His Glu Tyr Ser Asp Glu Ala Pro Gln Glu Asp
             60                  65                  70 gag ggc ttt atg ggc atg tcc cct ctc tta caa gcc cat cat gct atg     473
Glu Gly Phe Met Gly Met Ser Pro Leu Leu Gln Ala His His Ala Met
         75                  80                  85
```

```
gaa aaa atg gaa gaa ttt gtt tgt aag gta tgg gaa ggt cgg tgg cga        521
Glu Lys Met Glu Glu Phe Val Cys Lys Val Trp Glu Gly Arg Trp Arg
    90              95                  100 gtg atc cct cat gat gta cta cca gac tgg ctc aag gat aat gac ttc        569
Val Ile Pro His Asp Val Leu Pro Asp Trp Leu Lys Asp Asn Asp Phe
105             110                  115                     120 ctc ttg cat gga cac cgg cct cct atg cct tct ttc cgg gcc tgt ttt        617
Leu Leu His Gly His Arg Pro Pro Met Pro Ser Phe Arg Ala Cys Phe
                125                 130                 135 aag agc att ttc aga ata cac aca gaa aca ggc aac att tgg aca cat        665
Lys Ser Ile Phe Arg Ile His Thr Glu Thr Gly Asn Ile Trp Thr His
            140                 145                 150 ctc tta ggt tgt gta ttc ttc ctg tgc ctg ggg atc ttt tat atg ttt        713
Leu Leu Gly Cys Val Phe Phe Leu Cys Leu Gly Ile Phe Tyr Met Phe
        155                 160                 165 cgc cca aat atc tcc ttt gtg gcc cct ctg caa gag aag gtg gtc ttt        761
Arg Pro Asn Ile Ser Phe Val Ala Pro Leu Gln Glu Lys Val Val Phe
    170                 175                 180 gga tta ttt ttc tta gga gcc att ctc tgc ctt tct ttt tca tgg ctc        809
Gly Leu Phe Phe Leu Gly Ala Ile Leu Cys Leu Ser Phe Ser Trp Leu
185             190                 195                 200 ttc cac aca gtc tac tgc cac tca gag ggg gtc tct cgg ctc ttc tct        857
Phe His Thr Val Tyr Cys His Ser Glu Gly Val Ser Arg Leu Phe Ser
                205                 210                 215 aaa ctg gat tac tct ggt att gct ctt ctg att atg gga agt ttt gtt        905
Lys Leu Asp Tyr Ser Gly Ile Ala Leu Leu Ile Met Gly Ser Phe Val
            220                 225                 230 cct tgg ctt tat tat tct ttc tac tgt aat cca caa cct tgc ttc atc        953
Pro Trp Leu Tyr Tyr Ser Phe Tyr Cys Asn Pro Gln Pro Cys Phe Ile
        235                 240                 245 tac ttg att gtc atc tgt gtg ctg ggc att gca gcc att ata gtc tcc       1001
Tyr Leu Ile Val Ile Cys Val Leu Gly Ile Ala Ala Ile Ile Val Ser
    250                 255                 260 cag tgg gac atg ttt gcc acc cct cag tat cgg gga gta aga gca gga       1049
Gln Trp Asp Met Phe Ala Thr Pro Gln Tyr Arg Gly Val Arg Ala Gly
265             270                 275                 280 gtg ttt ttg ggc cta ggc ctg agt gga atc att cct acc ttg cac tat       1097
Val Phe Leu Gly Leu Gly Leu Ser Gly Ile Ile Pro Thr Leu His Tyr
                285                 290                 295 gtc atc tcg gag ggg ttc ctt aag gcc gcc acc ata ggg cag ata ggc       1145
Val Ile Ser Glu Gly Phe Leu Lys Ala Ala Thr Ile Gly Gln Ile Gly
            300                 305                 310 tgg ttg atg ctg atg gcc agc ctc tac atc aca gga gct gcc ctg tat       1193
Trp Leu Met Leu Met Ala Ser Leu Tyr Ile Thr Gly Ala Ala Leu Tyr
        315                 320                 325 gct gcc cgg atc ccc gaa cgc ttt ttc cct ggc aaa tgt gac atc tgg       1241
Ala Ala Arg Ile Pro Glu Arg Phe Phe Pro Gly Lys Cys Asp Ile Trp
    330                 335                 340 ttt cac tct cat cag ctg ttt cat atc ttt gtg gtt gct gga gct ttt       1289
Phe His Ser His Gln Leu Phe His Ile Phe Val Val Ala Gly Ala Phe
345             350                 355                 360 gtt cac ttc cat ggt gtc tca aac ctc cag gag ttt cgt ttc atg atc       1337
Val His Phe His Gly Val Ser Asn Leu Gln Glu Phe Arg Phe Met Ile
                365                 370                 375 ggc ggg ggc tgc agt gaa gag gat gca ctg tgataccctac cagtctccag       1387
Gly Gly Gly Cys Ser Glu Glu Asp Ala Leu
            380                 385 ggactatgac cctaaaccag ggcctgcggc acttgcgggc ctccctgctg gctactgatg    1447
ccagtaccag aggagcccca aaactttgac agcctcgtgg gctttgtgac ggcccagggg    1507
```
ctctgcgtgg tacatgactg agaagagaaa aacaaaaata aatcatacct caaaaaaaaa    1567
aaaaaaaaaa aaaaaaaa                                                  1585

<210> SEQ ID NO 2
<211> LENGTH: 386
<212> TYPE: PRT
<213> ORGANISM: Homo sapiens

<400> SEQUENCE: 2

Met Asn Glu Pro Thr Glu Asn Arg Leu Gly Cys Ser Arg Thr Pro Glu
1               5                   10                  15

Pro Asp Ile Arg Leu Arg Lys Gly His Gln Leu Asp Gly Thr Arg Arg
            20                  25                  30

Gly Asp Asn Asp Ser His Gln Gly Asp Leu Glu Pro Ile Leu Glu Ala
        35                  40                  45

Ser Val Leu Ser Ser His Lys Lys Ser Ser Glu Glu His Glu Tyr
    50                  55                  60

Ser Asp Glu Ala Pro Gln Glu Asp Glu Gly Phe Met Gly Met Ser Pro
65                  70                  75                  80

Leu Leu Gln Ala His His Ala Met Glu Lys Met Glu Glu Phe Val Cys
                85                  90                  95

Lys Val Trp Glu Gly Arg Trp Arg Val Ile Pro His Asp Val Leu Pro
            100                 105                 110

Asp Trp Leu Lys Asp Asn Asp Phe Leu Leu His Gly His Arg Pro Pro
        115                 120                 125

Met Pro Ser Phe Arg Ala Cys Phe Lys Ser Ile Phe Arg Ile His Thr
    130                 135                 140

Glu Thr Gly Asn Ile Trp Thr His Leu Leu Gly Cys Val Phe Phe Leu
145                 150                 155                 160

Cys Leu Gly Ile Phe Tyr Met Phe Arg Pro Asn Ile Ser Phe Val Ala
                165                 170                 175

Pro Leu Gln Glu Lys Val Val Phe Gly Leu Phe Phe Leu Gly Ala Ile
            180                 185                 190

Leu Cys Leu Ser Phe Ser Trp Leu Phe His Thr Val Tyr Cys His Ser
        195                 200                 205

Glu Gly Val Ser Arg Leu Phe Ser Lys Leu Asp Tyr Ser Gly Ile Ala
    210                 215                 220

Leu Leu Ile Met Gly Ser Phe Val Pro Trp Leu Tyr Tyr Ser Phe Tyr
225                 230                 235                 240

Cys Asn Pro Gln Pro Cys Phe Ile Tyr Leu Ile Val Ile Cys Val Leu
                245                 250                 255

Gly Ile Ala Ala Ile Ile Val Ser Gln Trp Asp Met Phe Ala Thr Pro
            260                 265                 270

Gln Tyr Arg Gly Val Arg Ala Gly Val Phe Leu Gly Leu Gly Leu Ser
        275                 280                 285

Gly Ile Ile Pro Thr Leu His Tyr Val Ile Ser Glu Gly Phe Leu Lys
    290                 295                 300

Ala Ala Thr Ile Gly Gln Ile Gly Trp Leu Met Leu Met Ala Ser Leu
305                 310                 315                 320

Tyr Ile Thr Gly Ala Ala Leu Tyr Ala Ala Arg Ile Pro Glu Arg Phe
                325                 330                 335

Phe Pro Gly Lys Cys Asp Ile Trp Phe His Ser His Gln Leu Phe His
            340                 345                 350

```
Ile Phe Val Val Ala Gly Ala Phe Val His Phe His Gly Val Ser Asn
        355                 360                 365

Leu Gln Glu Phe Arg Phe Met Ile Gly Gly Cys Ser Glu Glu Asp
        370                 375                 380

Ala Leu
385

<210> SEQ ID NO 3
<211> LENGTH: 3975
<212> TYPE: DNA
<213> ORGANISM: Mus musculus
<220> FEATURE:
<221> NAME/KEY: CDS
<222> LOCATION: (153)..(1310)

<400> SEQUENCE: 3
```

| | |
|---|---:|
| cacaagaatc cgtggagctc agcagtaccc tcagactctg gtctacaact ctgacaggat | 60 |
| ttggggtcaa cttaccatcc cttaaaaatc cattctccca agaagaaggg acagaaagaa | 120 |
| agaccacttt gtaagaaagg ctttggtatc cc atg aac gag cca gcc aaa cac | 173 |
|                                    Met Asn Glu Pro Ala Lys His     |     |
|                                      1               5              |     |
| cga ttg ggg tgc acc agg act cca gag cca gat ata cgg ctc aga aaa | 221 |
| Arg Leu Gly Cys Thr Arg Thr Pro Glu Pro Asp Ile Arg Leu Arg Lys |     |
|             10                  15                  20          |     |
| ggg cac caa ctt gat gat aca agg gga agt aat aat gac aac tac caa | 269 |
| Gly His Gln Leu Asp Asp Thr Arg Gly Ser Asn Asn Asp Asn Tyr Gln |     |
|     25                  30                  35                  |     |
| gga gat ttg gag ccc agc tta gag aca cct gtt tgt tct tcc tat tat | 317 |
| Gly Asp Leu Glu Pro Ser Leu Glu Thr Pro Val Cys Ser Ser Tyr Tyr |     |
| 40                  45                  50                  55  |     |
| gaa aat agc ccg gag gag ccc gag tgt cat gat gac aat tcc cag gaa | 365 |
| Glu Asn Ser Pro Glu Glu Pro Glu Cys His Asp Asp Asn Ser Gln Glu |     |
|                 60                  65                  70      |     |
| gat gaa ggg ttt atg ggc atg tcc ccg ctc cta cag gcc cat cat gct | 413 |
| Asp Glu Gly Phe Met Gly Met Ser Pro Leu Leu Gln Ala His His Ala |     |
|             75                  80                  85          |     |
| atg gaa cga atg gaa gag ttt gtt tgt aag gtg tgg gaa ggc cga tgg | 461 |
| Met Glu Arg Met Glu Glu Phe Val Cys Lys Val Trp Glu Gly Arg Trp |     |
|         90                  95                 100              |     |
| cga gtg atc cct cac gat gtg cta ccg gat tgg ctt aag gat aat gac | 509 |
| Arg Val Ile Pro His Asp Val Leu Pro Asp Trp Leu Lys Asp Asn Asp |     |
| 105                 110                 115                     |     |
| ttc ctt ctc cat gga cac cgg cct cct atg cct tcc ttt cgg gcc tgt | 557 |
| Phe Leu Leu His Gly His Arg Pro Pro Met Pro Ser Phe Arg Ala Cys |     |
| 120                 125                 130                 135 |     |
| ttt aag agc att ttt aga ata cac aca gag acg ggc aac att tgg aca | 605 |
| Phe Lys Ser Ile Phe Arg Ile His Thr Glu Thr Gly Asn Ile Trp Thr |     |
|                 140                 145                 150     |     |
| cat ctc cta ggt tgt gta ttc ctg tgc ctg ggg atc ttt tat atg | 653 |
| His Leu Leu Gly Cys Val Phe Leu Cys Leu Gly Ile Phe Tyr Met     |     |
|             155                 160                 165         |     |
| ttt cgc cca aat ata tct ttt gtg gcc cct ctg caa gag aaa gtg gtc | 701 |
| Phe Arg Pro Asn Ile Ser Phe Val Ala Pro Leu Gln Glu Lys Val Val |     |
|         170                 175                 180             |     |
| ttt ggc ttg ttc ttc ttg gga gcc att ctc tgc ctt tcc ttt tca tgg | 749 |
| Phe Gly Leu Phe Phe Leu Gly Ala Ile Leu Cys Leu Ser Phe Ser Trp |     |
|     185                 190                 195                 |     |
| ctc ttc cac acg gtg tac tgc cac tca gaa ggg gtc tcc cga ctc ttc | 797 |
| Leu Phe His Thr Val Tyr Cys His Ser Glu Gly Val Ser Arg Leu Phe |     |
| 200                 205                 210                 215 |     |

```
tct aaa ttg gat tac tct ggt att gct ctt ctg atc atg gga agt ttt        845
Ser Lys Leu Asp Tyr Ser Gly Ile Ala Leu Leu Ile Met Gly Ser Phe
            220                 225                 230 gtt cct tgg ctt tat tat tct ttc tac tgt aac cca caa cct tgc ttc        893
Val Pro Trp Leu Tyr Tyr Ser Phe Tyr Cys Asn Pro Gln Pro Cys Phe
        235                 240                 245 atc tac ctg att gtc atc tgt gtg ctg ggc att gca gcc att atc gtc        941
Ile Tyr Leu Ile Val Ile Cys Val Leu Gly Ile Ala Ala Ile Ile Val
250                 255                 260 tct cag tgg gac atg ttt gcc acc cct cag tat cgg ggg gtc aga gca        989
Ser Gln Trp Asp Met Phe Ala Thr Pro Gln Tyr Arg Gly Val Arg Ala
    265                 270                 275 gga gtg ttc gtg ggc tta ggc ctg agt gga atc atc cct acc ttg cat       1037
Gly Val Phe Val Gly Leu Gly Leu Ser Gly Ile Ile Pro Thr Leu His
280                 285                 290                 295 tat gtc atc tca gaa ggg ttc ctg aag gct gcc acc ata ggg cag ata       1085
Tyr Val Ile Ser Glu Gly Phe Leu Lys Ala Ala Thr Ile Gly Gln Ile
            300                 305                 310 ggc tgg cta atg ctt atg gct agc ctc tat atc acc gga gct gcc ctc       1133
Gly Trp Leu Met Leu Met Ala Ser Leu Tyr Ile Thr Gly Ala Ala Leu
        315                 320                 325 tat gcg gcc cgt atc cct gag cgc ttc ttt cct ggc aaa tgt gac atc       1181
Tyr Ala Ala Arg Ile Pro Glu Arg Phe Phe Pro Gly Lys Cys Asp Ile
330                 335                 340 tgg ttt cac tct cat cag ctc ttc cac atc ttt gtg gtt gct ggt gcc       1229
Trp Phe His Ser His Gln Leu Phe His Ile Phe Val Val Ala Gly Ala
    345                 350                 355 ttt gtt cac ttc cac gga gtc tca aac ctg cag gaa ttt cgt ttc atg       1277
Phe Val His Phe His Gly Val Ser Asn Leu Gln Glu Phe Arg Phe Met
360                 365                 370                 375 att ggc ggg ggc tgc act gaa gag gat gca ctg tgatactctc caggaaccag     1330
Ile Gly Gly Gly Cys Thr Glu Glu Asp Ala Leu
            380                 385 ggactctgac cctgagccag gcctgcaggt cctgcaggcc ttcttactgg ctgtcggtgc     1390
cagtgccaga gaagccccaa aacttggaca gcctcatggg ccttgtgttg gcccaagggc     1450
tccatggggt acaagactaa gaagagaaaa acaaaaataa atcataccatc aaaggatgga    1510 atgcatcgat taggagagaa ggagaaatgg ctcatcccct ggcttcctct tgggatctac    1570
cgattgaaag caactctgca agaccctcgc ctgacaggct ggcttctgat gtgatcgtat    1630
ttatttgtag aagatgggga aacagtttag ttggtggtct ttcttctccc ttccttgctc    1690
cttgcagcag taacatgtat gagtaccatg caccaactga tcgtgccatt ggagctcctt    1750
aaacagtaat cacaaccaag ctaggggaac atttgtatcc aataaagggg tgggagtgcg    1810
gttttaggca ctcctttggg agaacaaaga aattaatgta aataagattt ctaatttact    1870
gtttaaataa gaatttatat aaacatttaa gacataggggg cagggaggga gggagacttt   1930
ttttaaaaag aatgaaacat gcaagtacca cacactgttt caattttgca caagtgatgg    1990
gaggaggatg gagtggtagc cccagaatgc acgatgtctt ggtgcaccaa ggtgccttcc    2050
ctaggccgat aacacttgga ccctgctggg gcagagtgga cagccccagc ccaggaactt    2110
cctggccact ctcaagactg agagcctttg gcattcaga gggggaggga tgtggaagtc     2170
gtgtgtgctt ttcaatggaa gcagcacagg ttgtcatagt ggctctagag aaagtgtcat    2230
ttgggagact gttatgtagg ctagtgatga ccctttgaa gagtgaagcc acctggttct     2290
actgtagatg tagtagagac ttgatgaagg ggaggaggac ctgggggcat cagcatagga    2350
```

-continued

```
ctggtctgct tctccctggt gtctcgtttg accaggtggt agttcttatc tgaatagagg    2410
tatggccatt ttccagaccc tctctgtgga gctctgagcc attctgcaaa ttttgctcta    2470
ttgagaatca ctgccctaac tgtccttcct cctggaaatc aaaaactgcc ccccccccc     2530 cagcatcaaa gctccttcgt ggagccggcc actagtgaga ttctgatgag catgggtccc    2590
acctgaagtc atgcaggcag gtgtggagga ccatcccttg gactaggaat ggtggcgctt    2650
ttctctggtg caggcttggc aggcttggca tgacaacaga ttcttctccc gttgaacaag    2710
aaagtcagta atacctactg tggagttgtt agcacgcact gaatgccatt tgcaagacct    2770
gtgctacaga gttgaaaagg aagtggactg ttattaccag gtagtcggat agaattaaac    2830
ccacaatttt gaattgctgc tagaagttac aaataatttc tttgtcctag ggccttcttg    2890
ttatgggttt tagagagtgg cagtgagttg ggtcttggct cctaagtgag aaaccaagca    2950
cttgagtctc ttagactcta ggcctcactc cttgggctg gtgggtattg cagtgtaaca     3010
tgggcctcgg gcatcccaaa aggggtgctg gcagtatga ggaggtcctg ttttacagt      3070 agtgttttct tggtcgttgt tgtccttcct ctaccttcag atcgccaccc agctgcagct    3130
gggacccagg aaggagtcca ttgaaaacct gggaagaact tcagagtatt gggttgtgga    3190
taaggtcact gccctaggta ggcccaacag gaagctctgg gtgaacagca ttgtgccaga    3250
caactaagaa cagtgttaat tcctcaagaa gcagttcatc aagacagtgt ccatccggaa    3310
ggaagctcac ctaggcttgt ggtagcaaca gcacatatca gcagccagac gcactctctg    3370
gtcgtgcact ttgggacatg agtttgagac gcttcctcat gacacctaca ggagtagagg    3430
tctttgggac tggtcatccc tcttcccaaa gcagggagac tctggttcaa catagcacaa    3490
actcttaggg aaccgaatca ccaccaccac tgtagtccag taacttccct tcggtgtgtg    3550
tgtgtgggca tgtgtgtgcc ctgtatgtct gcgcagctca ctaccaacag cctccatgtg    3610
cacttgacct tgtggtgcct ccgggaactt tccaggttgg cacctgaatg ccttactctc    3670
agcagtctga ggctcgcttg ctctgcgcac acatttcagt ctccttttt ggccctaggc     3730 tggttaggaa cctgtacacc ttcactctct catcattaaa tagtggcctt tttcagtatt    3790
tcctctctcc cctctataag ttgctgaaat cacaaagcac acttttgggg atcatagaag    3850 gttgggttc cagaaaggca tctctgtgat ggttccattc actatgggga tttccctact     3910
tgctgtcttc ttgatttctc taataaaaag agccaaatgg aaaatgaaaa aaaaaaaaa     3970 aaaaa                                                                3975
```

<210> SEQ ID NO 4
<211> LENGTH: 386
<212> TYPE: PRT
<213> ORGANISM: Mus musculus

<400> SEQUENCE: 4

```
Met Asn Glu Pro Ala Lys His Arg Leu Gly Cys Thr Arg Thr Pro Glu
1               5                   10                  15

Pro Asp Ile Arg Leu Arg Lys Gly His Gln Leu Asp Asp Thr Arg Gly
            20                  25                  30

Ser Asn Asn Asp Asn Tyr Gln Gly Asp Leu Glu Pro Ser Leu Glu Thr
        35                  40                  45

Pro Val Cys Ser Ser Tyr Tyr Glu Asn Ser Pro Glu Glu Pro Glu Cys
    50                  55                  60

His Asp Asp Asn Ser Gln Glu Asp Glu Gly Phe Met Gly Met Ser Pro
65                  70                  75                  80
```

-continued

```
Leu Leu Gln Ala His His Ala Met Glu Arg Met Glu Phe Val Cys
                 85                  90                  95

Lys Val Trp Glu Gly Arg Trp Arg Val Ile Pro His Asp Val Leu Pro
            100                 105                 110

Asp Trp Leu Lys Asp Asn Asp Phe Leu His Gly His Arg Pro Pro
        115                 120                 125

Met Pro Ser Phe Arg Ala Cys Phe Lys Ser Ile Phe Arg Ile His Thr
130                 135                 140

Glu Thr Gly Asn Ile Trp Thr His Leu Leu Gly Cys Val Phe Phe Leu
145                 150                 155                 160

Cys Leu Gly Ile Phe Tyr Met Phe Arg Pro Asn Ile Ser Phe Val Ala
                165                 170                 175

Pro Leu Gln Glu Lys Val Val Phe Gly Leu Phe Phe Leu Gly Ala Ile
                180                 185                 190

Leu Cys Leu Ser Phe Ser Trp Leu Phe His Thr Val Tyr Cys His Ser
            195                 200                 205

Glu Gly Val Ser Arg Leu Phe Ser Lys Leu Asp Tyr Ser Gly Ile Ala
        210                 215                 220

Leu Leu Ile Met Gly Ser Phe Val Pro Trp Leu Tyr Tyr Ser Phe Tyr
225                 230                 235                 240

Cys Asn Pro Gln Pro Cys Phe Ile Tyr Leu Ile Val Ile Cys Val Leu
                245                 250                 255

Gly Ile Ala Ala Ile Ile Val Ser Gln Trp Asp Met Phe Ala Thr Pro
                260                 265                 270

Gln Tyr Arg Gly Val Arg Ala Gly Val Phe Val Gly Leu Gly Leu Ser
            275                 280                 285

Gly Ile Ile Pro Thr Leu His Tyr Val Ile Ser Glu Gly Phe Leu Lys
        290                 295                 300

Ala Ala Thr Ile Gly Gln Ile Gly Trp Leu Met Leu Met Ala Ser Leu
305                 310                 315                 320

Tyr Ile Thr Gly Ala Ala Leu Tyr Ala Ala Arg Ile Pro Glu Arg Phe
                325                 330                 335

Phe Pro Gly Lys Cys Asp Ile Trp Phe His Ser His Gln Leu Phe His
            340                 345                 350

Ile Phe Val Val Ala Gly Ala Phe Val His Phe His Gly Val Ser Asn
        355                 360                 365

Leu Gln Glu Phe Arg Phe Met Ile Gly Gly Gly Cys Thr Glu Glu Asp
370                 375                 380

Ala Leu
385
```

<210> SEQ ID NO 5
<211> LENGTH: 867
<212> TYPE: DNA
<213> ORGANISM: Homo sapiens
<220> FEATURE:
<221> NAME/KEY: CDS
<222> LOCATION: (1)..(864)

<400> SEQUENCE: 5

```
atg att ctg ttg gaa ggc ttt gag gag aat ggg tgt gaa ttt atg att    48
Met Ile Leu Leu Glu Gly Phe Glu Glu Asn Gly Cys Glu Phe Met Ile
1               5                   10                  15 gca gag aag ggc aaa tgg gta atc acc aac cca aac aaa gct gaa gaa    96
Ala Glu Lys Gly Lys Trp Val Ile Thr Asn Pro Asn Lys Ala Glu Glu
            20                  25                  30
```

```
gag caa aca tgc cca gtg ccc cag gaa gaa gag gag gag gtg tgg gta       144
Glu Gln Thr Cys Pro Val Pro Gln Glu Glu Glu Glu Glu Val Trp Val
         35                  40                  45 ctg aca ctt ccc ctg caa gcc cac cac acc atg gag aag atg gag gag       192
Leu Thr Leu Pro Leu Gln Ala His His Thr Met Glu Lys Met Glu Glu
 50                  55                  60 ttt gtg tac aag ccg cag ctc cag aca agc tgc tgc cac cat caa tat       240
Phe Val Tyr Lys Pro Gln Leu Gln Thr Ser Cys Cys His His Gln Tyr
 65                  70                  75                  80 gat ggg ctc cct gac tgg ctg aag gac aat gac tgt ctg cag gac aat       288
Asp Gly Leu Pro Asp Trp Leu Lys Asp Asn Asp Cys Leu Gln Asp Asn
                 85                  90                  95 gac tgt ctg ctc tat ggc cat aga caa ccc atg tcc tcc ttc tgg gct       336
Asp Cys Leu Leu Tyr Gly His Arg Gln Pro Met Ser Ser Phe Trp Ala
            100                 105                 110 tgc ttc aag agc atc ttc tat atc cat aca gaa acc ggc agc agc cgg       384
Cys Phe Lys Ser Ile Phe Tyr Ile His Thr Glu Thr Gly Ser Ser Arg
        115                 120                 125 aca cat ctg ctt ggt ttc gtg ctg ttt ctc ttt ttg gaa atc ttg acc       432
Thr His Leu Leu Gly Phe Val Leu Phe Leu Phe Leu Glu Ile Leu Thr
    130                 135                 140 atg ctc aga cca aat atg tac ttc acg gcc cct cta cag gag aaa gtg       480
Met Leu Arg Pro Asn Met Tyr Phe Thr Ala Pro Leu Gln Glu Lys Val
145                 150                 155                 160 att tgg agg ata ttc ctt ttg gag aaa gtc tct cgg act ttt tcc aaa       528
Ile Trp Arg Ile Phe Leu Leu Glu Lys Val Ser Arg Thr Phe Ser Lys
                165                 170                 175 ctg tac tat tca ggg att gct cca ctg ctc ata agg agc ttc gtc ccc       576
Leu Tyr Tyr Ser Gly Ile Ala Pro Leu Leu Ile Arg Ser Phe Val Pro
            180                 185                 190 tgg ctc tgt tac tcc ttc tac tgc tcg cca cag cca cgg ctc atc tac       624
Trp Leu Cys Tyr Ser Phe Tyr Cys Ser Pro Gln Pro Arg Leu Ile Tyr
        195                 200                 205 ttc tcc atc atc tat gtc ctg ggc atc tct gcc atc att gtg aca tgg       672
Phe Ser Ile Ile Tyr Val Leu Gly Ile Ser Ala Ile Ile Val Thr Trp
    210                 215                 220 gac cgg ttt gtc act cct aag cac cgg cag aca agg gca ggg gtg ttg       720
Asp Arg Phe Val Thr Pro Lys His Arg Gln Thr Arg Ala Gly Val Leu
225                 230                 235                 240 ctg gga ctt ggc ttg agc ggt att gtg ccc acc atg cac ttt cct att       768
Leu Gly Leu Gly Leu Ser Gly Ile Val Pro Thr Met His Phe Pro Ile
                245                 250                 255 gct gag ggt ttc gtc aag gcc acc aca gtg ggc cag atg ggc tgg ttc       816
Ala Glu Gly Phe Val Lys Ala Thr Thr Val Gly Gln Met Gly Trp Phe
            260                 265                 270 ttc ctc gtg gct gtg atg tac atc acc aga gct ggc ctt tat gct gct       864
Phe Leu Val Ala Val Met Tyr Ile Thr Arg Ala Gly Leu Tyr Ala Ala
        275                 280                 285 taa                                                                   867

<210> SEQ ID NO 6
<211> LENGTH: 288
<212> TYPE: PRT
<213> ORGANISM: Homo sapiens

<400> SEQUENCE: 6

Met Ile Leu Leu Glu Gly Phe Glu Glu Asn Gly Cys Glu Phe Met Ile
1               5                  10                  15

Ala Glu Lys Gly Lys Trp Val Ile Thr Asn Pro Asn Lys Ala Glu Glu
                20                  25                  30
```

```
Glu Gln Thr Cys Pro Val Pro Gln Glu Glu Glu Val Trp Val
            35                  40                  45

Leu Thr Leu Pro Leu Gln Ala His His Thr Met Glu Lys Met Glu Glu
 50                  55                  60

Phe Val Tyr Lys Pro Gln Leu Gln Thr Ser Cys Cys His His Gln Tyr
 65                  70                  75                  80

Asp Gly Leu Pro Asp Trp Leu Lys Asp Asn Asp Cys Leu Gln Asp Asn
                 85                  90                  95

Asp Cys Leu Leu Tyr Gly His Arg Gln Pro Met Ser Ser Phe Trp Ala
            100                 105                 110

Cys Phe Lys Ser Ile Phe Tyr Ile His Thr Glu Thr Gly Ser Ser Arg
            115                 120                 125

Thr His Leu Leu Gly Phe Val Leu Phe Leu Phe Leu Glu Ile Leu Thr
            130                 135                 140

Met Leu Arg Pro Asn Met Tyr Phe Thr Ala Pro Leu Gln Glu Lys Val
145                 150                 155                 160

Ile Trp Arg Ile Phe Leu Leu Glu Lys Val Ser Arg Thr Phe Ser Lys
                165                 170                 175

Leu Tyr Tyr Ser Gly Ile Ala Pro Leu Leu Ile Arg Ser Phe Val Pro
            180                 185                 190

Trp Leu Cys Tyr Ser Phe Tyr Cys Ser Pro Gln Pro Arg Leu Ile Tyr
            195                 200                 205

Phe Ser Ile Ile Tyr Val Leu Gly Ile Ser Ala Ile Ile Val Thr Trp
            210                 215                 220

Asp Arg Phe Val Thr Pro Lys His Arg Gln Thr Arg Ala Gly Val Leu
225                 230                 235                 240

Leu Gly Leu Gly Leu Ser Gly Ile Val Pro Thr Met His Phe Pro Ile
                245                 250                 255

Ala Glu Gly Phe Val Lys Ala Thr Thr Val Gly Gln Met Gly Trp Phe
            260                 265                 270

Phe Leu Val Ala Val Met Tyr Ile Thr Arg Ala Gly Leu Tyr Ala Ala
            275                 280                 285

<210> SEQ ID NO 7
<211> LENGTH: 375
<212> TYPE: PRT
<213> ORGANISM: Homo sapiens

<400> SEQUENCE: 7

Met Ser Ser His Lys Gly Ser Val Val Ala Gln Gly Asn Gly Ala Pro
 1               5                  10                  15

Ala Ser Asn Arg Glu Ala Asp Thr Val Glu Leu Ala Glu Leu Gly Pro
            20                  25                  30

Leu Leu Glu Glu Lys Gly Lys Arg Val Ile Ala Asn Pro Pro Lys Ala
            35                  40                  45

Glu Glu Gln Thr Cys Pro Val Pro Gln Glu Glu Glu Glu Val
 50                  55                  60

Arg Val Leu Thr Leu Pro Leu Gln Ala His His Ala Met Glu Lys Met
 65                  70                  75                  80

Glu Glu Phe Val Tyr Lys Val Trp Glu Gly Arg Trp Arg Val Ile Pro
                 85                  90                  95

Tyr Asp Val Leu Pro Asp Trp Leu Lys Asp Asn Asp Tyr Leu Leu His
            100                 105                 110

Gly His Arg Pro Pro Met Pro Ser Phe Arg Ala Cys Phe Lys Ser Ile
```

-continued

```
                115                 120                 125
Phe Arg Ile His Thr Glu Thr Gly Asn Ile Trp Thr His Leu Leu Gly
    130                 135                 140
Phe Val Leu Phe Leu Phe Leu Gly Ile Leu Thr Met Leu Arg Pro Asn
145                 150                 155                 160
Met Tyr Phe Met Ala Pro Leu Gln Glu Lys Val Val Phe Gly Met Phe
                165                 170                 175
Phe Leu Gly Ala Val Leu Cys Leu Ser Phe Ser Trp Leu Phe His Thr
                180                 185                 190
Val Tyr Cys His Ser Glu Lys Val Ser Arg Thr Phe Ser Lys Leu Asp
                195                 200                 205
Tyr Ser Gly Ile Ala Leu Leu Ile Met Gly Ser Phe Val Pro Trp Leu
    210                 215                 220
Tyr Tyr Ser Phe Tyr Cys Ser Pro Gln Pro Arg Leu Ile Tyr Leu Ser
225                 230                 235                 240
Ile Val Cys Val Leu Gly Ile Ser Ala Ile Val Ala Gln Trp Asp
                245                 250                 255
Arg Phe Ala Thr Pro Lys His Arg Gln Thr Arg Ala Gly Val Phe Leu
                260                 265                 270
Gly Leu Gly Leu Ser Gly Val Val Pro Thr Met His Phe Thr Ile Ala
    275                 280                 285
Glu Gly Phe Val Lys Ala Thr Thr Val Gly Gln Met Gly Trp Phe Phe
290                 295                 300
Leu Met Ala Val Met Tyr Ile Thr Gly Ala Gly Leu Tyr Ala Ala Arg
305                 310                 315                 320
Ile Pro Glu Arg Phe Phe Pro Gly Lys Phe Asp Ile Trp Phe Gln Ser
                325                 330                 335
His Gln Ile Phe His Val Leu Val Ala Ala Ala Phe Val His Phe
                340                 345                 350
Tyr Gly Val Ser Asn Leu Gln Glu Phe Arg Tyr Gly Leu Glu Gly Gly
                355                 360                 365
Cys Thr Asp Asp Thr Leu Leu
                370                 375

<210> SEQ ID NO 8
<211> LENGTH: 375
<212> TYPE: PRT
<213> ORGANISM: Mus musculus

<400> SEQUENCE: 8

Met Ser Ser His Lys Gly Ser Ala Gly Ala Gln Gly Asn Gly Ala Pro
1               5                   10                  15
Ser Gly Asn Arg Glu Ala Asp Thr Val Glu Leu Ala Glu Leu Gly Pro
                20                  25                  30
Leu Leu Glu Glu Lys Gly Lys Arg Ala Ala Ser Ser Pro Ala Lys Ala
            35                  40                  45
Glu Glu Asp Gln Ala Cys Pro Val Pro Gln Glu Glu Glu Glu Glu Val
        50                  55                  60
Arg Val Leu Thr Leu Pro Leu Gln Ala His His Ala Met Glu Lys Met
65                  70                  75                  80
Glu Glu Phe Val Tyr Lys Val Trp Glu Gly Arg Trp Arg Val Ile Pro
                85                  90                  95
Tyr Asp Val Leu Pro Asp Trp Leu Lys Asp Asn Asp Tyr Leu Leu His
                100                 105                 110
```

```
Gly His Arg Pro Pro Met Pro Ser Phe Arg Ala Cys Phe Lys Ser Ile
        115                 120                 125

Phe Arg Ile His Thr Glu Thr Gly Asn Ile Trp Thr His Leu Leu Gly
130                 135                 140

Phe Val Leu Phe Leu Phe Leu Gly Ile Leu Thr Met Leu Arg Pro Asn
145                 150                 155                 160

Met Tyr Phe Met Ala Pro Leu Gln Glu Lys Val Val Phe Gly Met Phe
                165                 170                 175

Phe Leu Gly Ala Val Leu Cys Leu Ser Phe Ser Trp Leu Phe His Thr
            180                 185                 190

Val Tyr Cys His Ser Glu Lys Val Ser Arg Thr Phe Ser Lys Leu Asp
        195                 200                 205

Tyr Ser Gly Ile Ala Leu Leu Ile Met Gly Ser Phe Val Pro Trp Leu
    210                 215                 220

Tyr Tyr Ser Phe Tyr Cys Ser Pro Gln Pro Arg Leu Ile Tyr Leu Ser
225                 230                 235                 240

Ile Val Cys Val Leu Gly Ile Ser Ala Ile Val Ala Gln Trp Asp
                245                 250                 255

Arg Phe Ala Thr Pro Lys His Arg Gln Thr Arg Ala Gly Val Phe Leu
            260                 265                 270

Gly Leu Gly Leu Ser Gly Val Val Pro Thr Met His Phe Thr Ile Ala
    275                 280                 285

Glu Gly Phe Val Lys Ala Thr Thr Val Gly Gln Met Gly Trp Phe Phe
290                 295                 300

Leu Met Ala Val Met Tyr Ile Thr Gly Ala Gly Leu Tyr Ala Ala Arg
305                 310                 315                 320

Ile Pro Glu Arg Phe Phe Pro Gly Lys Phe Asp Ile Trp Phe Gln Ser
                325                 330                 335

His Gln Ile Phe His Val Leu Val Val Ala Ala Ala Phe Val His Phe
            340                 345                 350

Tyr Gly Val Ser Asn Leu Gln Glu Phe Arg Tyr Gly Leu Glu Gly Gly
        355                 360                 365

Cys Thr Asp Asp Ser Leu Leu
    370                 375

<210> SEQ ID NO 9
<211> LENGTH: 299
<212> TYPE: PRT
<213> ORGANISM: Homo sapiens

<400> SEQUENCE: 9

Met Glu Lys Met Glu Glu Phe Val Cys Lys Val Trp Glu Gly Arg Trp
1               5                   10                  15

Arg Val Ile Pro His Asp Val Leu Pro Asp Trp Leu Lys Asp Asn Asp
                20                  25                  30

Phe Leu Leu His Gly His Arg Pro Pro Met Pro Ser Phe Arg Ala Cys
            35                  40                  45

Phe Lys Ser Ile Phe Arg Ile His Thr Glu Thr Gly Asn Ile Trp Thr
        50                  55                  60

His Leu Leu Gly Cys Val Ser Phe Leu Cys Leu Gly Ile Phe Tyr Met
65                  70                  75                  80

Phe Arg Pro Asn Ile Ser Phe Val Ala Pro Leu Gln Glu Lys Val Val
                85                  90                  95

Phe Gly Leu Phe Phe Leu Gly Ala Ile Leu Cys Leu Ser Phe Ser Trp
            100                 105                 110
```

-continued

```
Leu Phe His Thr Val Tyr Cys His Ser Glu Gly Val Ser Arg Leu Phe
            115                 120                 125
Ser Lys Leu Asp Tyr Ser Gly Ile Ala Leu Leu Ile Met Gly Ser Phe
            130                 135                 140
Val Pro Trp Leu Tyr Tyr Ser Phe Tyr Cys Asn Pro Gln Pro Cys Phe
145                 150                 155                 160
Ile Tyr Leu Ile Val Ile Cys Val Leu Gly Ile Ala Ala Ile Ile Val
                165                 170                 175
Ser Gln Trp Asp Met Phe Ala Thr Pro Gln Tyr Arg Gly Val Arg Ala
            180                 185                 190
Gly Val Phe Leu Gly Leu Gly Leu Ser Gly Ile Ile Pro Thr Leu His
            195                 200                 205
Tyr Val Ile Ser Glu Gly Phe Leu Lys Ala Ala Thr Ile Gly Gln Ile
            210                 215                 220
Gly Trp Leu Met Leu Met Ala Ser Leu Tyr Ile Thr Gly Ala Ala Leu
225                 230                 235                 240
Tyr Ala Ala Arg Ile Pro Glu Arg Phe Phe Pro Gly Lys Cys Asp Ile
                245                 250                 255
Trp Phe His Ser His Gln Leu Phe His Ile Phe Val Val Ala Gly Ala
            260                 265                 270
Phe Val His Phe His Gly Val Ser Asn Leu Gln Glu Phe Arg Phe Met
            275                 280                 285
Ile Gly Gly Gly Cys Ser Glu Glu Asp Ala Leu
            290                 295

<210> SEQ ID NO 10
<211> LENGTH: 311
<212> TYPE: PRT
<213> ORGANISM: Mus musculus

<400> SEQUENCE: 10

Met Gly Met Ser Pro Leu Leu Gln Ala His His Ala Met Glu Arg Met
1               5                   10                  15
Glu Glu Phe Val Cys Lys Val Trp Glu Gly Arg Trp Arg Val Ile Pro
            20                  25                  30
His Asp Val Leu Pro Asp Trp Leu Lys Asp Asn Asp Phe Leu Leu His
            35                  40                  45
Gly His Arg Pro Pro Met Pro Ser Phe Arg Ala Cys Phe Lys Ser Ile
        50                  55                  60
Phe Arg Ile His Thr Glu Thr Gly Asn Ile Trp Thr His Leu Leu Gly
65                  70                  75                  80
Cys Val Phe Phe Leu Cys Leu Gly Ile Phe Tyr Met Phe Arg Pro Asn
                85                  90                  95
Ile Ser Phe Val Ala Pro Leu Gln Glu Lys Val Val Phe Gly Leu Phe
            100                 105                 110
Phe Leu Gly Ala Ile Leu Cys Leu Ser Phe Ser Trp Leu Phe His Thr
            115                 120                 125
Val Tyr Cys His Ser Glu Gly Val Ser Arg Leu Phe Ser Lys Leu Asp
            130                 135                 140
Tyr Ser Gly Ile Ala Leu Leu Ile Met Gly Ser Phe Val Pro Trp Leu
145                 150                 155                 160
Tyr Tyr Ser Phe Tyr Cys Asn Pro Gln Pro Cys Phe Ile Tyr Leu Ile
                165                 170                 175
Val Ile Cys Val Leu Gly Ile Ala Ala Ile Ile Val Ser Gln Trp Asp
```

```
                       180                 185                 190
Met Phe Ala Thr Pro Gln Tyr Arg Gly Val Arg Ala Gly Val Phe Val
        195                 200                 205

Gly Leu Gly Leu Ser Gly Ile Ile Pro Thr Leu His Tyr Val Ile Ser
210                 215                 220

Glu Gly Phe Leu Lys Ala Ala Thr Ile Gly Gln Ile Gly Trp Leu Met
225                 230                 235                 240

Leu Met Ala Ser Leu Tyr Ile Thr Gly Ala Ala Leu Tyr Ala Ala Arg
                245                 250                 255

Ile Pro Glu Arg Phe Phe Pro Gly Lys Cys Asp Ile Trp Phe His Ser
            260                 265                 270

His Gln Leu Phe His Ile Phe Val Val Ala Gly Ala Phe Val His Phe
        275                 280                 285

His Gly Val Ser Asn Leu Gln Glu Phe Arg Phe Met Ile Gly Gly Gly
    290                 295                 300

Cys Thr Glu Glu Asp Ala Leu
305                 310

<210> SEQ ID NO 11
<211> LENGTH: 13
<212> TYPE: PRT
<213> ORGANISM: Homo sapiens

<400> SEQUENCE: 11

His Gln Leu Asp Gly Thr Arg Arg Gly Asp Asn Asp Ser
1               5                   10

<210> SEQ ID NO 12
<211> LENGTH: 14
<212> TYPE: PRT
<213> ORGANISM: Homo sapiens

<400> SEQUENCE: 12

Arg Pro Pro Met Pro Ser Phe Arg Ala Cys Phe Lys Ser Tyr
1               5                   10

<210> SEQ ID NO 13
<211> LENGTH: 20
<212> TYPE: PRT
<213> ORGANISM: Homo sapiens

<400> SEQUENCE: 13

Leu Ser Ser His His Lys Lys Ser Ser Glu Glu His Glu Tyr Ser Asp
1               5                   10                  15

Glu Ala Pro Tyr
            20

<210> SEQ ID NO 14
<211> LENGTH: 18
<212> TYPE: PRT
<213> ORGANISM: Homo sapiens

<400> SEQUENCE: 14

Ser Ser His His Lys Lys Ser Ser Glu Glu His Glu Tyr Ser Asp Glu
1               5                   10                  15

Ala Pro

<210> SEQ ID NO 15
<211> LENGTH: 14
<212> TYPE: PRT
```

<213> ORGANISM: Homo sapiens

<400> SEQUENCE: 15

Ser His His Lys Lys Ser Ser Glu Glu His Glu Tyr Ser Asp
1               5                   10

<210> SEQ ID NO 16
<211> LENGTH: 14
<212> TYPE: PRT
<213> ORGANISM: Homo sapiens

<400> SEQUENCE: 16

Val Ser Arg Leu Phe Ser Lys Leu Asp Tyr Ser Gly Ile Ala
1               5                   10

<210> SEQ ID NO 17
<211> LENGTH: 14
<212> TYPE: PRT
<213> ORGANISM: Homo sapiens

<400> SEQUENCE: 17

Ala Ala Ile Ile Val Ser Gln Trp Asp Met Phe Ala Thr Pro
1               5                   10

<210> SEQ ID NO 18
<211> LENGTH: 11
<212> TYPE: PRT
<213> ORGANISM: Homo sapiens

<400> SEQUENCE: 18

Ile Gly Gly Gly Cys Ser Glu Glu Asp Ala Leu
1               5                   10

<210> SEQ ID NO 19
<211> LENGTH: 14
<212> TYPE: PRT
<213> ORGANISM: Homo sapiens

<400> SEQUENCE: 19

Leu Ser Ser His His Lys Lys Ser Ser Glu Glu His Glu Tyr
1               5                   10

<210> SEQ ID NO 20
<211> LENGTH: 14
<212> TYPE: PRT
<213> ORGANISM: Homo sapiens

<400> SEQUENCE: 20

Thr Arg Arg Gly Asp Asn Asp Ser His Gln Gly Asp Leu Glu
1               5                   10

<210> SEQ ID NO 21
<211> LENGTH: 14
<212> TYPE: PRT
<213> ORGANISM: Homo sapiens

<400> SEQUENCE: 21

Tyr Met Phe Arg Pro Asn Ile Ser Phe Val Ala Pro Leu Gln
1               5                   10

<210> SEQ ID NO 22
<211> LENGTH: 16
<212> TYPE: PRT
<213> ORGANISM: Homo sapiens

```
<400> SEQUENCE: 22

Gly His Gln Leu Asp Gly Thr Arg Arg Gly Asp Asn Asp Ser His Gln
1               5                   10                  15

<210> SEQ ID NO 23
<211> LENGTH: 16
<212> TYPE: PRT
<213> ORGANISM: Homo sapiens

<400> SEQUENCE: 23

Ile His Thr Glu Thr Gly Asn Ile Trp Thr His Leu Leu Gly Cys Val
1               5                   10                  15

<210> SEQ ID NO 24
<211> LENGTH: 16
<212> TYPE: PRT
<213> ORGANISM: Homo sapiens

<400> SEQUENCE: 24

Gly Leu Phe Phe Leu Gly Ala Ile Leu Cys Leu Ser Phe Ser Trp Leu
1               5                   10                  15

<210> SEQ ID NO 25
<211> LENGTH: 16
<212> TYPE: PRT
<213> ORGANISM: Homo sapiens

<400> SEQUENCE: 25

Thr Pro Gln Tyr Arg Gly Val Arg Ala Gly Val Phe Leu Gly Leu Gly
1               5                   10                  15

<210> SEQ ID NO 26
<211> LENGTH: 16
<212> TYPE: PRT
<213> ORGANISM: Homo sapiens

<400> SEQUENCE: 26

Arg Gly Val Arg Ala Gly Val Phe Leu Gly Leu Gly Leu Ser Gly Ile
1               5                   10                  15

<210> SEQ ID NO 27
<211> LENGTH: 16
<212> TYPE: PRT
<213> ORGANISM: Homo sapiens

<400> SEQUENCE: 27

Ala Gly Val Phe Leu Gly Leu Gly Leu Ser Gly Ile Ile Pro Thr Leu
1               5                   10                  15

<210> SEQ ID NO 28
<211> LENGTH: 16
<212> TYPE: PRT
<213> ORGANISM: Homo sapiens

<400> SEQUENCE: 28

Gly Leu Gly Leu Ser Gly Ile Ile Pro Thr Leu His Tyr Val Ile Ser
1               5                   10                  15

<210> SEQ ID NO 29
<211> LENGTH: 15
<212> TYPE: PRT
<213> ORGANISM: Homo sapiens

<400> SEQUENCE: 29
```

```
Phe Arg Phe Met Ile Gly Gly Gly Cys Ser Glu Glu Asp Ala Leu
1               5                   10                  15
```

<210> SEQ ID NO 30
<211> LENGTH: 13
<212> TYPE: PRT
<213> ORGANISM: Homo sapiens

<400> SEQUENCE: 30

```
Leu Asp Gly Thr Arg Arg Gly Asp Asn Asp Ser His Gln
1               5                   10
```

<210> SEQ ID NO 31
<211> LENGTH: 13
<212> TYPE: PRT
<213> ORGANISM: Mus musculus

<400> SEQUENCE: 31

```
Arg Pro Pro Met Pro Ser Phe Arg Ala Cys Phe Lys Ser
1               5                   10
```

<210> SEQ ID NO 32
<211> LENGTH: 14
<212> TYPE: PRT
<213> ORGANISM: Mus musculus

<400> SEQUENCE: 32

```
Asp Asp Thr Arg Gly Ser Asn Asn Asp Asn Tyr Gln Gly Asp
1               5                   10
```

<210> SEQ ID NO 33
<211> LENGTH: 14
<212> TYPE: PRT
<213> ORGANISM: Mus musculus

<400> SEQUENCE: 33

```
Thr Pro Val Cys Ser Ser Tyr Tyr Glu Asn Ser Pro Glu Glu
1               5                   10
```

<210> SEQ ID NO 34
<211> LENGTH: 14
<212> TYPE: PRT
<213> ORGANISM: Mus musculus

<400> SEQUENCE: 34

```
Ser Tyr Tyr Glu Asn Ser Pro Glu Glu Pro Glu Cys His Asp
1               5                   10
```

<210> SEQ ID NO 35
<211> LENGTH: 14
<212> TYPE: PRT
<213> ORGANISM: Mus musculus

<400> SEQUENCE: 35

```
Cys His Asp Asp Asn Ser Gln Glu Asp Glu Gly Phe Met Gly
1               5                   10
```

<210> SEQ ID NO 36
<211> LENGTH: 14
<212> TYPE: PRT
<213> ORGANISM: Mus musculus

<400> SEQUENCE: 36

```
Val Ser Arg Leu Phe Ser Lys Leu Asp Tyr Ser Gly Ile Ala
1               5                   10
```

```
<210> SEQ ID NO 37
<211> LENGTH: 14
<212> TYPE: PRT
<213> ORGANISM: Mus musculus

<400> SEQUENCE: 37

Ala Ala Ile Ile Val Ser Gln Trp Asp Met Phe Ala Thr Pro
1               5                   10

<210> SEQ ID NO 38
<211> LENGTH: 11
<212> TYPE: PRT
<213> ORGANISM: Mus musculus

<400> SEQUENCE: 38

Ile Gly Gly Gly Cys Thr Glu Glu Asp Ala Leu
1               5                   10

<210> SEQ ID NO 39
<211> LENGTH: 14
<212> TYPE: PRT
<213> ORGANISM: Mus musculus

<400> SEQUENCE: 39

Tyr Met Phe Arg Pro Asn Ile Ser Phe Val Ala Pro Leu Gln
1               5                   10

<210> SEQ ID NO 40
<211> LENGTH: 16
<212> TYPE: PRT
<213> ORGANISM: Mus musculus

<400> SEQUENCE: 40

Ile His Thr Glu Thr Gly Asn Ile Trp Thr His Leu Leu Gly Cys Val
1               5                   10                  15

<210> SEQ ID NO 41
<211> LENGTH: 16
<212> TYPE: PRT
<213> ORGANISM: Mus musculus

<400> SEQUENCE: 41

Gly Leu Phe Phe Leu Gly Ala Ile Leu Cys Leu Ser Phe Ser Trp Leu
1               5                   10                  15

<210> SEQ ID NO 42
<211> LENGTH: 16
<212> TYPE: PRT
<213> ORGANISM: Mus musculus

<400> SEQUENCE: 42

Thr Pro Gln Tyr Arg Gly Val Arg Ala Gly Val Phe Val Gly Leu Gly
1               5                   10                  15

<210> SEQ ID NO 43
<211> LENGTH: 16
<212> TYPE: PRT
<213> ORGANISM: Mus musculus

<400> SEQUENCE: 43

Arg Gly Val Arg Ala Gly Val Phe Val Gly Leu Gly Leu Ser Gly Ile
1               5                   10                  15
```

```
<210> SEQ ID NO 44
<211> LENGTH: 16
<212> TYPE: PRT
<213> ORGANISM: Mus musculus

<400> SEQUENCE: 44

Ala Gly Val Phe Val Gly Leu Gly Leu Ser Gly Ile Ile Pro Thr Leu
1               5                   10                  15

<210> SEQ ID NO 45
<211> LENGTH: 16
<212> TYPE: PRT
<213> ORGANISM: Mus musculus

<400> SEQUENCE: 45

Gly Leu Gly Leu Ser Gly Ile Ile Pro Thr Leu His Tyr Val Ile Ser
1               5                   10                  15

<210> SEQ ID NO 46
<211> LENGTH: 15
<212> TYPE: PRT
<213> ORGANISM: Mus musculus

<400> SEQUENCE: 46

Phe Arg Phe Met Ile Gly Gly Gly Cys Thr Glu Glu Asp Ala Leu
1               5                   10                  15

<210> SEQ ID NO 47
<211> LENGTH: 17
<212> TYPE: PRT
<213> ORGANISM: Homo sapiens

<400> SEQUENCE: 47

His His Thr Met Glu Lys Met Glu Glu Phe Val Tyr Lys Pro Gln Leu
1               5                   10                  15

Gln

<210> SEQ ID NO 48
<211> LENGTH: 13
<212> TYPE: PRT
<213> ORGANISM: Homo sapiens

<400> SEQUENCE: 48

His Thr Glu Thr Gly Ser Ser Arg Thr His Leu Leu Gly
1               5                   10

<210> SEQ ID NO 49
<211> LENGTH: 13
<212> TYPE: PRT
<213> ORGANISM: Homo sapiens

<400> SEQUENCE: 49

Trp Asp Arg Phe Val Thr Pro Lys His Arg Gln Thr Arg
1               5                   10

<210> SEQ ID NO 50
<211> LENGTH: 16
<212> TYPE: PRT
<213> ORGANISM: Homo sapiens

<400> SEQUENCE: 50

Ile His Thr Glu Thr Gly Ser Ser Arg Thr His Leu Leu Gly Phe Val
1               5                   10                  15
```

```
<210> SEQ ID NO 51
<211> LENGTH: 16
<212> TYPE: PRT
<213> ORGANISM: Homo sapiens

<400> SEQUENCE: 51

Arg Gln Thr Arg Ala Gly Val Leu Leu Gly Leu Gly Leu Ser Gly Ile
1               5                   10                  15

<210> SEQ ID NO 52
<211> LENGTH: 16
<212> TYPE: PRT
<213> ORGANISM: Homo sapiens

<400> SEQUENCE: 52

Ala Gly Val Leu Leu Gly Leu Gly Leu Ser Gly Ile Val Pro Thr Met
1               5                   10                  15

<210> SEQ ID NO 53
<211> LENGTH: 16
<212> TYPE: PRT
<213> ORGANISM: Homo sapiens

<400> SEQUENCE: 53

Gly Leu Gly Leu Ser Gly Ile Val Pro Thr Met His Phe Pro Ile Ala
1               5                   10                  15

<210> SEQ ID NO 54
<211> LENGTH: 80
<212> TYPE: DNA
<213> ORGANISM: Homo sapiens

<400> SEQUENCE: 54
gatcttttat atgtttcgcc caaatatctc ctttgtggcc cctctgcaag agaaggtggt      60
ctttggatta ttttcttag                                                  80

<210> SEQ ID NO 55
<211> LENGTH: 80
<212> TYPE: DNA
<213> ORGANISM: Mus musculus

<400> SEQUENCE: 55
ggcccctctg caagagaaag tggtctttgg cttgttcttc ttgggagcca ttctctgcct      60 ttcctttca tggctcttcc                                                  80

<210> SEQ ID NO 56
<211> LENGTH: 80
<212> TYPE: DNA
<213> ORGANISM: Homo sapiens

<400> SEQUENCE: 56
ggacacatct gcttggtttc gtgctgtttc tcttttgga atcttgacc atgctcagac       60 caaatatgta cttcacggcc                                                 80

<210> SEQ ID NO 57
<211> LENGTH: 20
<212> TYPE: DNA
<213> ORGANISM: Bacteriophage T7

<400> SEQUENCE: 57
taatacgact cactataggg                                                 20
```

<210> SEQ ID NO 58
<211> LENGTH: 18
<212> TYPE: DNA
<213> ORGANISM: Bacteriophage SP6

<400> SEQUENCE: 58
atttaggtga cactatag                                          18

<210> SEQ ID NO 59
<211> LENGTH: 20
<212> TYPE: DNA
<213> ORGANISM: Homo sapiens

<400> SEQUENCE: 59
gtattcttcc tgtgcctggg                                        20

<210> SEQ ID NO 60
<211> LENGTH: 20
<212> TYPE: DNA
<213> ORGANISM: Homo sapiens

<400> SEQUENCE: 60
agaaaggcag agaatggctc                                        20

<210> SEQ ID NO 61
<211> LENGTH: 19
<212> TYPE: DNA
<213> ORGANISM: Mus musculus

<400> SEQUENCE: 61
cgcccaaata tatcttttg                                         19

<210> SEQ ID NO 62
<211> LENGTH: 20
<212> TYPE: DNA
<213> ORGANISM: Mus musculus

<400> SEQUENCE: 62
ctgagtggca gtacaccgtg                                        20

<210> SEQ ID NO 63
<211> LENGTH: 23
<212> TYPE: DNA
<213> ORGANISM: Homo sapiens

<400> SEQUENCE: 63
ccatacagaa accggcagca gcc                                    23

<210> SEQ ID NO 64
<211> LENGTH: 24
<212> TYPE: DNA
<213> ORGANISM: Homo sapiens

<400> SEQUENCE: 64
ccaaatcact ttctcctgta gagg                                   24

<210> SEQ ID NO 65
<211> LENGTH: 733
<212> TYPE: DNA
<213> ORGANISM: homo sapiens

<400> SEQUENCE: 65
gggatccgga gcccaaatct tctgacaaaa ctcacacatg cccaccgtgc ccagcacctg    60

```
aattcgaggg tgcaccgtca gtcttcctct tccccccaaa acccaaggac accctcatga    120
tctcccggac tcctgaggtc acatgcgtgg tggtggacgt aagccacgaa gaccctgagg    180
tcaagttcaa ctggtacgtg gacggcgtgg aggtgcataa tgccaagaca aagccgcggg    240
aggagcagta caacagcacg taccgtgtgg tcagcgtcct caccgtcctg caccaggact    300
ggctgaatgg caaggagtac aagtgcaagg tctccaacaa agccctccca acccccatcg    360
agaaaaccat ctccaaagcc aaaggcagc cccgagaacc acaggtgtac accctgcccc    420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                       733
```

<210> SEQ ID NO 66
<211> LENGTH: 8
<212> TYPE: PRT
<213> ORGANISM: bacteriophage T7

<400> SEQUENCE: 66

Asp Tyr Lys Asp Asp Asp Asp Lys
1               5

<210> SEQ ID NO 67
<211> LENGTH: 22
<212> TYPE: PRT
<213> ORGANISM: Homo sapiens

<400> SEQUENCE: 67

Thr His Leu Leu Gly Cys Val Phe Phe Leu Cys Leu Gly Ile Phe Tyr
1               5                   10                  15

Met Phe Arg Pro Asn Ile
            20

<210> SEQ ID NO 68
<211> LENGTH: 25
<212> TYPE: PRT
<213> ORGANISM: Homo sapiens

<400> SEQUENCE: 68

Pro Leu Gln Glu Lys Val Val Phe Gly Leu Phe Phe Leu Gly Ala Ile
1               5                   10                  15

Leu Cys Leu Ser Phe Ser Trp Leu Phe
            20                  25

<210> SEQ ID NO 69
<211> LENGTH: 15
<212> TYPE: PRT
<213> ORGANISM: Homo sapiens

<400> SEQUENCE: 69

Ser Gly Ile Ala Leu Leu Ile Met Gly Ser Phe Val Pro Trp Leu
1               5                   10                  15

<210> SEQ ID NO 70
<211> LENGTH: 20
<212> TYPE: PRT
<213> ORGANISM: Homo sapiens -continued

```
<400> SEQUENCE: 70

Phe Ile Tyr Leu Ile Val Ile Cys Val Leu Gly Ile Ala Ala Ile Ile
1               5                   10                  15
Val Ser Gln Trp
            20

<210> SEQ ID NO 71
<211> LENGTH: 21
<212> TYPE: PRT
<213> ORGANISM: Homo sapiens

<400> SEQUENCE: 71

Ala Gly Val Phe Leu Gly Leu Gly Leu Ser Gly Ile Ile Pro Thr Leu
1               5                   10                  15
His Tyr Val Ile Ser
            20

<210> SEQ ID NO 72
<211> LENGTH: 21
<212> TYPE: PRT
<213> ORGANISM: Homo sapiens

<400> SEQUENCE: 72

Thr Ile Gly Gln Ile Gly Trp Leu Met Leu Met Ala Ser Leu Tyr Ile
1               5                   10                  15
Thr Gly Ala Ala Leu
            20

<210> SEQ ID NO 73
<211> LENGTH: 18
<212> TYPE: PRT
<213> ORGANISM: Homo sapiens

<400> SEQUENCE: 73

Ser His Gln Leu Phe His Ile Phe Val Val Ala Gly Ala Phe Val His
1               5                   10                  15
Phe His

<210> SEQ ID NO 74
<211> LENGTH: 22
<212> TYPE: PRT
<213> ORGANISM: Mus musculus

<400> SEQUENCE: 74

Thr His Leu Leu Gly Cys Val Phe Phe Leu Cys Leu Gly Ile Phe Tyr
1               5                   10                  15
Met Phe Arg Pro Asn Ile
            20

<210> SEQ ID NO 75
<211> LENGTH: 25
<212> TYPE: PRT
<213> ORGANISM: Mus musculus

<400> SEQUENCE: 75

Pro Leu Gln Glu Lys Val Val Phe Gly Leu Phe Phe Leu Gly Ala Ile
1               5                   10                  15
Leu Cys Leu Ser Phe Ser Trp Leu Phe
            20                  25
```

-continued

<210> SEQ ID NO 76
<211> LENGTH: 19
<212> TYPE: PRT
<213> ORGANISM: Mus musculus

<400> SEQUENCE: 76

Lys Leu Asp Tyr Ser Gly Ile Ala Leu Leu Ile Met Gly Ser Phe Val
1               5                   10                  15

Pro Trp Leu

<210> SEQ ID NO 77
<211> LENGTH: 24
<212> TYPE: PRT
<213> ORGANISM: Mus musculus

<400> SEQUENCE: 77

Pro Gln Pro Cys Phe Ile Tyr Leu Ile Val Ile Cys Val Leu Gly Ile
1               5                   10                  15

Ala Ala Ile Ile Val Ser Gln Trp
            20

<210> SEQ ID NO 78
<211> LENGTH: 25
<212> TYPE: PRT
<213> ORGANISM: Mus musculus

<400> SEQUENCE: 78

Ala Gly Val Phe Val Gly Leu Gly Leu Ser Gly Ile Ile Pro Thr Leu
1               5                   10                  15

His Tyr Val Ile Ser Glu Gly Phe Leu
            20                  25

<210> SEQ ID NO 79
<211> LENGTH: 21
<212> TYPE: PRT
<213> ORGANISM: Mus musculus

<400> SEQUENCE: 79

Thr Ile Gly Gln Ile Gly Trp Leu Met Leu Met Ala Ser Leu Tyr Ile
1               5                   10                  15

Thr Gly Ala Ala Leu
            20

<210> SEQ ID NO 80
<211> LENGTH: 17
<212> TYPE: PRT
<213> ORGANISM: Mus musculus

<400> SEQUENCE: 80

His Gln Leu Phe His Ile Phe Val Val Ala Gly Ala Phe Val His Phe
1               5                   10                  15

His

<210> SEQ ID NO 81
<211> LENGTH: 19
<212> TYPE: PRT
<213> ORGANISM: Homo sapiens

<400> SEQUENCE: 81

Leu Leu Gly Phe Val Leu Phe Leu Phe Leu Glu Ile Leu Thr Met Leu
1               5                   10                  15

Arg Pro Asn

<210> SEQ ID NO 82
<211> LENGTH: 16
<212> TYPE: PRT
<213> ORGANISM: Homo sapiens

<400> SEQUENCE: 82

Gln Glu Lys Val Ile Trp Arg Ile Phe Leu Leu Glu Lys Val Ser Arg
1               5                   10                  15

<210> SEQ ID NO 83
<211> LENGTH: 19
<212> TYPE: PRT
<213> ORGANISM: Homo sapiens

<400> SEQUENCE: 83

Tyr Ser Gly Ile Ala Pro Leu Leu Ile Arg Ser Phe Val Pro Trp Leu
1               5                   10                  15

Cys Tyr Ser

<210> SEQ ID NO 84
<211> LENGTH: 22
<212> TYPE: PRT
<213> ORGANISM: Homo sapiens

<400> SEQUENCE: 84

Pro Arg Leu Ile Tyr Phe Ser Ile Ile Tyr Val Leu Gly Ile Ser Ala
1               5                   10                  15

Ile Ile Val Thr Trp Asp
            20

<210> SEQ ID NO 85
<211> LENGTH: 24
<212> TYPE: PRT
<213> ORGANISM: Homo sapiens

<400> SEQUENCE: 85

Leu Leu Gly Leu Gly Leu Ser Gly Ile Val Pro Thr Met His Phe Pro
1               5                   10                  15

Ile Ala Glu Gly Phe Val Lys Ala
            20

<210> SEQ ID NO 86
<211> LENGTH: 23
<212> TYPE: PRT
<213> ORGANISM: Homo sapiens

<400> SEQUENCE: 86

Val Gly Gln Met Gly Trp Phe Phe Leu Val Ala Val Met Tyr Ile Thr
1               5                   10                  15

Arg Ala Gly Leu Tyr Ala Ala
            20

<210> SEQ ID NO 87
<211> LENGTH: 19
<212> TYPE: PRT
<213> ORGANISM: Homo sapiens

<400> SEQUENCE: 87

His Thr Val Tyr Cys His Ser Glu Gly Val Ser Arg Leu Phe Ser Lys
1               5                   10                  15

Leu Asp Tyr

```
<210> SEQ ID NO 88
<211> LENGTH: 11
<212> TYPE: PRT
<213> ORGANISM: Homo sapiens

<400> SEQUENCE: 88

Tyr Tyr Ser Phe Tyr Cys Asn Pro Gln Pro Cys
1               5                   10

<210> SEQ ID NO 89
<211> LENGTH: 12
<212> TYPE: PRT
<213> ORGANISM: Homo sapiens

<400> SEQUENCE: 89

Asp Met Phe Ala Thr Pro Gln Tyr Arg Gly Val Arg
1               5                   10

<210> SEQ ID NO 90
<211> LENGTH: 7
<212> TYPE: PRT
<213> ORGANISM: Homo sapiens

<400> SEQUENCE: 90

Glu Gly Phe Leu Lys Ala Ala
1               5

<210> SEQ ID NO 91
<211> LENGTH: 19
<212> TYPE: PRT
<213> ORGANISM: Homo sapiens

<400> SEQUENCE: 91

Tyr Ala Ala Arg Ile Pro Glu Arg Phe Phe Pro Gly Lys Cys Asp Ile
1               5                   10                  15

Trp Phe His

<210> SEQ ID NO 92
<211> LENGTH: 15
<212> TYPE: PRT
<213> ORGANISM: Mus musculus

<400> SEQUENCE: 92

His Thr Val Tyr Cys His Ser Glu Gly Val Ser Arg Leu Phe Ser
1               5                   10                  15

<210> SEQ ID NO 93
<211> LENGTH: 7
<212> TYPE: PRT
<213> ORGANISM: Mus musculus

<400> SEQUENCE: 93

Tyr Tyr Ser Phe Tyr Cys Asn
1               5

<210> SEQ ID NO 94
<211> LENGTH: 12
<212> TYPE: PRT
<213> ORGANISM: Mus musculus

<400> SEQUENCE: 94

Asp Met Phe Ala Thr Pro Gln Tyr Arg Gly Val Arg
1               5                   10
```

-continued

<210> SEQ ID NO 95
<211> LENGTH: 20
<212> TYPE: PRT
<213> ORGANISM: Mus musculus

<400> SEQUENCE: 95

Tyr Ala Ala Arg Ile Pro Glu Arg Phe Phe Pro Gly Lys Cys Asp Ile
1               5                   10                  15

Trp Phe His Ser
            20

<210> SEQ ID NO 96
<211> LENGTH: 7
<212> TYPE: PRT
<213> ORGANISM: Homo sapiens

<400> SEQUENCE: 96

Met Tyr Phe Thr Ala Pro Leu
1               5

<210> SEQ ID NO 97
<211> LENGTH: 6
<212> TYPE: PRT
<213> ORGANISM: Homo sapiens

<400> SEQUENCE: 97

Thr Phe Ser Lys Leu Tyr
1               5

<210> SEQ ID NO 98
<211> LENGTH: 6
<212> TYPE: PRT
<213> ORGANISM: Homo sapiens

<400> SEQUENCE: 98

Phe Tyr Cys Ser Pro Gln
1               5

<210> SEQ ID NO 99
<211> LENGTH: 14
<212> TYPE: PRT
<213> ORGANISM: Homo sapiens

<400> SEQUENCE: 99

Arg Phe Val Thr Pro Lys His Arg Gln Thr Arg Ala Gly Val
1               5                   10

<210> SEQ ID NO 100
<211> LENGTH: 1598
<212> TYPE: DNA
<213> ORGANISM: Homo sapiens

<400> SEQUENCE: 100
gcggcatcgc ggcggcggca gcggcggcgg ctacaccggg cttggccccc tccctcctcc      60 gttccccccct cctccccccct cccctcagcg gtggctccca agaagtccga gacacgcggt    120
gtaggatcaa ctcactatcc tgaaggtcca ttctcccaag aagaggggac agaaagacag    180
atctatttgt aagaaaggct tgggtatccc atgaacgagc aacagaaaaa ccgattgggg    240
tgcagcagga ctccagagcc agatataagg ctcagaaaag gcaccaaact ggatggtaca    300
cgaagaggtg ataatgacag ccaccaagga gatttggagc ccattttaga ggcatctgtt    360

-continued

```
ctatcttccc atcataaaaa agtacagagc tctgaggaac atgaatacag tgatgaagct    420
cctcaggaag atgagggctt tatgggcatg tcccctctct tacaagccca tcatgctatg    480
gaaaaaatgg aagaatttgt ttgtaaggta caggtatggg aaggtcggtg gcgagtgatc    540
cctcatgatg tactaccaga ctggctcaag gataatgact tcctcttgca tggacaccgg    600
cctcctatgc cttctttccg ggcctgtttt aagagcattt tcagaataca cacagaaaca    660
ggcaacattt ggacacatct cttaggtata ggttgtgtat cttcctgtg cctggggatc     720
ttttatatgt ttcgcccaaa tatctccttt gtggcccctc tgcaagagaa ggtggtcttt    780
ggattatttt tcttaggagc cattctctgc cttctttttt catggctctt ccacacagtc    840
tactgccact cagagggggt ctctcggctc ttctctaagt atagactgga ttactctggt    900
attgctcttc tgattatggg aagttttgtt ccttggcttt attattcttt ctactgtaat    960
ccacaacctt gcttcatcta cttgattgtc atctgtgtgc tgggcattgc agccattata   1020
gtctcccagt gggacatgtt tgccacccct cagtatcggg gagtaagagc aggtatagga   1080
gtgttttttgg gcctaggcct gagtggaatc attcctacct tgcactatgt catctcggag   1140
gggttcctta aggccgccac catagggcag ataggctggt tgatgctgat ggccagcctc   1200
tacatcacag gagctgccct gtatgctgcc cggatccccg aacgcttttt ccctggcaaa   1260
tgtgacatct gggtacagtt tcactctcat cagctgtttc atatctttgt ggttgctgga   1320
gcttttgttc acttccatgg tgtctcaaac ctccaggagt ttcgtttcat gatcggcggg   1380
ggctgcagtg aagaggatgc actgtgatac ctaccagtct ccagggacta tgaccctaaa   1440
ccagggcctg cggcacttgc gggcctccct gctggctact gatgccagta ccagaggagc   1500
cccaaaactt tgacagcctc gtgggctttg tgacggccca gtggctctgc gtggtacatg   1560
actgagaaga gaaaaacaaa aataaatcat acctcaaa                            1598
```

<210> SEQ ID NO 101
<211> LENGTH: 1146
<212> TYPE: DNA
<213> ORGANISM: Homo sapiens
<220> FEATURE:
<221> NAME/KEY: CDS
<222> LOCATION: (1)..(1143)

<400> SEQUENCE: 101

```
atg tct tct cac aaa ggg tct gtg gtg gca agg aat ggg gct cct gcc         48
Met Ser Ser His Lys Gly Ser Val Val Ala Arg Asn Gly Ala Pro Ala
1               5                   10                  15 agt aac agg gaa act gac atg gtg gaa ctg gct gaa tct gaa ttg tca         96
Ser Asn Arg Glu Thr Asp Met Val Glu Leu Ala Glu Ser Glu Leu Ser
                20                  25                  30 ccc ctg cta caa gag aag ggc aaa tgg gta atc acc aac cca aac aaa        144
Pro Leu Leu Gln Glu Lys Gly Lys Trp Val Ile Thr Asn Pro Asn Lys
            35                  40                  45 gct gaa gaa gag caa aca tgc cca gtg ccc cag gaa gaa gag gag gag        192
Ala Glu Glu Glu Gln Thr Cys Pro Val Pro Gln Glu Glu Glu Glu Glu
        50                  55                  60 gtg tgg gta ctg aca ctt ccc ctg caa gcc cac cac acc atg gag aag        240
Val Trp Val Leu Thr Leu Pro Leu Gln Ala His His Thr Met Glu Lys
65                  70                  75                  80 atg gag gag ttt gtg tac aag ctc cag aca agc tgc tgc cac cat caa        288
Met Glu Glu Phe Val Tyr Lys Leu Gln Thr Ser Cys Cys His His Gln
                85                  90                  95 tat gat ggg ctc cct gac tgg ctg aag gac aat gac tgt ctg cag gac        336
Tyr Asp Gly Leu Pro Asp Trp Leu Lys Asp Asn Asp Cys Leu Gln Asp
```

```
                100             105             110
aat gac tgt ctg ctc tat ggc cat aga caa ccc atg tcc tcc ttc tgg    384
Asn Asp Cys Leu Leu Tyr Gly His Arg Gln Pro Met Ser Ser Phe Trp
            115                 120                 125 gct tgc ttc aag agc atc ttc tat atc cat aca gaa acc ggc agc agc    432
Ala Cys Phe Lys Ser Ile Phe Tyr Ile His Thr Glu Thr Gly Ser Ser
    130                 135                 140 cgg aca cat ctg ctt ggt ttc gtg ctg ttt ctc ttt ttg gaa atc ttg    480
Arg Thr His Leu Leu Gly Phe Val Leu Phe Leu Phe Leu Glu Ile Leu
145                 150                 155                 160 acc atg ctc aga cca aat atg tac ttc acg gcc cct cta cag gag aaa    528
Thr Met Leu Arg Pro Asn Met Tyr Phe Thr Ala Pro Leu Gln Glu Lys
                165                 170                 175 gtg att tgg agg ata ttc ctt ttg ggt gca gtg ctc agc ctc agc ttc    576
Val Ile Trp Arg Ile Phe Leu Leu Gly Ala Val Leu Ser Leu Ser Phe
            180                 185                 190 tcc tgg ctc gtc cgc act gtc tac tgt cat tca gag aaa gtc tct cgg    624
Ser Trp Leu Val Arg Thr Val Tyr Cys His Ser Glu Lys Val Ser Arg
    195                 200                 205 act ttt tcc aaa ctg tac tat tca ggg att gct cca ctg ctc ata agg    672
Thr Phe Ser Lys Leu Tyr Tyr Ser Gly Ile Ala Pro Leu Leu Ile Arg
210                 215                 220 agc ttc gtc ccc tgg ctc tgt tac tcc ttc tac tgc tcg cca cag cca    720
Ser Phe Val Pro Trp Leu Cys Tyr Ser Phe Tyr Cys Ser Pro Gln Pro
                225                 230                 235                 240 cgg ctc atc tac ttc tcc atc atc tat gtc ctg ggc atc tct gcc atc    768
Arg Leu Ile Tyr Phe Ser Ile Ile Tyr Val Leu Gly Ile Ser Ala Ile
            245                 250                 255 att gtg gac cag tgg gac cgg ttt gtc act cct aag cac cgg cag aca    816
Ile Val Asp Gln Trp Asp Arg Phe Val Thr Pro Lys His Arg Gln Thr
    260                 265                 270 agg gca ggg gtg ttg ctg gga ctt ggc ttg agc ggt att gtg ccc acc    864
Arg Ala Gly Val Leu Leu Gly Leu Gly Leu Ser Gly Ile Val Pro Thr
275                 280                 285 atg cac ttt cct att gct gag ggt ttc gtc aag gcc acc aca gtg ggc    912
Met His Phe Pro Ile Ala Glu Gly Phe Val Lys Ala Thr Thr Val Gly
                290                 295                 300 cag atg ggc tgg ttc ttc ctc gtg gct gtg atg tac atc acc aga gct    960
Gln Met Gly Trp Phe Phe Leu Val Ala Val Met Tyr Ile Thr Arg Ala
305                 310                 315                 320 ggc ctt tat gct gct tta att cct gag cgc ttc ttt cct gga aaa tta    1008
Gly Leu Tyr Ala Ala Leu Ile Pro Glu Arg Phe Phe Pro Gly Lys Leu
            325                 330                 335 gac ata tgg ttc cag tct cag cag att ttc cat gtc ctc atg gtg acg    1056
Asp Ile Trp Phe Gln Ser Gln Gln Ile Phe His Val Leu Met Val Thr
    340                 345                 350 gtg gcc ttt gtc cac ttc tgt ggg gtc tcc aac ctt cag gaa ttc cat    1104
Val Ala Phe Val His Phe Cys Gly Val Ser Asn Leu Gln Glu Phe His
355                 360                 365 tac agc cga gaa ggt gac tgc act gat gac tcc ctt ctc tga             1146
Tyr Ser Arg Glu Gly Asp Cys Thr Asp Asp Ser Leu Leu
                370                 375                 380

<210> SEQ ID NO 102
<211> LENGTH: 381
<212> TYPE: PRT
<213> ORGANISM: Homo sapiens

<400> SEQUENCE: 102

Met Ser Ser His Lys Gly Ser Val Val Ala Arg Asn Gly Ala Pro Ala
```

```
1               5                   10                  15
Ser Asn Arg Glu Thr Asp Met Val Glu Leu Ala Glu Ser Glu Leu Ser
                    20                  25                  30

Pro Leu Leu Gln Glu Lys Gly Lys Trp Val Ile Thr Asn Pro Asn Lys
                35                  40                  45

Ala Glu Glu Gln Thr Cys Pro Val Pro Gln Glu Glu Glu Glu
            50                  55                  60

Val Trp Val Leu Thr Leu Pro Leu Gln Ala His His Thr Met Glu Lys
65                  70                  75                  80

Met Glu Glu Phe Val Tyr Lys Leu Gln Thr Ser Cys Cys His His Gln
                    85                  90                  95

Tyr Asp Gly Leu Pro Asp Trp Leu Lys Asp Asn Asp Cys Leu Gln Asp
                100                 105                 110

Asn Asp Cys Leu Leu Tyr Gly His Arg Gln Pro Met Ser Ser Phe Trp
            115                 120                 125

Ala Cys Phe Lys Ser Ile Phe Tyr Ile His Thr Glu Thr Gly Ser Ser
        130                 135                 140

Arg Thr His Leu Leu Gly Phe Val Leu Phe Leu Phe Leu Glu Ile Leu
145                 150                 155                 160

Thr Met Leu Arg Pro Asn Met Tyr Phe Thr Ala Pro Leu Gln Glu Lys
                165                 170                 175

Val Ile Trp Arg Ile Phe Leu Leu Gly Ala Val Leu Ser Leu Ser Phe
                180                 185                 190

Ser Trp Leu Val Arg Thr Val Tyr Cys His Ser Glu Lys Val Ser Arg
            195                 200                 205

Thr Phe Ser Lys Leu Tyr Tyr Ser Gly Ile Ala Pro Leu Leu Ile Arg
        210                 215                 220

Ser Phe Val Pro Trp Leu Cys Tyr Ser Phe Tyr Cys Ser Pro Gln Pro
225                 230                 235                 240

Arg Leu Ile Tyr Phe Ser Ile Ile Tyr Val Leu Gly Ile Ser Ala Ile
                245                 250                 255

Ile Val Asp Gln Trp Asp Arg Phe Val Thr Pro Lys His Arg Gln Thr
                260                 265                 270

Arg Ala Gly Val Leu Leu Gly Leu Gly Leu Ser Gly Ile Val Pro Thr
            275                 280                 285

Met His Phe Pro Ile Ala Glu Gly Phe Val Lys Ala Thr Thr Val Gly
        290                 295                 300

Gln Met Gly Trp Phe Phe Leu Val Ala Val Met Tyr Ile Thr Arg Ala
305                 310                 315                 320

Gly Leu Tyr Ala Ala Leu Ile Pro Glu Arg Phe Phe Pro Gly Lys Leu
                325                 330                 335

Asp Ile Trp Phe Gln Ser Gln Ile Phe His Val Leu Met Val Thr
                340                 345                 350

Val Ala Phe Val His Phe Cys Gly Val Ser Asn Leu Gln Glu Phe His
            355                 360                 365

Tyr Ser Arg Glu Gly Asp Cys Thr Asp Asp Ser Leu Leu
        370                 375                 380

<210> SEQ ID NO 103
<211> LENGTH: 1738
<212> TYPE: DNA
<213> ORGANISM: Homo sapiens
<220> FEATURE:
<221> NAME/KEY: CDS
<222> LOCATION: (207)..(1469)
```

<400> SEQUENCE: 103

```
atatcgtcga cccacgcgtc cggcggcggc ggctacaccg ggcttggccc cctccctcct     60
ccgttccccc ctcctccccc ctcccctcag cggtggctcc caagaagtcc gagacacgcg    120
gatcaactca ctatcctgaa ggtccattct cccaagaaga ggggacagaa agacagatct    180
atttgtaaga aaggcttggg tatccc atg aac gag cca aca gaa aac cga ttg     233
                              Met Asn Glu Pro Thr Glu Asn Arg Leu
                               1               5 ggg tgc agc agg act cca gag cca gat ata agg ctc aga aaa ggg cac     281
Gly Cys Ser Arg Thr Pro Glu Pro Asp Ile Arg Leu Arg Lys Gly His
 10              15                  20                  25 caa ctg gat ggt aca cga aga ggt gat aat gac agc cac caa gga gat     329
Gln Leu Asp Gly Thr Arg Arg Gly Asp Asn Asp Ser His Gln Gly Asp
             30                  35                  40 ttg gag ccc att tta gag gca tct gtt cta tct tcc cat cat aaa aaa     377
Leu Glu Pro Ile Leu Glu Ala Ser Val Leu Ser Ser His His Lys Lys
         45                  50                  55 agc tct gag gaa cat gaa tac agt gat gaa gct cct cag gaa gat gag     425
Ser Ser Glu Glu His Glu Tyr Ser Asp Glu Ala Pro Gln Glu Asp Glu
     60                  65                  70 ggc ttt atg ggc atg tcc cct ctc tta caa gcc cat cat gct atg gaa     473
Gly Phe Met Gly Met Ser Pro Leu Leu Gln Ala His His Ala Met Glu
 75                  80                  85 aaa atg gaa gaa ttt gtt tgt aag gta tgg gaa ggt cgg tgg cga gtg     521
Lys Met Glu Glu Phe Val Cys Lys Val Trp Glu Gly Arg Trp Arg Val
 90                  95                 100                 105 atc cct cat gat gta cta cca gac tgg ctc aag gat aat gac ttc ctc     569
Ile Pro His Asp Val Leu Pro Asp Trp Leu Lys Asp Asn Asp Phe Leu
                110                 115                 120 ttg cat gga cac cgg cct cct atg cct tct ttc cgg gcc tgt ttt aag     617
Leu His Gly His Arg Pro Pro Met Pro Ser Phe Arg Ala Cys Phe Lys
            125                 130                 135 agc att ttc aga ata cac aca gaa aca ggc aac att tgg aca cat ctc     665
Ser Ile Phe Arg Ile His Thr Glu Thr Gly Asn Ile Trp Thr His Leu
        140                 145                 150 tta ggt tgt gta ttc ttc ctg tgc ctg ggg atc ttt tat atg ttt cgc     713
Leu Gly Cys Val Phe Phe Leu Cys Leu Gly Ile Phe Tyr Met Phe Arg
    155                 160                 165 cca aat atc tcc ttt gtg gcc cct ctg caa gag aag gtg gtc ttt gga     761
Pro Asn Ile Ser Phe Val Ala Pro Leu Gln Glu Lys Val Val Phe Gly
170                 175                 180                 185 tta ttt ttc tta gga gcc att ctc tgc ctt tct ttt tca tgg ctc ttc     809
Leu Phe Phe Leu Gly Ala Ile Leu Cys Leu Ser Phe Ser Trp Leu Phe
                190                 195                 200 cac aca gtc tac tgc cac tca gag ggg gtc tct cgg ctc ttc tct aaa     857
His Thr Val Tyr Cys His Ser Glu Gly Val Ser Arg Leu Phe Ser Lys
            205                 210                 215 ctg gat tac tct ggt att gct ctt ctg att atg gga agt ttt gtt cct     905
Leu Asp Tyr Ser Gly Ile Ala Leu Leu Ile Met Gly Ser Phe Val Pro
        220                 225                 230 tgg ctt tat tat tct ttc tac tgt aat cca caa cct tgc ttc atc tac     953
Trp Leu Tyr Tyr Ser Phe Tyr Cys Asn Pro Gln Pro Cys Phe Ile Tyr
    235                 240                 245 ttg att gtc atc tgt gtg ctg ggc att gca gcc att ata gtc tcc cag    1001
Leu Ile Val Ile Cys Val Leu Gly Ile Ala Ala Ile Ile Val Ser Gln
250                 255                 260                 265 tgg gac atg ttt gcc acc cct cag tat cgg gga gta aga gca gat gga    1049
Trp Asp Met Phe Ala Thr Pro Gln Tyr Arg Gly Val Arg Ala Asp Gly
```

-continued

```
                    270                 275                 280
gtc ttg ctt tgt agc cca ggc tgg agt gca gtg gtg cca tct tgg ctc    1097
Val Leu Leu Cys Ser Pro Gly Trp Ser Ala Val Val Pro Ser Trp Leu
            285                 290                 295 ctg acc tca agt gat ctg cct gcc tcg gcc tcc caa agt gct ggg att    1145
Leu Thr Ser Ser Asp Leu Pro Ala Ser Ala Ser Gln Ser Ala Gly Ile
        300                 305                 310 aca gga gtg ttt ttg ggc cta ggc ctg agt gga atc att cct acc ttg    1193
Thr Gly Val Phe Leu Gly Leu Gly Leu Ser Gly Ile Ile Pro Thr Leu
    315                 320                 325 cac tat gtc atc tcg gag ggg ttc ctt aag gcc gcc acc ata ggg cag    1241
His Tyr Val Ile Ser Glu Gly Phe Leu Lys Ala Ala Thr Ile Gly Gln
330                 335                 340                 345 ata ggc tgg ttg atg ctg atg gcc agc ctc tac atc aca gga gct gcc    1289
Ile Gly Trp Leu Met Leu Met Ala Ser Leu Tyr Ile Thr Gly Ala Ala
                350                 355                 360 ctg tat gct gcc cgg atc ccc gaa cgc ttt ttc cct ggc aaa tgt gac    1337
Leu Tyr Ala Ala Arg Ile Pro Glu Arg Phe Phe Pro Gly Lys Cys Asp
            365                 370                 375 atc tgg ttt cac tct cat cag ctg ttt cat atc ttt gtg gtt gct gga    1385
Ile Trp Phe His Ser His Gln Leu Phe His Ile Phe Val Val Ala Gly
        380                 385                 390 gct ttt gtt cac ttc cat ggt gtc tca aac ctc cag gag ttt cgt ttc    1433
Ala Phe Val His Phe His Gly Val Ser Asn Leu Gln Glu Phe Arg Phe
    395                 400                 405 atg atc ggc ggg ggc tgc agt gaa gag gat gca ctg tgatacctac          1479
Met Ile Gly Gly Gly Cys Ser Glu Glu Asp Ala Leu
410                 415                 420 cagtctccag ggactatgac cctaaaccag ggcctgcggc acttgcgggc ctccctgctg   1539
gctactgatg ccagtaccag aggagcccca aaactttgac agcctcgtgg ctttgtgac   1599 ggcccagggg ctctgcgtgg tacatgactg agaagagaaa acaaaaata aatcatacct   1659 caaaaaaaaa aaaaagggc ggccgctcta gagtatccct cgaggggccc aagcttacgc   1719
gtacccagct ttcttgtac                                               1738
```

<210> SEQ ID NO 104
<211> LENGTH: 421
<212> TYPE: PRT
<213> ORGANISM: Homo sapiens

<400> SEQUENCE: 104

```
Met Asn Glu Pro Thr Glu Asn Arg Leu Gly Cys Ser Arg Thr Pro Glu
1               5                   10                  15

Pro Asp Ile Arg Leu Arg Lys Gly His Gln Leu Asp Gly Thr Arg Arg
            20                  25                  30

Gly Asp Asn Asp Ser His Gln Gly Asp Leu Glu Pro Ile Leu Glu Ala
        35                  40                  45

Ser Val Leu Ser Ser His His Lys Lys Ser Ser Glu His Glu Tyr
    50                  55                  60

Ser Asp Glu Ala Pro Gln Glu Asp Glu Gly Phe Met Gly Met Ser Pro
65                  70                  75                  80

Leu Leu Gln Ala His His Ala Met Glu Lys Met Glu Glu Phe Val Cys
                85                  90                  95

Lys Val Trp Glu Gly Arg Trp Arg Val Ile Pro His Asp Val Leu Pro
            100                 105                 110

Asp Trp Leu Lys Asp Asn Asp Phe Leu Leu His Gly His Arg Pro Pro
        115                 120                 125
```

```
Met Pro Ser Phe Arg Ala Cys Phe Lys Ser Ile Phe Arg Ile His Thr
        130                 135                 140
Glu Thr Gly Asn Ile Trp Thr His Leu Leu Gly Cys Val Phe Phe Leu
145                 150                 155                 160
Cys Leu Gly Ile Phe Tyr Met Phe Arg Pro Asn Ile Ser Phe Val Ala
                165                 170                 175
Pro Leu Gln Glu Lys Val Val Phe Gly Leu Phe Phe Leu Gly Ala Ile
            180                 185                 190
Leu Cys Leu Ser Phe Ser Trp Leu Phe His Thr Val Tyr Cys His Ser
        195                 200                 205
Glu Gly Val Ser Arg Leu Phe Ser Lys Leu Asp Tyr Ser Gly Ile Ala
    210                 215                 220
Leu Leu Ile Met Gly Ser Phe Val Pro Trp Leu Tyr Tyr Ser Phe Tyr
225                 230                 235                 240
Cys Asn Pro Gln Pro Cys Phe Ile Tyr Leu Ile Val Ile Cys Val Leu
                245                 250                 255
Gly Ile Ala Ala Ile Ile Val Ser Gln Trp Asp Met Phe Ala Thr Pro
            260                 265                 270
Gln Tyr Arg Gly Val Arg Ala Asp Gly Val Leu Leu Cys Ser Pro Gly
        275                 280                 285
Trp Ser Ala Val Val Pro Ser Trp Leu Leu Thr Ser Ser Asp Leu Pro
    290                 295                 300
Ala Ser Ala Ser Gln Ser Ala Gly Ile Thr Gly Val Phe Leu Gly Leu
305                 310                 315                 320
Gly Leu Ser Gly Ile Ile Pro Thr Leu His Tyr Val Ile Ser Glu Gly
                325                 330                 335
Phe Leu Lys Ala Ala Thr Ile Gly Gln Ile Gly Trp Leu Met Leu Met
            340                 345                 350
Ala Ser Leu Tyr Ile Thr Gly Ala Ala Leu Tyr Ala Ala Arg Ile Pro
        355                 360                 365
Glu Arg Phe Phe Pro Gly Lys Cys Asp Ile Trp Phe His Ser His Gln
    370                 375                 380
Leu Phe His Ile Phe Val Val Ala Gly Ala Phe Val His Phe His Gly
385                 390                 395                 400
Val Ser Asn Leu Gln Glu Phe Arg Phe Met Ile Gly Gly Gly Cys Ser
                405                 410                 415
Glu Glu Asp Ala Leu
            420

<210> SEQ ID NO 105
<211> LENGTH: 17
<212> TYPE: PRT
<213> ORGANISM: Homo sapiens

<400> SEQUENCE: 105

His His Thr Met Glu Lys Met Glu Glu Phe Val Tyr Lys Leu Gln Thr
1               5                   10                  15
Ser

<210> SEQ ID NO 106
<211> LENGTH: 10
<212> TYPE: PRT
<213> ORGANISM: Homo sapiens

<400> SEQUENCE: 106
```

```
Met Ser Ser His Lys Gly Ser Val Val Ala
1               5                   10
```

<210> SEQ ID NO 107
<211> LENGTH: 13
<212> TYPE: PRT
<213> ORGANISM: Homo sapiens

<400> SEQUENCE: 107

```
Asn Gly Ala Pro Ala Ser Asn Arg Glu Thr Asp Met Val
1               5                   10
```

<210> SEQ ID NO 108
<211> LENGTH: 13
<212> TYPE: PRT
<213> ORGANISM: Homo sapiens

<400> SEQUENCE: 108

```
His Thr Glu Thr Gly Ser Ser Arg Thr His Leu Leu Gly
1               5                   10
```

<210> SEQ ID NO 109
<211> LENGTH: 13
<212> TYPE: PRT
<213> ORGANISM: Homo sapiens

<400> SEQUENCE: 109

```
Thr Val Tyr Cys His Ser Glu Lys Val Ser Arg Thr Phe
1               5                   10
```

<210> SEQ ID NO 110
<211> LENGTH: 13
<212> TYPE: PRT
<213> ORGANISM: Homo sapiens

<400> SEQUENCE: 110

```
Trp Asp Arg Phe Val Thr Pro Lys His Arg Gln Thr Arg
1               5                   10
```

<210> SEQ ID NO 111
<211> LENGTH: 14
<212> TYPE: PRT
<213> ORGANISM: Homo sapiens

<400> SEQUENCE: 111

```
Asn Gly Ala Pro Ala Ser Asn Arg Glu Thr Asp Met Val Glu
1               5                   10
```

<210> SEQ ID NO 112
<211> LENGTH: 16
<212> TYPE: PRT
<213> ORGANISM: Homo sapiens

<400> SEQUENCE: 112

```
Met Ser Ser His Lys Gly Ser Val Val Ala Arg Asn Gly Ala Pro Ala
1               5                   10                  15
```

<210> SEQ ID NO 113
<211> LENGTH: 16
<212> TYPE: PRT
<213> ORGANISM: Homo sapiens

<400> SEQUENCE: 113

```
Val Val Ala Arg Asn Gly Ala Pro Ala Ser Asn Arg Glu Thr Asp Met
1               5                   10                  15
```

-continued

<210> SEQ ID NO 114
<211> LENGTH: 16
<212> TYPE: PRT
<213> ORGANISM: Homo sapiens

<400> SEQUENCE: 114

Ile His Thr Glu Thr Gly Ser Ser Arg Thr His Leu Leu Gly Phe Val
1               5                   10                  15

<210> SEQ ID NO 115
<211> LENGTH: 16
<212> TYPE: PRT
<213> ORGANISM: Homo sapiens

<400> SEQUENCE: 115

Arg Ile Phe Leu Leu Gly Ala Val Leu Ser Leu Ser Phe Ser Trp Leu
1               5                   10                  15

<210> SEQ ID NO 116
<211> LENGTH: 16
<212> TYPE: PRT
<213> ORGANISM: Homo sapiens

<400> SEQUENCE: 116

Arg Gln Thr Arg Ala Gly Val Leu Leu Gly Leu Gly Leu Ser Gly Ile
1               5                   10                  15

<210> SEQ ID NO 117
<211> LENGTH: 16
<212> TYPE: PRT
<213> ORGANISM: Homo sapiens

<400> SEQUENCE: 117

Ala Gly Val Leu Leu Gly Leu Gly Leu Ser Gly Ile Val Pro Thr Met
1               5                   10                  15

<210> SEQ ID NO 118
<211> LENGTH: 16
<212> TYPE: PRT
<213> ORGANISM: Homo sapiens

<400> SEQUENCE: 118

Gly Leu Gly Leu Ser Gly Ile Val Pro Thr Met His Phe Pro Ile Ala
1               5                   10                  15

<210> SEQ ID NO 119
<211> LENGTH: 16
<212> TYPE: PRT
<213> ORGANISM: Homo sapiens

<400> SEQUENCE: 119

Tyr Ile Thr Arg Ala Gly Leu Tyr Ala Ala Leu Ile Pro Glu Arg Phe
1               5                   10                  15

<210> SEQ ID NO 120
<211> LENGTH: 25
<212> TYPE: PRT
<213> ORGANISM: Homo sapiens

<400> SEQUENCE: 120

Trp Thr His Leu Leu Gly Cys Val Phe Phe Leu Cys Leu Gly Ile Phe
1               5                   10                  15

Tyr Met Phe Arg Pro Asn Ile Ser Phe 20              25

<210> SEQ ID NO 121
<211> LENGTH: 33
<212> TYPE: PRT
<213> ORGANISM: Homo sapiens

<400> SEQUENCE: 121

Ala Pro Leu Gln Glu Lys Val Val Phe Gly Leu Phe Phe Leu Gly Ala
1               5                   10                  15

Ile Leu Cys Leu Ser Phe Ser Trp Leu Phe His Thr Val Tyr Cys His
            20                  25                  30

Ser

<210> SEQ ID NO 122
<211> LENGTH: 21
<212> TYPE: PRT
<213> ORGANISM: Homo sapiens

<400> SEQUENCE: 122

Lys Leu Asp Tyr Ser Gly Ile Ala Leu Leu Ile Met Gly Ser Phe Val
1               5                   10                  15

Pro Trp Leu Tyr Tyr
            20

<210> SEQ ID NO 123
<211> LENGTH: 26
<212> TYPE: PRT
<213> ORGANISM: Homo sapiens

<400> SEQUENCE: 123

Pro Gln Pro Cys Phe Ile Tyr Leu Ile Val Ile Cys Val Leu Gly Ile
1               5                   10                  15

Ala Ala Ile Ile Val Ser Gln Trp Asp Met
            20                  25

<210> SEQ ID NO 124
<211> LENGTH: 23
<212> TYPE: PRT
<213> ORGANISM: Homo sapiens

<400> SEQUENCE: 124

Val Leu Leu Cys Ser Pro Gly Trp Ser Ala Val Val Pro Ser Trp Leu
1               5                   10                  15

Leu Thr Ser Ser Asp Leu Pro
            20

<210> SEQ ID NO 125
<211> LENGTH: 29
<212> TYPE: PRT
<213> ORGANISM: Homo sapiens

<400> SEQUENCE: 125

Ser Gln Ser Ala Gly Ile Thr Gly Val Phe Leu Gly Leu Gly Leu Ser
1               5                   10                  15

Gly Ile Ile Pro Thr Leu His Tyr Val Ile Ser Glu Gly
            20                  25

<210> SEQ ID NO 126
<211> LENGTH: 29
<212> TYPE: PRT
<213> ORGANISM: Homo sapiens

```
<400> SEQUENCE: 126

Phe Leu Lys Ala Ala Thr Ile Gly Gln Ile Gly Trp Leu Met Leu Met
1               5                   10                  15

Ala Ser Leu Tyr Ile Thr Gly Ala Ala Leu Tyr Ala Ala
            20                  25

<210> SEQ ID NO 127
<211> LENGTH: 19
<212> TYPE: PRT
<213> ORGANISM: Homo sapiens

<400> SEQUENCE: 127

Ser His Gln Leu Phe His Ile Phe Val Val Ala Gly Ala Phe Val His
1               5                   10                  15

Phe His Gly

<210> SEQ ID NO 128
<211> LENGTH: 8
<212> TYPE: PRT
<213> ORGANISM: Homo sapiens

<400> SEQUENCE: 128

Glu Gly Val Ser Arg Leu Phe Ser
1               5

<210> SEQ ID NO 129
<211> LENGTH: 5
<212> TYPE: PRT
<213> ORGANISM: Homo sapiens

<400> SEQUENCE: 129

Ser Phe Tyr Cys Asn
1               5

<210> SEQ ID NO 130
<211> LENGTH: 13
<212> TYPE: PRT
<213> ORGANISM: Homo sapiens

<400> SEQUENCE: 130

Phe Ala Thr Pro Gln Tyr Arg Gly Val Arg Ala Asp Gly
1               5                   10

<210> SEQ ID NO 131
<211> LENGTH: 16
<212> TYPE: PRT
<213> ORGANISM: Homo sapiens

<400> SEQUENCE: 131

Arg Ile Pro Glu Arg Phe Phe Pro Gly Lys Cys Asp Ile Trp Phe His
1               5                   10                  15

<210> SEQ ID NO 132
<211> LENGTH: 20
<212> TYPE: PRT
<213> ORGANISM: Homo sapiens

<400> SEQUENCE: 132

Leu Ser Ser His His Lys Lys Ser Ser Glu Glu His Glu Tyr Ser Asp
1               5                   10                  15

Glu Ala Pro Tyr
            20
```

<210> SEQ ID NO 133
<211> LENGTH: 18
<212> TYPE: PRT
<213> ORGANISM: Homo sapiens

<400> SEQUENCE: 133

Ser Ser His His Lys Lys Ser Ser Glu Glu His Glu Tyr Ser Asp Glu
1               5                   10                  15

Ala Pro

<210> SEQ ID NO 134
<211> LENGTH: 13
<212> TYPE: PRT
<213> ORGANISM: Homo sapiens

<400> SEQUENCE: 134

His Gln Leu Asp Gly Thr Arg Arg Gly Asp Asn Asp Ser
1               5                   10

<210> SEQ ID NO 135
<211> LENGTH: 13
<212> TYPE: PRT
<213> ORGANISM: Homo sapiens

<400> SEQUENCE: 135

Arg Pro Pro Met Pro Ser Phe Arg Ala Cys Phe Lys Ser
1               5                   10

<210> SEQ ID NO 136
<211> LENGTH: 14
<212> TYPE: PRT
<213> ORGANISM: Homo sapiens

<400> SEQUENCE: 136

Ser His His Lys Lys Ser Ser Glu Glu His Glu Tyr Ser Asp
1               5                   10

<210> SEQ ID NO 137
<211> LENGTH: 14
<212> TYPE: PRT
<213> ORGANISM: Homo sapiens

<400> SEQUENCE: 137

Val Ser Arg Leu Phe Ser Lys Leu Asp Tyr Ser Gly Ile Ala
1               5                   10

<210> SEQ ID NO 138
<211> LENGTH: 14
<212> TYPE: PRT
<213> ORGANISM: Homo sapiens

<400> SEQUENCE: 138

Ala Ala Ile Ile Val Ser Gln Trp Asp Met Phe Ala Thr Pro
1               5                   10

<210> SEQ ID NO 139
<211> LENGTH: 14
<212> TYPE: PRT
<213> ORGANISM: Homo sapiens

<400> SEQUENCE: 139

Pro Ser Trp Leu Leu Thr Ser Ser Asp Leu Pro Ala Ser Ala
1               5                   10

<210> SEQ ID NO 140
<211> LENGTH: 11
<212> TYPE: PRT
<213> ORGANISM: Homo sapiens

<400> SEQUENCE: 140

Ile Gly Gly Gly Cys Ser Glu Glu Asp Ala Leu
1               5                   10

<210> SEQ ID NO 141
<211> LENGTH: 14
<212> TYPE: PRT
<213> ORGANISM: Homo sapiens

<400> SEQUENCE: 141

Leu Ser Ser His His Lys Lys Ser Ser Glu Glu His Glu Tyr
1               5                   10

<210> SEQ ID NO 142
<211> LENGTH: 14
<212> TYPE: PRT
<213> ORGANISM: Homo sapiens

<400> SEQUENCE: 142

Thr Arg Arg Gly Asp Asn Asp Ser His Gln Gly Asp Leu Glu
1               5                   10

<210> SEQ ID NO 143
<211> LENGTH: 14
<212> TYPE: PRT
<213> ORGANISM: Homo sapiens

<400> SEQUENCE: 143

Tyr Met Phe Arg Pro Asn Ile Ser Phe Val Ala Pro Leu Gln
1               5                   10

<210> SEQ ID NO 144
<211> LENGTH: 16
<212> TYPE: PRT
<213> ORGANISM: Homo sapiens

<400> SEQUENCE: 144

Gly His Gln Leu Asp Gly Thr Arg Arg Gly Asp Asn Asp Ser His Gln
1               5                   10                  15

<210> SEQ ID NO 145
<211> LENGTH: 16
<212> TYPE: PRT
<213> ORGANISM: Homo sapiens

<400> SEQUENCE: 145

Ile His Thr Glu Thr Gly Asn Ile Trp Thr His Leu Leu Gly Cys Val
1               5                   10                  15

<210> SEQ ID NO 146
<211> LENGTH: 16
<212> TYPE: PRT
<213> ORGANISM: Homo sapiens

<400> SEQUENCE: 146

Gly Leu Phe Phe Leu Gly Ala Ile Leu Cys Leu Ser Phe Ser Trp Leu
1               5                   10                  15

<210> SEQ ID NO 147
<211> LENGTH: 16
<212> TYPE: PRT
<213> ORGANISM: Homo sapiens

<400> SEQUENCE: 147

Gly Val Arg Ala Asp Gly Val Leu Leu Cys Ser Pro Gly Trp Ser Ala
1               5                   10                  15

<210> SEQ ID NO 148
<211> LENGTH: 16
<212> TYPE: PRT
<213> ORGANISM: Homo sapiens

<400> SEQUENCE: 148

Ser Ala Gly Ile Thr Gly Val Phe Leu Gly Leu Gly Leu Ser Gly Ile
1               5                   10                  15

<210> SEQ ID NO 149
<211> LENGTH: 16
<212> TYPE: PRT
<213> ORGANISM: Homo sapiens

<400> SEQUENCE: 149

Thr Gly Val Phe Leu Gly Leu Gly Leu Ser Gly Ile Ile Pro Thr Leu
1               5                   10                  15

<210> SEQ ID NO 150
<211> LENGTH: 16
<212> TYPE: PRT
<213> ORGANISM: Homo sapiens

<400> SEQUENCE: 150

Gly Leu Gly Leu Ser Gly Ile Ile Pro Thr Leu His Tyr Val Ile Ser
1               5                   10                  15

<210> SEQ ID NO 151
<211> LENGTH: 15
<212> TYPE: PRT
<213> ORGANISM: Homo sapiens

<400> SEQUENCE: 151

Phe Arg Phe Met Ile Gly Gly Gly Cys Ser Glu Glu Asp Ala Leu
1               5                   10                  15

<210> SEQ ID NO 152
<211> LENGTH: 13
<212> TYPE: PRT
<213> ORGANISM: Homo sapiens

<400> SEQUENCE: 152

Leu Asp Gly Thr Arg Arg Gly Asp Asn Asp Ser His Gln
1               5                   10

<210> SEQ ID NO 153
<211> LENGTH: 1149
<212> TYPE: DNA
<213> ORGANISM: Homo sapiens

<400> SEQUENCE: 153
atgtcttctc acaaagggtc tgtggtggca taggaatggg gctcctgcca gtaacaggga      60
aactgacatg gtggaactgg ctgaactctg aattgtgacc cctgctacaa gagaagggca     120
aatgggtaat caccaaccca aacaaagctg aagaagagca acatgccca gtgccccagg      180

-continued

```
aagaagagga ggaggtgtgg gtactgacac ttcccctgca agcccaccac accatggaga      240
agatggagga gtttgtgtac aagagctcca gacaagctgc tgccaccatc aatatgatgg      300
gctccctgac tggctgaagg acaatgactg tctgcaggac aatgactgtc tgctctatgg      360
ccatagacaa cccatgtcct ccttctgggc ttgcttcaag agcatcttct atatccatac      420
agaaaccggc agcagccgga cacatctgct tggtttcgtg ctgtttctct ttttggaaat      480
cttgaccatg ctcagaccaa atatgtactt cacggcccct ctacaggaga aagtgatttg      540
gaggatattc cttttgggtg cagtgctcta gcctcagctt ctcctggctc gtccgcactg      600
tctactgtca ttcagagaaa gtctctcgga ctttttccaa actgtactat tcagggattg      660
ctccactgct cataaggagc ttcgtcccct ggctctgtta ctccttctac tgctcgccac      720
agccacggct catctacttc tccatcatct atgtcctggg catctctgcc atcattgtga      780
cagtgggacc ggtttgtcac tcctaagcac cggcagacaa gggcaggggt gttgctggga      840
cttggcttga gcggtattgt gcccaccatg cactttccta ttgctgaggg tttcgtcaag      900
gccaccacag tgggccagat gggctggttc ttcctcgtgg ctgtgatgta catcaccaga      960
gctggccttt atgctgctta aattcctgag cgcttctttc ctggaaaatt agacatatgg     1020
ttccagtctc agcagatttt ccatgtcctc atggtgacgg tggcctttgt ccacttctgt     1080
ggggtctcca accttcagga attccattac agccgagaag gtgactgcac tgatgactcc     1140
cttctctga                                                              1149

<210> SEQ ID NO 154
<211> LENGTH: 31
<212> TYPE: DNA
<213> ORGANISM: Homo sapiens

<400> SEQUENCE: 154
atgtcttctc acaagggtc tgtggtggca a                                       31

<210> SEQ ID NO 155
<211> LENGTH: 25
<212> TYPE: DNA
<213> ORGANISM: Homo sapiens

<400> SEQUENCE: 155
tcagagttca gccagttcca ccatg                                             25

<210> SEQ ID NO 156
<211> LENGTH: 28
<212> TYPE: DNA
<213> ORGANISM: Homo sapiens

<400> SEQUENCE: 156
ctggctgaat ctgaattgtc acccctgc                                          28

<210> SEQ ID NO 157
<211> LENGTH: 29
<212> TYPE: DNA
<213> ORGANISM: Homo sapiens

<400> SEQUENCE: 157
gcttgtctgg agcttgtaca caaactcct                                         29

<210> SEQ ID NO 158
<211> LENGTH: 32
<212> TYPE: DNA
<213> ORGANISM: Homo sapiens
```

<400> SEQUENCE: 158
aggagtttgt gtacaagctc cagacaagct gc					32

<210> SEQ ID NO 159
<211> LENGTH: 27
<212> TYPE: DNA
<213> ORGANISM: Homo sapiens

<400> SEQUENCE: 159
gagcactgca cccaaaagga atatcct						27

<210> SEQ ID NO 160
<211> LENGTH: 25
<212> TYPE: DNA
<213> ORGANISM: Homo sapiens

<400> SEQUENCE: 160
tttgggtgca gtgctcagcc tcagc						25

<210> SEQ ID NO 161
<211> LENGTH: 28
<212> TYPE: DNA
<213> ORGANISM: Homo sapiens

<400> SEQUENCE: 161
tcacaatgat ggcagagatg cccaggac						28

<210> SEQ ID NO 162
<211> LENGTH: 31
<212> TYPE: DNA
<213> ORGANISM: Homo sapiens

<400> SEQUENCE: 162
catctctgcc atcattgtgg accagtggga c					31

<210> SEQ ID NO 163
<211> LENGTH: 24
<212> TYPE: DNA
<213> ORGANISM: Homo sapiens

<400> SEQUENCE: 163
tcagagaagg gagtcatcag tgca						24

<210> SEQ ID NO 164
<211> LENGTH: 1442
<212> TYPE: DNA
<213> ORGANISM: Rattus norvegicus
<220> FEATURE:
<221> NAME/KEY: CDS
<222> LOCATION: (225)..(1349)

<400> SEQUENCE: 164
ccacgcgtcc gcccacgcgt ccgcgggcag ggcgctgagg atccggcgcc cctcggccgc			60 aggccgcctc cagagccgcg ggatgtagcg ccccggcctg cggcccccag cagaggcagc			120 cagccaggcc tgtccatcat cactgggaga tctctgccct ctgggctga gagaccccaa			180 cctctcctca agctgaagct gcaaggcact gaggtaccag ccag atg tct tcc cac			236
                                              Met Ser Ser His
                                              1 aaa gga tct gcc gtg gcc cag ggc aat ggg gct cct tct agt aac aga			284
Lys Gly Ser Ala Val Ala Gln Gly Asn Gly Ala Pro Ser Ser Asn Arg
 5                  10                  15                  20

```
gaa gcg gac acg gtg gag ctg gct gag ctg ggg ccc ctg ctg gag gag        332
Glu Ala Asp Thr Val Glu Leu Ala Glu Leu Gly Pro Leu Leu Glu Glu
             25                  30                  35 aag ggt aag cgg gca gcc acc agc cca gcc aag gct gaa gaa gaa caa        380
Lys Gly Lys Arg Ala Ala Thr Ser Pro Ala Lys Ala Glu Glu Glu Gln
         40                  45                  50 gca tgc ccc gtg cct cag gag gag gag gag gtg cgg gtg ctg acc            428
Ala Cys Pro Val Pro Gln Glu Glu Glu Glu Val Arg Val Leu Thr
             55                  60                  65 ctt cct ctg caa gcc cac cat gcc atg gag aag atg gag gag ttc gta        476
Leu Pro Leu Gln Ala His His Ala Met Glu Lys Met Glu Glu Phe Val
 70                  75                  80 tat aag gtc tgg gag ggg cgt tgg agg gtc atc cca tac gat gtg ctt        524
Tyr Lys Val Trp Glu Gly Arg Trp Arg Val Ile Pro Tyr Asp Val Leu
 85                  90                  95                 100 cct gac tgg ctg aaa gac aat gac tac ctg cta cat ggc cac aga cca        572
Pro Asp Trp Leu Lys Asp Asn Asp Tyr Leu Leu His Gly His Arg Pro
                105                 110                 115 cct atg ccc tcc ttc cgg gct tgc ttc aag agc atc ttc cgc atc cac        620
Pro Met Pro Ser Phe Arg Ala Cys Phe Lys Ser Ile Phe Arg Ile His
            120                 125                 130 aca gaa act ggc aac atc tgg aca cat ttg ctt ggt ttt gtg cta ttt        668
Thr Glu Thr Gly Asn Ile Trp Thr His Leu Leu Gly Phe Val Leu Phe
            135                 140                 145 ctc ttt ctg gga atc ttg acc atg ctc aga cca aat atg tac ttc atg        716
Leu Phe Leu Gly Ile Leu Thr Met Leu Arg Pro Asn Met Tyr Phe Met
150                 155                 160 gct ccc ctc cag gag aag gtg gtc ttc ggg atg ttc ttc ctg ggt gca        764
Ala Pro Leu Gln Glu Lys Val Val Phe Gly Met Phe Phe Leu Gly Ala
165                 170                 175                 180 gtg ctc tgc ctc agc ttc tcc tgg ctt ttc cac acc gtc tac tgt cat        812
Val Leu Cys Leu Ser Phe Ser Trp Leu Phe His Thr Val Tyr Cys His
                185                 190                 195 tca gag aag gtc tct cgc act ttt tcc aaa ctg gac tat tca ggg att        860
Ser Glu Lys Val Ser Arg Thr Phe Ser Lys Leu Asp Tyr Ser Gly Ile
            200                 205                 210 gct cta ctg att atg ggg agc ttc gtc ccc tgg ctc tat tac tcc ttc        908
Ala Leu Leu Ile Met Gly Ser Phe Val Pro Trp Leu Tyr Tyr Ser Phe
            215                 220                 225 tac tgc tcc cca cag cca cgg ctc atc tac ctc tcc atc gtc tgt gtc        956
Tyr Cys Ser Pro Gln Pro Arg Leu Ile Tyr Leu Ser Ile Val Cys Val
230                 235                 240 ctg ggc atc tct gcc atc att gtg gca cag tgg gac cgg ttt gcc act       1004
Leu Gly Ile Ser Ala Ile Ile Val Ala Gln Trp Asp Arg Phe Ala Thr
245                 250                 255                 260 ccc aag cac cgg cag aca aga gca gga gtg ttc ctg gga ctt ggc ttg       1052
Pro Lys His Arg Gln Thr Arg Ala Gly Val Phe Leu Gly Leu Gly Leu
                265                 270                 275 agt ggt gtt gta ccc acc atg cac ttt act atc gct gag ggc ttt gtc       1100
Ser Gly Val Val Pro Thr Met His Phe Thr Ile Ala Glu Gly Phe Val
            280                 285                 290 aag gcc acc aca gtg ggc cag atg ggc tgg ttc ttc ctc atg gct gtg       1148
Lys Ala Thr Thr Val Gly Gln Met Gly Trp Phe Phe Leu Met Ala Val
            295                 300                 305 atg tac atc acc ggc gct ggc ctt tat gct gct cgg att cct gag cgc       1196
Met Tyr Ile Thr Gly Ala Gly Leu Tyr Ala Ala Arg Ile Pro Glu Arg
310                 315                 320 ttc ttt cct gga aaa ttt gac ata tgg ttc cag tct cat cag att ttc       1244
Phe Phe Pro Gly Lys Phe Asp Ile Trp Phe Gln Ser His Gln Ile Phe
```

```
                325                 330                 335                 340
cat gtc ctg gtg gtg gca gcg gct ttc gtc cac ttc tat ggg gtg tcc      1292
His Val Leu Val Val Ala Ala Ala Phe Val His Phe Tyr Gly Val Ser
                345                 350                 355 aac cta cag gaa ttc cgt tac ggc cta gag ggt gga tgt acc gat gac      1340
Asn Leu Gln Glu Phe Arg Tyr Gly Leu Glu Gly Gly Cys Thr Asp Asp
        360                 365                 370 tcc ctt ctc tgagccttcc cacctgaggg ttggtggagg aacttcccca              1389
Ser Leu Leu
        375 agtgctttta aaataacttc ctttgctgaa gtacgagaaa aaaaaaaaaa aaa           1442
```

<210> SEQ ID NO 165
<211> LENGTH: 375
<212> TYPE: PRT
<213> ORGANISM: Rattus norvegicus

<400> SEQUENCE: 165

```
Met Ser Ser His Lys Gly Ser Ala Val Ala Gln Gly Asn Gly Ala Pro
1               5                   10                  15

Ser Ser Asn Arg Glu Ala Asp Thr Val Glu Leu Ala Glu Leu Gly Pro
            20                  25                  30

Leu Leu Glu Glu Lys Gly Lys Arg Ala Ala Thr Ser Pro Ala Lys Ala
        35                  40                  45

Glu Glu Glu Gln Ala Cys Pro Val Pro Gln Glu Glu Glu Glu Val
    50                  55                  60

Arg Val Leu Thr Leu Pro Leu Gln Ala His His Ala Met Glu Lys Met
65                  70                  75                  80

Glu Glu Phe Val Tyr Lys Val Trp Glu Gly Arg Trp Arg Val Ile Pro
                85                  90                  95

Tyr Asp Val Leu Pro Asp Trp Leu Lys Asp Asn Asp Tyr Leu Leu His
            100                 105                 110

Gly His Arg Pro Pro Met Pro Ser Phe Arg Ala Cys Phe Lys Ser Ile
        115                 120                 125

Phe Arg Ile His Thr Glu Thr Gly Asn Ile Trp Thr His Leu Leu Gly
    130                 135                 140

Phe Val Leu Phe Leu Phe Leu Gly Ile Leu Thr Met Leu Arg Pro Asn
145                 150                 155                 160

Met Tyr Phe Met Ala Pro Leu Gln Glu Lys Val Val Phe Gly Met Phe
                165                 170                 175

Phe Leu Gly Ala Val Leu Cys Leu Ser Phe Ser Trp Leu Phe His Thr
            180                 185                 190

Val Tyr Cys His Ser Glu Lys Val Ser Arg Thr Phe Ser Lys Leu Asp
        195                 200                 205

Tyr Ser Gly Ile Ala Leu Leu Ile Met Gly Ser Phe Val Pro Trp Leu
    210                 215                 220

Tyr Tyr Ser Phe Tyr Cys Ser Pro Gln Pro Arg Leu Ile Tyr Leu Ser
225                 230                 235                 240

Ile Val Cys Val Leu Gly Ile Ser Ala Ile Val Ala Gln Trp Asp
                245                 250                 255

Arg Phe Ala Thr Pro Lys His Arg Gln Thr Arg Ala Gly Val Phe Leu
            260                 265                 270

Gly Leu Gly Leu Ser Gly Val Val Pro Thr Met His Phe Thr Ile Ala
        275                 280                 285

Glu Gly Phe Val Lys Ala Thr Thr Val Gly Gln Met Gly Trp Phe Phe
```

```
                 290                 295                 300
Leu Met Ala Val Met Tyr Ile Thr Gly Ala Gly Leu Tyr Ala Ala Arg
305                 310                 315                 320

Ile Pro Glu Arg Phe Phe Pro Gly Lys Phe Asp Ile Trp Phe Gln Ser
                325                 330                 335

His Gln Ile Phe His Val Leu Val Ala Ala Ala Phe Val His Phe
            340                 345                 350

Tyr Gly Val Ser Asn Leu Gln Glu Phe Arg Tyr Gly Leu Glu Gly Gly
        355                 360                 365

Cys Thr Asp Asp Ser Leu Leu
    370                 375

<210> SEQ ID NO 166
<211> LENGTH: 1369
<212> TYPE: DNA
<213> ORGANISM: Rattus norvegicus
<220> FEATURE:
<221> NAME/KEY: CDS
<222> LOCATION: (130)..(1287)

<400> SEQUENCE: 166
gcggcttccc gggctcagca gattgcctgg gtcggaagga gggtcaactc accatcccctt     60 ataaatccat tctcccaaga agaagggaca gaaagaaaga ccactttgta aggaaggctt    120 tggtatccc atg aac gag cca acc gaa cac cga ttg ggg tgc acc agg act    171
           Met Asn Glu Pro Thr Glu His Arg Leu Gly Cys Thr Arg Thr
             1               5                  10 cca gag cca gat ata agg ctc aga aaa ggg cac caa ctt gat gat aca      219
Pro Glu Pro Asp Ile Arg Leu Arg Lys Gly His Gln Leu Asp Asp Thr
 15                  20                  25                  30 agg gga ggt aac aat gac aac cac cac gga gat ttg gag ccc agt tta     267
Arg Gly Gly Asn Asn Asp Asn His His Gly Asp Leu Glu Pro Ser Leu
                 35                  40                  45 gag aca cct gtt tgt tct tcc tac tat gaa aat agc ccc gag gaa ctc     315
Glu Thr Pro Val Cys Ser Ser Tyr Tyr Glu Asn Ser Pro Glu Glu Leu
     50                  55                  60 gag tgt cat gat gac aac tcc caa gaa gat gaa ggg ttt atg ggc atg     363
Glu Cys His Asp Asp Asn Ser Gln Glu Asp Glu Gly Phe Met Gly Met
 65                  70                  75 tcc cct ctc cta caa gcc cat cat gct atg gaa cga atg gaa gag ttt     411
Ser Pro Leu Leu Gln Ala His His Ala Met Glu Arg Met Glu Glu Phe
 80                  85                  90 gtt tgt aag gtg tgg gaa ggt cga tgg cga gtg atc cct cat gat gtg     459
Val Cys Lys Val Trp Glu Gly Arg Trp Arg Val Ile Pro His Asp Val
 95                 100                 105                 110 ctg cca gat tgg ctt aag gac aat gac ttc ctt ctc cat gga cac cgg     507
Leu Pro Asp Trp Leu Lys Asp Asn Asp Phe Leu Leu His Gly His Arg
                115                 120                 125 cct cct atg cct tct ttc cgg gcc tgt ttt aag agc atc ttt aga ata     555
Pro Pro Met Pro Ser Phe Arg Ala Cys Phe Lys Ser Ile Phe Arg Ile
            130                 135                 140 cac aca gag acg ggc aac att tgg aca cat ctc cta ggt tgt gta ttc     603
His Thr Glu Thr Gly Asn Ile Trp Thr His Leu Leu Gly Cys Val Phe
        145                 150                 155 ttc ctg tgc ctg ggg atc ttt tat atg ttt cgc cca aat ata tct ttt     651
Phe Leu Cys Leu Gly Ile Phe Tyr Met Phe Arg Pro Asn Ile Ser Phe
160                 165                 170 gtg gcc cct ctg caa gag aaa gtg gtc ttc ggg ttg ttc ttc ttg gga     699
Val Ala Pro Leu Gln Glu Lys Val Val Phe Gly Leu Phe Phe Leu Gly
175                 180                 185                 190
```

```
gcc att ctc tgc ctt tcc ttt tca tgg ctc ttc cac acg gtg tac tgc      747
Ala Ile Leu Cys Leu Ser Phe Ser Trp Leu Phe His Thr Val Tyr Cys
            195                 200                 205 cac tca gaa ggg gtc tcc cga ctc ttc tct aaa ttg gat tac tct ggt      795
His Ser Glu Gly Val Ser Arg Leu Phe Ser Lys Leu Asp Tyr Ser Gly
            210                 215                 220 att gct ctt ctg atc atg gga agt ttt gtt cct tgg ctt tat tat tct     843
Ile Ala Leu Leu Ile Met Gly Ser Phe Val Pro Trp Leu Tyr Tyr Ser
            225                 230                 235 ttc tac tgt aac cca caa cct tgc ttc atc tac ctg att gtc atc tgt     891
Phe Tyr Cys Asn Pro Gln Pro Cys Phe Ile Tyr Leu Ile Val Ile Cys
    240                 245                 250 gtg ctg ggc att gca gcc att atc gtc tct cag tgg gac atg ttt gcc     939
Val Leu Gly Ile Ala Ala Ile Ile Val Ser Gln Trp Asp Met Phe Ala
255                 260                 265                 270 acc cct cag tat cgg ggg gtc aga gca gga gtg ttc gtg ggc tta ggt     987
Thr Pro Gln Tyr Arg Gly Val Arg Ala Gly Val Phe Val Gly Leu Gly
            275                 280                 285 ctg agt gga atc atc cct acc ttg cat tat gtc atc tca gaa ggg ttc     1035
Leu Ser Gly Ile Ile Pro Thr Leu His Tyr Val Ile Ser Glu Gly Phe
            290                 295                 300 ctg aag gct gcc acc ata agg cag ata ggc tgg cta atg ctc atg gct     1083
Leu Lys Ala Ala Thr Ile Arg Gln Ile Gly Trp Leu Met Leu Met Ala
            305                 310                 315 agc ctc tat atc aca gga gct gcc ctc tac gcg gcc cgt atc cct gag     1131
Ser Leu Tyr Ile Thr Gly Ala Ala Leu Tyr Ala Ala Arg Ile Pro Glu
            320                 325                 330 cgc ttc ttt cct ggc aaa tgt gac atc tgg ttt cac tct cat cag ctc     1179
Arg Phe Phe Pro Gly Lys Cys Asp Ile Trp Phe His Ser His Gln Leu
335                 340                 345                 350 ttc cac atc ttt gtg gtt gct ggt gcc ttt gtt cac ttc cat gga gtc     1227
Phe His Ile Phe Val Val Ala Gly Ala Phe Val His Phe His Gly Val
            355                 360                 365 tca aac ctg cag gaa ttt cgt ttc atg att ggt ggg ggc tgc act gaa     1275
Ser Asn Leu Gln Glu Phe Arg Phe Met Ile Gly Gly Gly Cys Thr Glu
            370                 375                 380 aaa gat gcg ctg tgatactctc caggaaccag ggactttgac cctgagccag         1327
Lys Asp Ala Leu
            385 gcctgcagct cccgcaggcc ttcttactgg ctgtctgtgc ca                      1369

<210> SEQ ID NO 167
<211> LENGTH: 386
<212> TYPE: PRT
<213> ORGANISM: Rattus norvegicus

<400> SEQUENCE: 167

Met Asn Glu Pro Thr Glu His Arg Leu Gly Cys Thr Arg Thr Pro Glu
1               5                   10                  15

Pro Asp Ile Arg Leu Arg Lys Gly His Gln Leu Asp Asp Thr Arg Gly
            20                  25                  30

Gly Asn Asn Asp Asn His His Gly Asp Leu Glu Pro Ser Leu Glu Thr
        35                  40                  45

Pro Val Cys Ser Ser Tyr Tyr Glu Asn Ser Pro Glu Glu Leu Glu Cys
    50                  55                  60

His Asp Asp Asn Ser Gln Glu Asp Glu Gly Phe Met Gly Met Ser Pro
65                  70                  75                  80

Leu Leu Gln Ala His His Ala Met Glu Arg Met Glu Glu Phe Val Cys
```

-continued

```
                85                  90                  95
Lys Val Trp Glu Gly Arg Trp Arg Val Ile Pro His Asp Val Leu Pro
            100                 105                 110
Asp Trp Leu Lys Asp Asn Asp Phe Leu Leu His Gly His Arg Pro Pro
            115                 120                 125
Met Pro Ser Phe Arg Ala Cys Phe Lys Ser Ile Phe Arg Ile His Thr
        130                 135                 140
Glu Thr Gly Asn Ile Trp Thr His Leu Leu Gly Cys Val Phe Phe Leu
145                 150                 155                 160
Cys Leu Gly Ile Phe Tyr Met Phe Arg Pro Asn Ile Ser Phe Val Ala
                165                 170                 175
Pro Leu Gln Glu Lys Val Val Phe Gly Leu Phe Phe Leu Gly Ala Ile
            180                 185                 190
Leu Cys Leu Ser Phe Ser Trp Leu Phe His Thr Val Tyr Cys His Ser
        195                 200                 205
Glu Gly Val Ser Arg Leu Phe Ser Lys Leu Asp Tyr Ser Gly Ile Ala
210                 215                 220
Leu Leu Ile Met Gly Ser Phe Val Pro Trp Leu Tyr Tyr Ser Phe Tyr
225                 230                 235                 240
Cys Asn Pro Gln Pro Cys Phe Ile Tyr Leu Ile Val Ile Cys Val Leu
                245                 250                 255
Gly Ile Ala Ala Ile Ile Val Ser Gln Trp Asp Met Phe Ala Thr Pro
            260                 265                 270
Gln Tyr Arg Gly Val Arg Ala Gly Val Phe Val Gly Leu Gly Leu Ser
        275                 280                 285
Gly Ile Ile Pro Thr Leu His Tyr Val Ile Ser Glu Gly Phe Leu Lys
    290                 295                 300
Ala Ala Thr Ile Arg Gln Ile Gly Trp Leu Met Leu Met Ala Ser Leu
305                 310                 315                 320
Tyr Ile Thr Gly Ala Ala Leu Tyr Ala Ala Arg Ile Pro Glu Arg Phe
                325                 330                 335
Phe Pro Gly Lys Cys Asp Ile Trp Phe His Ser His Gln Leu Phe His
            340                 345                 350
Ile Phe Val Val Ala Gly Ala Phe Val His Phe His Gly Val Ser Asn
        355                 360                 365
Leu Gln Glu Phe Arg Phe Met Ile Gly Gly Gly Cys Thr Glu Lys Asp
    370                 375                 380
Ala Leu
385

<210> SEQ ID NO 168
<211> LENGTH: 26
<212> TYPE: PRT
<213> ORGANISM: Rattus norvegicus

<400> SEQUENCE: 168

Asn Ile Trp Thr His Leu Leu Gly Phe Val Leu Phe Leu Phe Leu Gly
1               5                   10                  15
Ile Leu Thr Met Leu Arg Pro Asn Met Tyr
            20                  25

<210> SEQ ID NO 169
<211> LENGTH: 26
<212> TYPE: PRT
<213> ORGANISM: Rattus norvegicus
```

```
<400> SEQUENCE: 169

Leu Gln Glu Lys Val Val Phe Gly Met Phe Phe Leu Gly Ala Val Leu
1               5                   10                  15

Cys Leu Ser Phe Ser Trp Leu Phe His Thr
            20                  25

<210> SEQ ID NO 170
<211> LENGTH: 20
<212> TYPE: PRT
<213> ORGANISM: Rattus norvegicus

<400> SEQUENCE: 170

Asp Tyr Ser Gly Ile Ala Leu Leu Ile Met Gly Ser Phe Val Pro Trp
1               5                   10                  15

Leu Tyr Tyr Ser
            20

<210> SEQ ID NO 171
<211> LENGTH: 22
<212> TYPE: PRT
<213> ORGANISM: Rattus norvegicus

<400> SEQUENCE: 171

Pro Arg Leu Ile Tyr Leu Ser Ile Val Cys Val Leu Gly Ile Ser Ala
1               5                   10                  15

Ile Ile Val Ala Gln Trp
            20

<210> SEQ ID NO 172
<211> LENGTH: 23
<212> TYPE: PRT
<213> ORGANISM: Rattus norvegicus

<400> SEQUENCE: 172

Val Phe Leu Gly Leu Gly Leu Ser Gly Val Val Pro Thr Met His Phe
1               5                   10                  15

Thr Ile Ala Glu Gly Phe Val
            20

<210> SEQ ID NO 173
<211> LENGTH: 23
<212> TYPE: PRT
<213> ORGANISM: Rattus norvegicus

<400> SEQUENCE: 173

Gly Gln Met Gly Trp Phe Phe Leu Met Ala Val Met Tyr Ile Thr Gly
1               5                   10                  15

Ala Gly Leu Tyr Ala Ala Arg
            20

<210> SEQ ID NO 174
<211> LENGTH: 18
<212> TYPE: PRT
<213> ORGANISM: Rattus norvegicus

<400> SEQUENCE: 174

His Gln Ile Phe His Val Leu Val Val Ala Ala Ala Phe Val His Phe
1               5                   10                  15

Tyr Gly

<210> SEQ ID NO 175
```

-continued

```
<211> LENGTH: 22
<212> TYPE: PRT
<213> ORGANISM: Rattus norvegicus

<400> SEQUENCE: 175

Thr His Leu Leu Gly Cys Val Phe Phe Leu Cys Leu Gly Ile Phe Tyr
1               5                   10                  15

Met Phe Arg Pro Asn Ile
            20

<210> SEQ ID NO 176
<211> LENGTH: 24
<212> TYPE: PRT
<213> ORGANISM: Rattus norvegicus

<400> SEQUENCE: 176

Leu Gln Glu Lys Val Val Phe Gly Leu Phe Phe Leu Gly Ala Ile Leu
1               5                   10                  15

Cys Leu Ser Phe Ser Trp Leu Phe
            20

<210> SEQ ID NO 177
<211> LENGTH: 19
<212> TYPE: PRT
<213> ORGANISM: Rattus norvegicus

<400> SEQUENCE: 177

Lys Leu Asp Tyr Ser Gly Ile Ala Leu Leu Ile Met Gly Ser Phe Val
1               5                   10                  15

Pro Trp Leu

<210> SEQ ID NO 178
<211> LENGTH: 24
<212> TYPE: PRT
<213> ORGANISM: Rattus norvegicus

<400> SEQUENCE: 178

Pro Gln Pro Cys Phe Ile Tyr Leu Ile Val Ile Cys Val Leu Gly Ile
1               5                   10                  15

Ala Ala Ile Ile Val Ser Gln Trp
            20

<210> SEQ ID NO 179
<211> LENGTH: 25
<212> TYPE: PRT
<213> ORGANISM: Rattus norvegicus

<400> SEQUENCE: 179

Ala Gly Val Phe Val Gly Leu Gly Leu Ser Gly Ile Ile Pro Thr Leu
1               5                   10                  15

His Tyr Val Ile Ser Glu Gly Phe Leu
            20                  25

<210> SEQ ID NO 180
<211> LENGTH: 21
<212> TYPE: PRT
<213> ORGANISM: Rattus norvegicus

<400> SEQUENCE: 180

Thr Ile Arg Gln Ile Gly Trp Leu Met Leu Met Ala Ser Leu Tyr Ile
1               5                   10                  15

Thr Gly Ala Ala Leu
```

```
                20

<210> SEQ ID NO 181
<211> LENGTH: 17
<212> TYPE: PRT
<213> ORGANISM: Rattus norvegicus

<400> SEQUENCE: 181

His Gln Leu Phe His Ile Phe Val Val Ala Gly Ala Phe Val His Phe
1               5                   10                  15

His

<210> SEQ ID NO 182
<211> LENGTH: 15
<212> TYPE: PRT
<213> ORGANISM: Rattus norvegicus

<400> SEQUENCE: 182

Val Tyr Cys His Ser Glu Lys Val Ser Arg Thr Phe Ser Lys Leu
1               5                   10                  15

<210> SEQ ID NO 183
<211> LENGTH: 6
<212> TYPE: PRT
<213> ORGANISM: Rattus norvegicus

<400> SEQUENCE: 183

Phe Tyr Cys Ser Pro Gln
1               5

<210> SEQ ID NO 184
<211> LENGTH: 14
<212> TYPE: PRT
<213> ORGANISM: Rattus norvegicus

<400> SEQUENCE: 184

Asp Arg Phe Ala Thr Pro Lys His Arg Gln Thr Arg Ala Gly
1               5                   10

<210> SEQ ID NO 185
<211> LENGTH: 5
<212> TYPE: PRT
<213> ORGANISM: Rattus norvegicus

<400> SEQUENCE: 185

Lys Ala Thr Thr Val
1               5

<210> SEQ ID NO 186
<211> LENGTH: 16
<212> TYPE: PRT
<213> ORGANISM: Rattus norvegicus

<400> SEQUENCE: 186

Ile Pro Glu Arg Phe Phe Pro Gly Lys Phe Asp Ile Trp Phe Gln Ser
1               5                   10                  15

<210> SEQ ID NO 187
<211> LENGTH: 14
<212> TYPE: PRT
<213> ORGANISM: Rattus norvegicus

<400> SEQUENCE: 187

Tyr Met Phe Arg Pro Asn Ile Ser Phe Val Ala Pro Leu Gln
```

```
                1               5                  10

<210> SEQ ID NO 188
<211> LENGTH: 10
<212> TYPE: PRT
<213> ORGANISM: Rattus norvegicus

<400> SEQUENCE: 188

Met Ser Ser His Lys Gly Ser Ala Val Ala
1               5                  10

<210> SEQ ID NO 189
<211> LENGTH: 13
<212> TYPE: PRT
<213> ORGANISM: Rattus norvegicus

<400> SEQUENCE: 189

Asn Gly Ala Pro Ser Ser Asn Arg Glu Ala Asp Thr Val
1               5                  10

<210> SEQ ID NO 190
<211> LENGTH: 13
<212> TYPE: PRT
<213> ORGANISM: Rattus norvegicus

<400> SEQUENCE: 190

Arg Pro Pro Met Pro Ser Phe Arg Ala Cys Phe Lys Ser
1               5                  10

<210> SEQ ID NO 191
<211> LENGTH: 13
<212> TYPE: PRT
<213> ORGANISM: Rattus norvegicus

<400> SEQUENCE: 191

Thr Val Tyr Cys His Ser Glu Lys Val Ser Arg Thr Phe
1               5                  10

<210> SEQ ID NO 192
<211> LENGTH: 13
<212> TYPE: PRT
<213> ORGANISM: Rattus norvegicus

<400> SEQUENCE: 192

Trp Asp Arg Phe Ala Thr Pro Lys His Arg Gln Thr Arg
1               5                  10

<210> SEQ ID NO 193
<211> LENGTH: 14
<212> TYPE: PRT
<213> ORGANISM: Rattus norvegicus

<400> SEQUENCE: 193

Asn Gly Ala Pro Ser Ser Asn Arg Glu Ala Asp Thr Val Glu
1               5                  10

<210> SEQ ID NO 194
<211> LENGTH: 14
<212> TYPE: PRT
<213> ORGANISM: Rattus norvegicus

<400> SEQUENCE: 194

Val Ser Arg Thr Phe Ser Lys Leu Asp Tyr Ser Gly Ile Ala
1               5                  10
```

```
<210> SEQ ID NO 195
<211> LENGTH: 14
<212> TYPE: PRT
<213> ORGANISM: Rattus norvegicus

<400> SEQUENCE: 195

Pro Thr Met His Phe Thr Ile Ala Glu Gly Phe Val Lys Ala
1               5                   10

<210> SEQ ID NO 196
<211> LENGTH: 17
<212> TYPE: PRT
<213> ORGANISM: Rattus norvegicus

<400> SEQUENCE: 196

His His Ala Met Glu Lys Met Glu Glu Phe Val Tyr Lys Val Trp Glu
1               5                   10                  15

Gly

<210> SEQ ID NO 197
<211> LENGTH: 16
<212> TYPE: PRT
<213> ORGANISM: Rattus norvegicus

<400> SEQUENCE: 197

Met Ser Ser His Lys Gly Ser Ala Val Ala Gln Gly Asn Gly Ala Pro
1               5                   10                  15

<210> SEQ ID NO 198
<211> LENGTH: 16
<212> TYPE: PRT
<213> ORGANISM: Rattus norvegicus

<400> SEQUENCE: 198

Val Ala Gln Gly Asn Gly Ala Pro Ser Ser Asn Arg Glu Ala Asp Thr
1               5                   10                  15

<210> SEQ ID NO 199
<211> LENGTH: 16
<212> TYPE: PRT
<213> ORGANISM: Rattus norvegicus

<400> SEQUENCE: 199

Ile His Thr Glu Thr Gly Asn Ile Trp Thr His Leu Leu Gly Phe Val
1               5                   10                  15

<210> SEQ ID NO 200
<211> LENGTH: 16
<212> TYPE: PRT
<213> ORGANISM: Rattus norvegicus

<400> SEQUENCE: 200

Gly Met Phe Phe Leu Gly Ala Val Leu Cys Leu Ser Phe Ser Trp Leu
1               5                   10                  15

<210> SEQ ID NO 201
<211> LENGTH: 16
<212> TYPE: PRT
<213> ORGANISM: Rattus norvegicus

<400> SEQUENCE: 201

Arg Gln Thr Arg Ala Gly Val Phe Leu Gly Leu Gly Leu Ser Gly Val
1               5                   10                  15
```

```
<210> SEQ ID NO 202
<211> LENGTH: 16
<212> TYPE: PRT
<213> ORGANISM: Rattus norvegicus

<400> SEQUENCE: 202

Ala Gly Val Phe Leu Gly Leu Gly Leu Ser Gly Val Val Pro Thr Met
1               5                   10                  15

<210> SEQ ID NO 203
<211> LENGTH: 16
<212> TYPE: PRT
<213> ORGANISM: Rattus norvegicus

<400> SEQUENCE: 203

Gly Leu Gly Leu Ser Gly Val Val Pro Thr Met His Phe Thr Ile Ala
1               5                   10                  15

<210> SEQ ID NO 204
<211> LENGTH: 16
<212> TYPE: PRT
<213> ORGANISM: Rattus norvegicus

<400> SEQUENCE: 204

Tyr Ile Thr Gly Ala Gly Leu Tyr Ala Ala Arg Ile Pro Glu Arg Phe
1               5                   10                  15

<210> SEQ ID NO 205
<211> LENGTH: 16
<212> TYPE: PRT
<213> ORGANISM: Rattus norvegicus

<400> SEQUENCE: 205

Gln Glu Phe Arg Tyr Gly Leu Glu Gly Gly Cys Thr Asp Asp Ser Leu
1               5                   10                  15

<210> SEQ ID NO 206
<211> LENGTH: 14
<212> TYPE: PRT
<213> ORGANISM: Rattus norvegicus

<400> SEQUENCE: 206

Pro Leu Leu Glu Glu Lys Gly Lys Arg Ala Ala Thr Ser Pro
1               5                   10

<210> SEQ ID NO 207
<211> LENGTH: 4
<212> TYPE: PRT
<213> ORGANISM: Rattus norvegicus

<400> SEQUENCE: 207

Ser Phe Val Ala
1

<210> SEQ ID NO 208
<211> LENGTH: 15
<212> TYPE: PRT
<213> ORGANISM: Rattus norvegicus

<400> SEQUENCE: 208

His Thr Val Tyr Cys His Ser Glu Gly Val Ser Arg Leu Phe Ser
1               5                   10                  15

<210> SEQ ID NO 209
```

```
<211> LENGTH: 7
<212> TYPE: PRT
<213> ORGANISM: Rattus norvegicus

<400> SEQUENCE: 209

Tyr Tyr Ser Phe Tyr Cys Asn
1               5

<210> SEQ ID NO 210
<211> LENGTH: 12
<212> TYPE: PRT
<213> ORGANISM: Rattus norvegicus

<400> SEQUENCE: 210

Asp Met Phe Ala Thr Pro Gln Tyr Arg Gly Val Arg
1               5                   10

<210> SEQ ID NO 211
<211> LENGTH: 20
<212> TYPE: PRT
<213> ORGANISM: Rattus norvegicus

<400> SEQUENCE: 211

Tyr Ala Ala Arg Ile Pro Glu Arg Phe Phe Pro Gly Lys Cys Asp Ile
1               5                   10                  15

Trp Phe His Ser
            20

<210> SEQ ID NO 212
<211> LENGTH: 13
<212> TYPE: PRT
<213> ORGANISM: Rattus norvegicus

<400> SEQUENCE: 212

Arg Pro Pro Met Pro Ser Phe Arg Ala Cys Phe Lys Ser
1               5                   10

<210> SEQ ID NO 213
<211> LENGTH: 13
<212> TYPE: PRT
<213> ORGANISM: Rattus norvegicus

<400> SEQUENCE: 213

Phe Leu Lys Ala Ala Thr Ile Arg Gln Ile Gly Trp Leu
1               5                   10

<210> SEQ ID NO 214
<211> LENGTH: 11
<212> TYPE: PRT
<213> ORGANISM: Rattus norvegicus

<400> SEQUENCE: 214

Ile Gly Gly Gly Cys Thr Glu Lys Asp Ala Leu
1               5                   10

<210> SEQ ID NO 215
<211> LENGTH: 14
<212> TYPE: PRT
<213> ORGANISM: Rattus norvegicus

<400> SEQUENCE: 215

Thr Pro Val Cys Ser Ser Tyr Tyr Glu Asn Ser Pro Glu Glu
1               5                   10
```

```
<210> SEQ ID NO 216
<211> LENGTH: 14
<212> TYPE: PRT
<213> ORGANISM: Rattus norvegicus

<400> SEQUENCE: 216

Ser Tyr Tyr Glu Asn Ser Pro Glu Glu Leu Glu Cys His Asp
1               5                   10

<210> SEQ ID NO 217
<211> LENGTH: 14
<212> TYPE: PRT
<213> ORGANISM: Rattus norvegicus

<400> SEQUENCE: 217

Cys His Asp Asp Asn Ser Gln Glu Asp Glu Gly Phe Met Gly
1               5                   10

<210> SEQ ID NO 218
<211> LENGTH: 14
<212> TYPE: PRT
<213> ORGANISM: Rattus norvegicus

<400> SEQUENCE: 218

Val Ser Arg Leu Phe Ser Lys Leu Asp Tyr Ser Gly Ile Ala
1               5                   10

<210> SEQ ID NO 219
<211> LENGTH: 14
<212> TYPE: PRT
<213> ORGANISM: Rattus norvegicus

<400> SEQUENCE: 219

Ala Ala Ile Ile Val Ser Gln Trp Asp Met Phe Ala Thr Pro
1               5                   10

<210> SEQ ID NO 220
<211> LENGTH: 11
<212> TYPE: PRT
<213> ORGANISM: Rattus norvegicus

<400> SEQUENCE: 220

Ile Gly Gly Gly Cys Thr Glu Lys Asp Ala Leu
1               5                   10

<210> SEQ ID NO 221
<211> LENGTH: 16
<212> TYPE: PRT
<213> ORGANISM: Rattus norvegicus

<400> SEQUENCE: 221

Asp Asp Thr Arg Gly Gly Asn Asn Asp Asn His His Gly Asp Leu Glu
1               5                   10                  15

<210> SEQ ID NO 222
<211> LENGTH: 16
<212> TYPE: PRT
<213> ORGANISM: Rattus norvegicus

<400> SEQUENCE: 222

Ile His Thr Glu Thr Gly Asn Ile Trp Thr His Leu Leu Gly Cys Val
1               5                   10                  15

<210> SEQ ID NO 223
<211> LENGTH: 16
```

```
<212> TYPE: PRT
<213> ORGANISM: Rattus norvegicus

<400> SEQUENCE: 223

Gly Leu Phe Phe Leu Gly Ala Ile Leu Cys Leu Ser Phe Ser Trp Leu
1               5                   10                  15

<210> SEQ ID NO 224
<211> LENGTH: 16
<212> TYPE: PRT
<213> ORGANISM: Rattus norvegicus

<400> SEQUENCE: 224

Thr Pro Gln Tyr Arg Gly Val Arg Ala Gly Val Phe Val Gly Leu Gly
1               5                   10                  15

<210> SEQ ID NO 225
<211> LENGTH: 16
<212> TYPE: PRT
<213> ORGANISM: Rattus norvegicus

<400> SEQUENCE: 225

Arg Gly Val Arg Ala Gly Val Phe Val Gly Leu Gly Leu Ser Gly Ile
1               5                   10                  15

<210> SEQ ID NO 226
<211> LENGTH: 16
<212> TYPE: PRT
<213> ORGANISM: Rattus norvegicus

<400> SEQUENCE: 226

Ala Gly Val Phe Val Gly Leu Gly Leu Ser Gly Ile Ile Pro Thr Leu
1               5                   10                  15

<210> SEQ ID NO 227
<211> LENGTH: 16
<212> TYPE: PRT
<213> ORGANISM: Rattus norvegicus

<400> SEQUENCE: 227

Gly Leu Gly Leu Ser Gly Ile Ile Pro Thr Leu His Tyr Val Ile Ser
1               5                   10                  15

<210> SEQ ID NO 228
<211> LENGTH: 15
<212> TYPE: PRT
<213> ORGANISM: Rattus norvegicus

<400> SEQUENCE: 228

Phe Arg Phe Met Ile Gly Gly Gly Cys Thr Glu Lys Asp Ala Leu
1               5                   10                  15

<210> SEQ ID NO 229
<211> LENGTH: 18
<212> TYPE: DNA
<213> ORGANISM: Rattus norvegicus

<400> SEQUENCE: 229
tcatcactgg gagatctc                                                 18

<210> SEQ ID NO 230
<211> LENGTH: 20
<212> TYPE: DNA
<213> ORGANISM: Rattus norvegicus
```

<400> SEQUENCE: 230
cctccaccaa ccctcaggtg    20

<210> SEQ ID NO 231
<211> LENGTH: 20
<212> TYPE: DNA
<213> ORGANISM: Rattus norvegicus

<400> SEQUENCE: 231
gtcggaagga gggtcaactc    20

<210> SEQ ID NO 232
<211> LENGTH: 19
<212> TYPE: DNA
<213> ORGANISM: Rattus norvegicus

<400> SEQUENCE: 232
ctcagggtca aagtccctg    19

<210> SEQ ID NO 233
<211> LENGTH: 7
<212> TYPE: PRT
<213> ORGANISM: bacteriophage T7

<400> SEQUENCE: 233

Asp Tyr Lys Asp Asp Asp Asp
1               5

<210> SEQ ID NO 234
<211> LENGTH: 9
<212> TYPE: PRT
<213> ORGANISM: influenza A virus

<400> SEQUENCE: 234

Tyr Pro Tyr Asp Val Pro Asp Tyr Ala
1               5

<210> SEQ ID NO 235
<211> LENGTH: 73
<212> TYPE: DNA
<213> ORGANISM: Homo sapiens

<400> SEQUENCE: 235
ggccgaagcc ggatccgcca ccatgggcga ttataaagat gacgatgacg gctcttccca    60
caaaggatct gtg    73

<210> SEQ ID NO 236
<211> LENGTH: 46
<212> TYPE: DNA
<213> ORGANISM: Homo sapiens

<400> SEQUENCE: 236
ggccgaagcc ctcgagggct cagagaaggg tgtcatcagt acagcc    46

<210> SEQ ID NO 237
<211> LENGTH: 46
<212> TYPE: DNA
<213> ORGANISM: Homo sapiens

<400> SEQUENCE: 237
ggccgaagcc ggatccgcca ccatgtcttc ccacaaagga tctgtg    46

<210> SEQ ID NO 238
<211> LENGTH: 73
<212> TYPE: DNA
<213> ORGANISM: Homo sapiens

<400> SEQUENCE: 238
ggccgaagcc ctcgagggct caagcgtaat ctggaacatc gtatgggtag agaagggtgt    60
catcagtaca gcc                                                      73

<210> SEQ ID NO 239
<211> LENGTH: 71
<212> TYPE: DNA
<213> ORGANISM: Homo sapiens

<400> SEQUENCE: 239
ggccgaagcc gaattcgcca ccatgggcga ttataaagat gacgatgacg gcgaaaaaat    60
ggaagaattt g                                                        71

<210> SEQ ID NO 240
<211> LENGTH: 49
<212> TYPE: DNA
<213> ORGANISM: Homo sapiens

<400> SEQUENCE: 240
ggccgaagcc ctcgagggct cacagtgcat cctcttcact gcagccccc              49

<210> SEQ ID NO 241
<211> LENGTH: 44
<212> TYPE: DNA
<213> ORGANISM: Homo sapiens

<400> SEQUENCE: 241
ggccgaagcc gaattcgcca ccatggaaaa aatggaagaa tttg                    44

<210> SEQ ID NO 242
<211> LENGTH: 76
<212> TYPE: DNA
<213> ORGANISM: Homo sapiens

<400> SEQUENCE: 242
ggccgaagcc ctcgagggct caagcgtaat ctggaacatc gtatgggtac agtgcatcct    60
cttcactgca gccccc                                                   76

<210> SEQ ID NO 243
<211> LENGTH: 39
<212> TYPE: DNA
<213> ORGANISM: Homo sapiens

<400> SEQUENCE: 243
cggggagtaa gagcaggagt gtttttggga ctaggcctg                          39

<210> SEQ ID NO 244
<211> LENGTH: 39
<212> TYPE: DNA
<213> ORGANISM: Homo sapiens

<400> SEQUENCE: 244
caggcctagt cccaaaaaca ctcctgctct tactccccg                          39

<210> SEQ ID NO 245
<211> LENGTH: 79
<212> TYPE: DNA

```
<213> ORGANISM: Homo sapiens

<400> SEQUENCE: 245
ggccgaagcc gaattcgcca ccatgggcga ttataaagat gacgatgacg gcaacgagcc      60
aacagaaaac cgattgggg                                                   79

<210> SEQ ID NO 246
<211> LENGTH: 49
<212> TYPE: DNA
<213> ORGANISM: Homo sapiens

<400> SEQUENCE: 246
ggccgaagcc ctcgagggct cacagtgcat cctcttcact gcagccccc                  49

<210> SEQ ID NO 247
<211> LENGTH: 52
<212> TYPE: DNA
<213> ORGANISM: Homo sapiens

<400> SEQUENCE: 247
ggccgaagcc gaattcgcca ccatgaacga gccaacagaa aaccgattgg gg              52

<210> SEQ ID NO 248
<211> LENGTH: 76
<212> TYPE: DNA
<213> ORGANISM: Homo sapiens

<400> SEQUENCE: 248
ggccgaagcc ctcgagggct caagcgtaat ctggaacatc gtatgggtac agtgcatcct      60
cttcactgca gccccc                                                      76
```

What is claimed is:

1. An isolated polypeptide comprising a polypeptide sequence selected from the group consisting of:
   (a) an isolated polypeptide comprising amino acids 1 to 421 of SEQ ID NO:104; and
   (b) an isolated polypeptide comprising amino acids 2 to 421 of SEQ ID NO:104, wherein said polypeptide is capable of binding to adiponectin.

2. The isolated polypeptide of claim 1, wherein said polypeptide is (a).

3. The isolated polypeptide of claim 1, wherein said polypeptide is (b).

4. The isolated polypeptide of claim 1 further comprising a heterologous polypeptide sequence, wherein said heterologous polypeptide is the Fc domain of an immunoglobulin.

5. An isolated polypeptide comprising between 294 to 420 contiguous amino acids of SEQ ID NO:104, wherein said polypeptide is capable of binding to adiponectin.

6. An isolated polypeptide comprising amino acids 1 to 294 of SEQ ID NO:104, wherein said polypeptide is capable of binding to adiponectin.

7. An isolated polypeptide comprising amino acids 128 to 421 of SEQ ID NO:104, wherein said polypeptide is capable of binding to adiponectin.

8. An isolated polypeptide comprising the polypeptide encoded by the flag-tagged hAdipoR2V2 plasmid contained in ATCC Deposit No. PTA-6088.

9. An isolated polypeptide comprising the polypeptide encoded by the HA-tagged hAdipoR2V2 plasmid contained in ATCC Deposit No. PTA-6088.

10. An isolated polypeptide comprising at least 95.0% identity to amino acids 2 to 421 of SEQ ID NO: 104, wherein said polypeptide is capable of binding to adiponectin.

* * * * *

UNITED STATES PATENT AND TRADEMARK OFFICE
CERTIFICATE OF CORRECTION

PATENT NO. : 7,598,348 B2 Page 1 of 1
APPLICATION NO. : 12/148669
DATED : October 6, 2009
INVENTOR(S) : Chen et al.

It is certified that error appears in the above-identified patent and that said Letters Patent is hereby corrected as shown below:

Column (62) should read:

This application is a divisional application of non-provisional application U.S. Serial No. 10/874,923, filed June 23, 2004, which claims benefit to provisional application U.S. Serial No. 60/482,324 filed June 25, 2003; to provisional application U.S. Serial No. 60/486,036, filed July 10, 2003; to provisional application U.S. Serial No. 60/492,470, filed August 4, 2003; to provisional application U.S. Serial No. 60/508,225, filed October 2, 2003; and to provisional application U.S. Serial No. 60/552,084, filed March 11, 2004

Signed and Sealed this

Fifteenth Day of June, 2010

David J. Kappos
*Director of the United States Patent and Trademark Office*